(12) United States Patent
Flood et al.

(10) Patent No.: US 11,939,336 B2
(45) Date of Patent: Mar. 26, 2024

(54) ARYL TRIAZOLE CAGES

(71) Applicant: INDIANA UNIVERSITY RESEARCH AND TECHNOLOGY CORPORATION, Indianapolis, IN (US)

(72) Inventors: Amar H. Flood, Bloomington, IN (US); Yun Liu, Bloomington, IN (US); Wei Zhao, Bloomington, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 695 days.

(21) Appl. No.: 16/965,283

(22) PCT Filed: May 22, 2019

(86) PCT No.: PCT/US2019/033631
§ 371 (c)(1),
(2) Date: Jul. 27, 2020

(87) PCT Pub. No.: WO2019/226839
PCT Pub. Date: Nov. 28, 2019

(65) Prior Publication Data
US 2021/0363150 A1    Nov. 25, 2021

Related U.S. Application Data

(60) Provisional application No. 62/675,572, filed on May 23, 2018.

(51) Int. Cl.
| | | |
|---|---|---|
| *C07D 487/22* | (2006.01) | |
| *B01D 11/04* | (2006.01) | |
| *B01D 15/08* | (2006.01) | |
| *C02F 1/26* | (2023.01) | |
| *C07D 471/22* | (2006.01) | |
| *C07D 498/22* | (2006.01) | |
| *C08K 5/3472* | (2006.01) | |
| *C09D 5/08* | (2006.01) | |

(52) U.S. Cl.
CPC ........ *C07D 487/22* (2013.01); *B01D 11/0492* (2013.01); *B01D 15/08* (2013.01); *C02F 1/26* (2013.01); *C07D 471/22* (2013.01); *C07D 498/22* (2013.01); *C09D 5/086* (2013.01); *C08K 5/3472* (2013.01)

(58) Field of Classification Search
CPC .. C07D 487/22; C07D 471/22; C07D 498/22; B01D 11/0492; B01D 15/08; C02F 1/26; C09D 5/086; C08K 5/3472
See application file for complete search history.

(56) References Cited

U.S. PATENT DOCUMENTS

2016/0347758 A1\* 12/2016 Flood ....................... C02F 1/42

OTHER PUBLICATIONS

Couty et al., SYNLETT 2009, No. 12, pp. 1945-1948.\*
Written Opinion for International Patent Application No. PCT/US2019/033631 dated Nov. 28, 2019, 6 pages.
International Search Report for International Patent Application No. PCT/US2019/033631 dated Nov. 28, 2019, 4 pages.

\* cited by examiner

*Primary Examiner* — Alicia L Otton
(74) *Attorney, Agent, or Firm* — Quarles & Brady, LLP

(57) ABSTRACT

The present disclosure concerns synthesis, anion binding features, liquid-liquid extraction of salts, and anti-corrosion character of aryl-triazole bicyclic macrocycles of Formula (I) and related compounds:

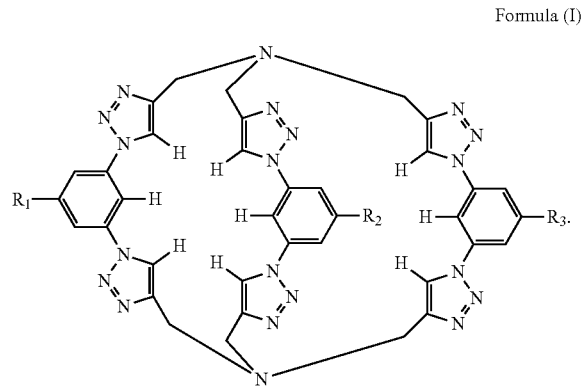

Formula (I)

48 Claims, 13 Drawing Sheets

Sequence 3: RXN 1, 2, 6

Sequence 4: RXN 5, 6

Triazolophane 2

Triazolotripod 3

ARYL TRIAZOLE CAGES

CROSS-REFERENCE TO RELATED APPLICATIONS

This application is the U.S. national stage application of International Patent Application No. PCT/US2019/033631, filed May 22, 2019, which claims benefit of priority under 35 U.S.C. 119 to U.S. Provisional Patent Application Ser. No. 62/675,572, filed May 23, 2018, which is entitled "ARYL TRIAZOLE CAGES," the contents of which are herein incorporated by reference in its entirety.

STATEMENT REGARDING FEDERALLY SPONSORED RESEARCH OR DEVELOPMENT

This invention was made with government support under DE-SC0002728 awarded by Department Of Energy. The government has certain rights in the invention.

FIELD OF THE INVENTION

This invention pertains to the design and preparation of triazole bicycle macrocycle compounds and complexes formed between the triazole compounds and anions. Methods of using the triazole compounds for removing anions from a solution and for preventing corrosion of a metal surface are also provided.

BACKGROUND OF THE INVENTION

Chloride is a ubiquitous anion present in natural waters and with growing penetration into areas relevant to modern society. Chloride is implicated in corrosion of metals (1) and impacts fit-for-purpose water quality such as for drinking and industrial use (2). Natural waters like rivers can carry as much as 50 mg/mL (~1 mM) of chloride. Intensive and extensive increases in the use of water in the energy and food sectors alter this balance raising salt concentrations that motivates interest in new approaches to better water management. The selective capture and extraction of chloride is needed and molecular recognition promises access to this characteristic.

Receptors capable of high extraction efficiency need to have sufficiently high affinities. Such receptors exist for cations (3) but are less prevalent for anions. Anions have higher hydration energies than cations, which inhibits phase transfer (4), e.g., transferring $Cl^-$ from water to 1,2-dichloroethane ($\varepsilon$=10.4) solvent is 52 kJ $mol^{-1}$ uphill while it is only 25 kJ $mol^{-1}$ for $Na^+$. Anions are larger than cations (5) requiring more covalent synthesis to construct a cavity fit for anions. Once constructed, the larger sizes of both receptor and anion lead to lower charge densities and intrinsically lower binding affinities. There are only a handful of receptors matching or exceeding the penalty of phase transfer ($\Delta G$ of 50 kJ $mol^{-1}$=$K_a$ ~$10^9$ $M^{-1}$): Maeda's pyrrole macrocycle ($10^{10}$ $M^{-1}$) measured in dichloromethane (6), Davis's steroidal tris-thiourea ($10^{11}$ $M^{-1}$) (7) and squaramide ($10^{14}$ $M^{-1}$) (8) both measured in wet chloroform. Surprisingly, these affinities are achieved using charge-neutral receptors, which circumvent the pH sensitivity that typically follows ionizable receptors.

Cryptands (9) are a class of cation binding receptor known to confer high selectivity as well as high affinity by virtue of the three-dimensional (3D) character of the binding pocket. The impact on cations is well known with the two-dimensional (2D) pocket of crown ethers being raised to a 3D pocket in cryptands enhancing $K^+$ affinity from 104 to $10^{10}$ $M^{-1}$ and selectivity of $K^+$ over $Na^+$ from 13 to 350-fold (10). The same design principle has been seen with Bowman-James's polyamide cryptands (11), Cummins and Nocera's peroxide receptors (12), Sessler's pyrrole-based cryptands (13), all of which are neutral, and Lehn's cationic (pH-dependent) aza-cryptands (10).

There is a need for compositions and formulations that enable one to readily complex with anions present in an aqueous solution. Such compositions would be desired for the purpose of providing methods that may extract salts from aqueous solutions and provide for certain beneficial properties.

BRIEF SUMMARY OF THE INVENTION

In a first aspect, an aryl-triazole bicyclic macrocycle of Formula (I) is provided:

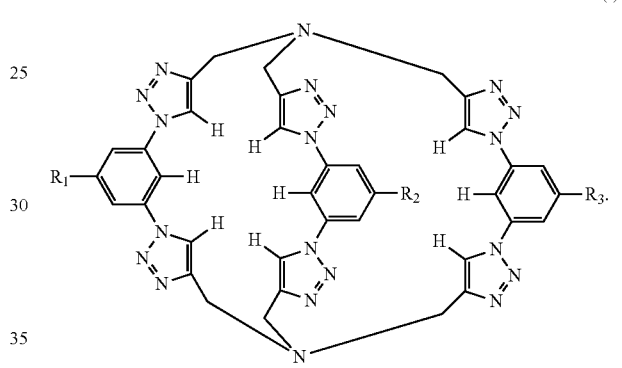

(I)

The $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

In a second aspect, a method of synthesizing an aryl-triazole bicyclic macrocycle of Formula (II) is disclosed:

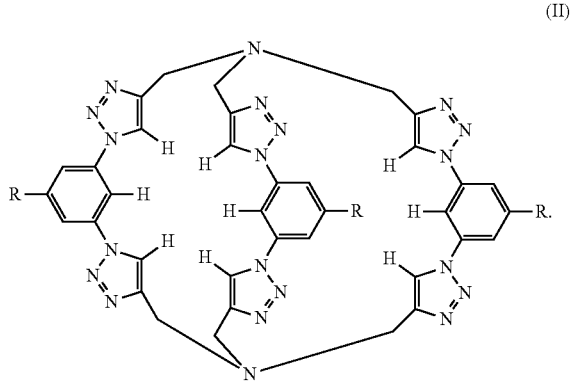

(II)

The R substituents are independently selected from the group consisting of alkenyl, alkyl, alkoxy, alkyl-NH-alkyl, aryl, cycloalkyl, heteroaryl, heterocycle, haloalkyl, hydrogen, iodo, —OR⁶, —N(R⁷R⁸), —CO₂R⁹, —C(O)—N(R¹⁰R¹¹), wherein R⁶, R⁷, R⁸, R⁹, R¹⁰, and R¹¹ are each independently selected from the group consisting of alkenyl, alkyl, aryl, arylalkyl, cycloalkyl, heteroaryl, heterocycle, haloalkyl, and hydrogen. The method includes several steps. A first step is forming a reaction mixture comprising:

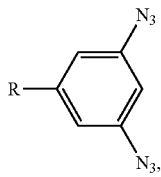

tripropargylamine; and a solvent. The

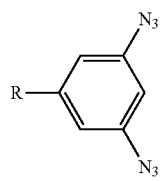

is selected from the group consisting of

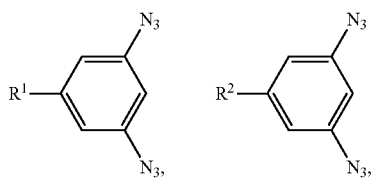

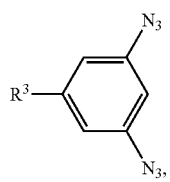

or a combination thereof.

The $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —OR⁴, —N(R⁵R⁶), —CO₂R⁷, —C(O)—N(R⁸R⁹), wherein R⁴, R⁵, R⁶, R⁷, R⁸, and R⁹ are each independently selected from the group consisting of alkenyl, alkyl, aryl, arylalkyl, cycloalkyl, heteroaryl, heterocycle, haloalkyl, and hydrogen. A second step is incubating the reaction mixture at an elevated reaction temperature for a reaction time to form the aryl-triazole bicyclic macrocycle of Formula (II). A third step is optionally purifying the aryl-triazole bicyclic macrocycle of Formula (II) from the reaction mixture to provide the aryl-triazole bicyclic macrocycle of Formula (II).

In a third aspect, method of synthesizing an aryl-triazole bicyclic macrocycle selected from Formulas (I) and (II) is presented:

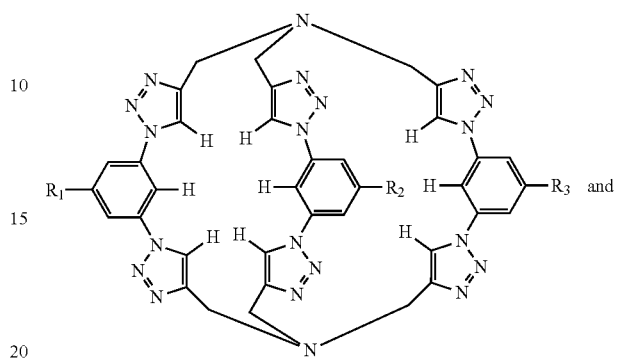

(I)

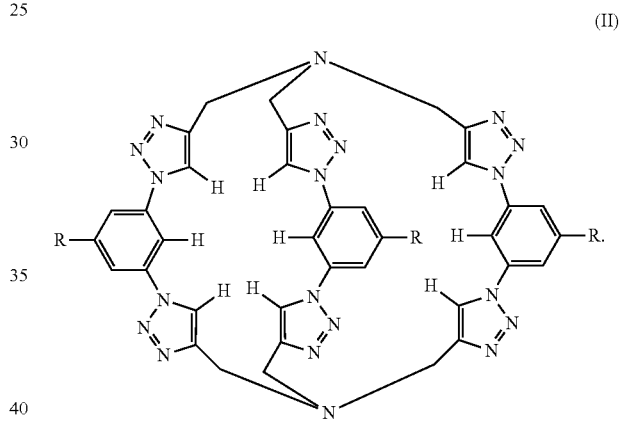

(II)

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —OR⁴, —N(R⁵R⁶), —CO₂R⁷, —C(O)—N(R⁸R⁹), wherein R⁴, R⁵, R⁶, R⁷, R⁸, and R⁹ are each independently selected from the group consisting of alkenyl, alkyl, aryl, arylalkyl, cycloalkyl, heteroaryl, heterocycle, haloalkyl, and hydrogen.

For (II), R is independently selected from the group consisting of alkenyl, alkyl, alkoxy, alkyl-NH-alkyl, aryl, cycloalkyl, heteroaryl, heterocycle, haloalkyl, hydrogen, iodo, —OR⁴, —N(R⁵R⁶), —CO₂R⁷, —C(O)—N(R⁸R⁹), wherein R⁴, R⁵, R⁶, R⁷, R⁸, and R⁹ are each independently selected from the group consisting of alkenyl, alkyl, aryl, arylalkyl, cycloalkyl, heteroaryl, heterocycle, haloalkyl, and hydrogen.

The method comprising a method of step-wise reactions selected from the group consisting of Sequences 1-4.

In a fourth aspect, an aryl-triazole bicyclic macrocycle of Formula (III) is presented:

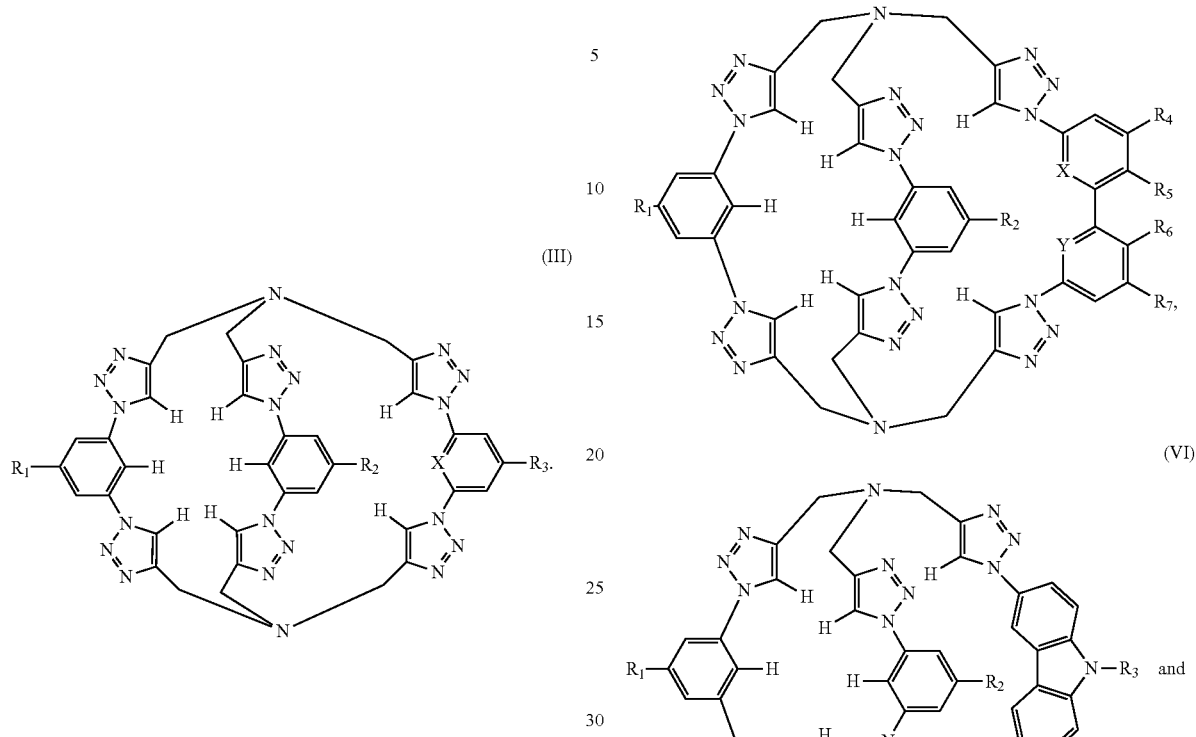

X is independently selected from the group consisting of CH, CF and N. The $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

In a fifth aspect, an aryl-triazole bicyclic macrocycle selected from the group consisting of Formulas (IV), (V), (VI) and (VII) is presented:

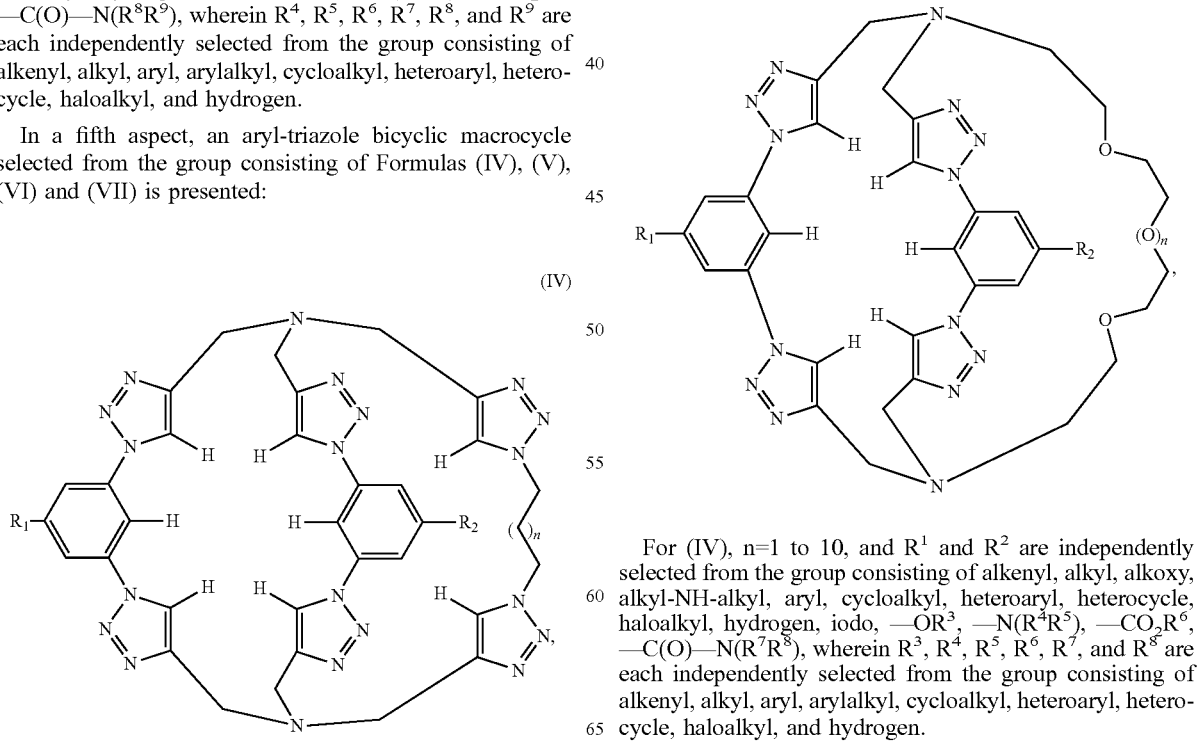

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —$C(O)$—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

In a sixth aspect, a method of synthesizing an aryl-triazole bicyclic macrocycle selected from Formulas (III), (IV), (V) and (VI) is presented:

(III)

(IV)

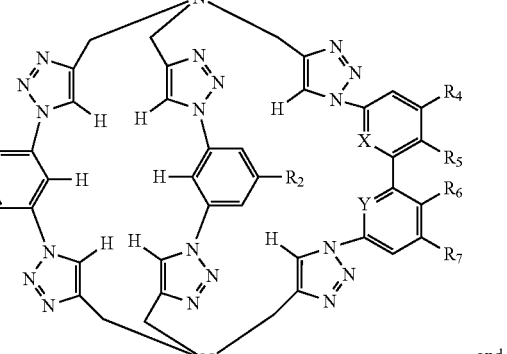

(V)

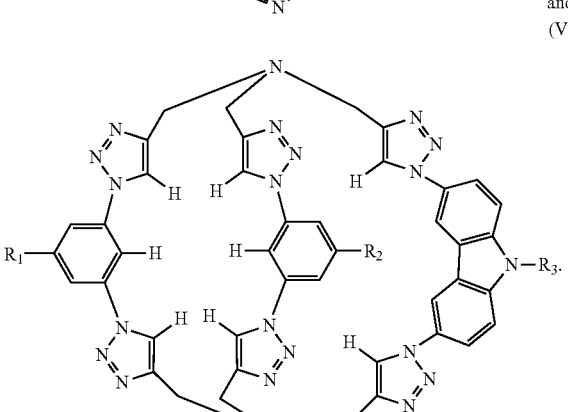

and (VI)

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —$C(O)$—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—N$(R^8R^9)$, wherein $R^4$, $R^5$, $R^6$, $R^7$, R, and $R^9$ are each independently selected from the group consisting of alkenyl, alkyl, aryl, arylalkyl, cycloalkyl, heteroaryl, heterocycle, haloalkyl, and hydrogen.

The method comprises a method of step-wise synthesis selected from Sequences 1-4.

In a seventh aspect, a method of synthesizing an aryl-triazole bicyclic macrocycle of Formula (VII) is presented:

(VII)

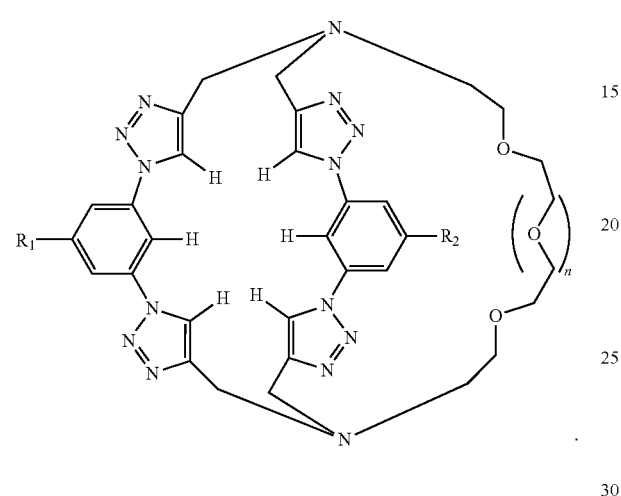

The value of n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

The method includes several steps. A first step includes preparing macrocycle intermediate MC1-1. A second step includes alkylating macrocycle intermediate MC1-1 to produce the aryl-triazole bicyclic macrocycle of Formula (VII).

In an eighth aspect, a complex is provided. The complex includes (a) an anion; (b) a cation and (c) an aryl-triazole bicyclic macrocycle selected from the group consisting of Formulas (I), (III), (IV), (V), (VI) and (VII):

(I)

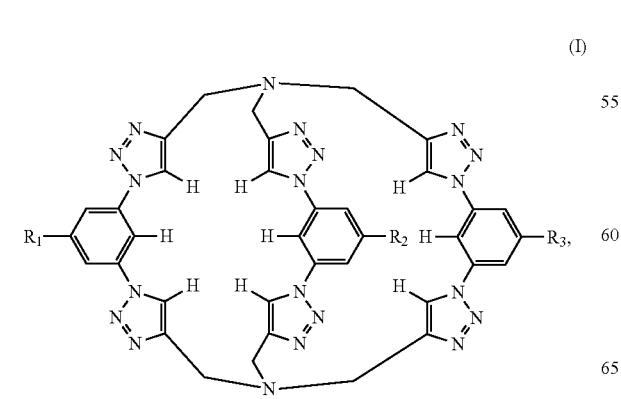

(III)

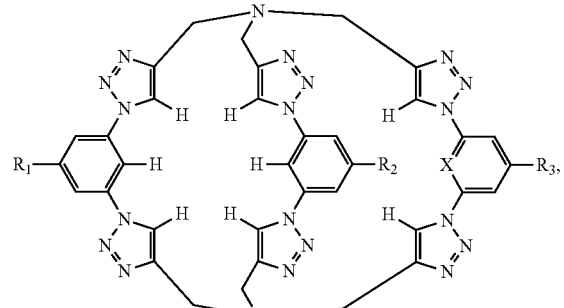

(IV)

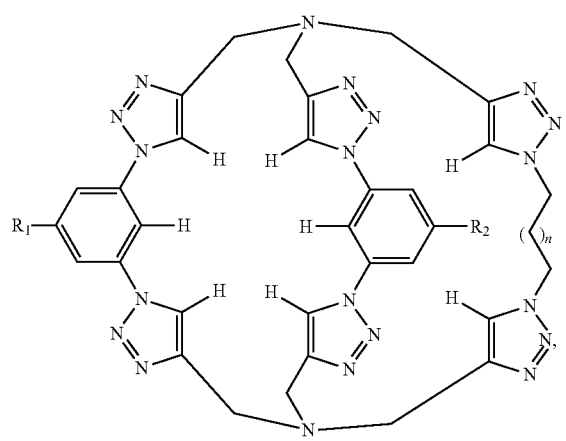

(V)

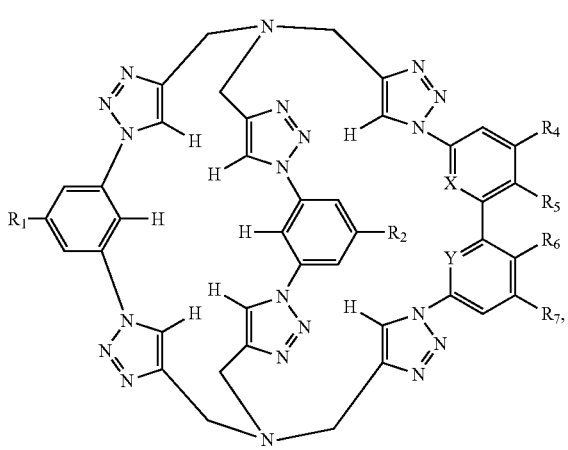

-continued (VI)

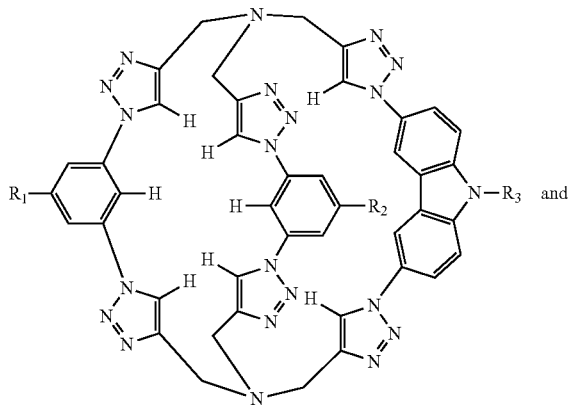

(VII)

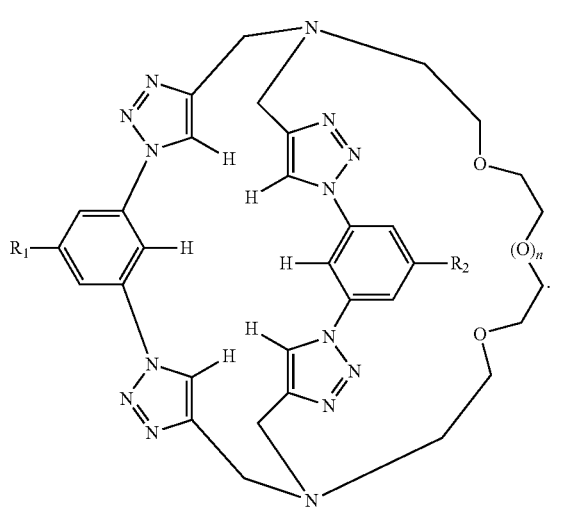

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—N($R^{12}R^{13}$), wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

In a ninth aspect, a method of removing an anion from an aqueous solution containing the anion is provided. The method includes several steps. The first step includes contacting the aqueous solution with an immiscible organic solution of an aryl-triazole bicyclic macrocycle selected from the group consisting of Formulas (I), (III), (IV), (V), (VI) and (VII):

(I)

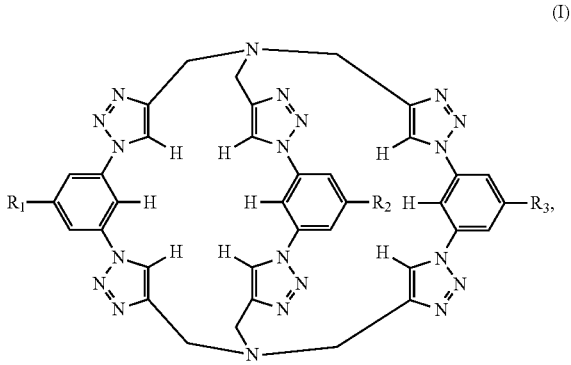

(III)

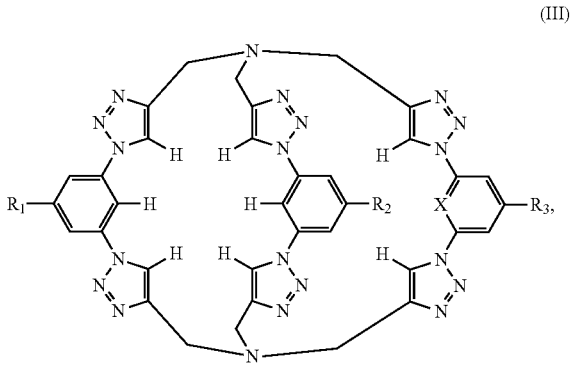

-continued (IV)
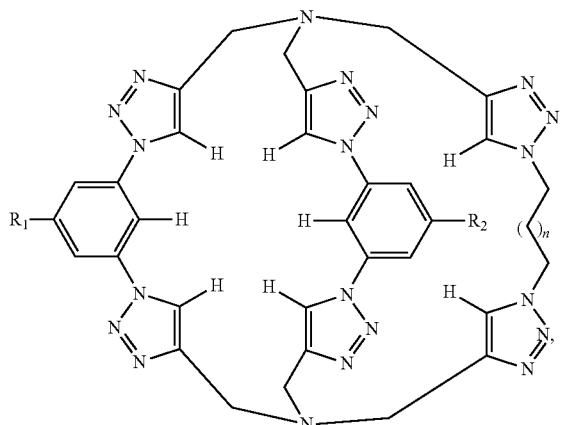

(V)
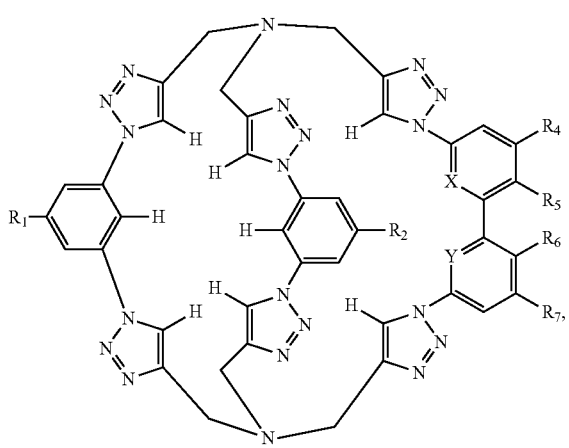

(VI)
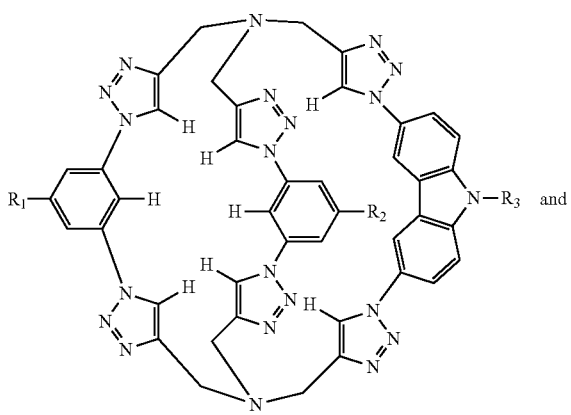

-continued (VII)
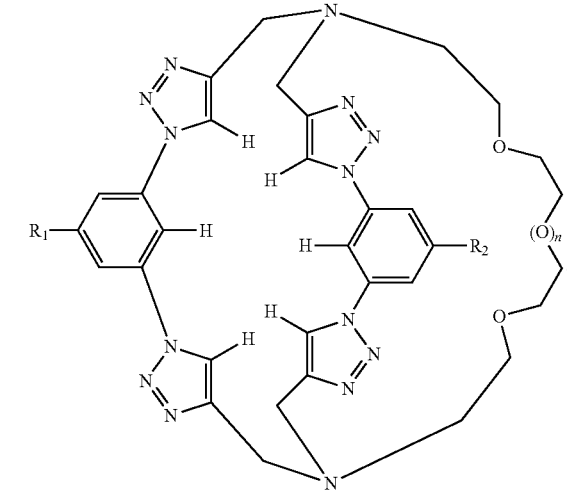

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—N($R^{12}R^{13}$), wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, $-OR^3$, $-N(R^4R^5)$, $-CO_2R^6$, $-C(O)-N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

The aqueous solution includes an anion and a cation. The second step includes forming a complex. The complex includes the anion, the cation and the aryl-triazole bicyclic macrocycle. The complex is formed in the organic layer. The third step includes separating the organic layer from aqueous layer, thereby removing the anion from the aqueous solution.

In a tenth aspect, a method of preventing corrosion of a metal surface is provided. The method includes several steps. The first step includes depositing a solution comprising an aryl-triazole bicyclic macrocycle in a solvent phase onto the metal surface to produce a coating on the metal surface. The aryl-triazole bicyclic macrocycle is selected from the group consisting of Formulas (I), (III), (IV), (V), (VI) and (VII):

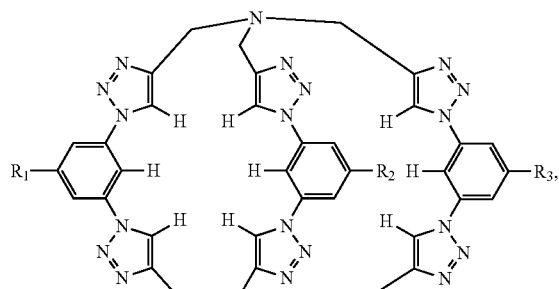

(I)

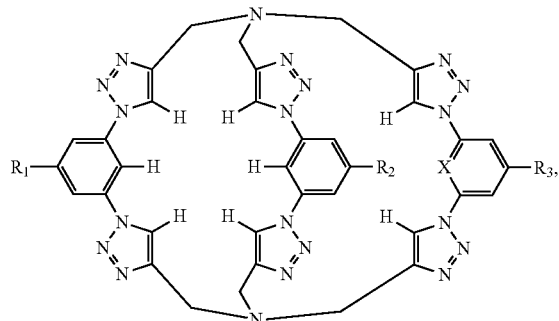

(III)

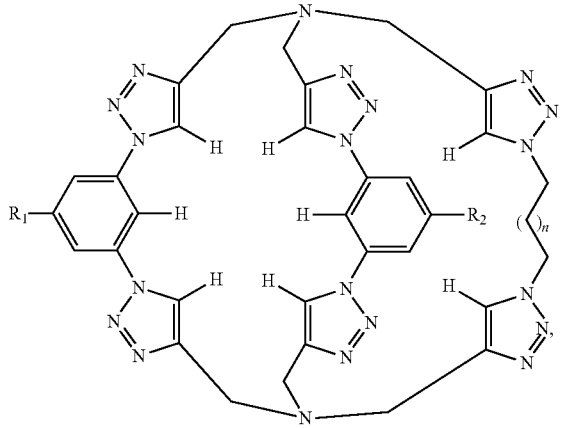

(IV)

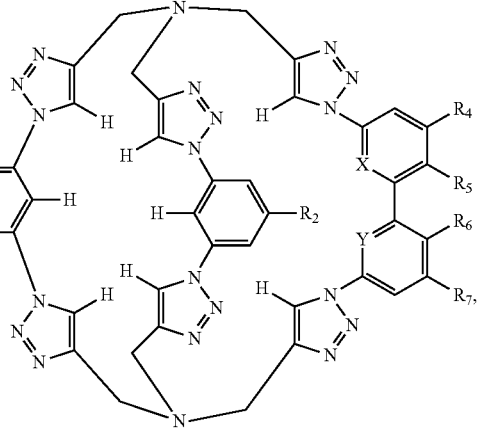

(V)

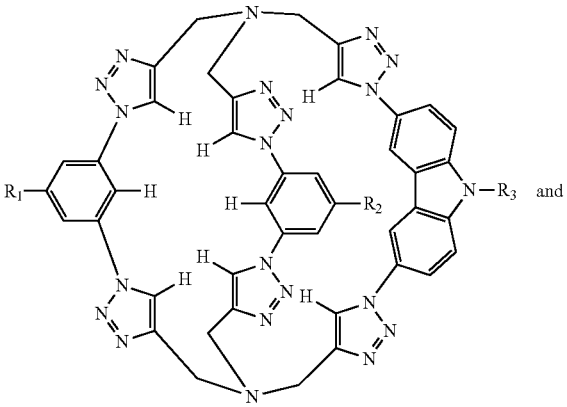

(VI)

and

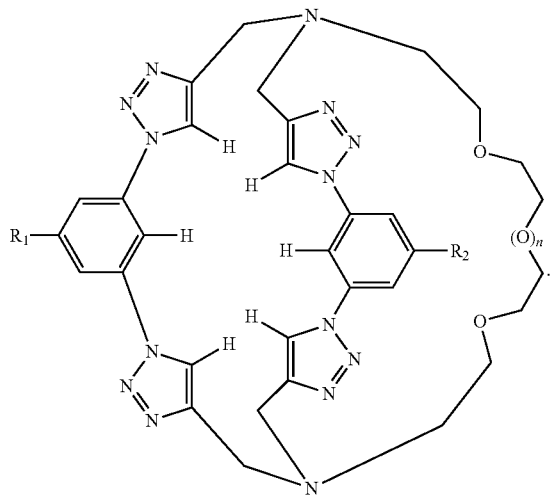

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

The second step includes removing the solvent phase from the coating to produce a metal surface having dried coating. The third step includes annealing the dried coating onto the metal surface by applying a neat solvent to the metal surface having the dried coating of the second step.

In an eleventh aspect, a composition is provided. The composition includes a metal surface and a coating. The coating includes an aryl-triazole bicyclic macrocycle selected from the group consisting of Formulas (I), (III), (IV), (V), (VI) and (VII):

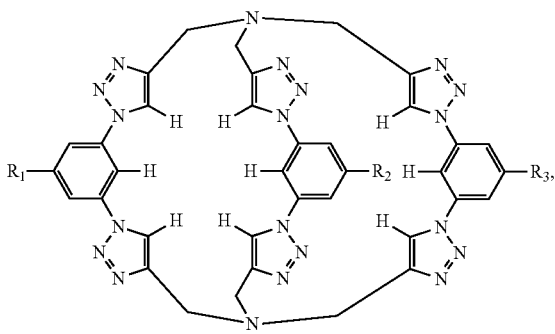

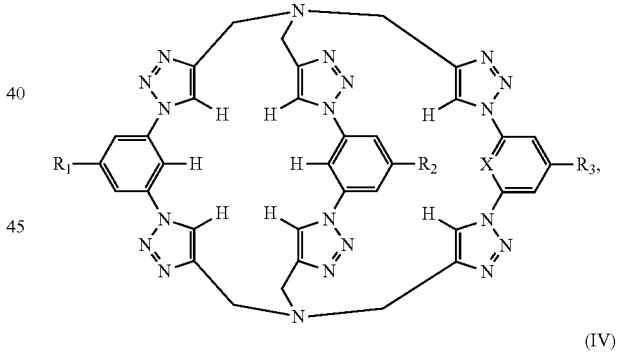

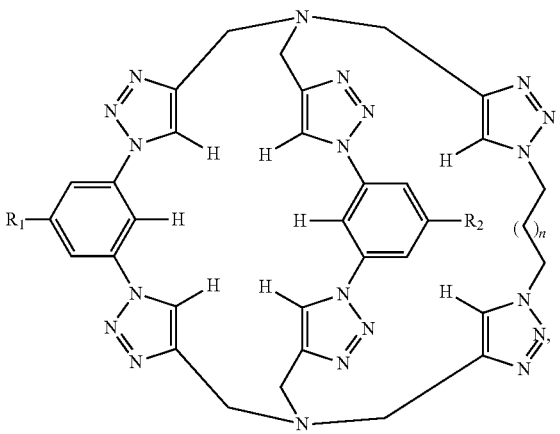

-continued

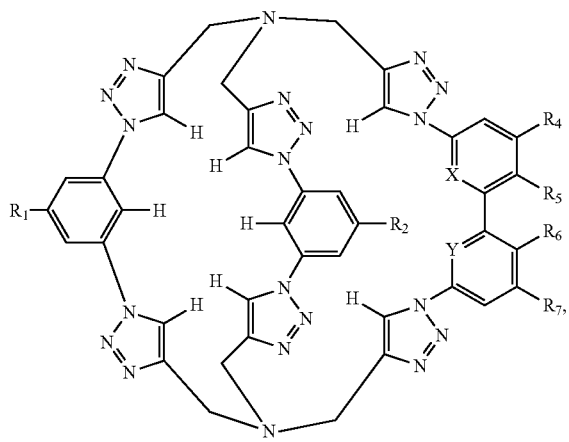
(V)

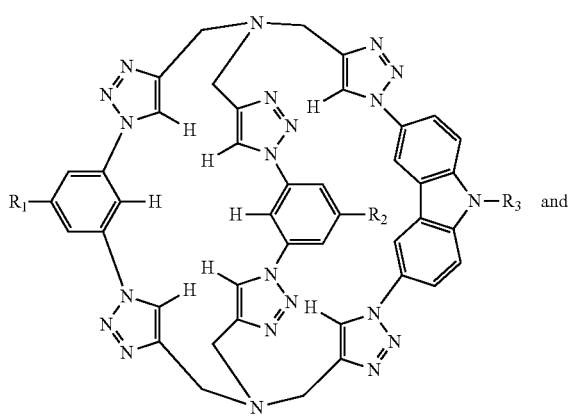
(VI) and

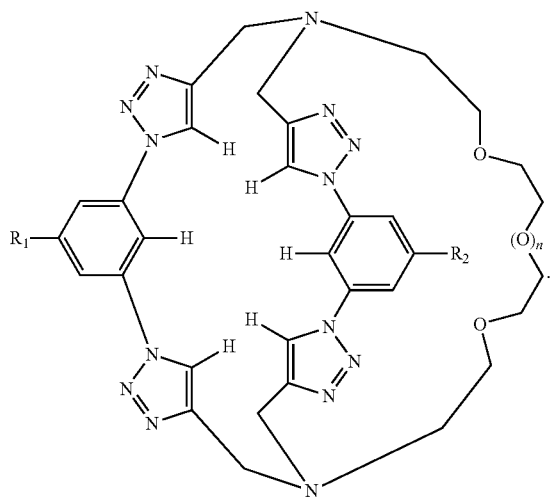
(VII)

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—N($R^{12}R^{13}$), wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

In a twelfth aspect, a formulation is provided. The formulation includes a coating and an aryl-triazole bicyclic macrocycle selected from the group consisting of Formulas (I), (III), (IV), (V), (VI) and (VII):

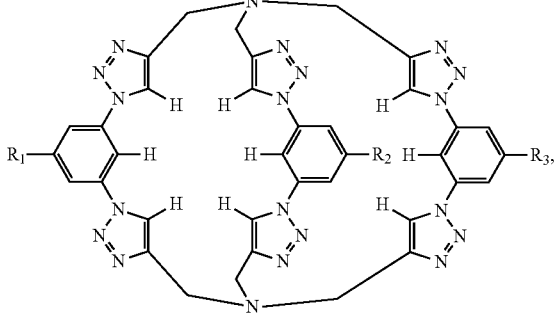
(I)

(III)
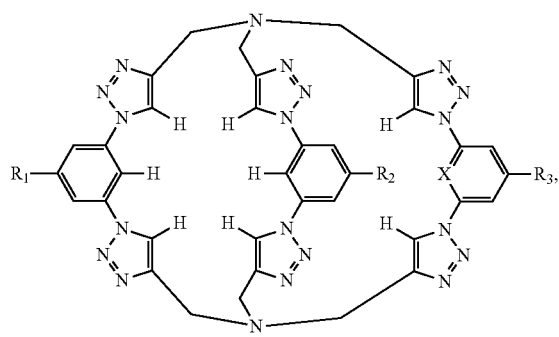

(IV)
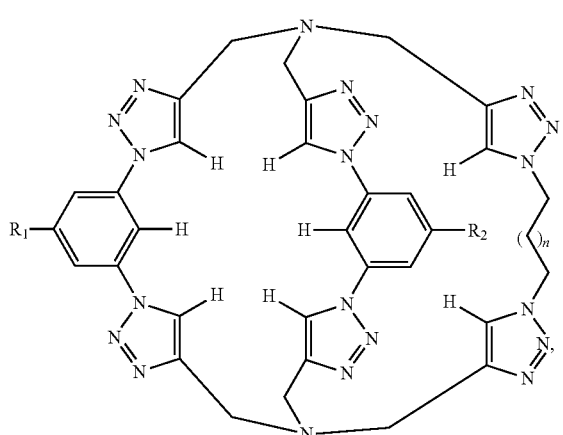

(V)
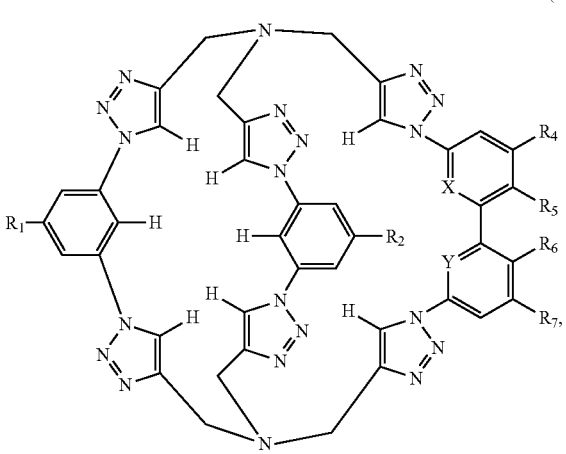

(VI)
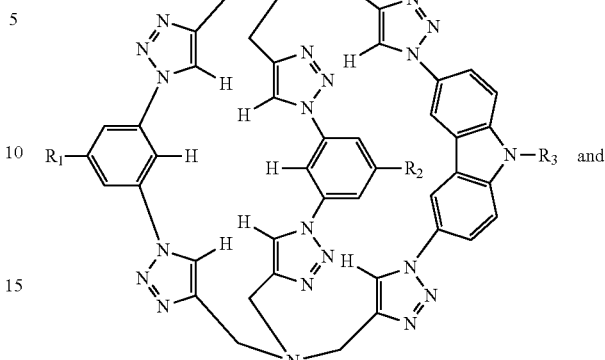
and (VII)
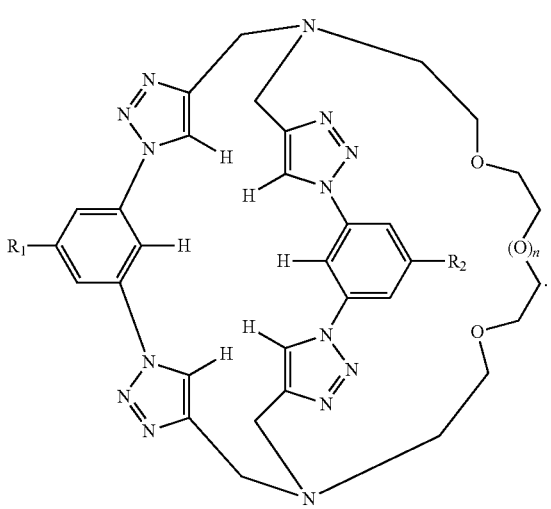

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

DETAILED DESCRIPTION

Figure 1A:
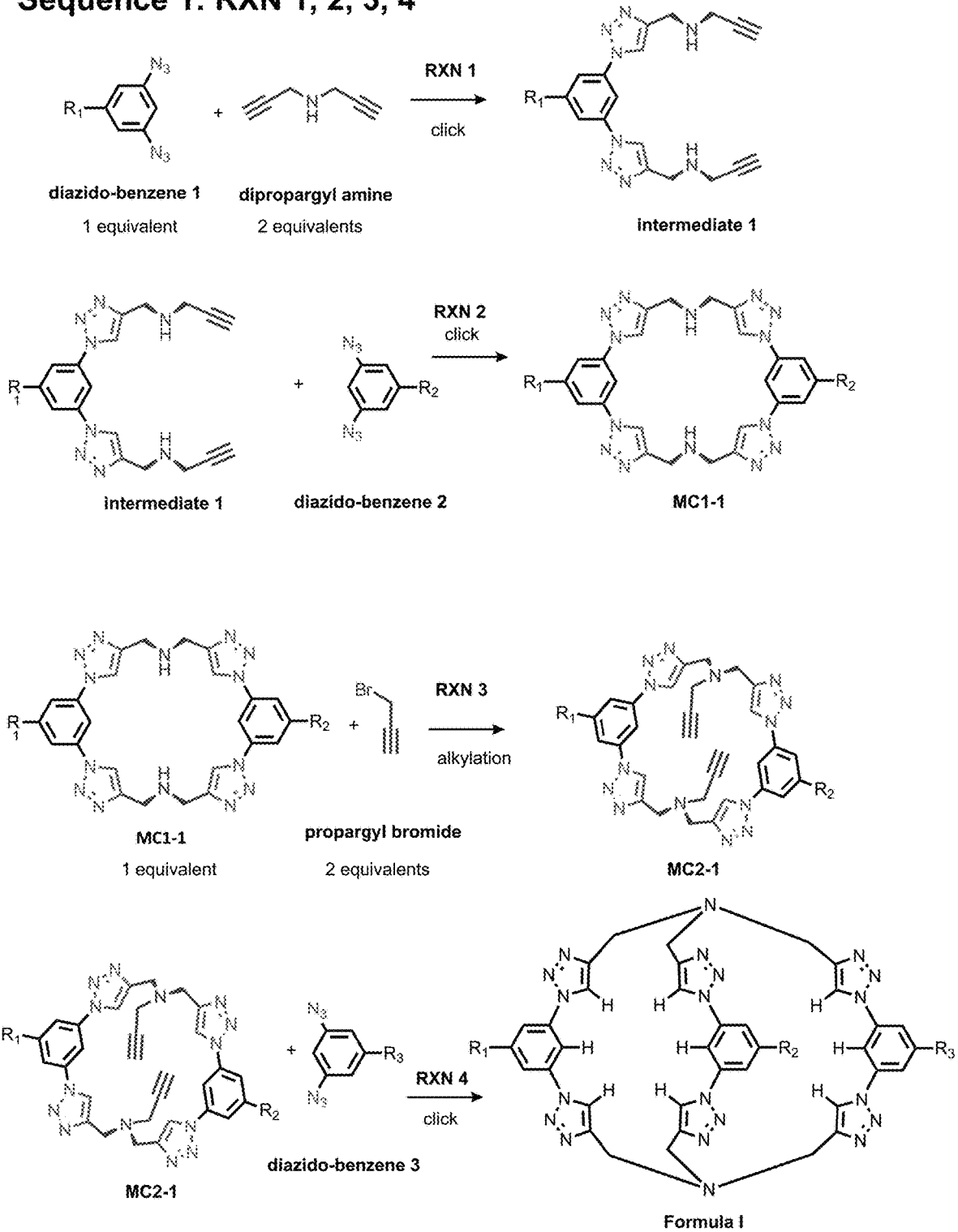
FIG. 1A depicts exemplary reaction strategies for preparing compounds of Formulas (I)-(VI) that includes step-wise synthesis reactions ("RXN") 1, 2, 3 and 4.

The present disclosure is based on the discovery of a novel class of aryl-triazole bicyclic macrocycles. The aryl-triazole bicyclic macrocycle compounds display high affinity for anions and can act as anion receptors or chelators. The compounds display robust affinity for chloride, having the highest chloride binding strength ever to be measured. The selectivity for chloride is also high relative to other anions tested (bromide, nitrate, iodide) and it may be the highest known. The compounds can be used in methods to desalinate salt water (NaCl) by extract NaCl into a suitable organic solvent (dichloromethane). Finally, coatings including aryl-triazole bicyclic macrocycle compounds can be applied to metal surfaces to inhibit corrosion of metal surfaces.

Definitions

When introducing elements of aspects of the disclosure or particular embodiments, the articles "a," "an," "the," and "said" are intended to mean that there are one or more of the elements. The terms "comprising," "including," and "having" are intended to be inclusive and mean that there may be additional elements other than the listed elements. The term "or" means any one member of a particular list and also includes any combination of members of that list, unless otherwise specified.

As intended herein, the terms "substantially," "approximately," and "about" and similar terms are intended to have a broad meaning in harmony with the common and accepted usage in the art to which the subject matter of this disclosure pertains. It should be understood by those of skill in the art who review this disclosure that these terms are intended to allow a description of certain features described and claimed without restricting the scope of these features to precise numerical ranges provided. Accordingly, these terms should be interpreted as indicating that insubstantial or inconsequential modifications or alterations of the subject matter described and claimed are considered to be within the scope of the invention as recited in the appended claims.

The compounds herein described may exhibit chirality and may be isolated in optically active or racemic forms. Methods for preparing optically active forms include, for instance, resolution of racemic forms or synthesis from optically active starting materials. Many geometric isomers of olefins, C=N double bonds, and the like can also be present in the compounds described herein, and all such stable isomers are contemplated in the present invention. All chiral, diastereomeric, racemic forms and all geometric isomeric forms of a structure are intended, unless the specific stereochemistry or isomeric form is specifically indicated.

The compounds of the composition and formulations disclosed herein may exist as salts. The term "salt," refers to salts or zwitterions of the compounds which are water or oil-soluble or dispersible. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, form ate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent, provided that the resulting bond is present in a stable compound.

The term "hydroxy" as used herein, refers to an —OH group. The term "oxo" as used herein, refers to a =O group. The term "oxy" as used herein, refers to a —O— group. The term "sulfonyl" as used herein, refers to a —S(O)$_2$— group. The term "carbonyl" as used herein refers to a —C(O)— group. The term "carboxy" as used herein refers to a —C(O)—OH group. The term "halo" or "halogen," as used herein, refers to —Cl, —Br, —I or —F.

The term "alkenyl" as used herein, refers to a straight or branched chain hydrocarbon group containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, hexyloxy, heptyloxy, octyloxy, nonyloxy, decyloxy, undecyloxy, dodecyloxy, trisdecyloxy, tetradecyloxy, and pentadecyloxy.

The term "alkyl" as used herein, refers to a straight or branched chain hydrocarbon group containing from 1 to 15 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkyl-NH" as used herein, refers to an alkyl group, as defined herein, appended to the parent molecular moiety through a nitrogen atom.

The term "alkyl-NH-alkyl" as used herein, refers to an alkyl-NH group, as defined herein, appended to the parent molecular moiety through an alkyl group, as defined herein.

The term "aryl" as used herein, means a phenyl group, or a bicyclic or a tricyclic fused ring system. Bicyclic fused ring systems are exemplified by a phenyl group appended to the parent molecular moiety and fused to a monocyclic cycloalkyl group, as defined herein, a phenyl group, a monocyclic heteroaryl group, as defined herein, or a monocyclic heterocycle, as defined herein. Tricyclic fused ring systems are exemplified by an aryl bicyclic fused ring system, as defined herein and fused to a monocyclic cycloalkyl group, as defined herein, a phenyl group, a monocyclic heteroaryl group, as defined herein, or a monocyclic heterocycle, as defined herein. Representative examples of aryl include, but are not limited to, anthracenyl, azulenyl, fluorenyl, indanyl, indenyl, naphthyl, phenyl and tetrahydronaphthyl.

The term "cycloalkyl" as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic fused ring systems are exemplified by a cycloalkyl group appended to the parent molecular moiety, which is fused to an additional cycloalkyl group, as defined herein, a phenyl group, a heteroaryl, as defined herein, or a heterocycle as defined herein. Tricyclic fused ring systems are exemplified by a cycloalkyl bicyclic fused ring system fused to an additional cycloalkyl group, as defined herein, a phenyl group, a heteroaryl, as defined herein, or a heterocycle as defined herein. Bicyclic ring systems are also exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Tricyclic ring systems are also exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0.3,7]nonane and tricyclo[3.3.1.13,7]decane (adamantane).

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, benzimidazolyl, benzofuranyl, benzothiazolyl, benzothienyl, benzoxazolyl, furyl, imidazolyl, indazolyl, indolyl, indolizinyl, isobenzofuranyl, isoindolyl, isoxazolyl, isoquinolinyl, isothiazolyl, naphthyridinyl, oxadiazolyl, oxazolyl, phthalazinyl, pyridinyl, pyridazinyl, pyridyl, pyrimidinyl, pyrazinyl, pyrazolyl, pyrrolyl, quinolinyl, quinolizinyl, quinoxalinyl, quinazolinyl, tetrazolyl, thiadiazolyl, thiazolyl, thienyl, triazolyl and triazinyl.

The term "heterocycle" as used herein, refers to a non-aromatic monocyclic ring or a non-aromatic bicyclic ring. The non-aromatic monocyclic ring is a three, four, five, six, seven, or eight membered ring containing at least one heteroatom, independently selected from the group consisting of N, O and S. Representative examples of monocyclic ring systems include, but are not limited to, azetidinyl, aziridinyl, diazepinyl, dithianyl, imidazolinyl, imidazolidinyl, isothiazolinyl, isoxazolinyl, isoxazolidinyl, morpholinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyranyl, tetrahydro-2H-pyran-2-yl, tetrahydro-2H-pyran-4-yl, tetrahydrothienyl, thiazolinyl, thiazolidinyl, thiomorpholinyl, 1,1-dioxidothiomorpholinyl (thiomorpholine sulfone) and thiopyranyl. The bicyclic heterocycles are exemplified by a monocyclic heterocycle appended to the parent molecular moiety and fused to a monocyclic cycloalkyl group, as defined herein, a monocyclic aryl group, a monocyclic heteroaryl group, as defined herein, or a monocyclic heterocycle, as defined herein. Bicyclic ring systems are also exemplified by a bridged monocyclic ring system in which two non-adjacent atoms of the monocyclic ring are linked by a bridge of between one and three atoms selected from the group consisting of carbon, nitrogen and oxygen. Representative examples of bicyclic ring systems include but are not limited to, for example, benzopyranyl, benzothiopyranyl, benzodioxinyl, 1,3-benzodioxolyl, cinnolinyl, 1,5-diazocanyl, 3,9-diaza-bicyclo[4.2.1]non-9-yl, 3,7-diazabicyclo[3.3.1] nonane, octahydro-pyrrolo[3,4-c]pyrrole, indolinyl, isoindolinyl, 2,3,4,5-tetrahydro-1H-benzo[c]azepine, 2,3,4, 5-tetrahydro-1H-benzo[b]azepine, 2,3,4,5-tetrahydro-TH-benzo[d]azepine, tetrahydroisoquinolinyl and tetrahydroquinolinyl.

The term "macrocycle" refers to a cyclic ring system that includes at least three cyclic rings covalently linked together.

The term "heteromacrocycle" refers to a macrocycle having at least one non-carbon atom included in the macrocycle structure.

Substituent R groups are variously designated without a numeral identifier or with a numeral identifier like "n", wherein n is selected from 1-20, such as represented, for example, by $R_n$ and R″. In all instances used throughout the disclosure and the figures, $R_n$ and R″ refer to the same substituent R group having numeral identifier n, wherein n is selected from 1-20.

Certain amine substituents having the structure —N(AB) (e.g., —N($R^5R^6$)) have the two substituents included in the parentheses each independently bonded to the N atom.

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that a compound name is misnamed or otherwise conflicts with the chemical structure disclosed herein.

The term "bicyclic macrocycle" refers to two macrocycles covalently fused together.

Aryl-Triazole Bicyclic Macrocycle Compounds

In a first aspect, an aryl-triazole bicyclic macrocycle of Formula (I) is provided:

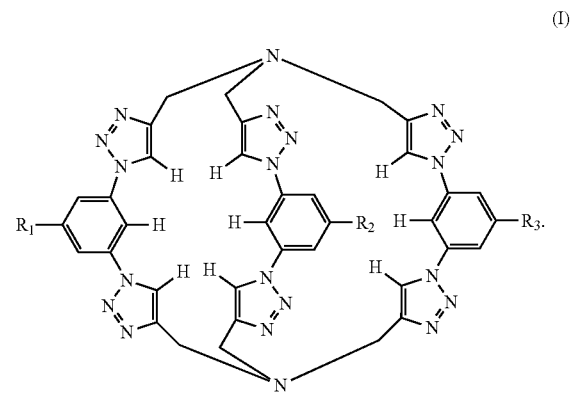

(I)

The $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —N($R^5R^6$), —$CO_2R^7$, —C(O)—N ($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

In a highly preferred embodiment, the aryl-triazole bicyclic macrocycle of Formula (I) includes $R^1$, $R^2$, and $R^3$ having N,N-dicyclohexylamide groups.

Exemplary species of aryl-triazole bicyclic macrocycles of Formula (I) include those selected from the group consisting of the following:

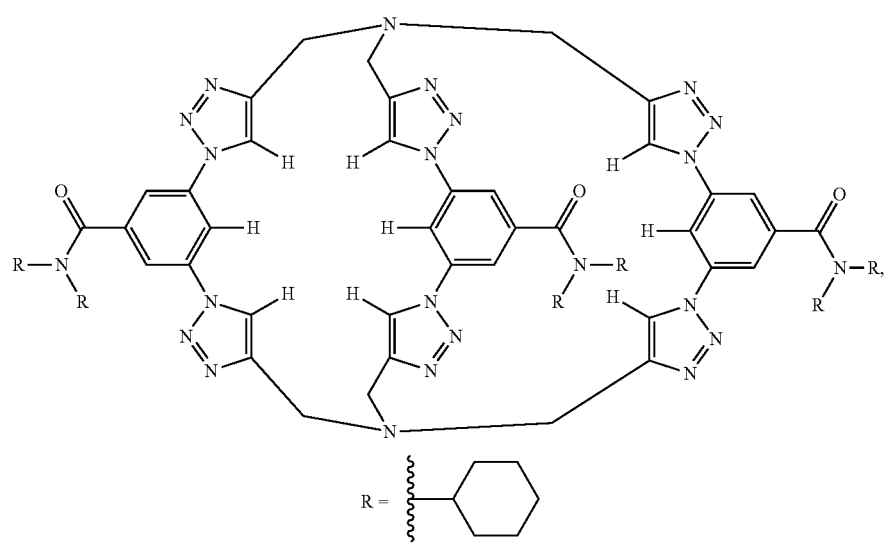
(T-Cage)
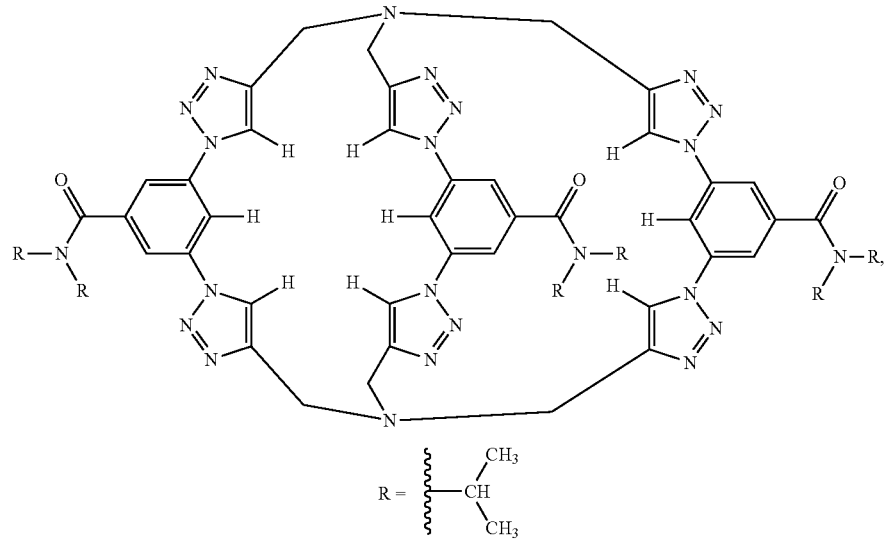
(I-Cage)

-continued
(B-Cage)
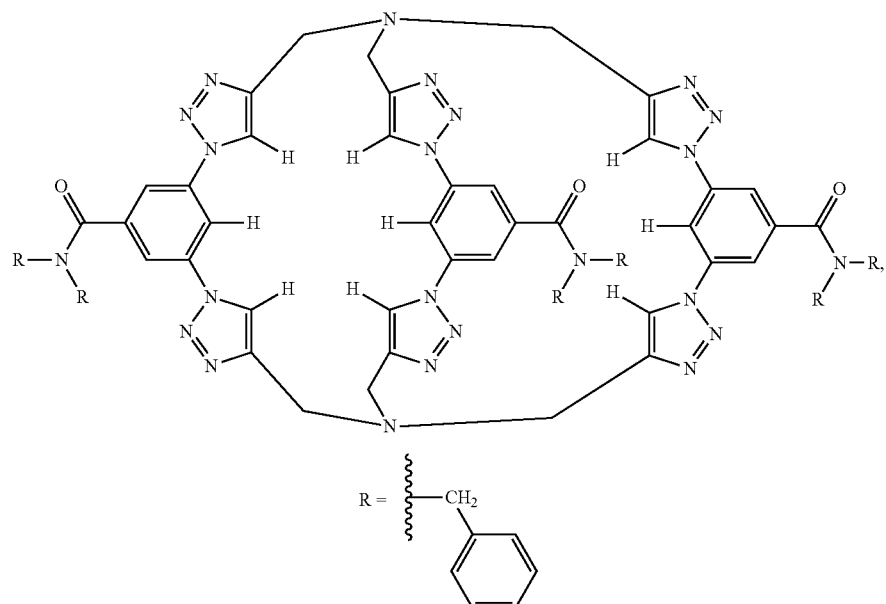
(E-Cage)
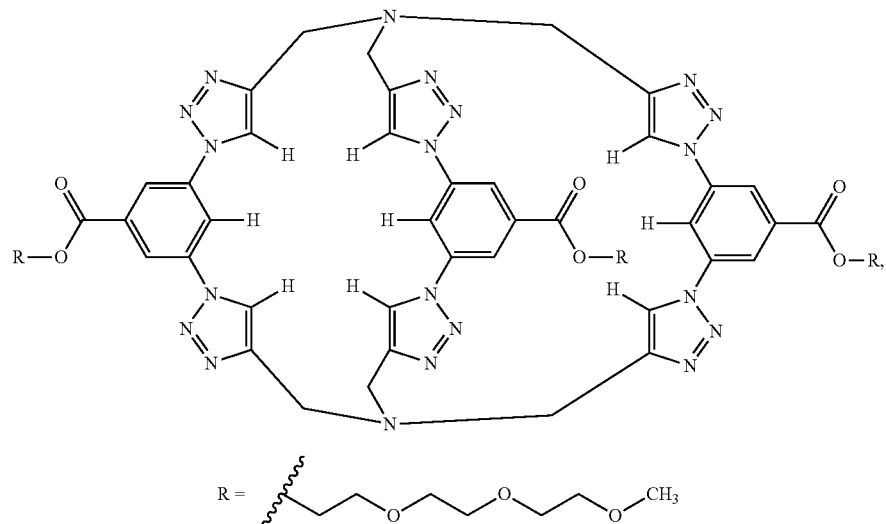
(G-Cage)
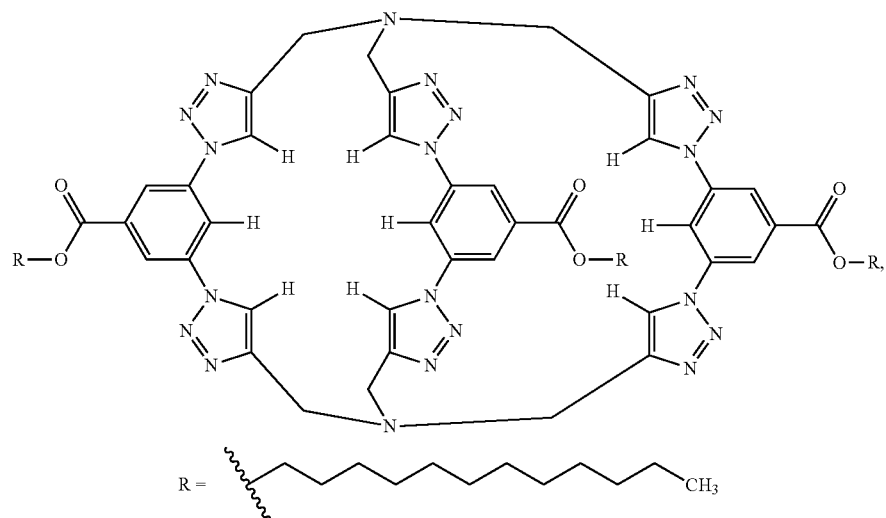

(P-Cage)
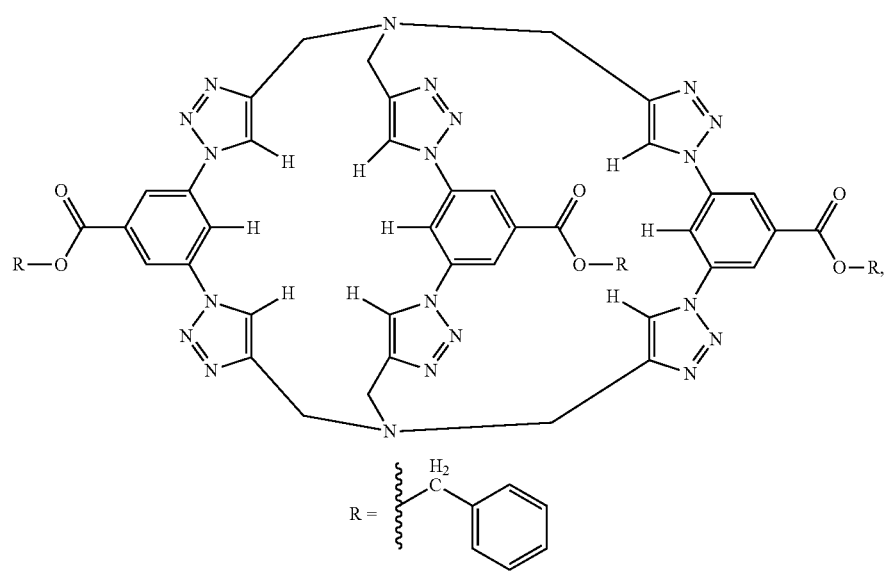
(A-Cage)
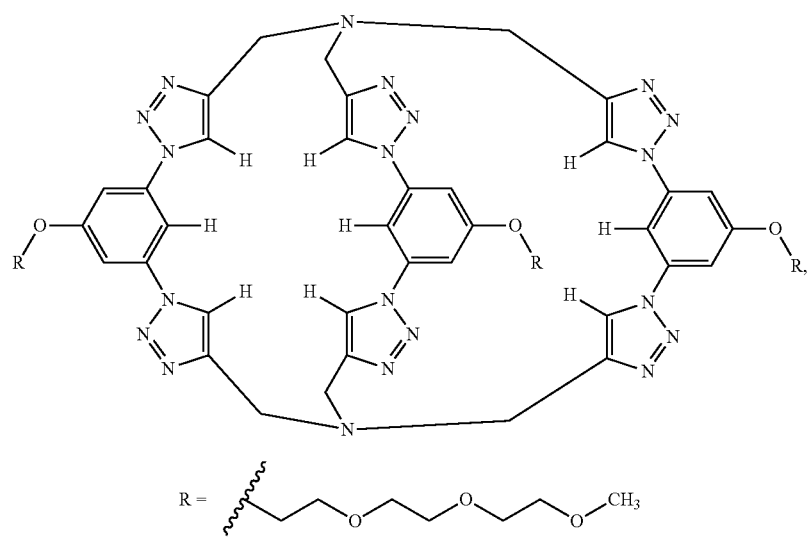
(D-Cage)
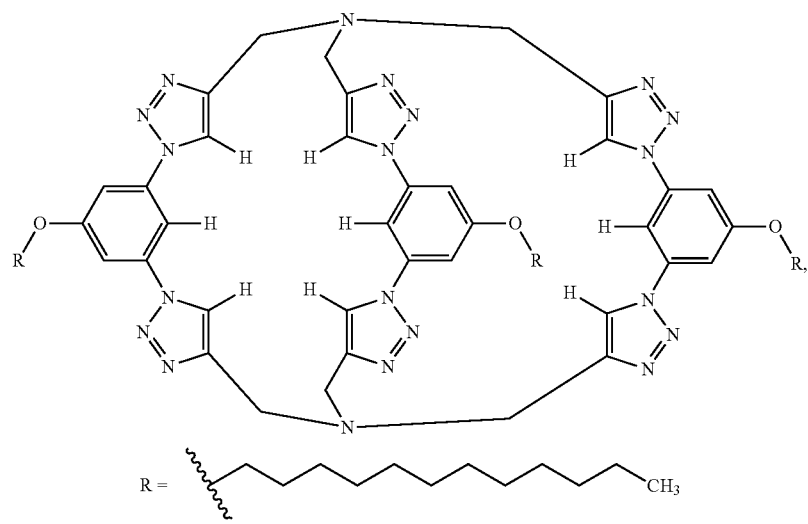

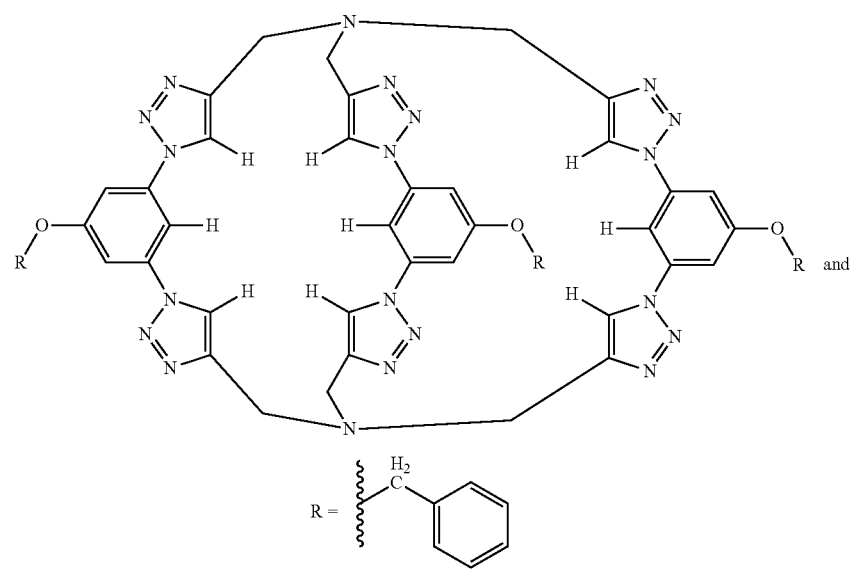
(Z-Cage)
and
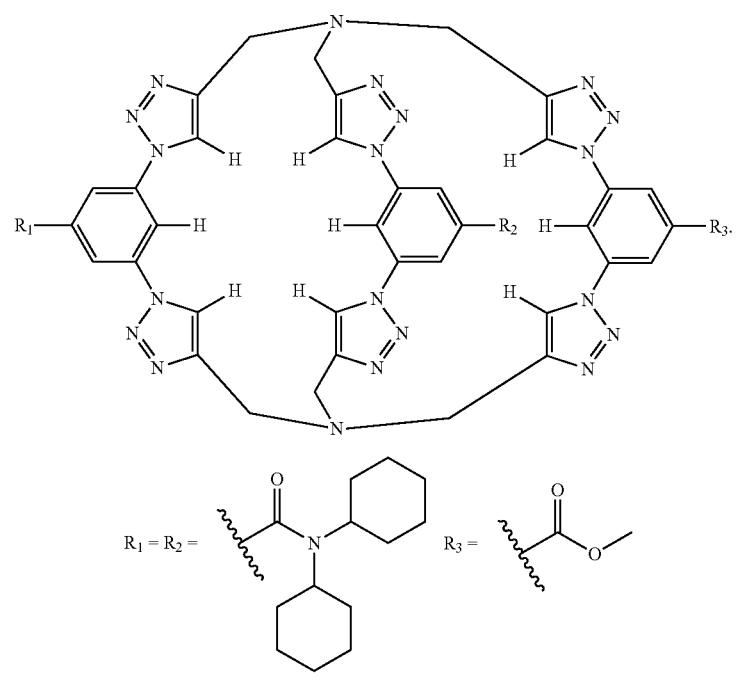
(T-cage-A₂B)

Synthetic Methods for Producing Compounds of Formula (I)

These exemplary species and others of the class of aryl-triazole bicyclic macrocycles of Formula (I) are amenable to synthesis using the methods described herein and in the Examples. A general scheme for synthesizing the aryl-triazole bicyclic macrocycles of Formula (I) is presented in Scheme I, where Formula (II) of Scheme I represents Formula (I) having $R_1$, $R_2$ and $R_3$ represented by R:

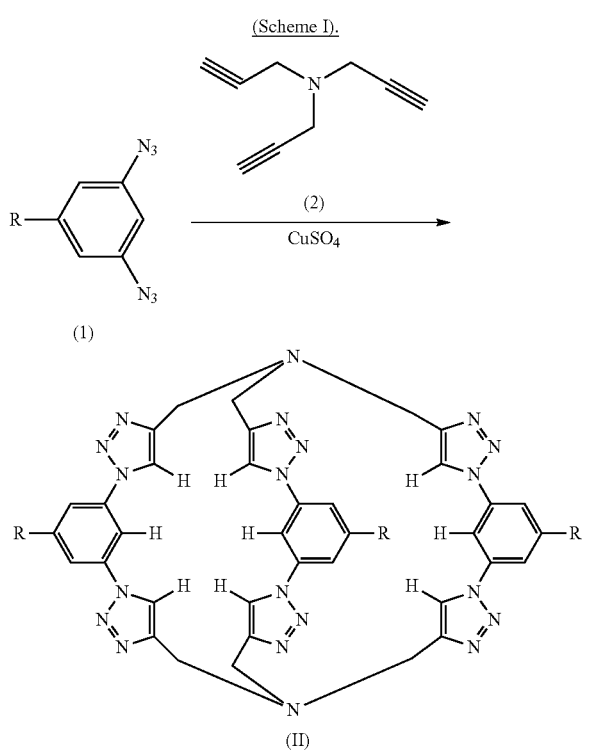

The aryl-triazole bicyclic macrocycles of Scheme I are amenable to production with a "one-pot" synthesis procedure using copper(I)-catalyzed alkyne-azide cycloaddition (CuAAC) (Meldal, M.; Tornoe, C. W. *Chem. Rev.* 2008, 108, 2952-3015) in which a 3:2 stoichiometric mixture of a suitably-substituted $C_2$ bisazide (reagent 1) and the $C_3$ building block tripropargylamine (reagent 2) are reacted together. Typical reaction conditions can be varied, consistent with the CuAAC reaction conditions reported in the literature. Exemplary conditions for the one-pot synthesis of Scheme I include, for example, a source of Cu(I), a reducing agent to regenerate Cu(I) from Cu(II), and a suitable reaction buffer. One preferred set of reaction conditions for Scheme I include $CuSO_4$, sodium ascorbate, and tris[(1-benzyl-1H-1,2,3-triazol-4-yl)methyl]amine (TBTA), THF:t-BuOH:$H_2O$ (3:1:1), where the reaction mixture is maintained 60° C. for 3 days.

The resulting product of the synthesis reaction can be purified using methods well understood and conventional in the art. A preferred purification method includes column chromatography. Typical yields of the aryl-triazole bicyclic macrocycles of Formula (II) are about 25% using the described synthesis procedure. Slight improvements in yield (e.g., about 30%) can be obtained by inclusion of a suitable salt, such as a chloride-based salt (e.g., tetraethylammonium chloride).

Accordingly, in a second aspect, a method of synthesizing an aryl-triazole bicyclic macrocycle of Formula (II) is presented:

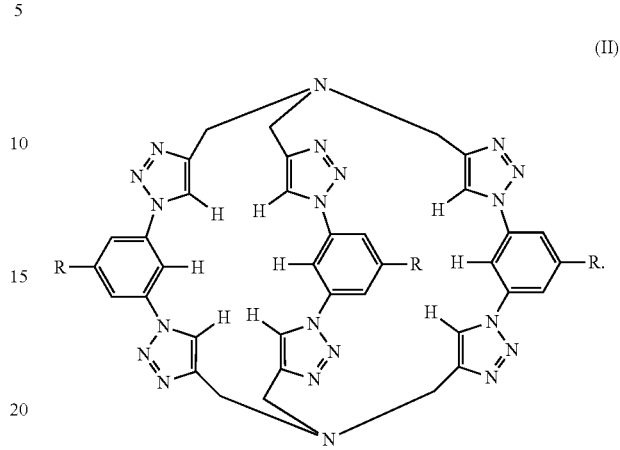

The R substituents are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

The method includes several steps. A first step is forming a reaction mixture comprising:

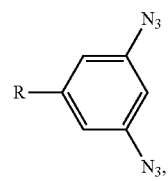

tripropargylamine; and a solvent. The

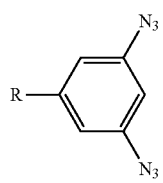

is selected from the group consisting of

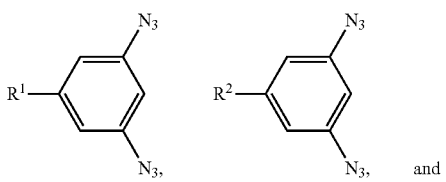

and

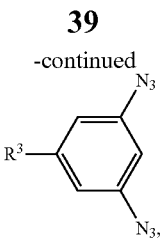

or a combination thereof.

The $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen. A second step is incubating the reaction mixture at an elevated reaction temperature for a reaction time to form the aryl-triazole bicyclic macrocycle of Formula (II). A third step is optionally purifying the aryl-triazole bicyclic macrocycle of Formula (II) from the reaction mixture to provide the aryl-triazole bicyclic macrocycle of Formula (II).

In another respect, the suitably-substituted $C_2$ bisazide (reagent 1) is selected from the group consisting of the following:

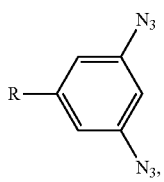

wherein R is selected from the group consisting of the following:

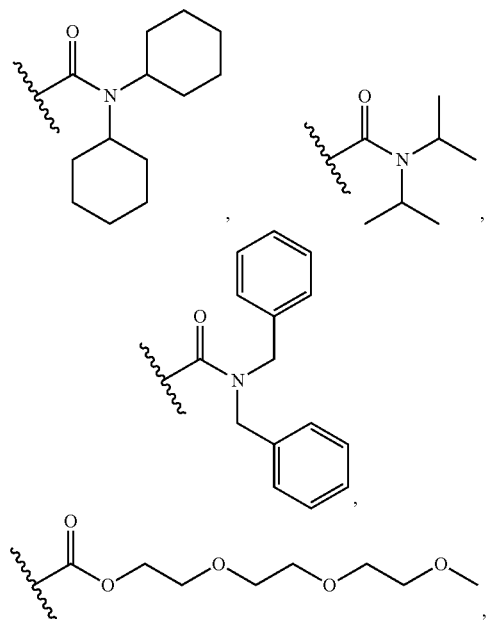

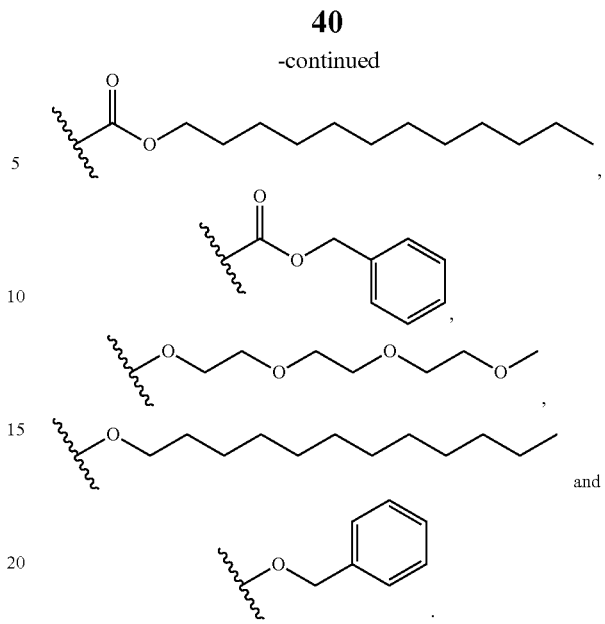

The solvent preferably includes a Cu(I) source, a reducing reagent and a buffer. A preferred Cu(I) source includes in-situ reduction of $CuSO_4$, among others, such as CuI, CuBr, CuCl, $Cu(CH_3CN)_4PF_6$, and $[N(n-Bu)_4]_2Cu_2I_4$. A preferred reducing reagent includes sodium ascorbate. A preferred buffer includes tris[(1-benzyl-1H-1,2,3-triazol-4-yl)methyl]amine (TBTA), THF:t-BuOH:$H_2O$ (3:1:1), among others such as 1,8-diazabicyclo[5.4.0]undec-7-ene (DBU) and toluene:$CH_3CN$ (1:1).

A preferred reaction temperature includes a temperature in the range from about 50° C. to about 70° C., including about 60° C., among other temperatures within this range.

A preferred reaction time includes reaction times up to and including 5 days, and a preferred range from about 1 day to about 5 days, including about 3 days.

A preferred third step of purifying the aryl-triazole bicyclic macrocycle of Formula (I) includes using chromatography, among other methods known in the art, such as recrystallization.

Figure 1B:
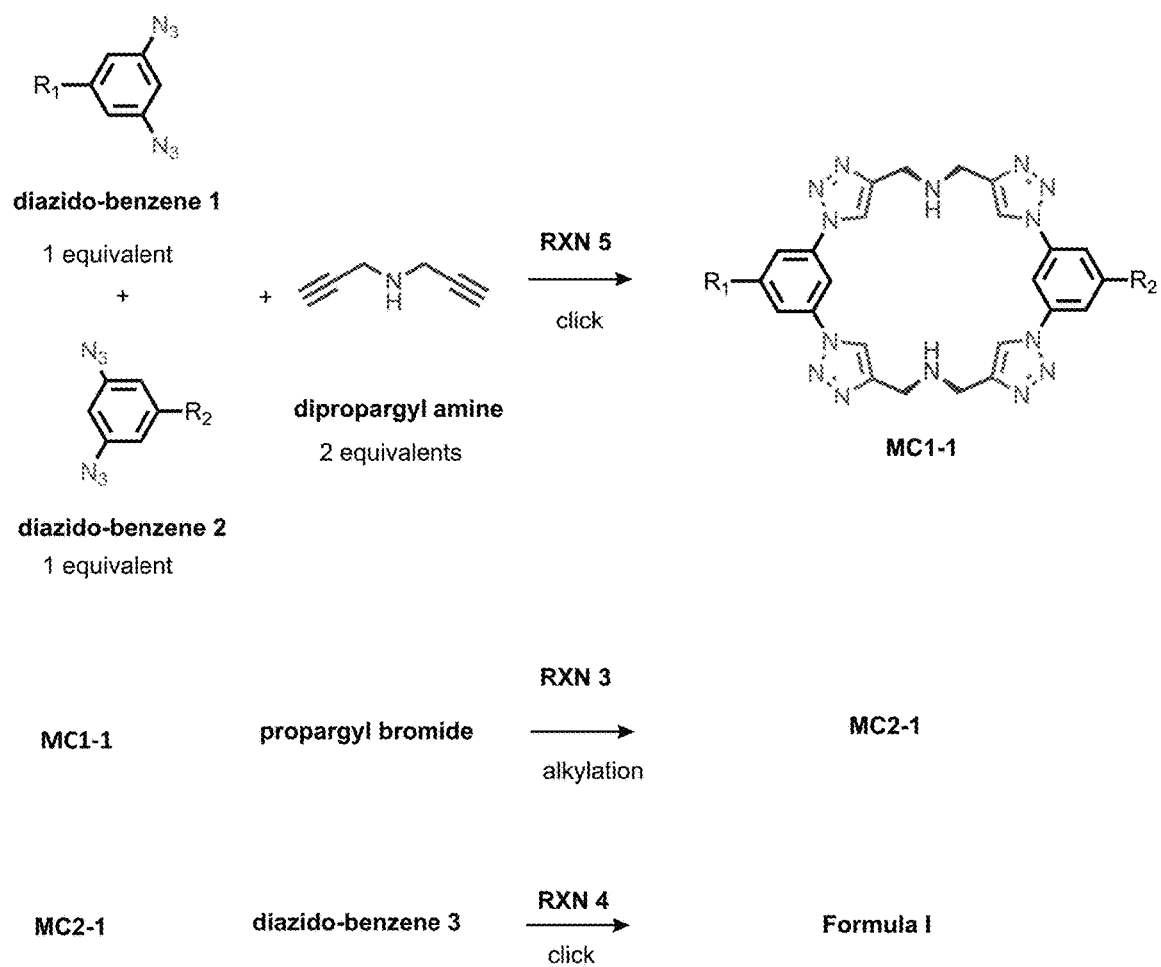
FIG. 1B depicts exemplary reaction strategies for preparing compounds of Formulas (I)-(VI) that includes step-wise synthesis reactions ("RXN") 5, 3 and 4.
Figure 1C:
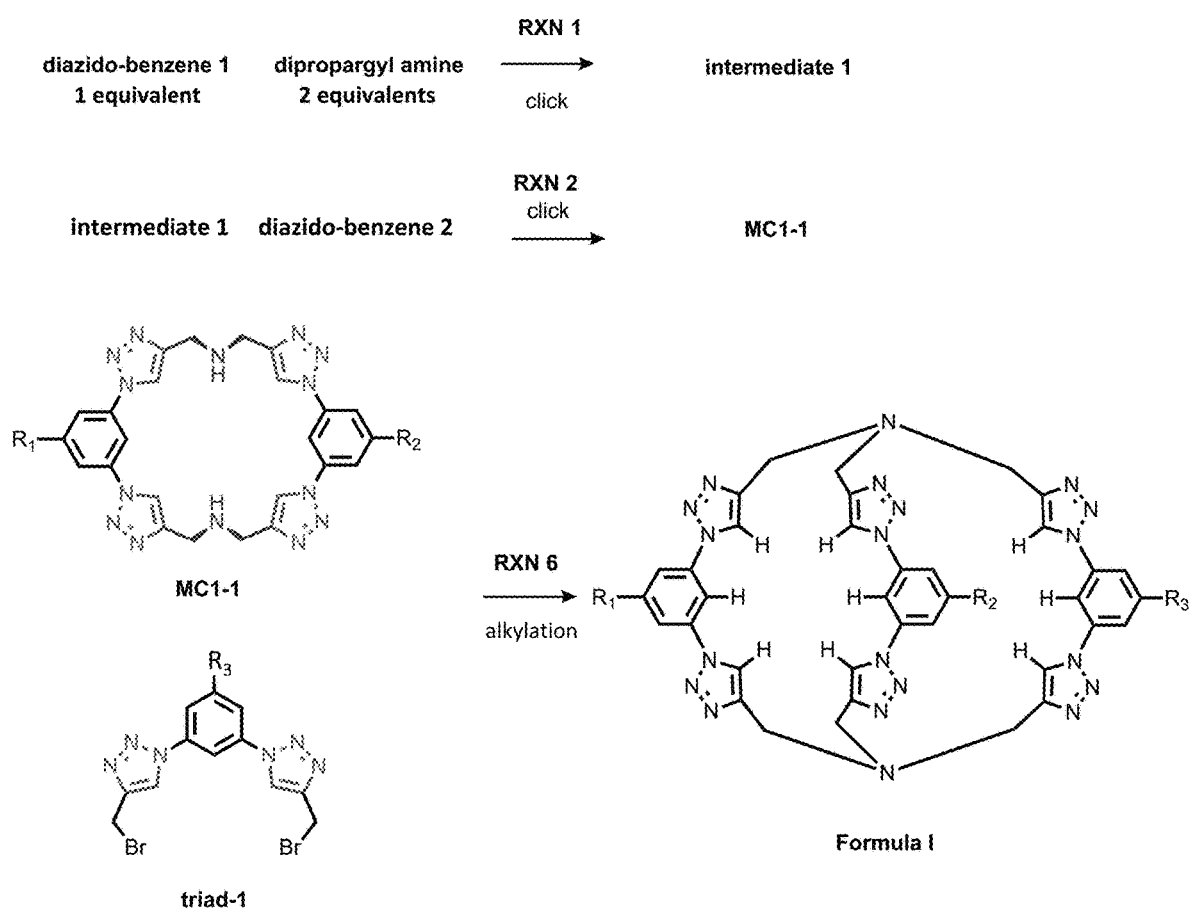
FIG. 1C depicts exemplary reaction strategies for preparing compounds of Formulas (I)-(VI) that includes step-wise synthesis reactions ("RXN") 1, 2 and 6.
Figure 1D:
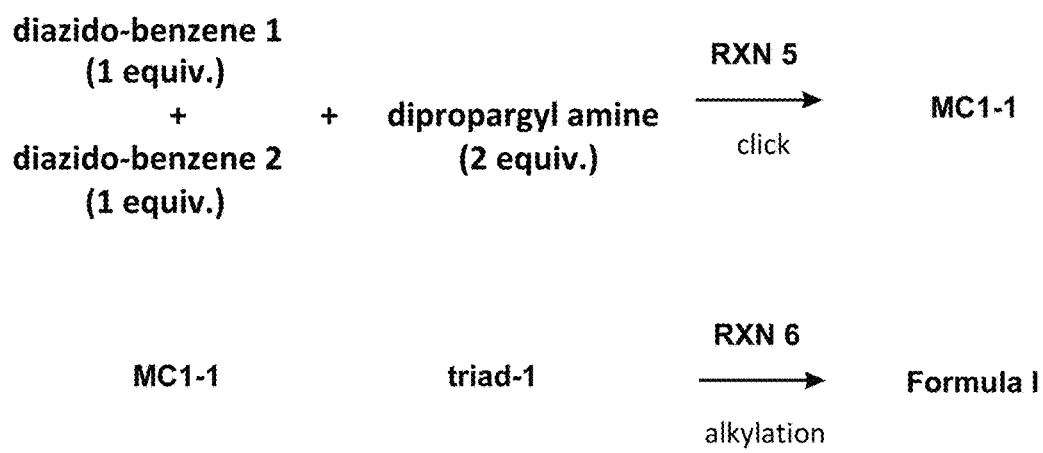
FIG. 1D depicts exemplary reaction strategies for preparing compounds of Formulas (I)-(VI) that includes step-wise synthesis reactions ("RXN") 5 and 6.
Figure 2:
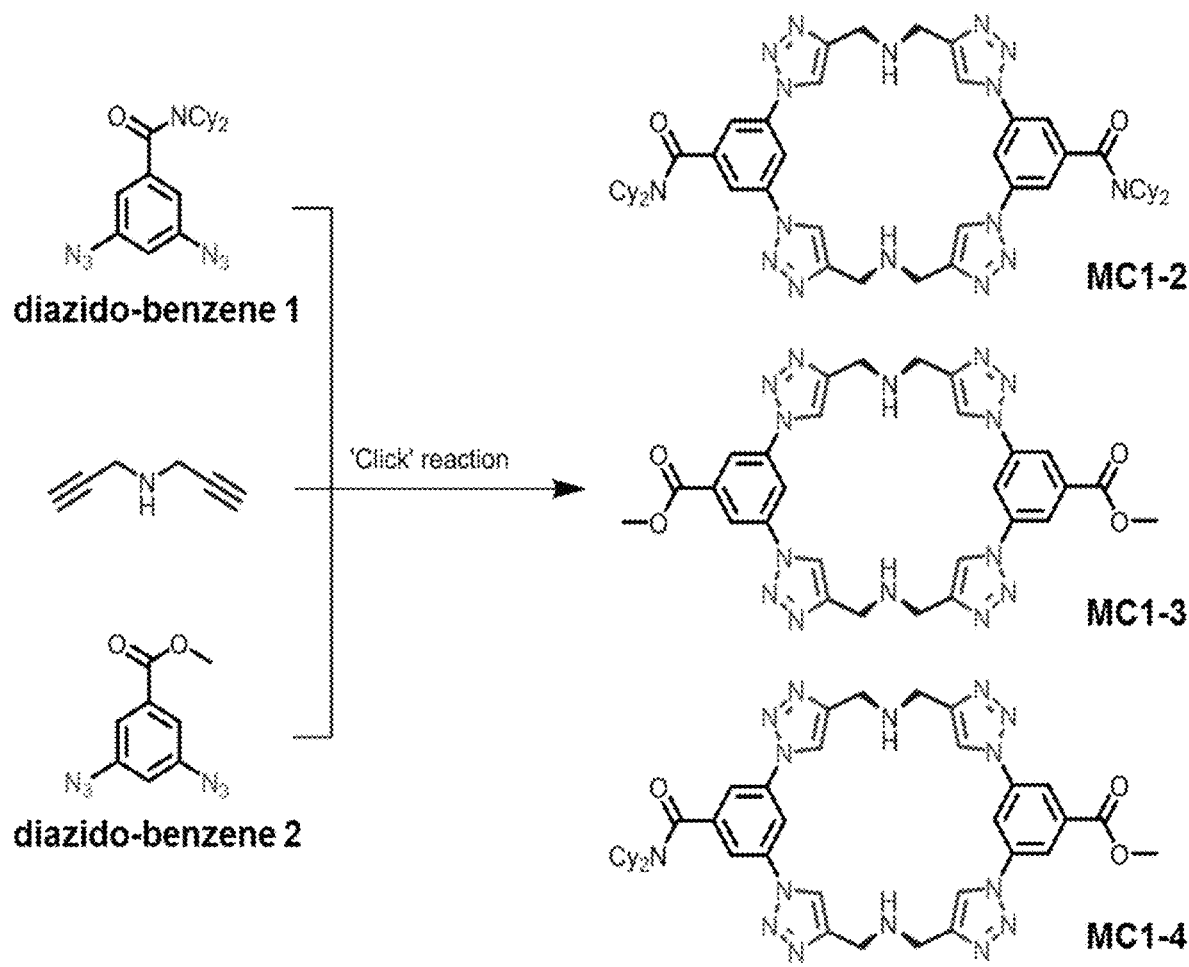
FIG. 2 depicts an exemplary one-pot synthesis strategy for preparing intermediate macrocycles MC1-2, MC1-3 and MC1-4 using diazido-benzene 1 (3,5-diazido-N.N-dicyclohexylbenzamide), dipropargyl amine and diazido-benzene 2 (3,5-diazidomethylbenzoate).

Additional synthetic reaction strategies for preparing aryl-triazole bicyclic macrocycles of Formula (I) and (II), as well as intermediate macrocycles, are outlined in FIGS. 1 and 2, respectively.

Referring to FIG. 1A, synthesis Sequence 1 provides a method for the step-wise synthesis of a compound of Formula (I) using a set of four reactions. Reaction 1 ("RXN 1") includes performing a click chemistry reaction with one equivalent of an $R^1$-substituted diazido-benzene 1 and two equivalents of dipropargyl amine to produce intermediate 1. Reaction 2 ("RXN 2") includes performing a click chemistry reaction with one equivalent of intermediate 1 and one equivalent of an $R^2$-substituted diazido-benzene 2 to produce MC1-1. Reaction 3 ("RXN 3") includes performing an alkylation reaction with one equivalent of MC1-1 with two equivalents propargyl bromide to produce MC2-1. Reaction 4 ("RXN 4") includes performing a click chemistry reaction between one equivalent of MC2-1 and one equivalent of an $R^3$-substituted diazido-benzene 3 to produce the compound of Formula (I).

Referring to FIG. 1B, synthesis Sequence 2 provides a method for the step-wise synthesis of a compound of Formula (I) using a set of three reactions. Reaction 5 ("RXN 5") includes performing a click chemistry reaction with one equivalent of an R¹-substituted diazido-benzene 1, one equivalent of an R²-substituted diazido-benzene 2 and two equivalents of dipropargyl amine to produce MC1-1. Reaction 3 ("RXN 3") includes performing an alkylation reaction with one equivalent of MC1-1 with two equivalents propargyl bromide to produce MC2-1. Reaction 4 ("RXN 4") includes performing a click chemistry reaction between one equivalent of MC2-1 and one equivalent of an R³-substituted diazido-benzene 3 to produce the compound of Formula (I).

Referring to FIG. 1C, synthesis Sequence 3 provides a method for the step-wise synthesis of a compound of Formula (I) using a set of three reactions. Reaction 1 ("RXN 1") includes performing a click chemistry reaction with one equivalent of an R¹-substituted diazido-benzene 1 and two equivalents of dipropargyl amine to produce intermediate 1. Reaction 2 ("RXN 2") includes performing a click chemistry reaction with one equivalent of intermediate 1 and one equivalent of an R²-substituted diazido-benzene 2 to produce MC1-1. Reaction 6 ("RXN 6") includes performing an alkylation reaction between one equivalent of MC1-1 and one equivalent of an R³-substituted diazido-benzene triad 3 to produce the compound of Formula (I).

Referring to FIG. 1D, synthesis Sequence 4 provides a method for the step-wise synthesis of a compound of Formula (I) using a set of two reactions. Reaction 5 ("RXN 5") includes performing a click chemistry reaction with one equivalent of an R¹-substituted diazido-benzene 1, one equivalent of an R²-substituted diazido-benzene 2 and two equivalents of dipropargyl amine to produce MC1-1. Reaction 6 ("RXN 6") includes performing an alkylation reaction between one equivalent of MC1-1 and one equivalent of an R³-substituted diazido-benzene triad 3 to produce the compound of Formula (I).

Referring to FIG. 2, an exemplary one-pot synthesis of intermediate macrocycles MCT-2, MCT-3 and MCT-4 using a click chemistry reaction with one equivalent of an R¹-substituted diazido-benzene 1 (3,5-diazido-N.N-dicyclohexylbenzamide), one equivalent of an R²-substituted diazido-benzene 2 (3,5-diazidomethylbenzoate) and two equivalents of dipropargyl amine is presented.

In a third aspect, method of synthesizing an aryl-triazole bicyclic macrocycle selected from Formulas (I) and (II):

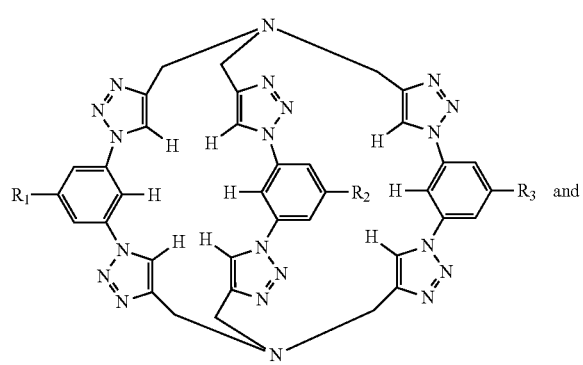

(I)

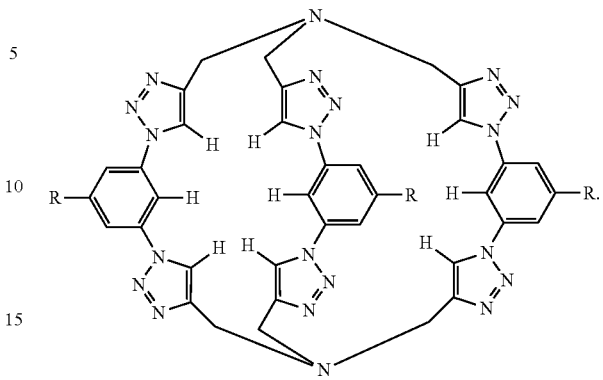

(II)

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (II), R is independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R'$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

The method comprising a method of step-wise reactions selected from the group consisting of Sequences 1-4.

In one respect, the aryl-triazole bicyclic macrocycle is Formula (I) in which at least one of $R^1$, $R^2$ and $R^3$ differs from the other two R-substituents. In a second respect, the aryl-triazole bicyclic macrocycle is Formula (I), in which $R^1$, $R^2$ and $R^3$ differ from each other. In a third respect, the method includes a method of step-wise synthesis according to Sequence 1. In a fourth respect, the method includes a method of step-wise synthesis of the aryl-triazole bicyclic macrocycle of Formula (I) from macrocycle intermediate MC1-1 by an alkylation using synthetic reaction 6. In a fifth respect, intermediate macrocycle MC1-1 is prepared in a one-pot synthesis using synthetic reaction 5.

Additional Aryl-Triazole Bicyclic Macrocycles and their Syntheses

In a fourth aspect, an aryl-triazole bicyclic macrocycle of Formula (III) is disclosed:

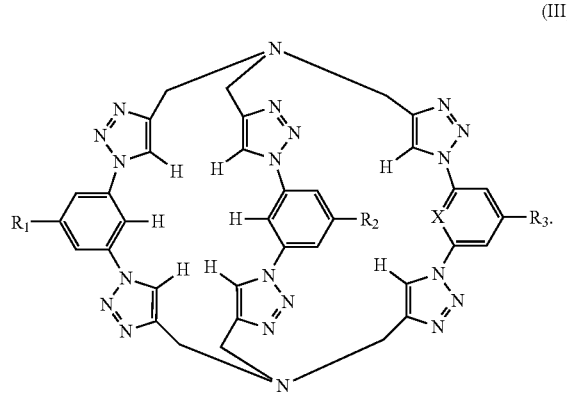
(III)

The X is independently selected from the group consisting of CH, CF and N. The $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

In one respect, the aryl-triazole bicyclic macrocycle is selected from the group consisting of the following:

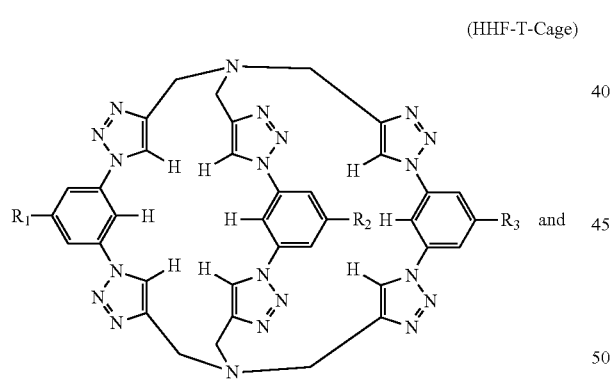
(HHF-T-Cage)

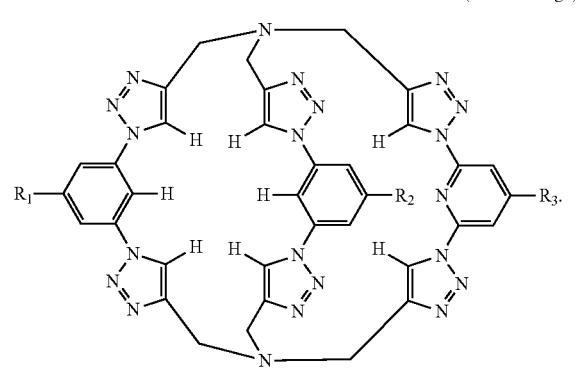
(HHN-T-Cage)

In a fifth aspect, an aryl-triazole bicyclic macrocycle selected from the group consisting of Formulas (IV), (V), (VI) and (VII) is disclosed:

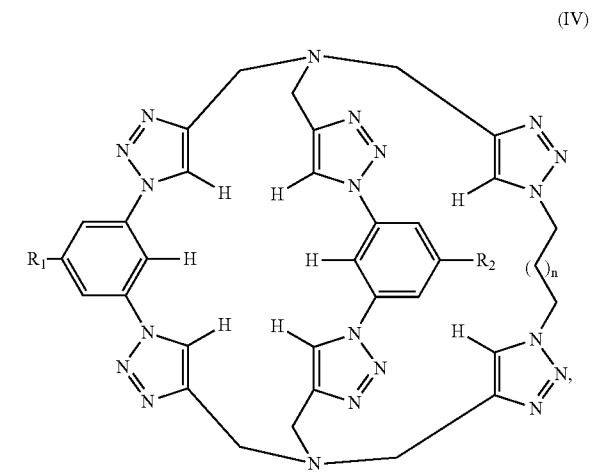
(IV)

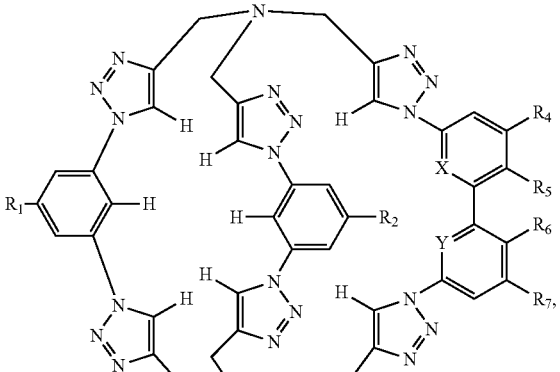
(V)

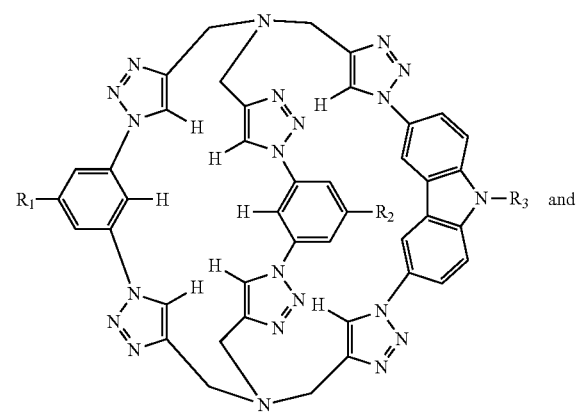
(VI)

and

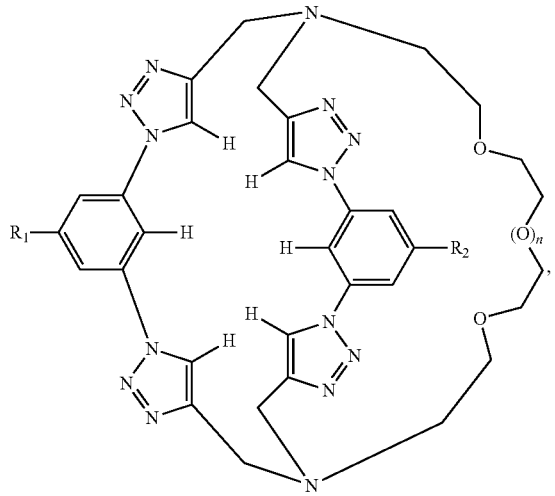

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —$C(O)$—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

In a sixth aspect, a method of synthesizing an aryl-triazole bicyclic macrocycle selected from Formulas (III), (IV), (V) and (VI) is provided:

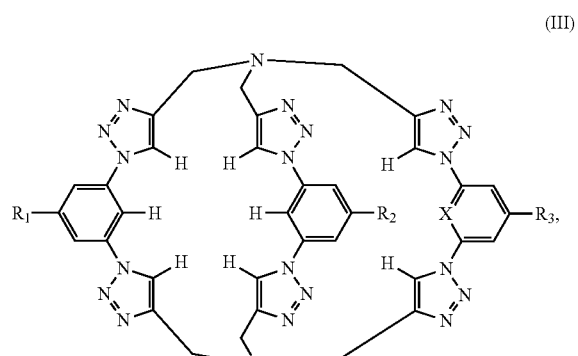

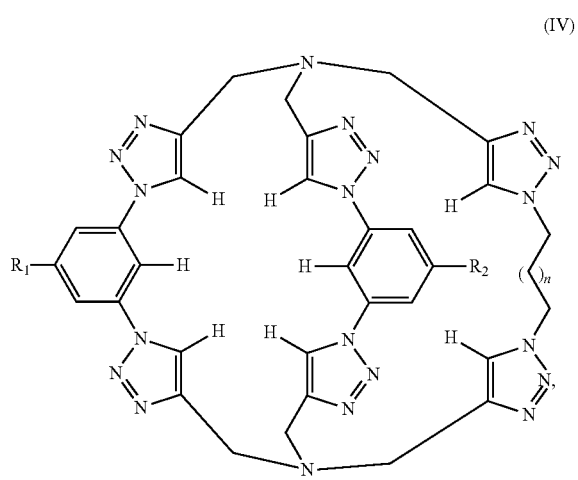

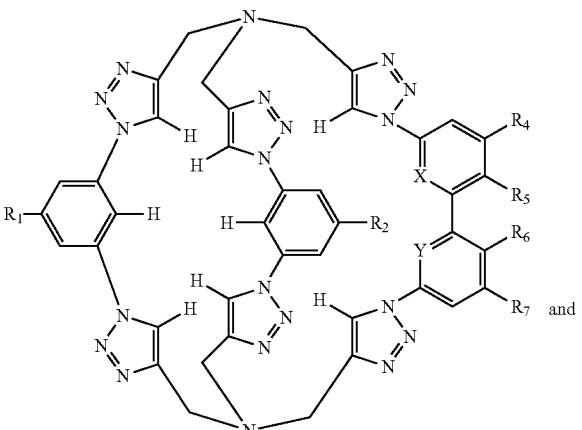

-continued

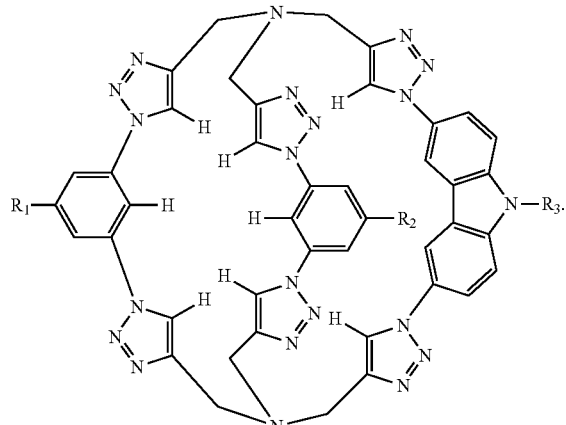

(VI)

In a seventh aspect, a method of synthesizing an aryl-triazole bicyclic macrocycle of Formula (VII) is provided:

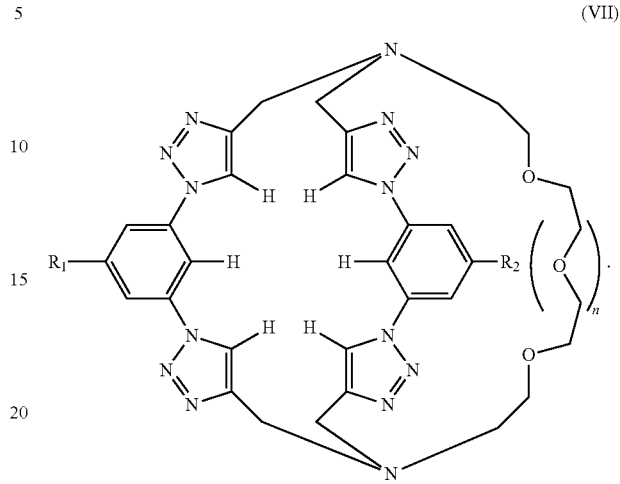

(VII)

For (III), X is independently selected from the group consisting of CH, CF and N, and R, $R^2$, and R are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and RY are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^8$, $R^9$, $R^{10}$, $R^{11}$, $R^{12}$ and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

The method comprises a method of step-wise synthesis selected from Sequences 1-4.

The value of n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

The method includes several steps. A first step includes preparing macrocycle intermediate MC1-1. A second step includes alkylating macrocycle intermediate MC1-1 to produce the aryl-triazole bicyclic macrocycle of Formula (VII).

Complexes

Figure 3A:
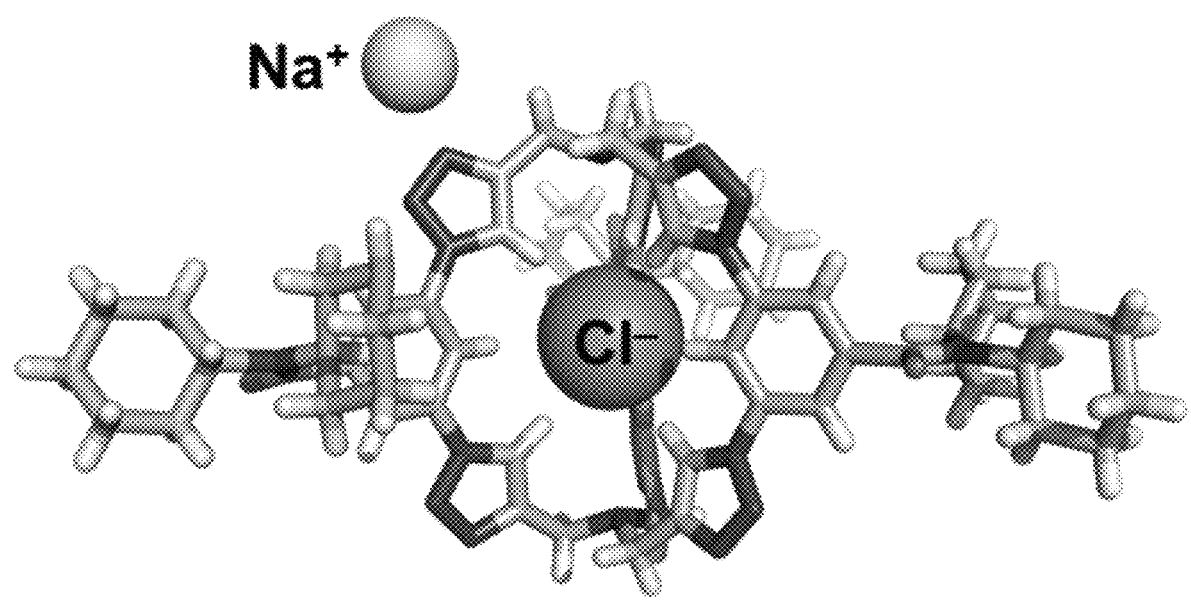
FIG. 3A illustrates exemplary a single-crystal X-ray diffraction structure of T-Cage·NaCl (CCDC No. 1533500).
Figure 3B:
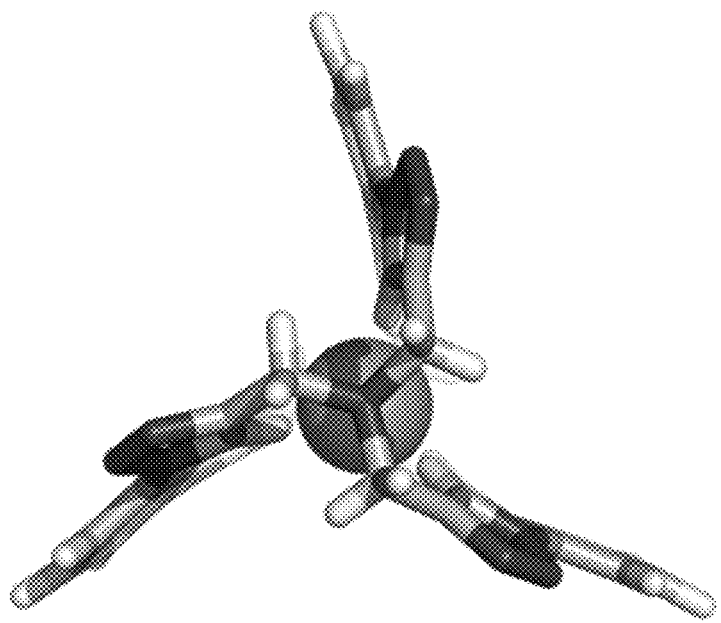
FIG. 3B illustrates a top view perspective of the structure presented in FIG. 3A, wherein the substituents are omitted in the side view for clarity.

The aryl-triazole bicyclic macrocycles of Formula (I) display surprisingly robust affinity and selectivity for anions present in salt solutions. The first indication of this behavior was revealed by single-crystal X-ray diffraction studies of an exemplary aryl-triazole bicyclic macrocycle of Formula (I) (T-Cage) following synthesis and purification by column chromatography (FIGS. 3A and 3B). The coordinated chloride and extra-cavity sodium were not introduced and must have been scavenged during column chromatography. Chloride is stabilized by six short CH·Cl⁻ hydrogen bonds from the triazoles ($d_{H \cdots Cl}$=2.7 Å) and three from the phenylenes ($d_{H \cdots Cl}$=2.9 Å). The Na⁺ counter cations are disordered over two locations. Half are stabilized by a square pyramidal coordination environment provided by carbonyl oxygen atoms and triazole nitrogen atoms and the other half are monohydrated and in the interstitial space between cages. The overall affinity for NaCl is so high that the sample still retains 10-20 mol % of salt after six extractions using de-ionized water. By contrast, all salts are completely removed from triazolophane macrocycles with one or two extractions.

Figure 4A:
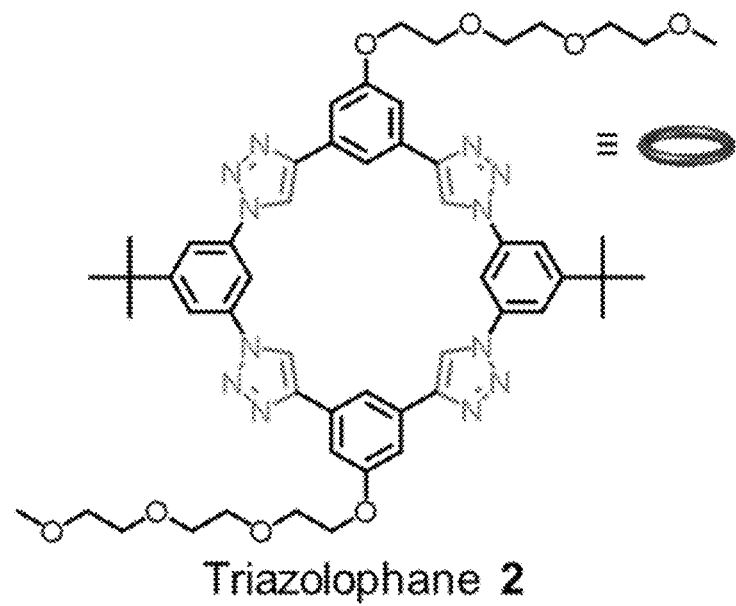
FIG. 4A depicts chemical structures of 2D triazolophane macrocycle 2 and 3D flexible receptor 3.
Figure 4A:
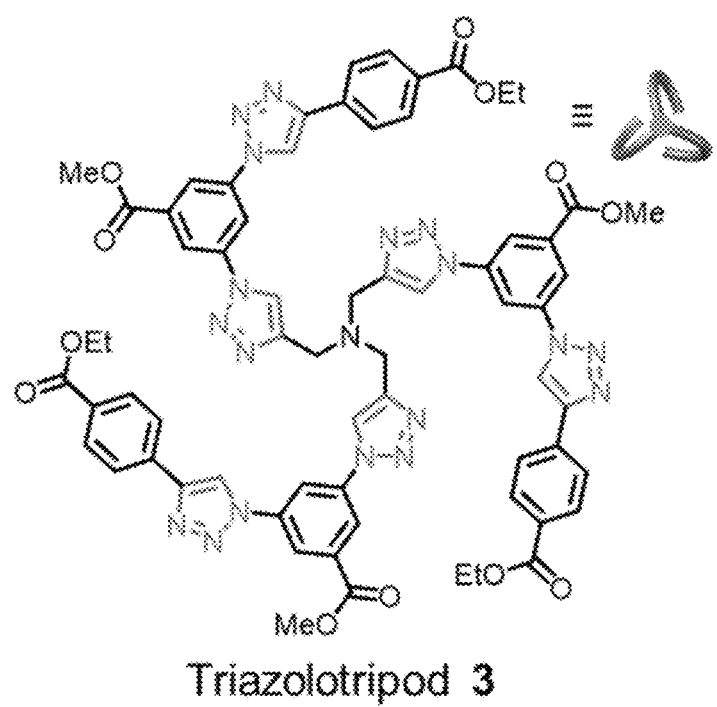
Figure 4B:
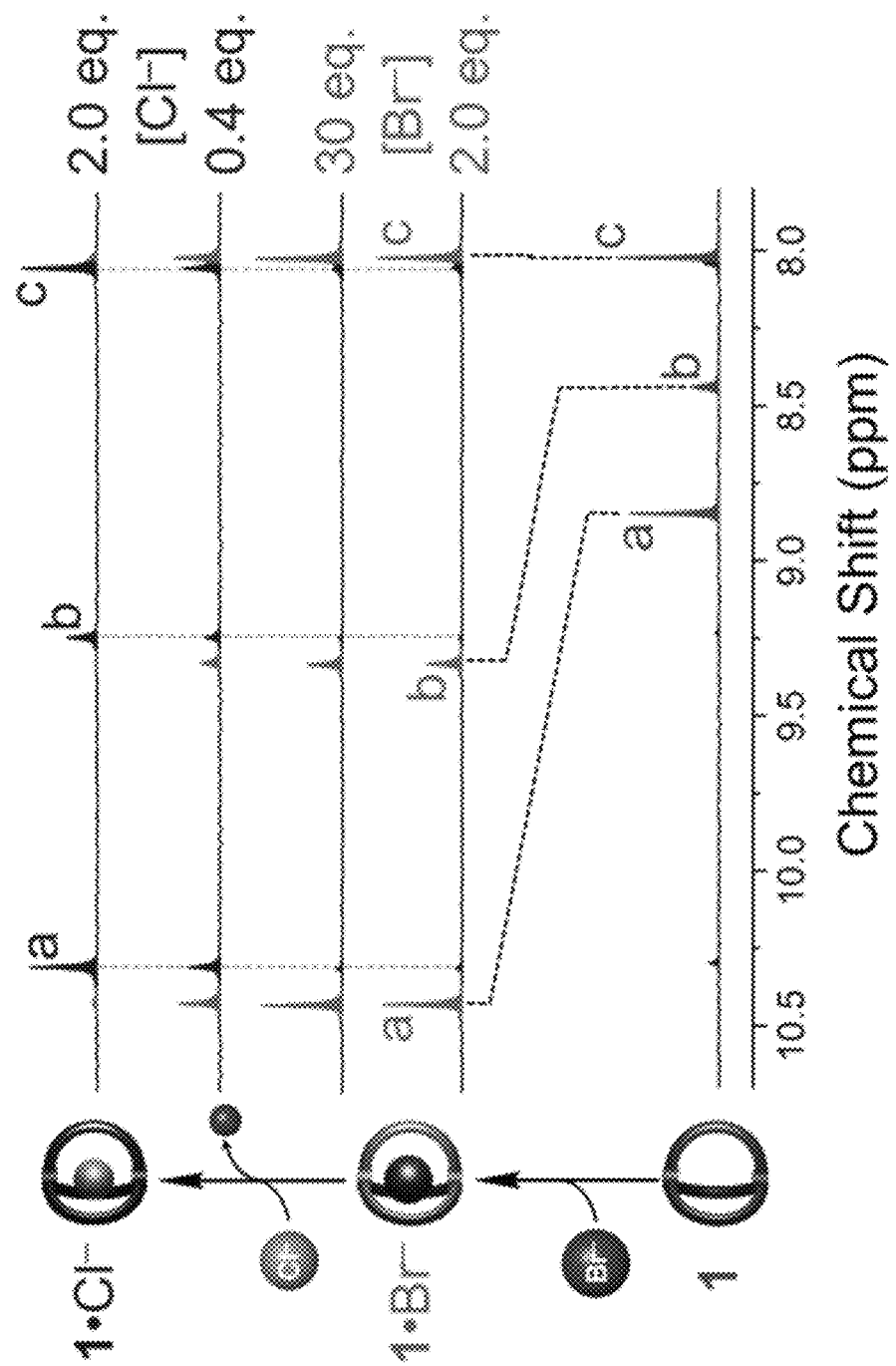
FIG. 4B depicts exemplary $^1$H NMR spectra of the competitive replacement of excess $Br^-$ by $Cl^-$ in DMSO-$d_6$ (0.5 mM, 298 K, 500 MHz). Proton peaks associated with free T-Cage (1) are colored in red, 1·$Br^-$ in magenta, and 1·$Cl^-$ in blue.
Figure 4C:
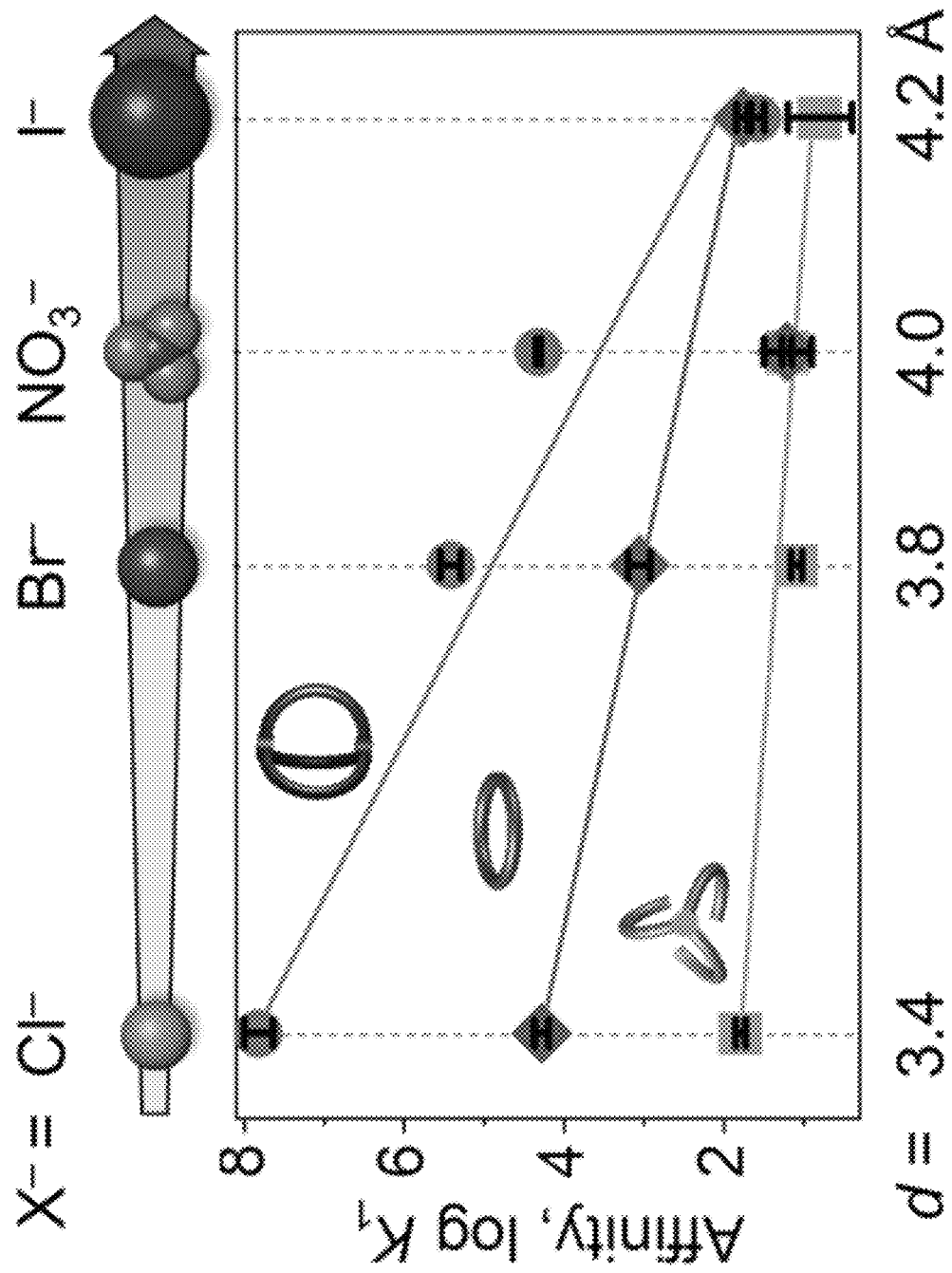
FIG. 4C depicts anion affinities ($K_1$) determined in DMSO-$d_6$ for $Cl^-$, $Br^-$, $NO_3^-$, and $I^-$. Colored lines indicate differences in selectivity.

Based on the solid-state behavior observed from the single-crystal X-ray diffraction studies, the binding strength of the T-Cage for chloride was measured. For comparison, the chloride binding affinities to an exemplary 2D triazolophane macrocycle 2 and 3D flexible receptor 3 were also determined (see FIG. 4A for these model compound structures). To help with affinity determination, high-dielectric dimethylsulfoxide (DMSO) was used as solvent, which is known to weaken binding, and made use of an affinity ladder after the fashion of pH ladders. Titrations were followed by $^1$H NMR spectroscopy. The addition of Cl$^-$ leads to significant downfield shifts of the CH hydrogen-bonded donor protons (triazole H$^a$ 1.6-ppm, phenylene H$^b$ 0.8 ppm) indicating chloride complexation. The outer phenylene CH protons H$^c$ showed little movement. The changes in peak position/intensity were used to construct the affinity ladder. The ladder was stepped from nitrate (~$10^4$ M$^{-1}$), to bromide (~$10^5$ M$^{-1}$), and then chloride (FIG. 4B) in separate competition experiments. Using the relative integration of proton peaks, chloride was found to almost have nanomolar affinity (~$10^8$ M$^{-1}$) in DMSO. This affinity exceeds the affinity seen with the 2D triazolophane (~$10^4$ M$^{-1}$; FIG. 4C) by four orders of magnitude. Interestingly, despite the moderate affinity differences between these anions, i.e., $10^1$ and $10^3$ M$^{-1}$, the displacement of nitrate with bromide and bromide with chloride both display slow exchange kinetics on the NMR time scale.

The superior binding affinity conferred by the multiple hydrogen bonding contacts strongly suggested that the T-Cage macrocycle would also be able to confer the types of selectivities seen with cryptands. Size selectivity across the spherical halides Cl$^-$, Br$^-$ and I$^-$, representing an increase in ionic diameter of 0.8 Å was examined, and a significant 1,000,000-fold drop with the triazolocage was observed. This is a significantly better selectivity compared to triazolophane compound 2, which only shows a 500-fold difference in this solvent. The enhanced selectivity can be attributed to the greater spatial confinement imposed by the cage. A third control compound, triazolotripod compound 3, can form a similar 3D cavity as the cage but is not pre-organized only displays 10-fold selectivity. Thus, the higher dimensionality and the rigidity of the cage is responsible for the observed selectivity. The 3D cavity precludes stable association with size-mismatched anions.

Importantly, the anion-binding cavity of the aryl-triazole bicyclic macrocycles of Formula (I) are expected to be of similar size, owing to the chemical bonding configuration of the bicyclic macrocycle core. Thus, the R substituents of the bicyclic macrocycles (i.e., R$_1$, R$^2$ and R$^3$) are predicted to contribute to modulating aqueous/non-aqueous partition coefficient properties with respect to the solubility of the bicyclic macrocycles in different solvents without affecting the overall anion-binding properties. Without the present invention being limited to any particular mechanism or mode of action, it is believed that the aryl-triazole bicyclic macrocycles of Formula (I) would possess comparable binding affinity for a given anion due to the size of the anion-binding cavity being comparable for each member of the family of structures of Formula (I). Any variations in binding affinity would be expected to vary with the electron withdrawing and donating ability of the various R substituents following documented knowledge in the field.

Accordingly, in an eighth aspect, a complex is disclosed. The complex includes (a) an anion, (b) a cation and (c) an aryl-triazole bicyclic macrocycle selected from the group consisting of Formulas (I), (III), (IV), (V), (VI) and (VII):

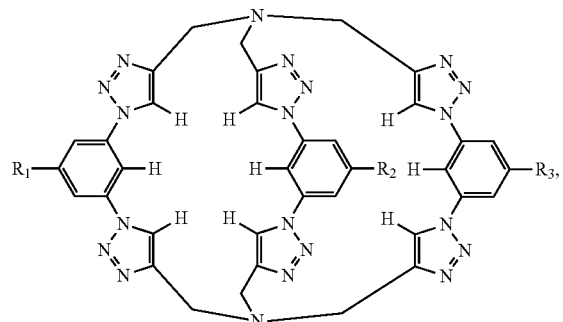

(I)

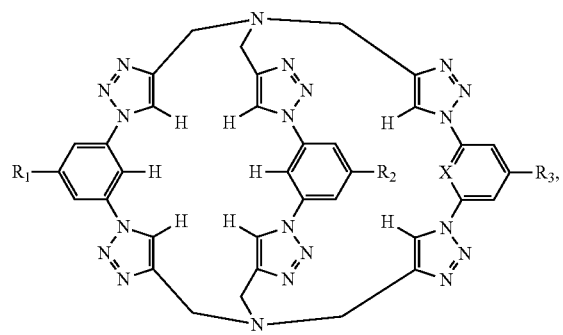

(III)

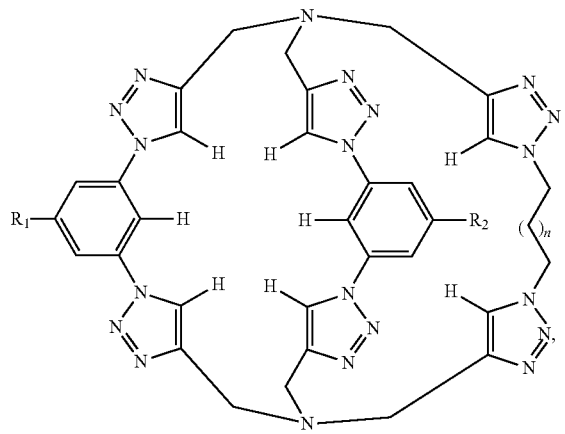

(IV)

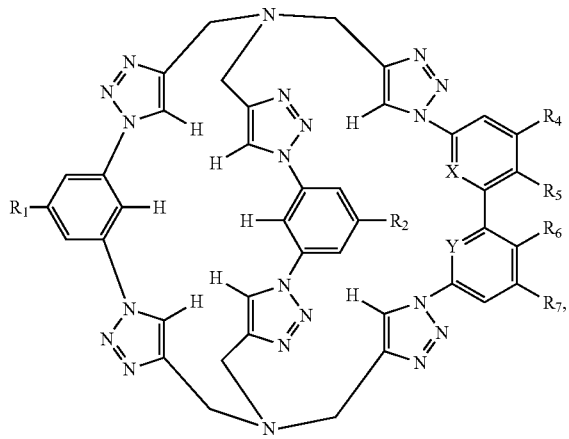

(V)

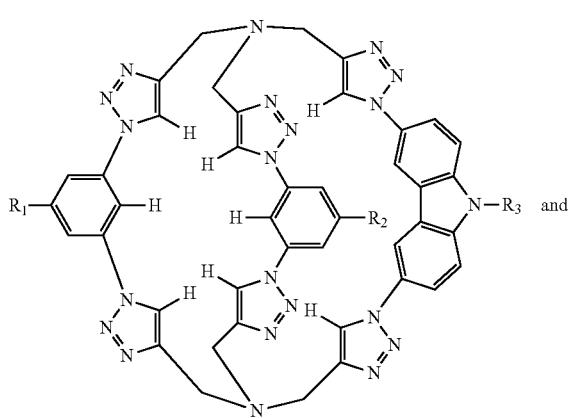

(VI)

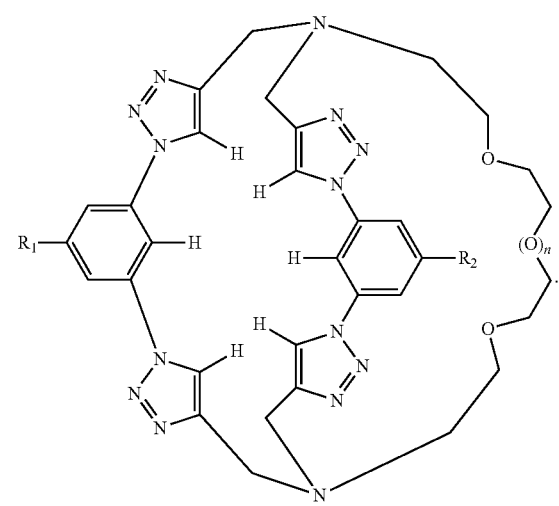

(VII)

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —$C(O)$—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

In one respect, the $R^1$, $R^2$, and $R^3$ of the aryl-triazole bicyclic macrocycle of Formula (I) include N,N-dicyclohexylamide groups. Highly preferred species of the aryl-triazole bicyclic macrocycle of Formula (I) include those selected from the following:

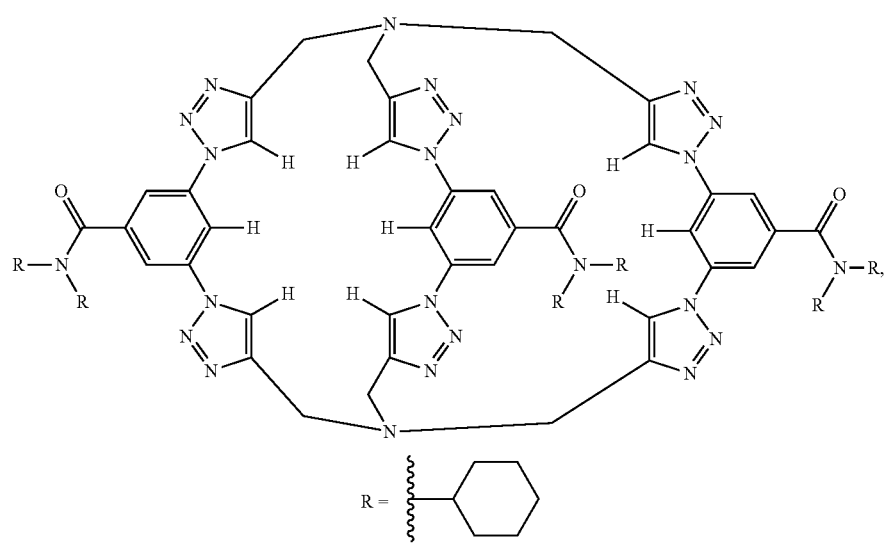
(T-Cage)
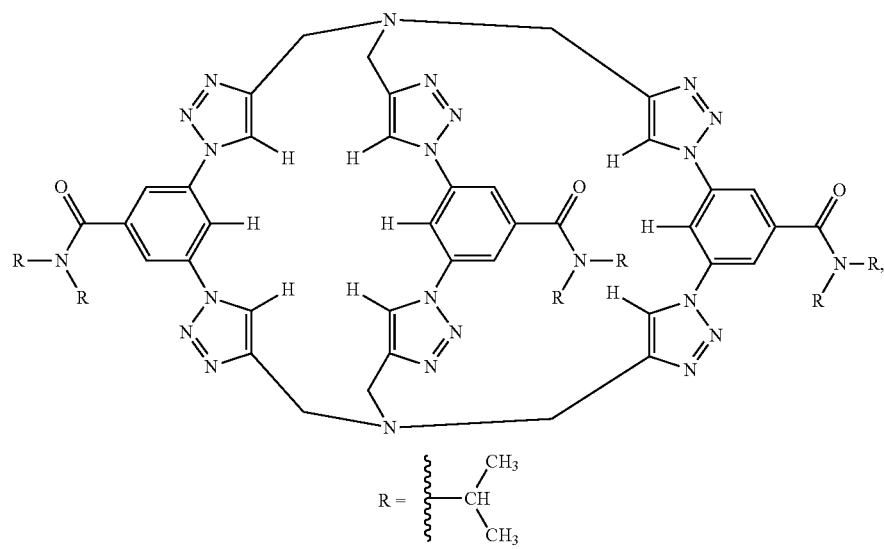
(I-Cage)

-continued
(B-Cage)
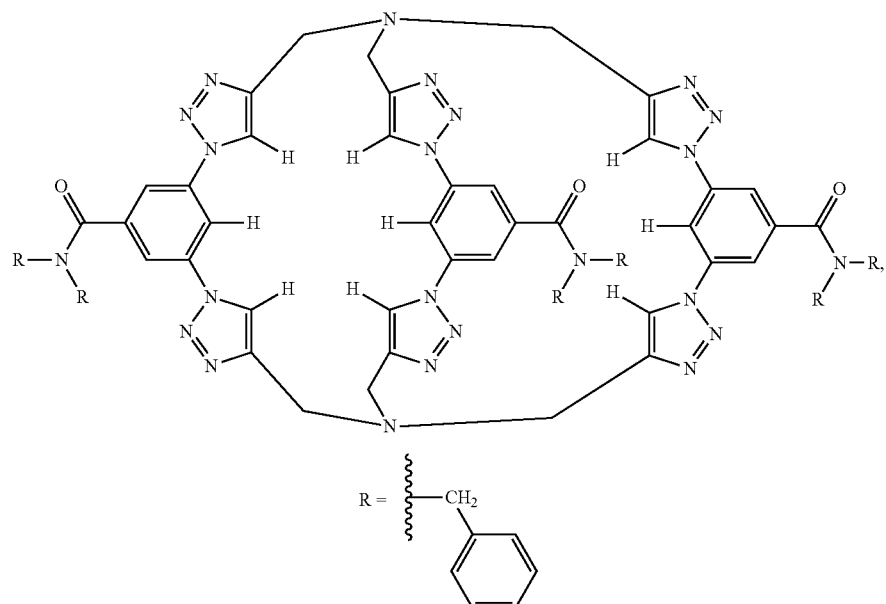
(E-Cage)
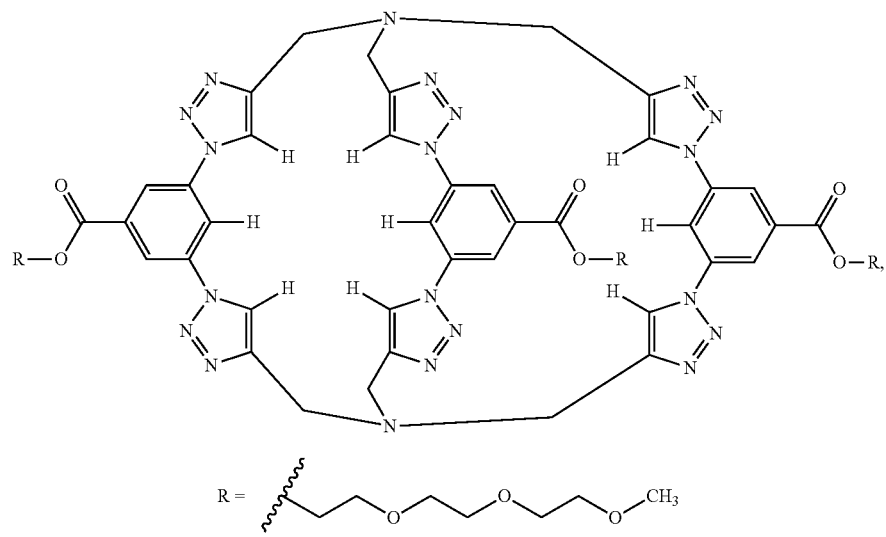
(G-Cage)
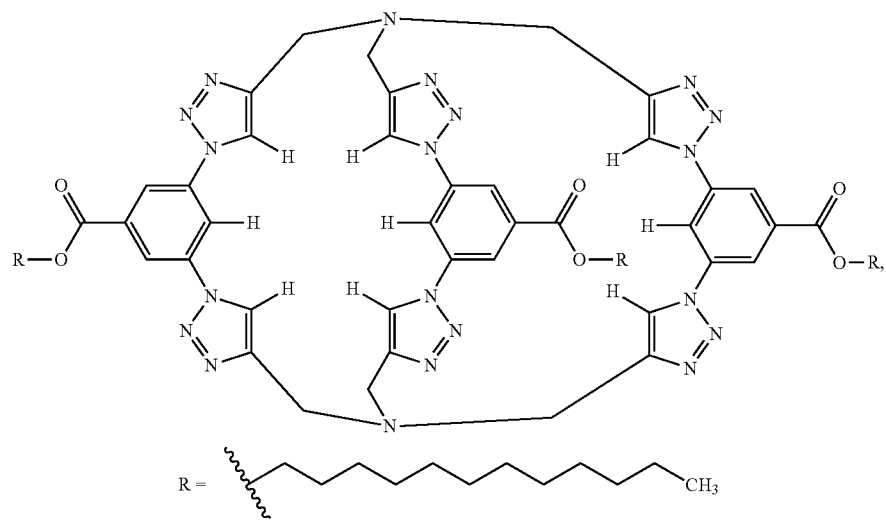

-continued
(P-Cage)
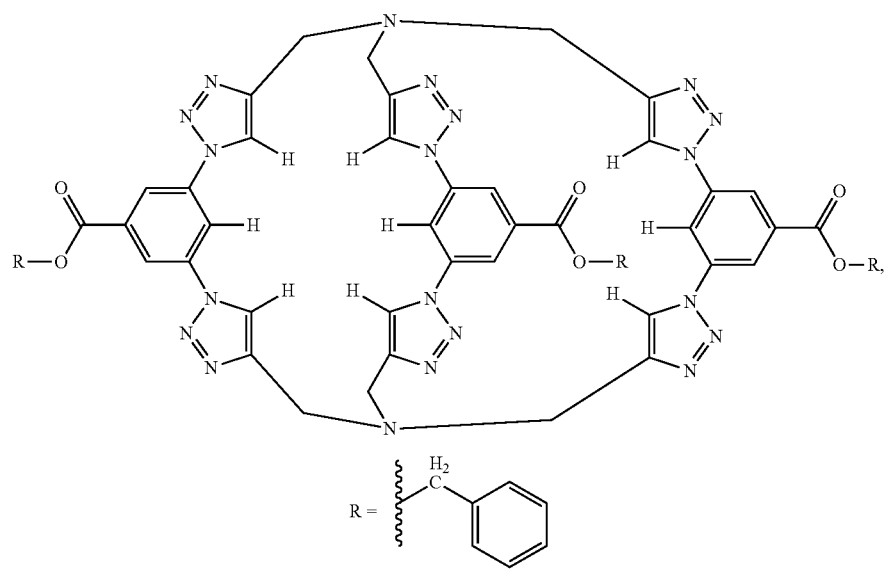
(A-Cage)
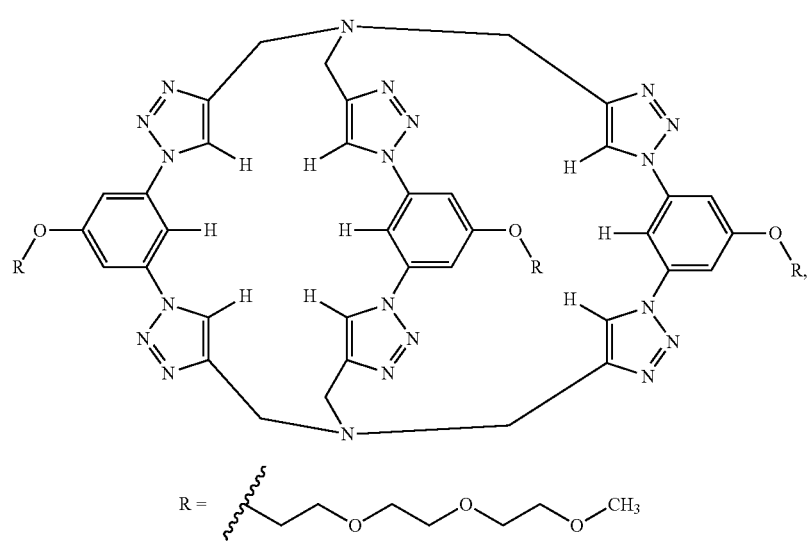
(D-Cage)
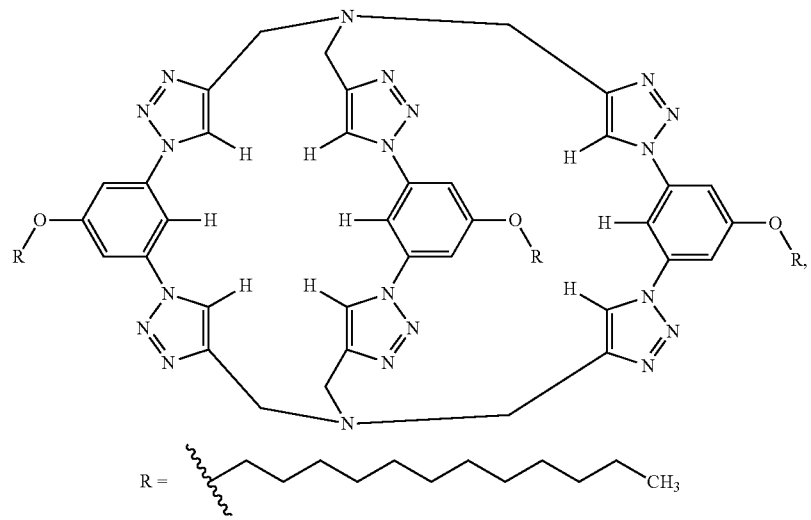

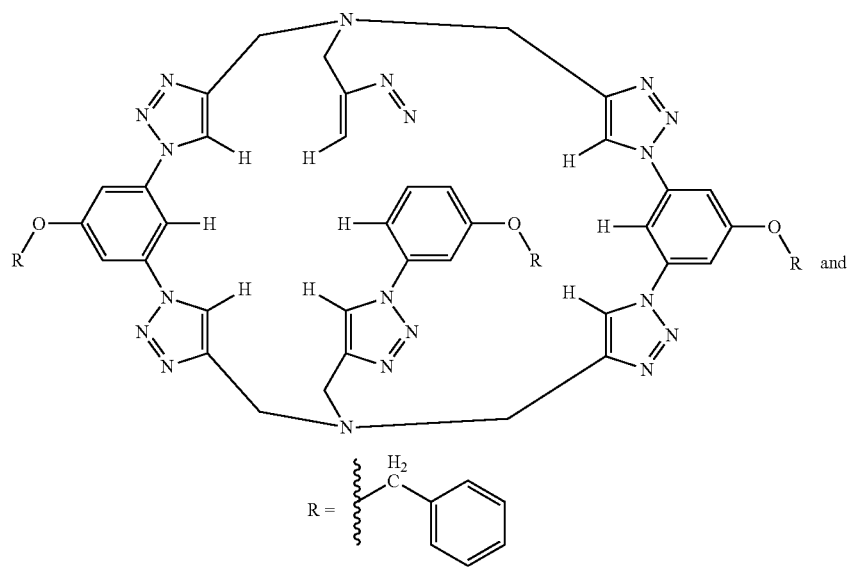

(Z-Cage)

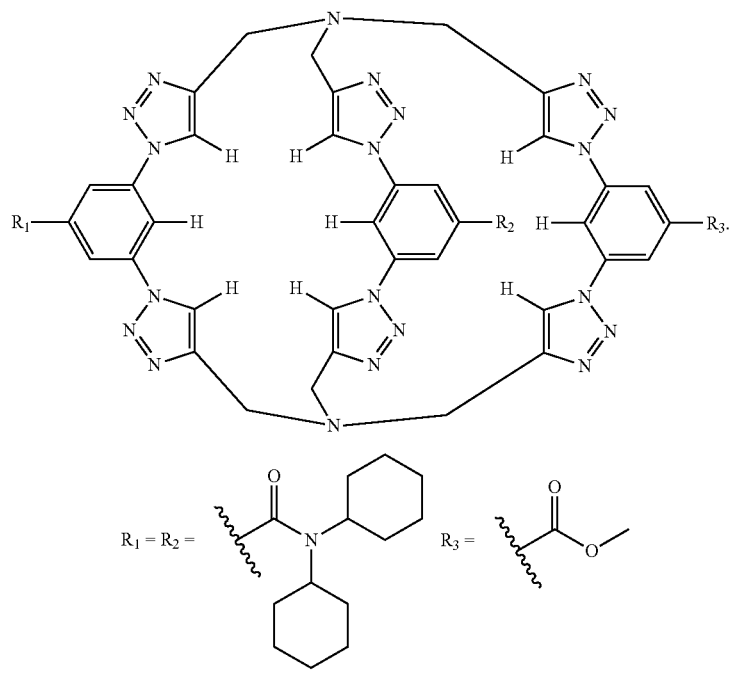

(T-cage-A₂B)

In yet other respects, the complex includes an anion selected from Cl⁻, Br⁻, I⁻, CN⁻, F⁻, $HF_2^-$, SCN⁻, $N_3^-$, $O_2^-$, $O_2^{2-}$, $NO_2^-$, $NO_3^-$, $CO_3^{2-}$, $HCO_3^-$, $S^{2-}$, $S_n^{x-}$ where $n \geq 1$ and $x = 1$ or 2, and ArO⁻. In preferred embodiments, the anion is a halide ion. In a highly preferred embodiment, the anion is chloride.

In other respects, the complex includes as a cation any cation needed for charge balance and, optionally, to confer any material property upon the complex. Exemplary material properties include, without limitation, solubility for a particular solvent, differential solubility (for example, partition coefficient-based differences between two media), spectral emission or absorption properties (for example, fluorescence, phosphorescence, colorimetric attributes, catalytic attributes, redox active attributes etc.).

Figure 5A:
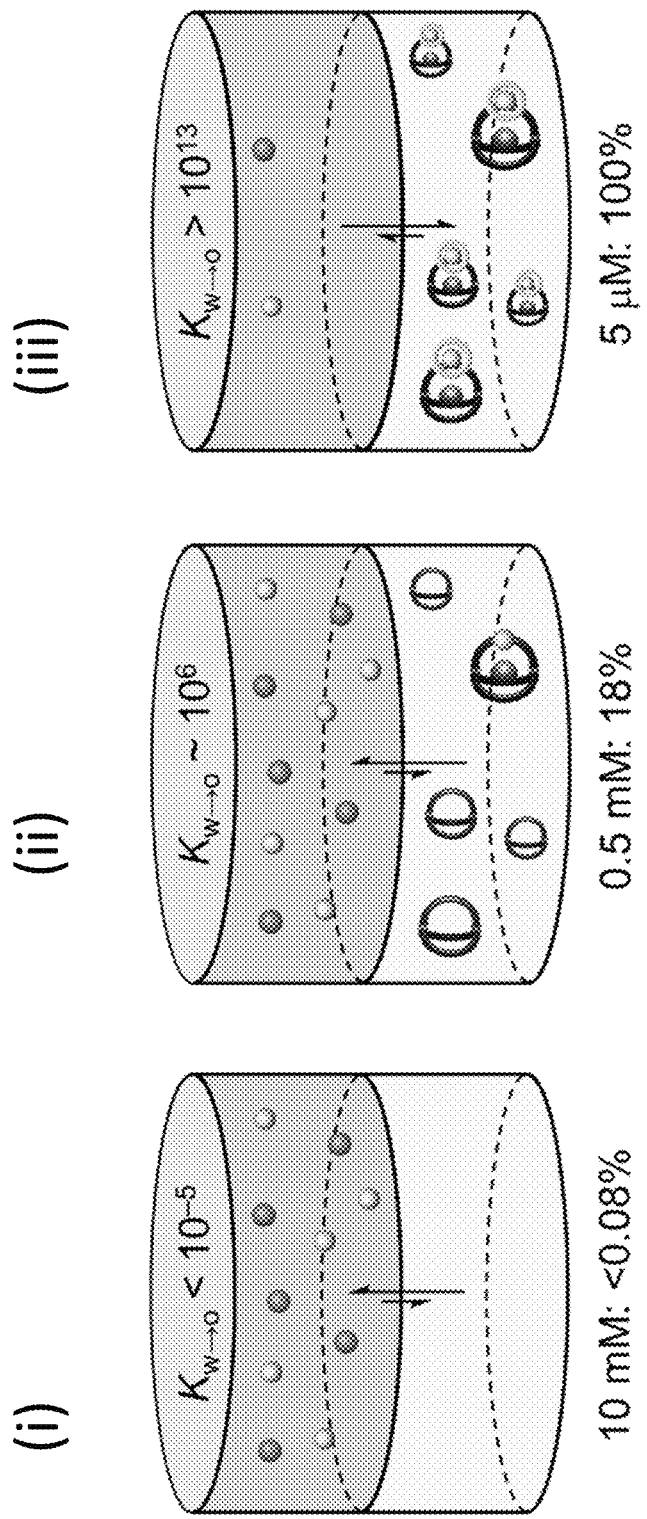
FIG. 5A depicts a cartoon representation of direct extraction of NaCl from water (blue) to $CH_2Cl_2$ (yellow) with the corresponding extraction equilibrium constant, $K_{w-o}$. Green ball: $Cl^-$; yellow ball: $Na^+$ (panel (i)); T-Cage-assisted extraction of NaCl (panel (ii)) and receptor-assisted extraction of NaCl using both cage and 18-C-6 (pink circles) (panel (iii)).
Figure 5B:
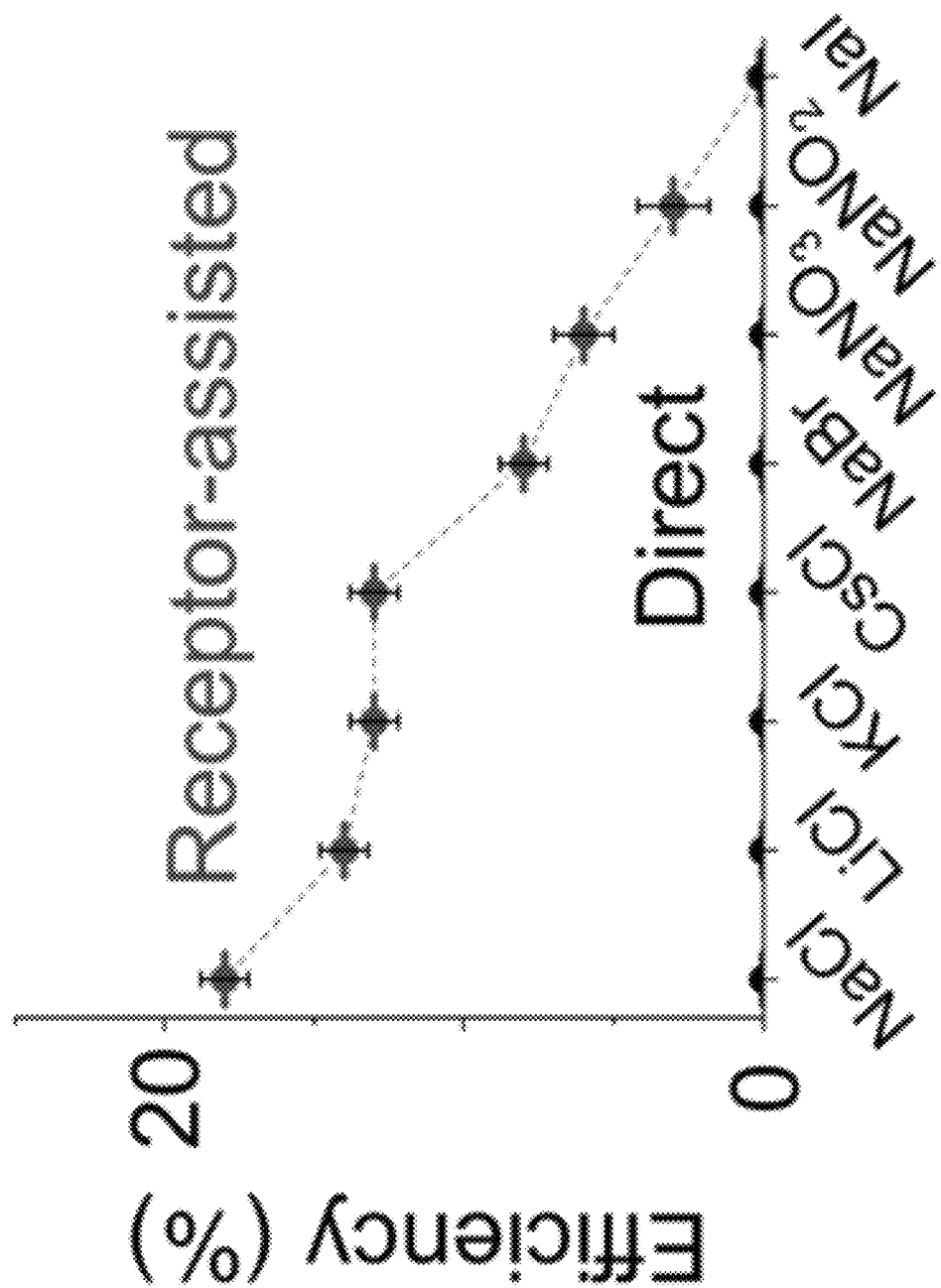
FIG. 5B depicts an exemplary plot of extraction efficiencies for salts with organic ammonium cations directly by $CH_2Cl_2$ (black) or assisted by T-Cage (red); $[1]_0$=0.2 mM, $[X^-]_0$=0.24 mM.

Methods Using an Aryl-Triazole Bicyclic Macrocycle to Remove an Anion from a Solution The ability to form high affinity complexes with anions makes it possible to use an aryl-triazole bicyclic macrocycle in a method to facilitate extracting alkali metal salts without the presence of a complementary cation-binding site. Referring to FIG. 5A, the extraction efficiency is best for NaCl (18%), using the T-Cage as an exemplary aryl-triazole bicyclic macrocycle of Formula (I). The extraction efficiency of NaCl from water to dichloromethane is enhanced by at least $10^8$-fold in the presence of T-Cage. Extraction efficiency is seen to follow the selectivity defined by the cage with Br being two-fold weaker than Cl⁻ (8%), and not observable for NaI (FIG. 5B). The Na⁺ salt has better extraction efficiency than other alkali cations. Presumably, the hydration energy penalty for Na⁺ is nicely counterbalanced by its ability to form favorable ion pairs with the negatively charged cage·Cl⁻ complex in dichloromethane. Quantitative extraction of NaCl was effected by addition of 18-crown-6 to overcome the penalty of co-extraction of sodium.

The extraction efficiency of tetraethylammonium chloride (TEACl) was quantitative. The presence of a cation like the tetraethylammonium cation (TEA⁺) with a lower hydration energy than alkali cations like Na⁺, enhances the extraction efficiency of the chloride salt. Cations with lower hydration energies are expected to behave in the same manner.

The measured extraction efficiency of TEACl ($K_{W \rightarrow O}$) can be used to quantify the strong binding affinity ($K_1$) of Cl⁻ in nonpolar solvents, e.g., dichloromethane and chloroform. Extraction is a function of the known transfer energies of the individual ions ($K_t^+$ and $K_t^-$), and of ion pairing between TEAT and cage·Cl⁻ ($K_{ipc}$) measured independently from variable concentration ¹H NMR studies.

$$K_{w \rightarrow o} = \frac{[Cage \cdot TEACl]_o}{[Cage]_o [TAE^+]_w [Cl^-]_w} = K_{ipc} \cdot K_1 \cdot K_t^+ \cdot K_t^- \quad (Eq\ 1)$$

Using Equation 1, the lower limit of T-Cage's Cl⁻ affinity, $K_1$, is estimated to be $10^{14}$ M⁻¹ in dichloromethane and $10^{16}$ M⁻¹ in chloroform. This extremely high affinity is consistent with the challenges encountered when trying to completely remove Cl⁻ from the cage, and the T-Cage's ability to readily extract NaCl from its surroundings during purification. Thus, the aryl-triazole bicyclic macrocycles of Formula (I) display is the best 1:1 Cl⁻ affinity of any neutral receptors known to date.

As explained previously, the anion-binding cavity of the aryl-triazole bicyclic macrocycles of Formula (I) are expected to be of similar size, owing to the chemical bonding configuration of the core of the bicyclic macrocycle. For this reason, the aryl-triazole bicyclic macrocycles of Formula (I) are expected possess comparable binding affinity for a given anion due to the size of the anion-binding cavity being comparable for each member of the family of structures of Formula (I). Each aryl-triazole bicyclic macrocycle of Formula (I), owing to differences in the R substituents of the bicyclic macrocycles (i.e., $R_1$, $R_2$ and $R_3$), will likely have different anion extraction efficiencies, however. Without the present invention being limited to any particular mechanism or mode of action, it is believed that aryl-triazole bicyclic macrocycles of Formula (I) having apolar, aprotic R substituents would display greater partition coefficients for organic solvents having low miscibility with aqueous solvents and yield higher anion extraction efficiencies than aryl-triazole bicyclic macrocycles of Formula (I) having polar, protic R substituents.

Without the present invention being limited to any particular mechanism or mode of action, it is believed that aryl-triazole bicyclic macrocycles of Formula (I) having heteroatoms like oxygen or nitrogen would display greater affinity for alkali cations in organic solvents having low miscibility with aqueous solvents and yield higher anion extraction efficiencies than aryl-triazole bicyclic macrocycles of Formula (I) having all carbon-hydrogen based R substituents.

Accordingly, in a ninth aspect, a method of removing an anion from an aqueous solution containing the anion is provided. The method includes several steps. The first step includes contacting the aqueous solution with an immiscible organic solution of an aryl-triazole bicyclic macrocycle selected from the group consisting of Formulas (I), (III), (IV), (V), (VI) and (VII):

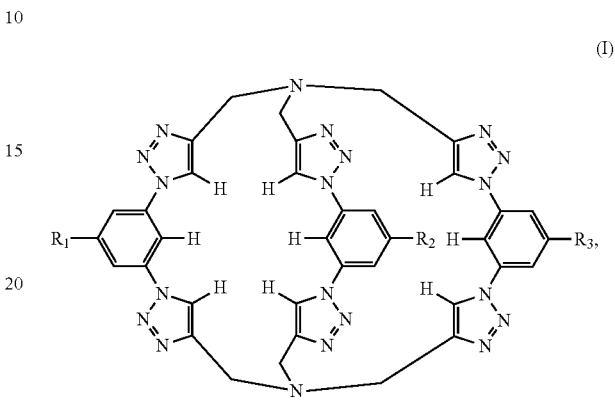

(I)

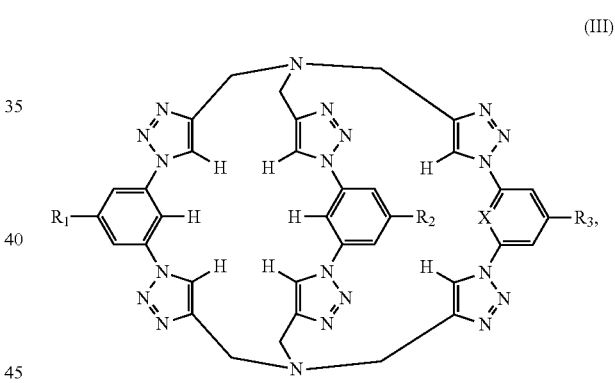

(III)

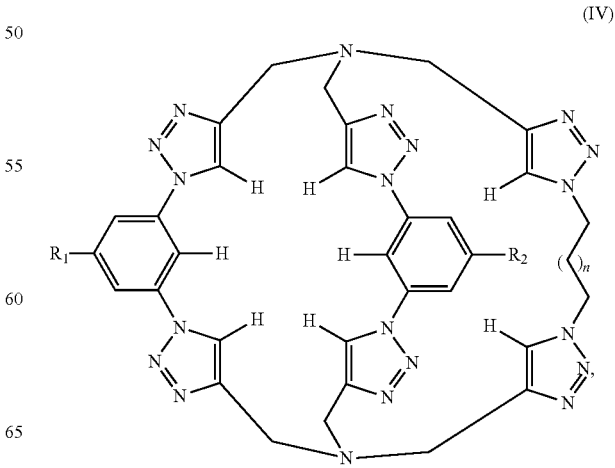

(IV)

(V)

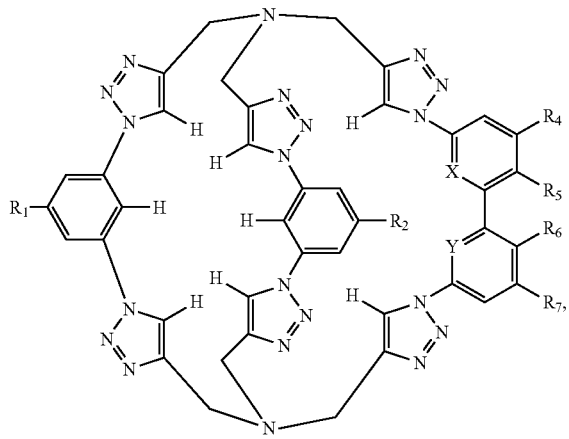

(VI)

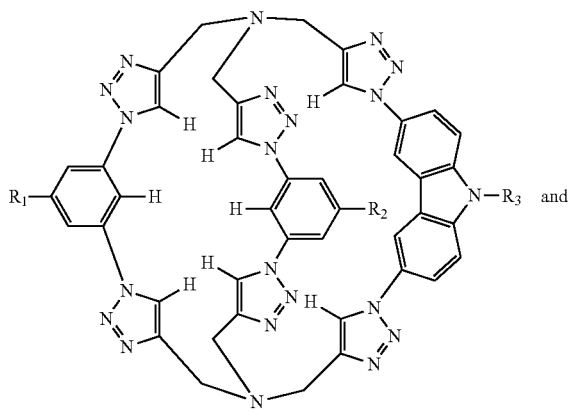

(VII)

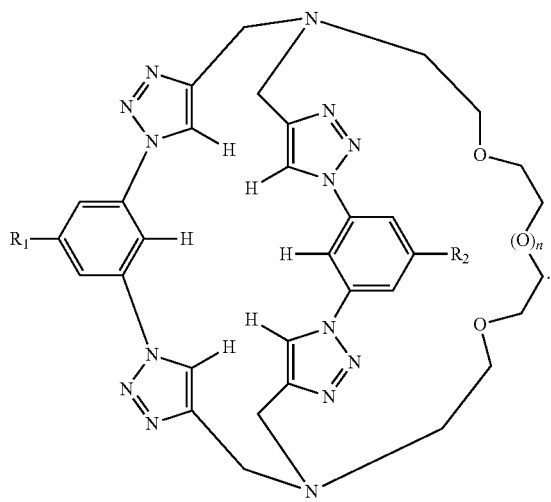

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, $-OR^4$, $-N(R^5R^6)$, $-CO_2R^7$, $-C(O)-N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, $-OR^4$, $-N(R^5R^6)$, $-CO_2R^7$, $-C(O)-N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, $-OR^3$, $-N(R^4R^5)$, $-CO_2R^6$, $-C(O)-N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, $-OR^8$, $-N(R^9R^{10})$, $-CO_2R^{11}$, $-C(O)-N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, $-OR^4$, $-N(R^5R^6)$, $-CO_2R^7$, $-C(O)-N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, $-OR^3$, $-N(R^4R^5)$, $-CO_2R^6$, $-C(O)-N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

The aqueous solution includes an anion and a cation. The second step includes forming a complex. The complex includes the anion, the cation and the aryl-triazole bicyclic macrocycle of Formula (I). The complex forms in the organic layer. The third step includes separating the organic layer from aqueous layer, thereby removing the anion from the aqueous solution.

In a first respect, the method is directed to the use of an aryl-triazole bicyclic macrocycle of Formula (I) in which the $R^1$, $R^2$, and $R^3$ include N,N-dicyclohexylamide groups. In a second respect, the method is directed to the use of an aryl-triazole bicyclic macrocycle of Formula (I) selected from one of the following:

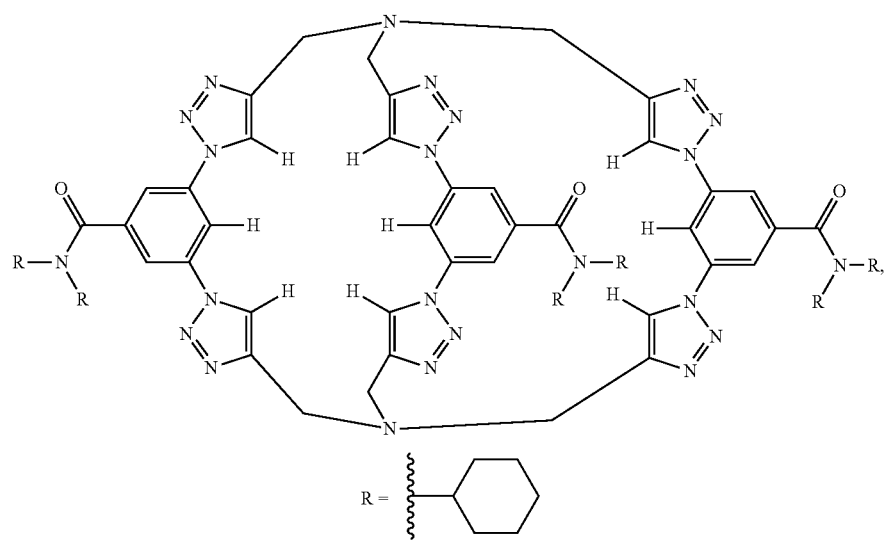
(T-Cage)
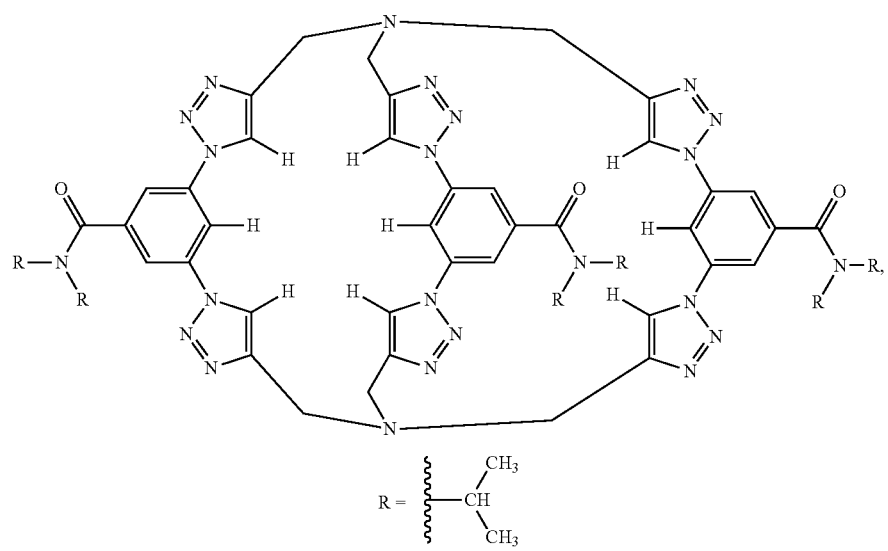
(I-Cage)

-continued
(B-Cage)
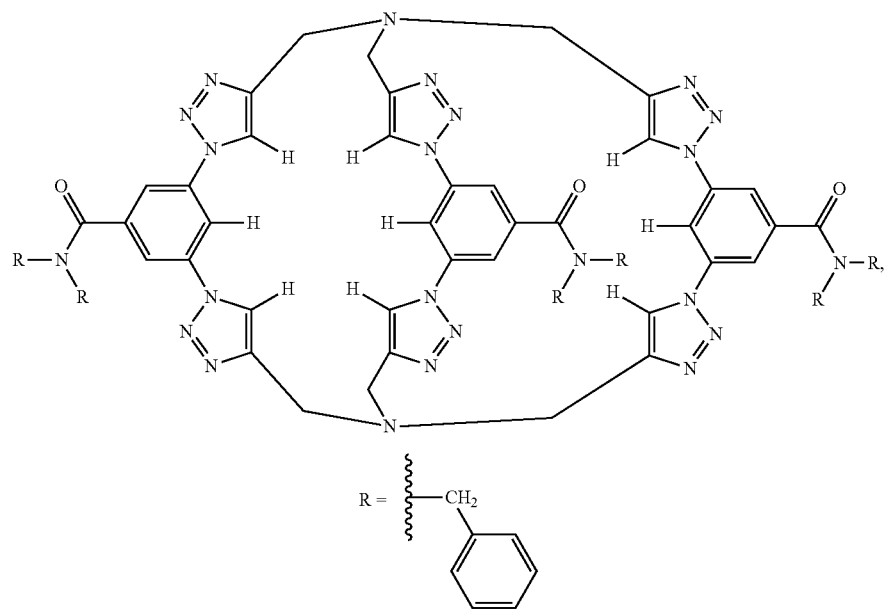
(E-Cage)
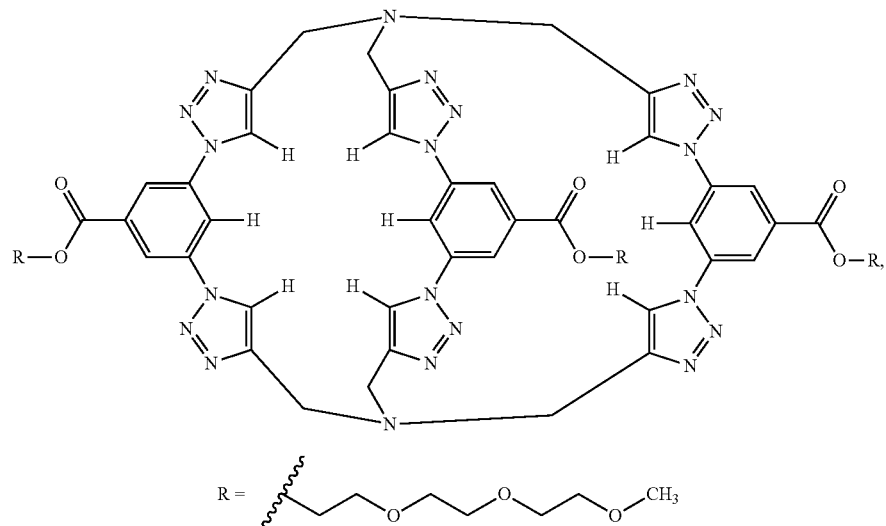
(G-Cage)
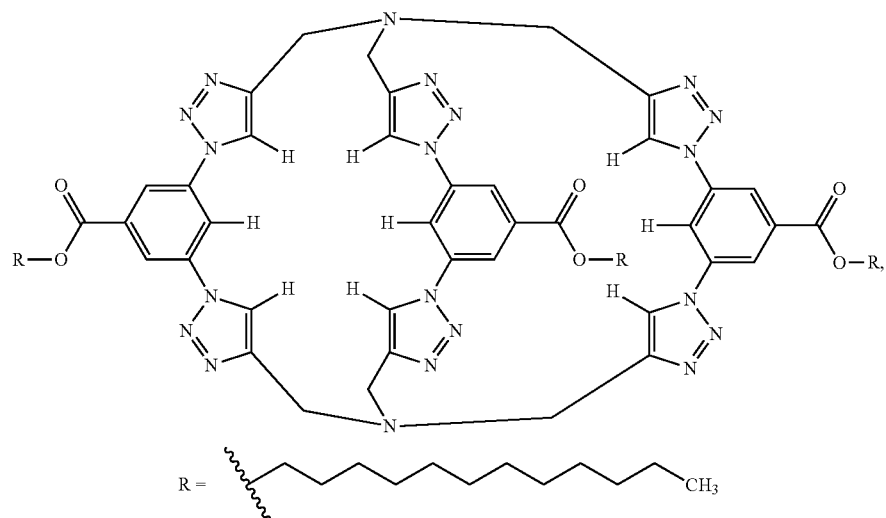

(P-Cage)
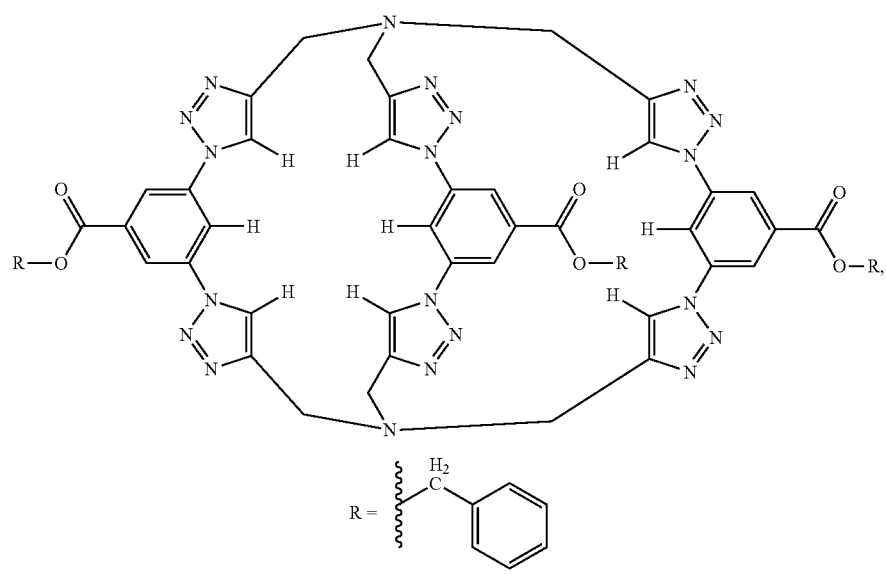
(A-Cage)
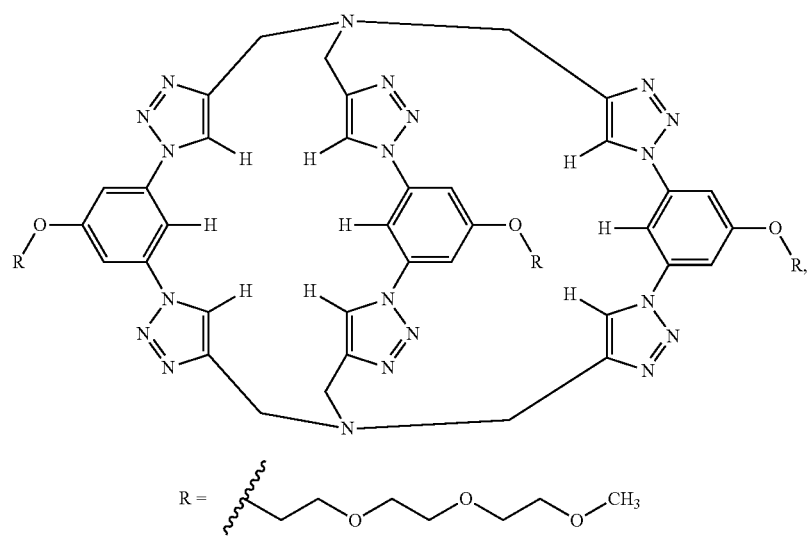
(D-Cage)
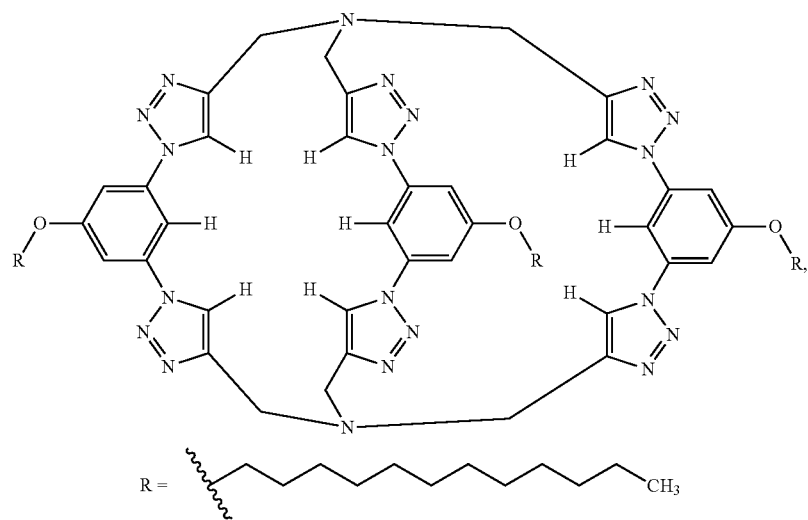

(Z-Cage)

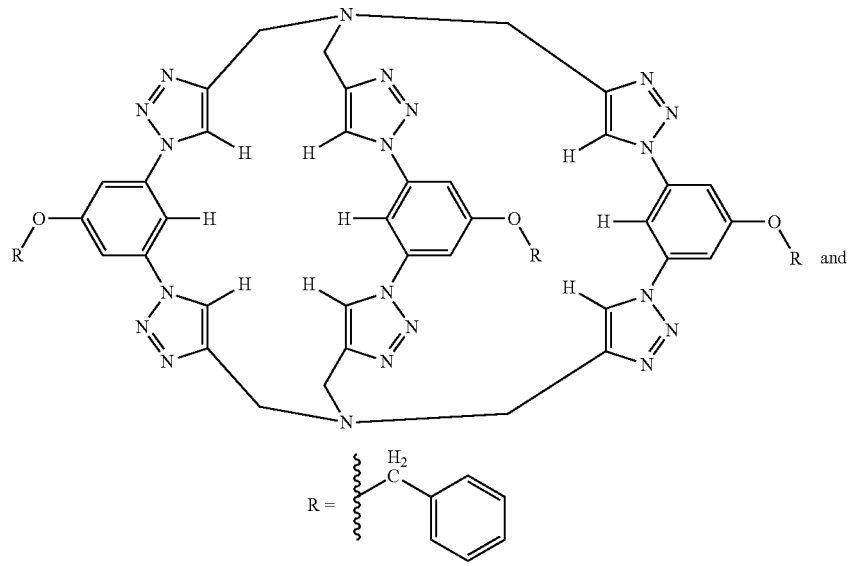

(T-cage-A₂B)

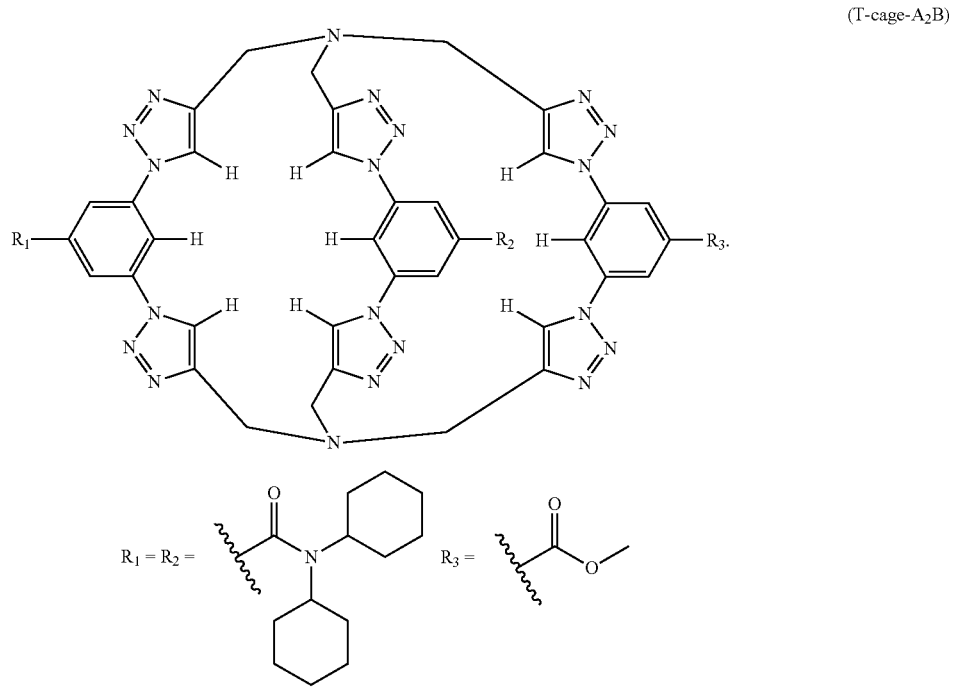

Figure 6:
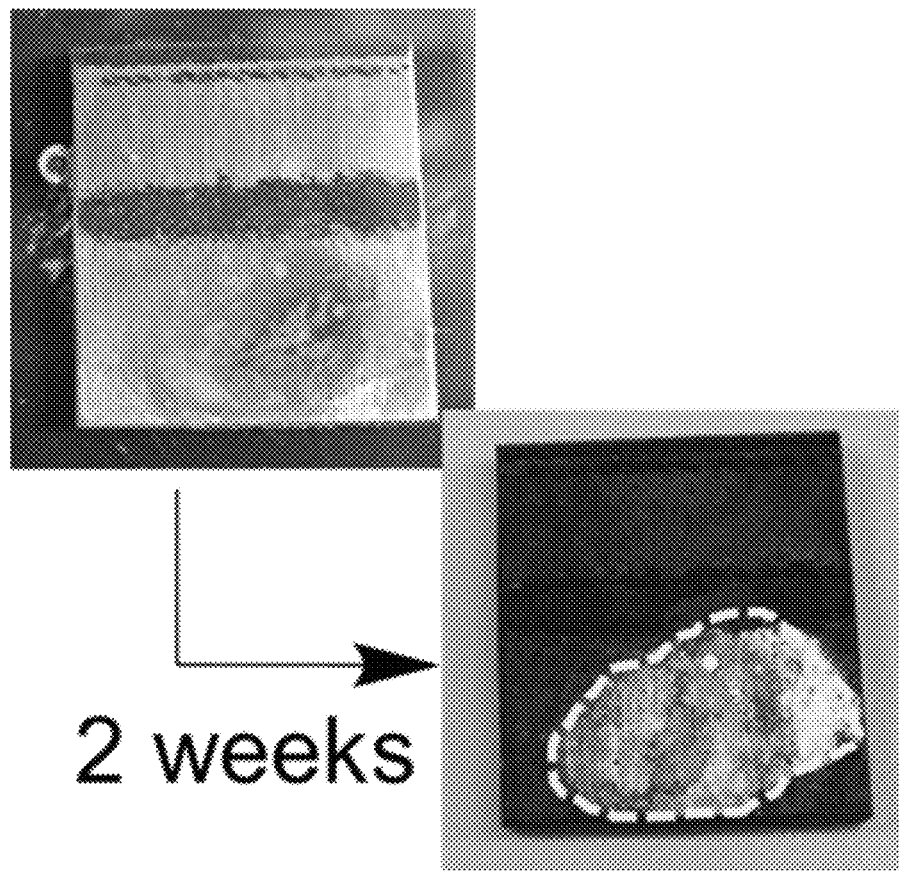
FIG. 6 depicts exemplary images of a thin film of T-Cage protected mild stainless steel from corrosion in saturated brine solution (5.4 M of NaCl) following a two-week exposure to the brine solution.

Methods, Compositions and Articles Using an Aryl-Triazole Bicyclic Macrocycle to Prevent Corrosion of Metal Surfaces Referring to FIG. 6, a small patch (~1 cm$^2$) of the T-cage compound (20 mg) was applied as a coating on a test sample of steel. This test sample was compared to a reference sample of steel treated with triazolophane (2, FIG. 4A) (20 mg) prepared in the same manner. Both samples were examined under the same conditions conducive for corrosion of the metal. The two samples were submerged in saline solution (5.6 M, NaCl) for 2 weeks and over that period of time only the T-cage inhibited the corrosion seen on the bare steel. The small patch of the test sample of steel that was coated with the T-cage does not show the extent of corrosion seen on the bare steel (FIG. 6).

A smooth film coating of the T-Cage compound was formed on the metal surface upon solvent-vapor annealing, in contrast to the sample coated with the triazolophane. The film coating of the T-Cage compound remained adhered during the course of the experiment. The T-cage compound coating provided an anti-corrosion property to the treated metal surface.

In a tenth aspect, a method of preventing corrosion of a metal surface is provided. The method includes several steps. The first step includes depositing a solution comprising an aryl-triazole bicyclic macrocycle in a solvent phase onto the metal surface to produce a coating on the metal surface. The aryl-triazole bicyclic macrocycle comprises a compound selected from the group consisting of Formulas (I), (III), (IV), (V), (VI) and (VII):

(I)

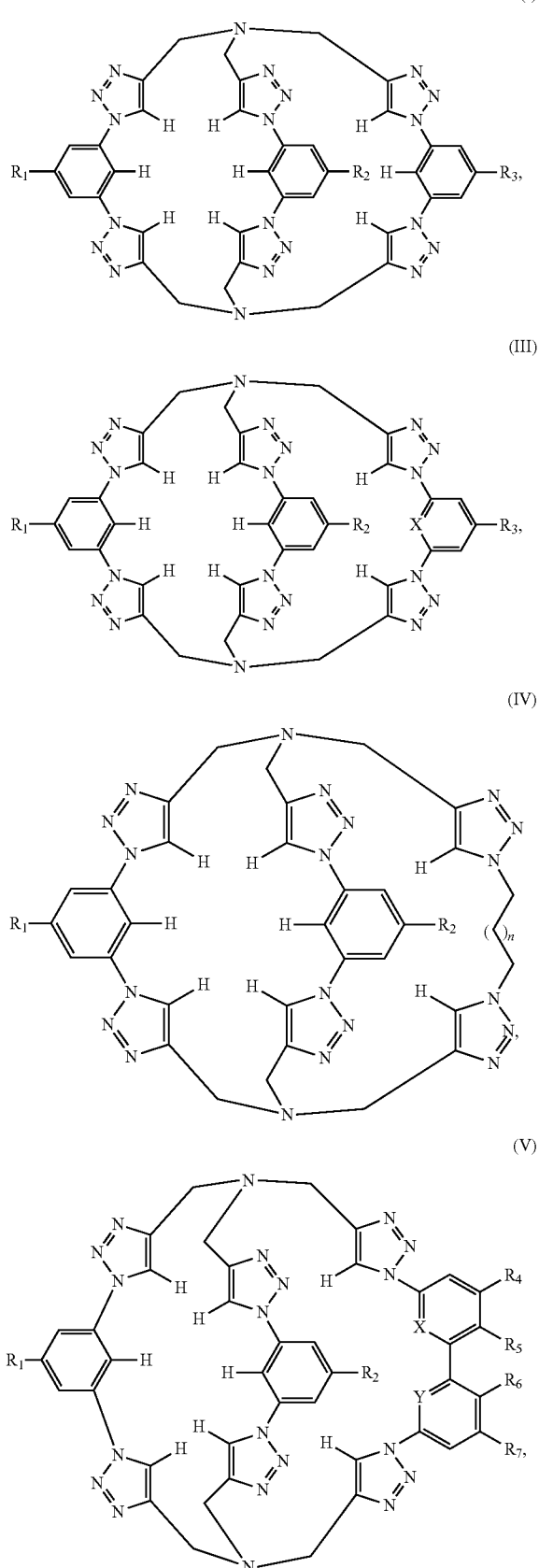

(VI)

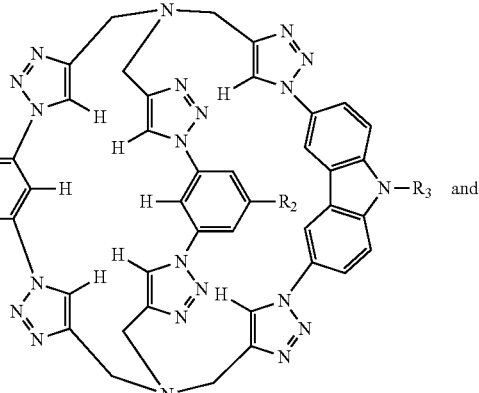

and (VII)

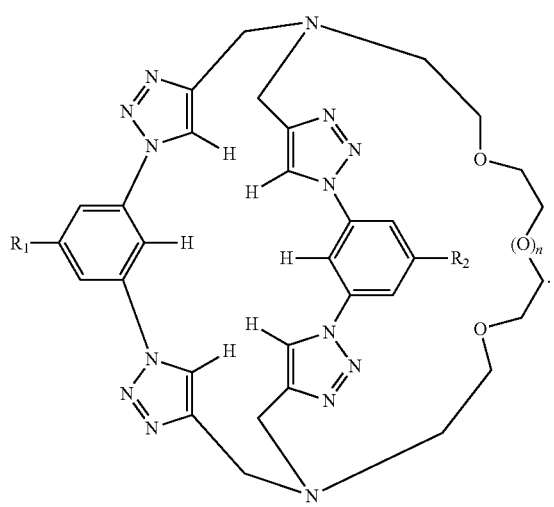

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^5$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —$C(O)$—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

The second step includes removing the solvent phase from the coating to produce a metal surface having dried coating. The third step includes annealing the dried coating onto the metal surface by applying a neat solvent to the metal surface having the dried coating of the second step. The neat solvent could include one of a mixture from the following: dichloromethane, chloroform, 1,2-dichloroethane, tetrahydrofuran, acetone, and ethyl acetate.

In a first respect, the method is directed the use of an aryl-triazole bicyclic macrocycle of Formula (I) in which $R^1$, $R^2$, and $R^3$ include N,N-dicyclohexylamide groups. In a second respect, the method is directed the use of an aryl-triazole bicyclic macrocycle of Formula (I) selected from one of the following:

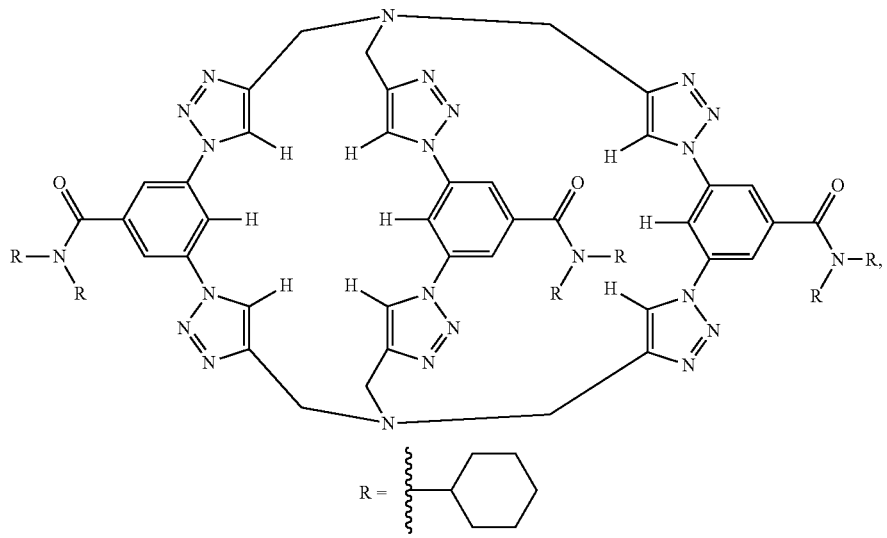

(T-Cage)

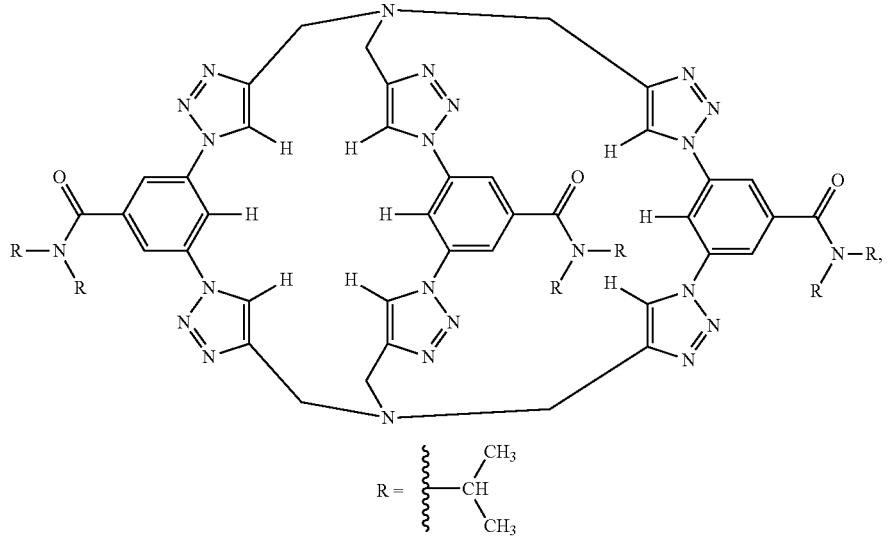

(I-Cage)

-continued
(B-Cage)
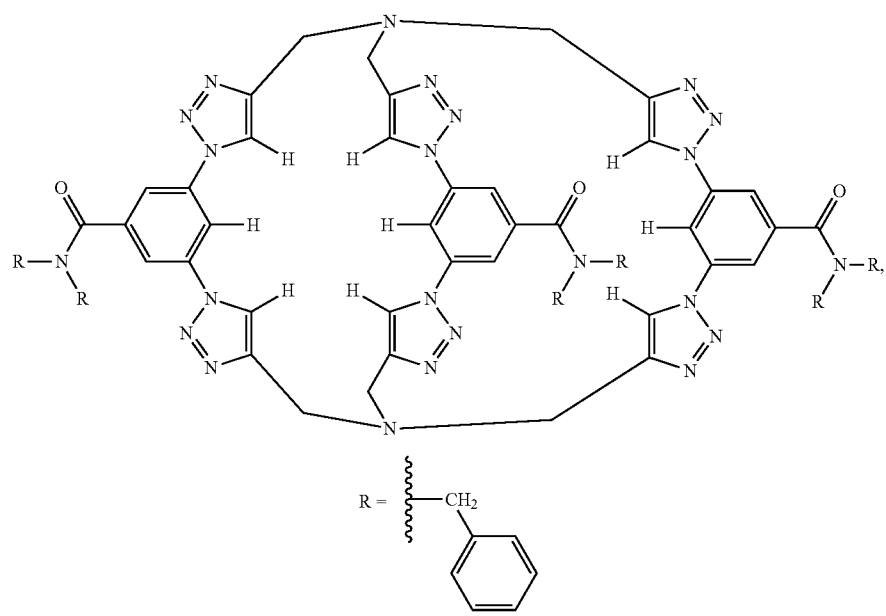
(E-Cage)
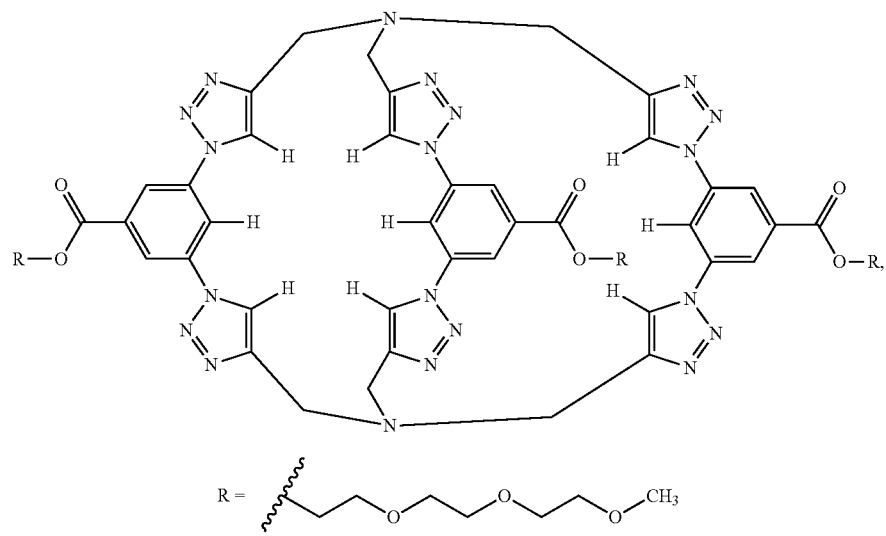
(G-Cage)
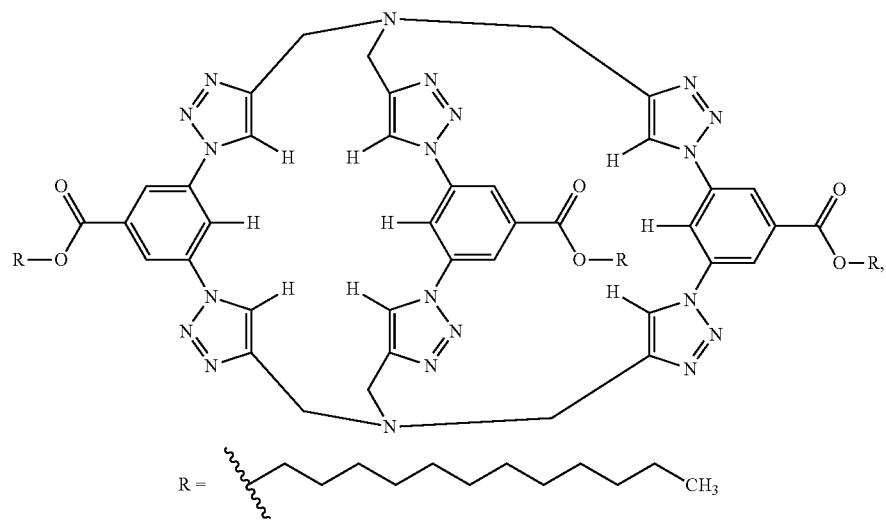

-continued
(P-Cage)
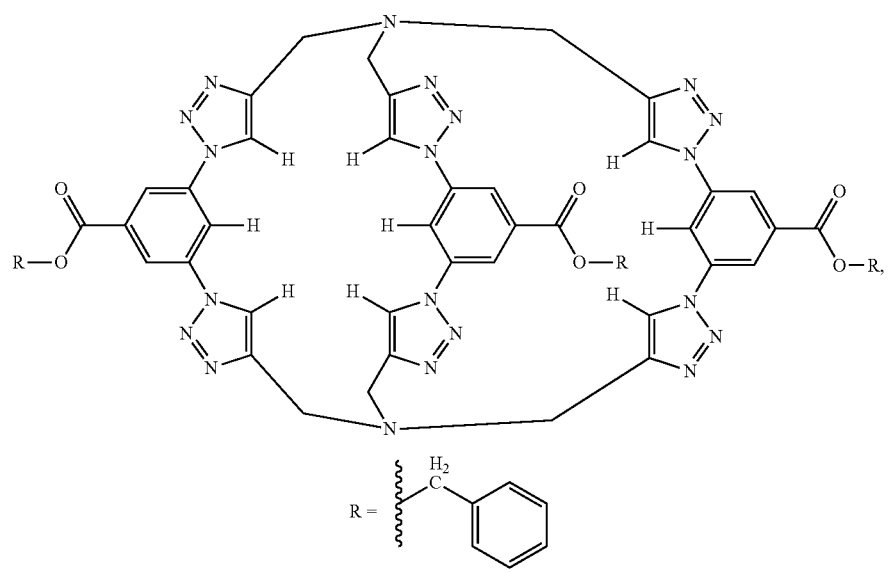
(A-Cage)
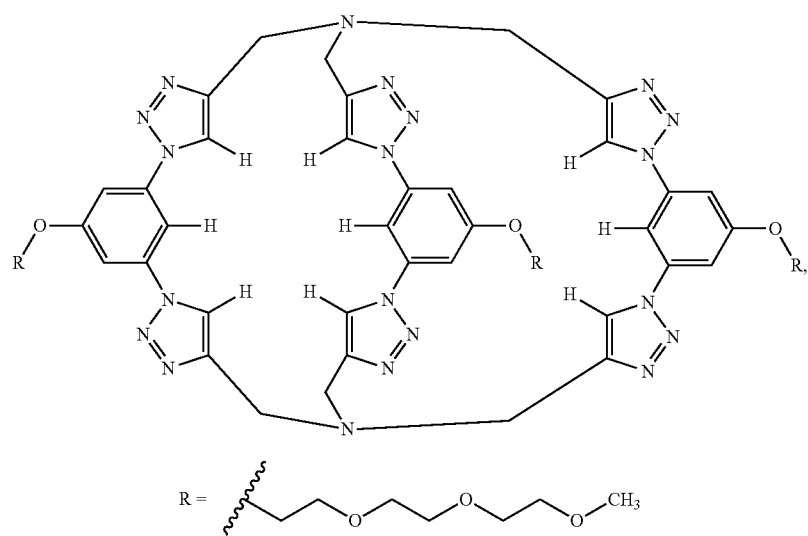
(D-Cage)
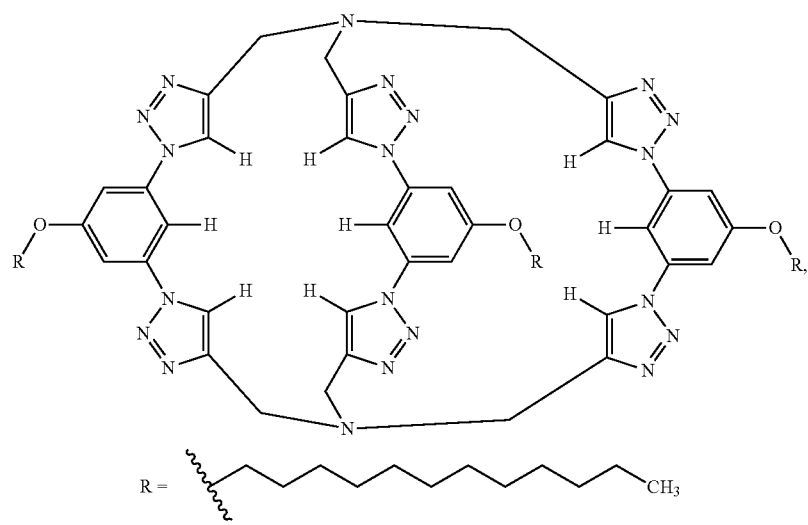

-continued (Z-Cage)

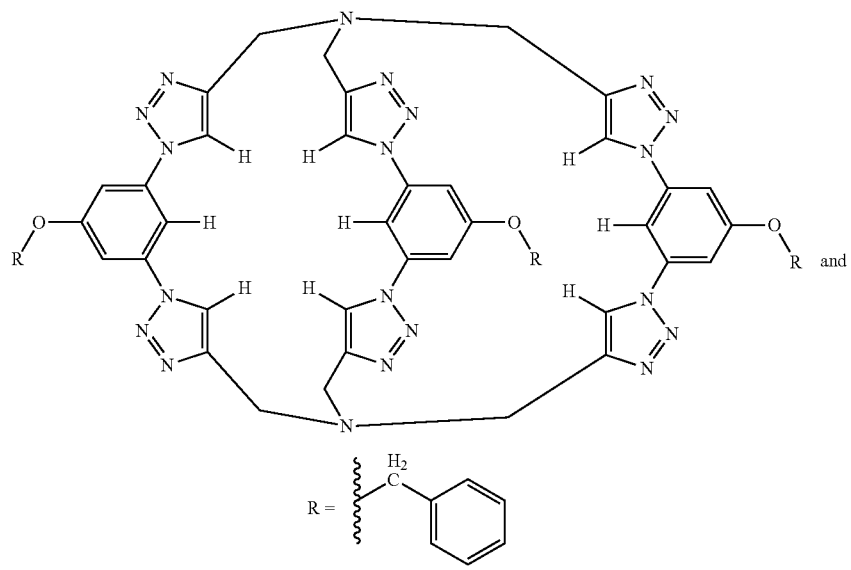

(T-cage-A₂B)

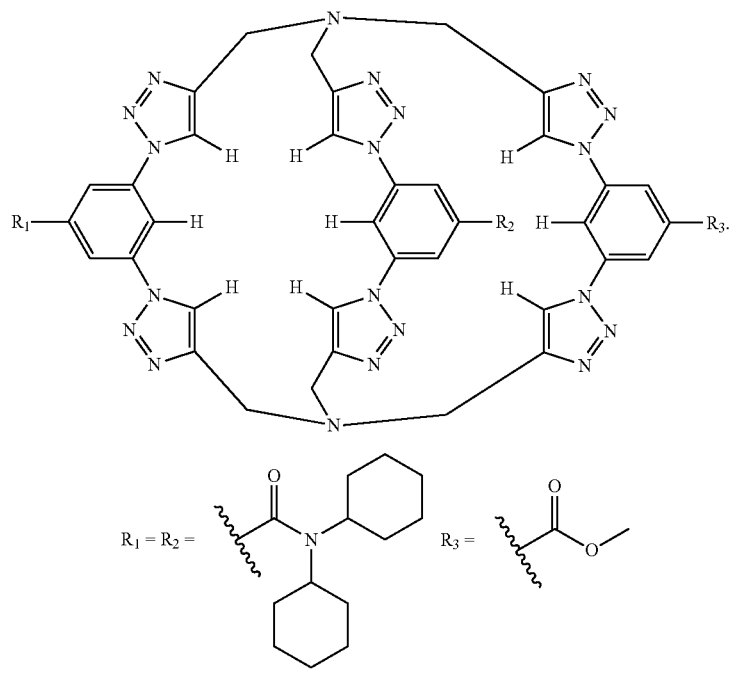

In additional respects, the solution comprising an aryl-triazole bicyclic macrocycle can be applied onto the metal surface by spin coating, drop casting, solvent-vapor annealing of drop-cast film chemical vapor deposition, physical vapor deposition, or applying it as a paint. Such deposition techniques are well understood to those of ordinary skill in the art.

In an eleventh aspect, a composition is provided. The composition includes a metal surface and a coating. The coating includes an aryl-triazole bicyclic macrocycle selected from the group consisting of Formulas (I), (III), (IV), (V), (VI) and (VII):

(I)

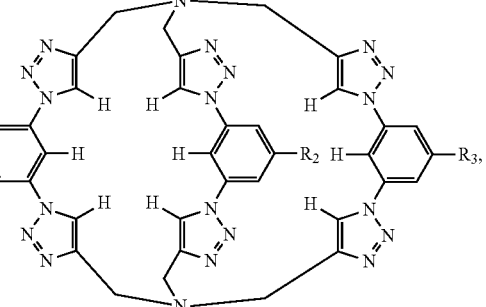

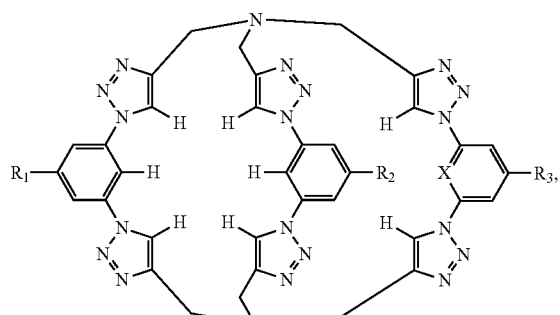

(III)

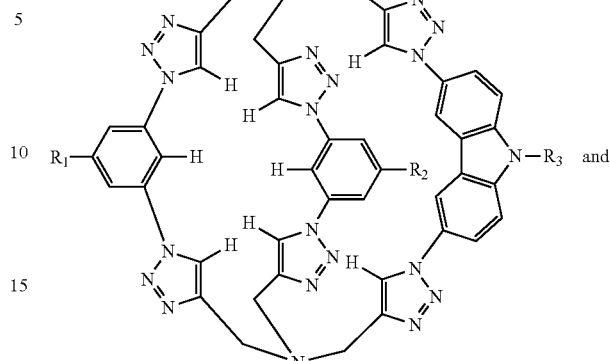

(VI)

and

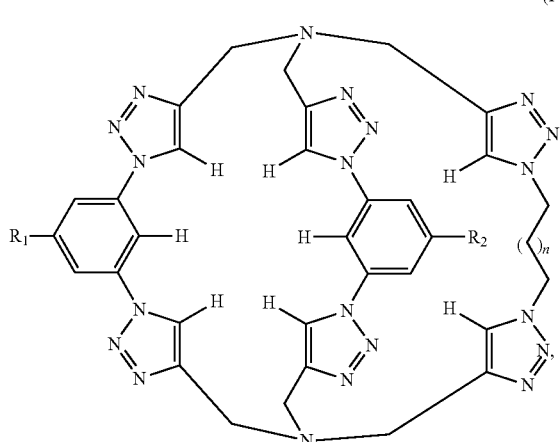

(IV)

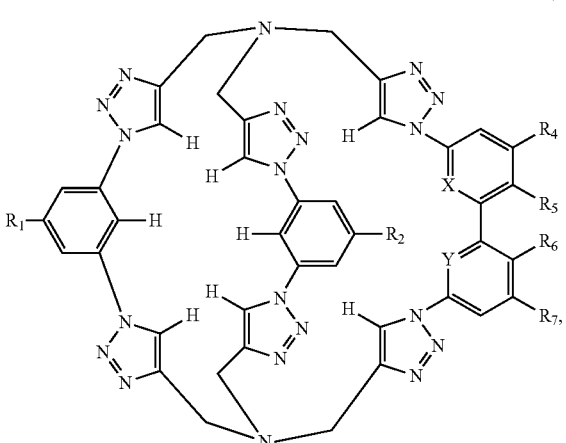

(V)

(VII)

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —$C(O)$—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

In a highly preferred embodiment of the composition, the aryl-triazole bicyclic macrocycle of Formula (I) includes $R^1$, $R^2$, and $R^3$ having N,N-dicyclohexylamide groups. Exemplary species of aryl-triazole bicyclic macrocycles of Formula (I) include those selected from the group consisting of the following:

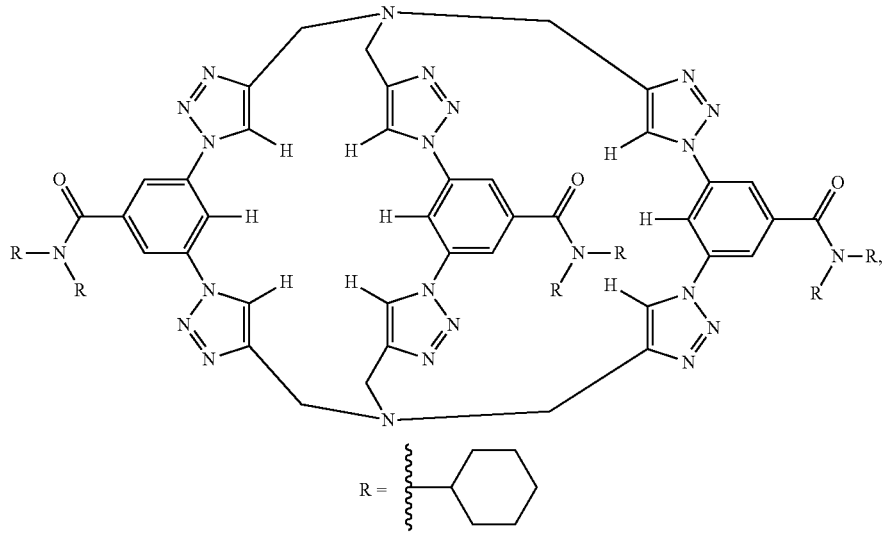

(T-Cage)

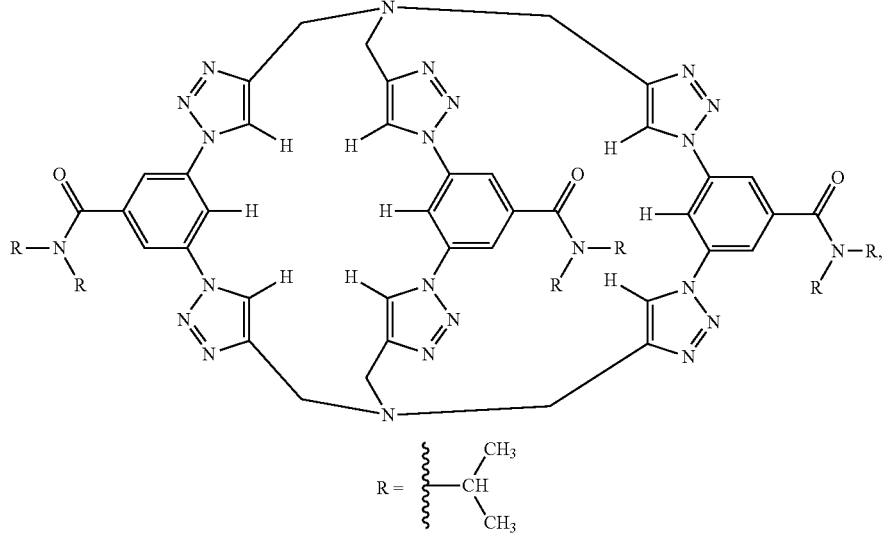

(I-Cage)

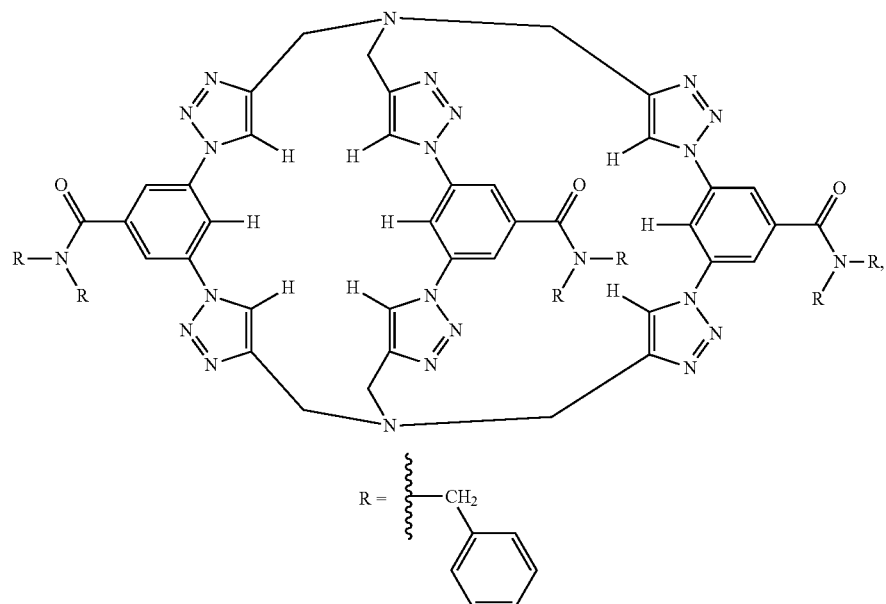
(B-Cage)
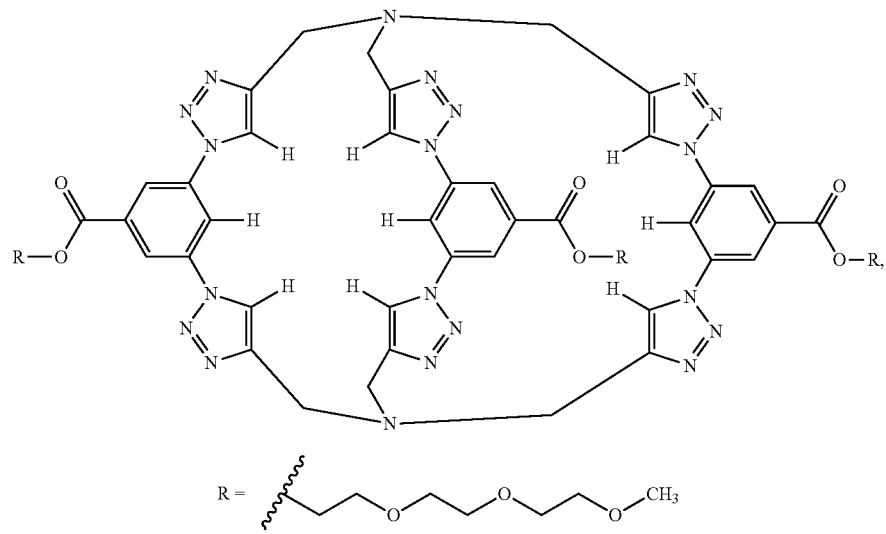
(E-Cage)
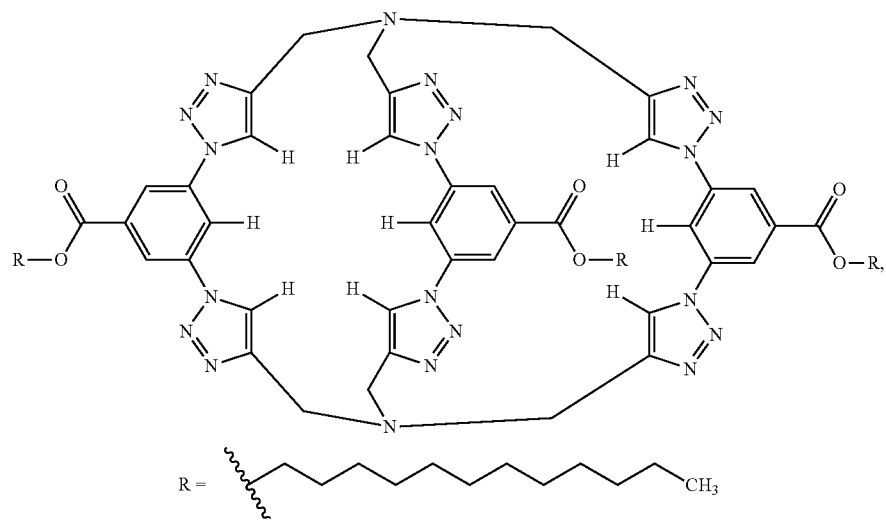
(G-Cage)

(P-Cage)
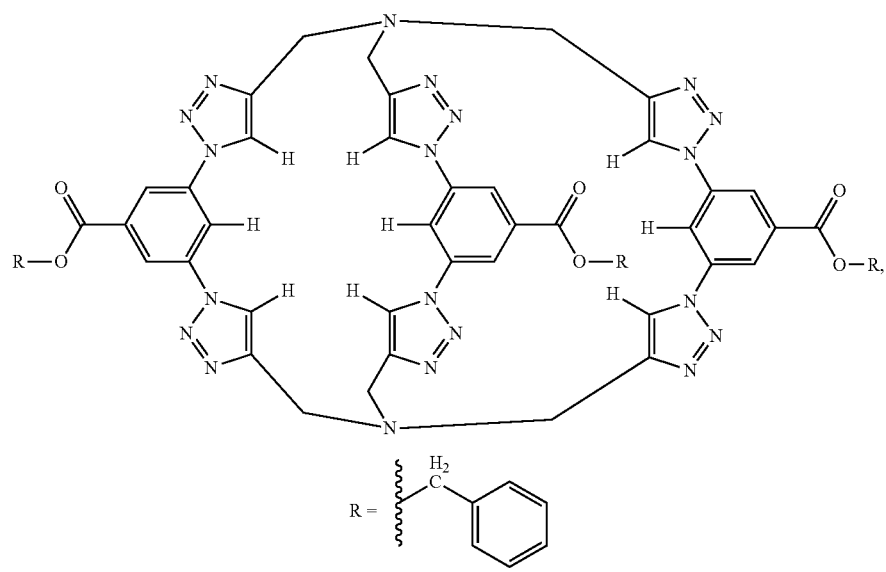
(A-Cage)
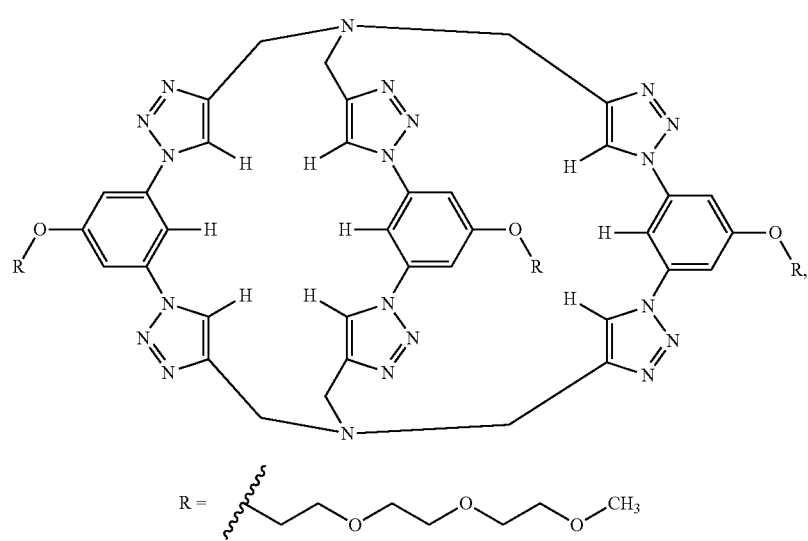
(D-Cage)
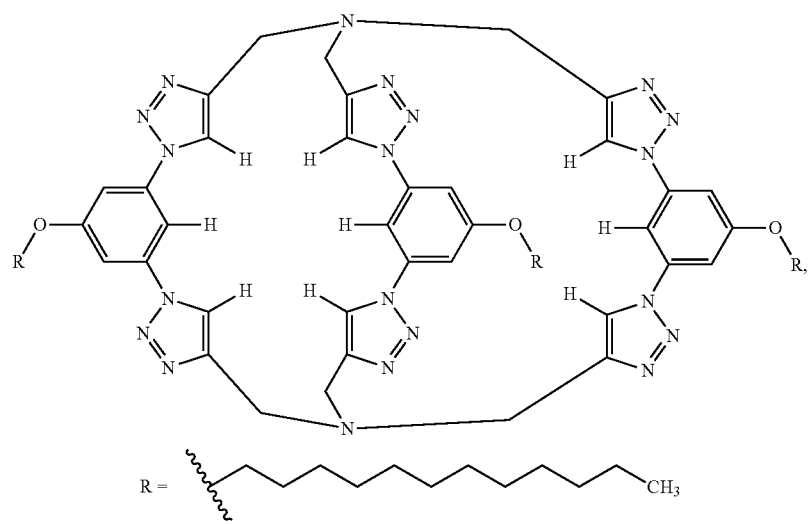

(Z-Cage)

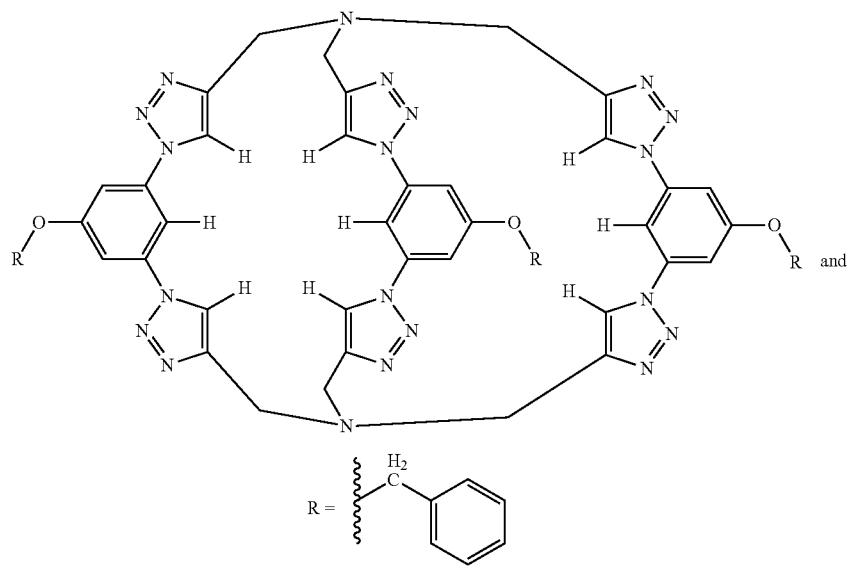

(T-cage-A₂B)

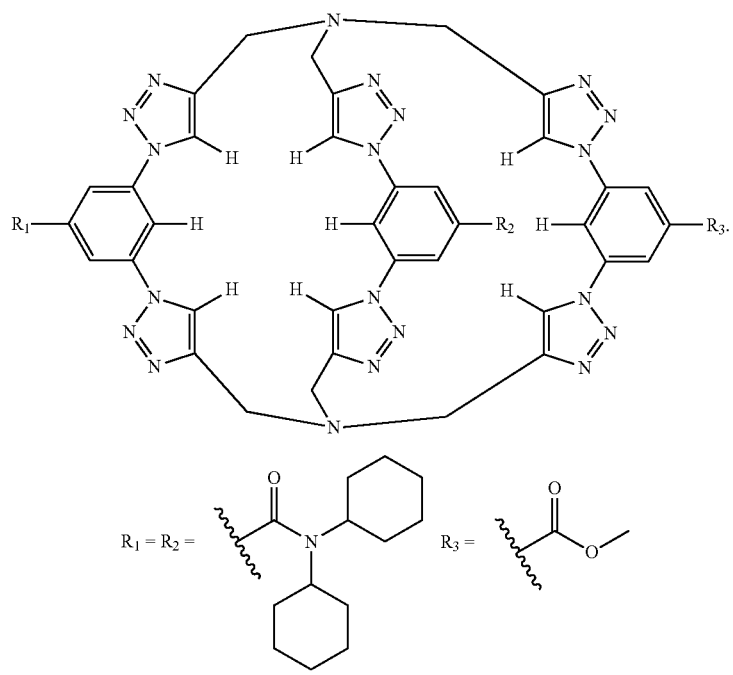

In another respect, the composition is directed to a metal surface having metal composed of stainless steel. Other metal surfaces subject to any corrosion that is facilitated by chloride ions will also be considered, such as but not limited to, iron-containing alloys, copper and copper alloys.

Formulations

In a twelfth aspect, a formulation is provided. The formulation includes a coating and an aryl-triazole bicyclic macrocycle selected from the group consisting of Formulas (I), (III), (IV), (V), (VI) and (VII):

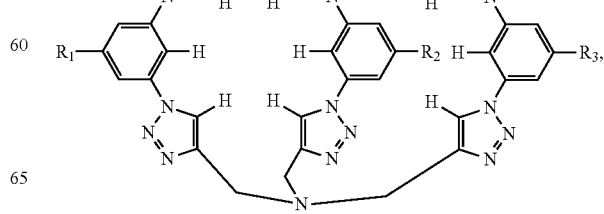

(I)

(III)

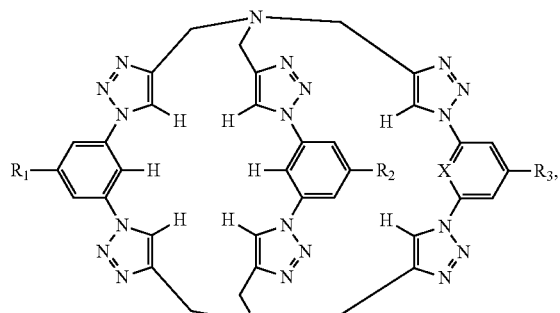

(IV)

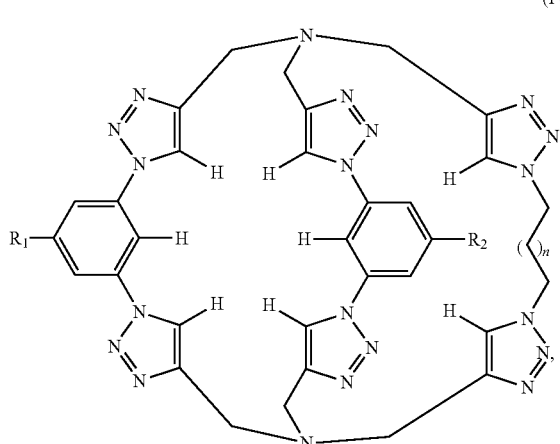

(V)

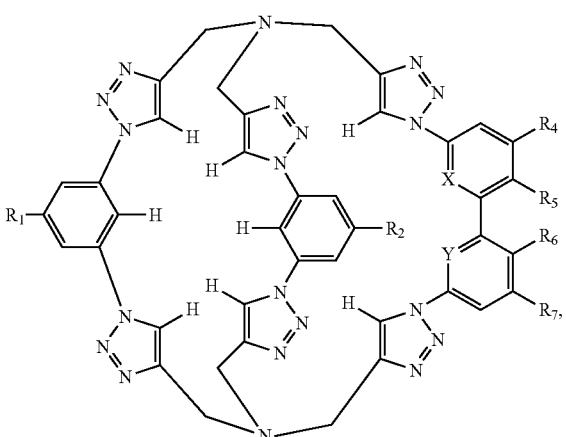

(VI)

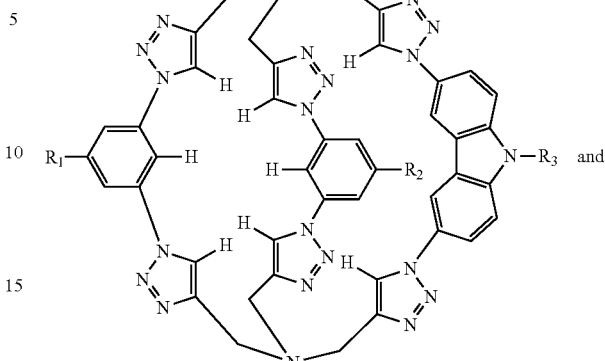

and (VII)

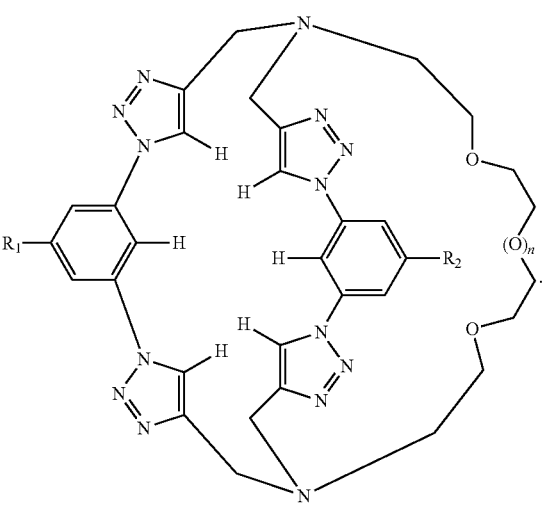

For (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—N($R^8R^9$), wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O)—N($R^7R^8$), wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

For (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —$C(O)$—$N(R^{12}R^{13})$, wherein $R^8$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen.

For (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—N$(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

For (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

In a first respect, the $R^1$, $R^2$, and $R^3$ include N,N-dicyclohexylamide groups. In a second respect, the aryl-triazole bicyclic macrocycle having Formula (I) is selected from the following:

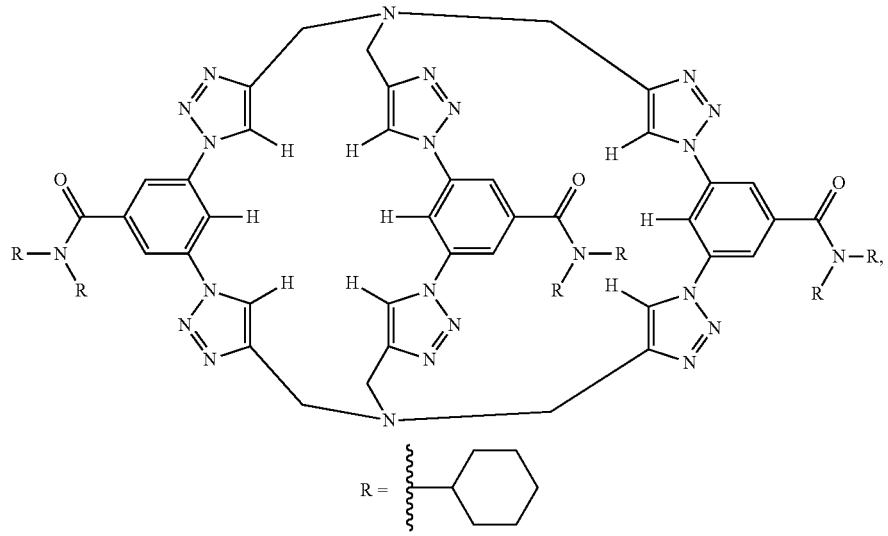
(T-Cage)

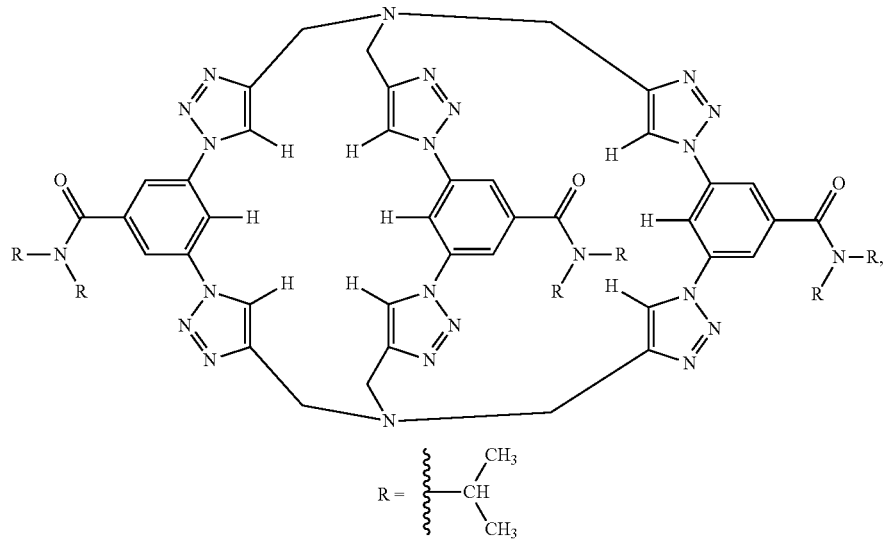
(I-Cage)

-continued
(B-Cage)
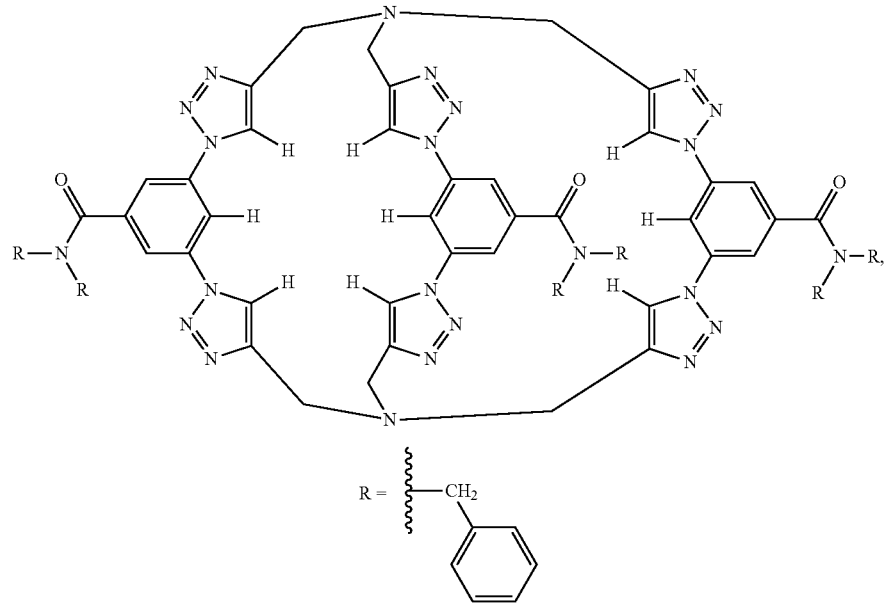
(E-Cage)
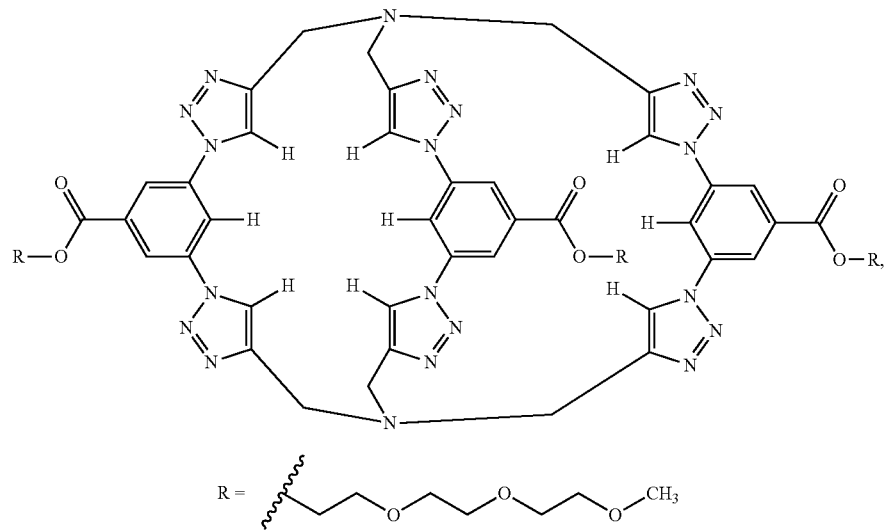
(G-Cage)
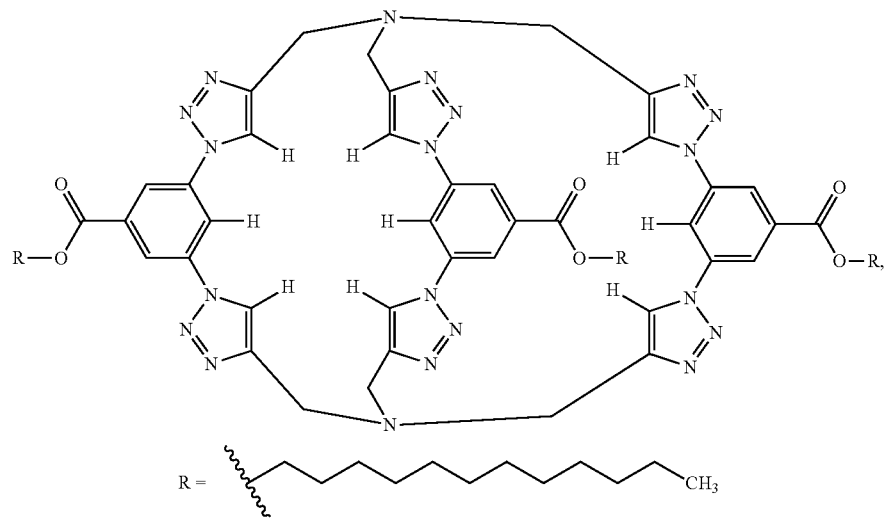

-continued
(P-Cage)
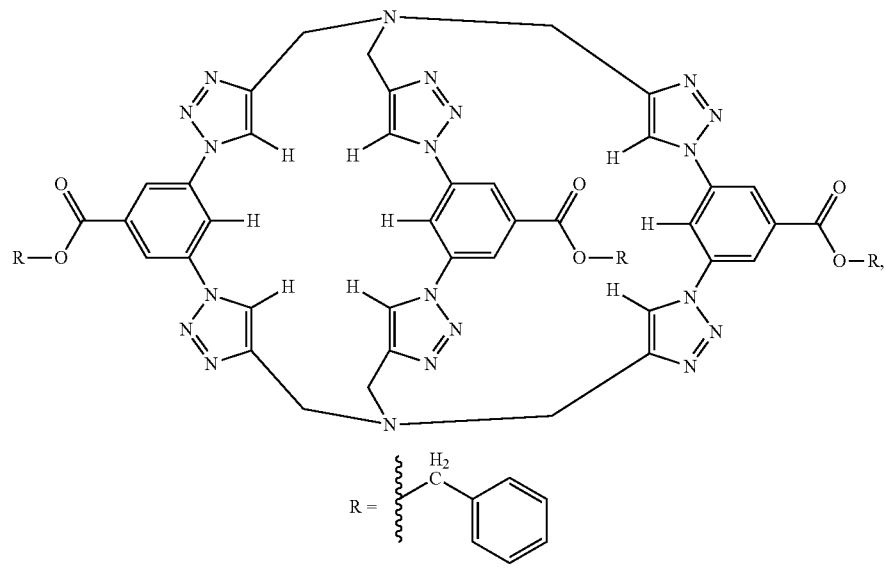
(A-Cage)
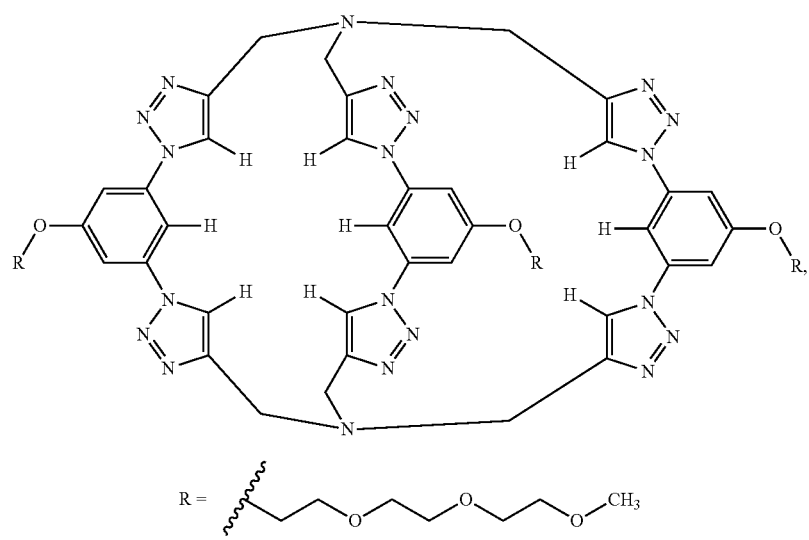
(D-Cage)
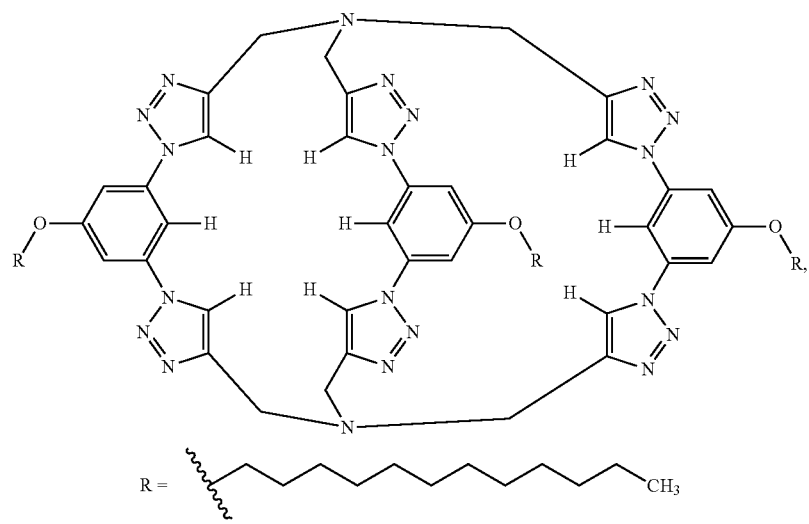

-continued (Z-Cage)

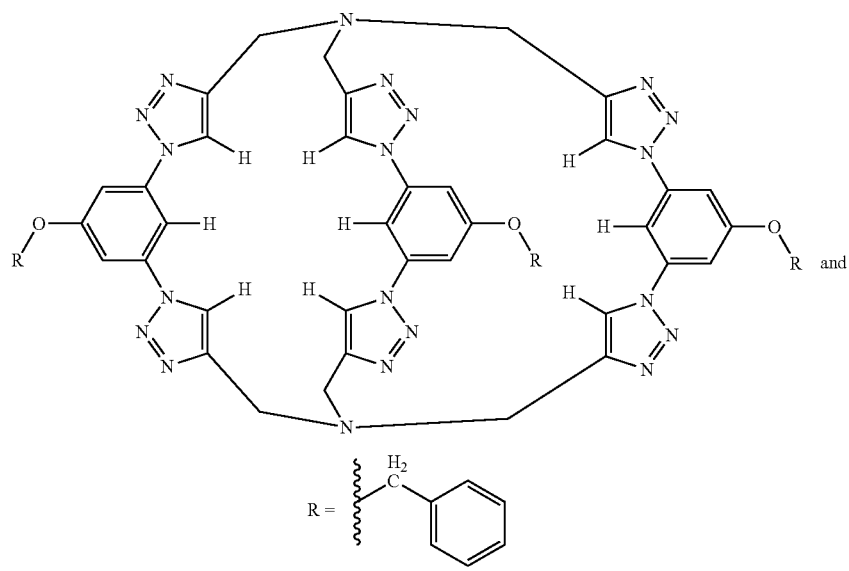

(T-cage-A₂B)

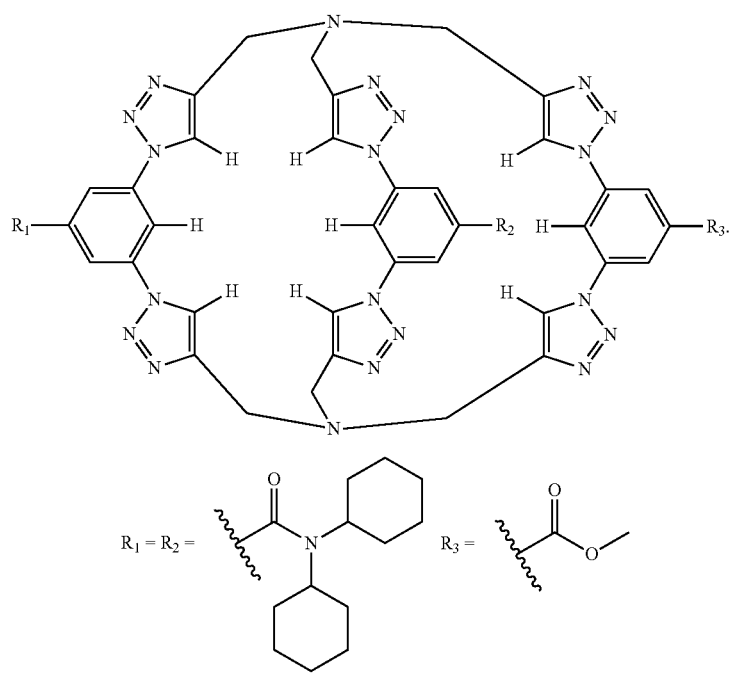

In a third respect, the coating includes a polymer, such as polymethyl methacrylate, polymethyl acrylate, acrylic polymers, latex, epoxy, and polyester. In a fourth respect, the coating includes a pigment. The pigment may include a colorant, such as a dye configured as one imparting a color. Such coatings can be useful as a paint.

EXAMPLES

Example 1. Synthesis of Triazolocage 1 and Triazolotripod 3

Syntheses of T-Cage and tiazolotripod 3 (NaAsc: sodium ascorbate; TBTA: tris[(1-benzyl-1H-1,2,3-triazol-4-yl)methyl]amine; TEACl: tetra-n-ethylammonium chloride) is presented below:

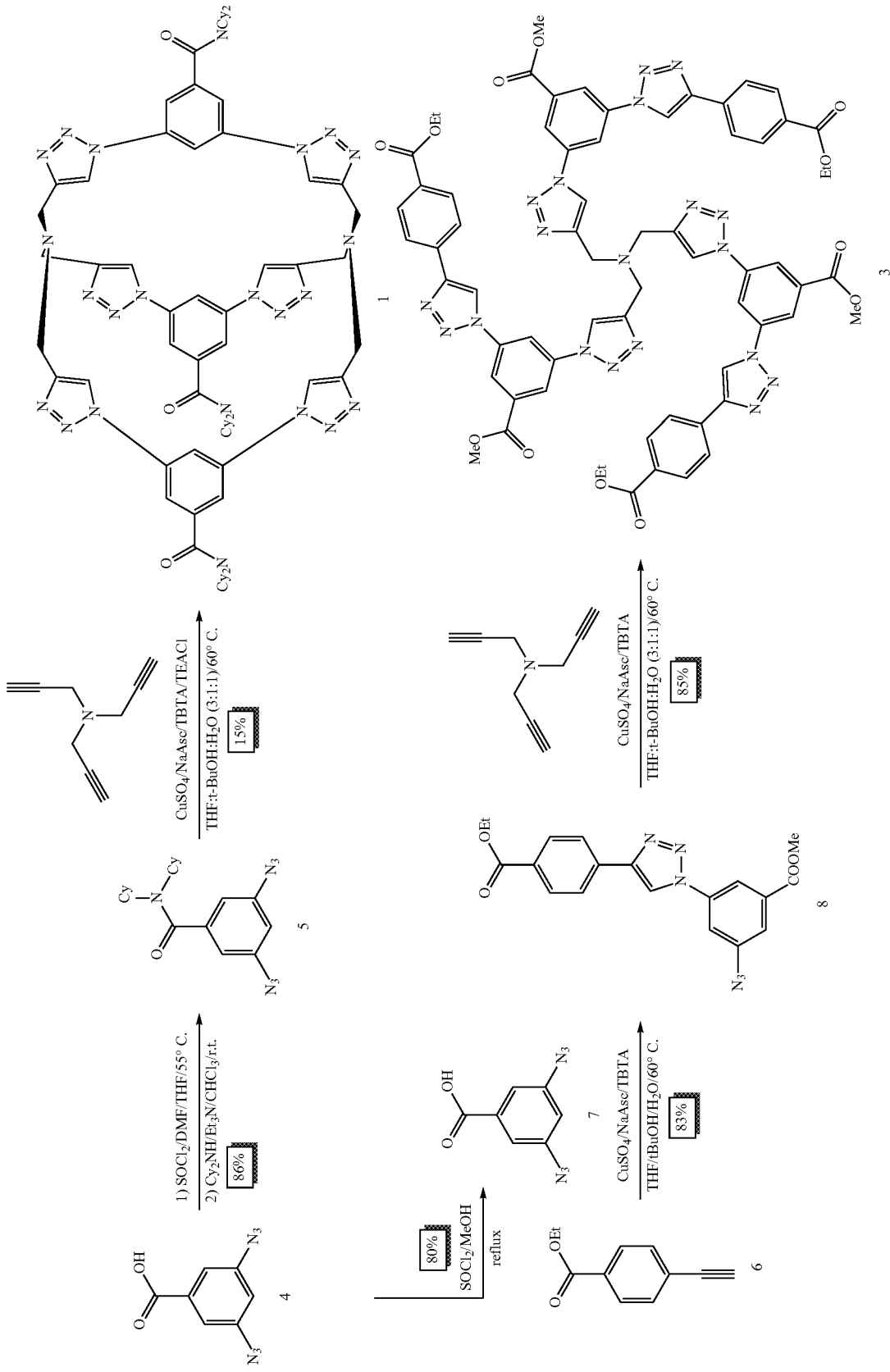

-continued
Cy =
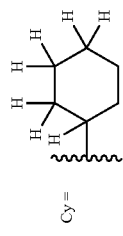

3,5-Diazido-N,N-dicyclohexylbenzamide (5)

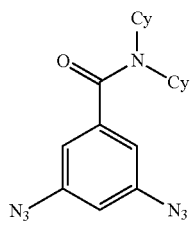

3,5-Diazido-benzoic acid (4, 10 g, 49 mmol) was dissolved in THF (100 mL), after which SOCl$_2$ (17.5 g, 147 mmol) and 3 drops of DMF were added at room temperature. The solution was heated to 55° C. for 10 h. Then the solution was cooled to room temperature, concentrated, and dried in vacuo. The resulting waxy oil was then dissolved in CHCl$_3$ (100 mL), to which dicyclohexylamine (17.8 g, 98 mmol) and triethylamine (50 mL) were added. The solution was stirred vigorously at room temperature overnight. The suspension was filtered over celite and concentrated in vacuo. The solid crude is purified by recrystallization from hot isopropanol to afford 5 (15.5 g, 42 mmol) as a yellow crystalline solid. Yield: 86%. $^1$H NMR (500 MHz, DMSO-d$_6$), δ=6.85 (t, J=2.0 Hz, 1H), 6.77 (d, J=2.0 Hz, 2H), 3.18 (tt, J=11.8, 3.7 Hz, 2H), 2.00 (br, 4H), 1.79-1.70 (m, 4H), 1.68-1.61 (m, 4H), 1.56 (d, J=10.4 Hz, 2H), 1.24-1.04 (m, 6H). $^{13}$C NMR (125 MHz, CDCl$_3$), δ=168.91, 142.35, 142.29, 112.86, 109.95, 58.42, 30.85, 26.23, 25.27. HR-CI-MS: C$_{19}$H$_{26}$N$_7$O (M+H)$^+$, Calculated: 368.2199; Found: 368.2191.

3,5-Diazidomethylbenzoate (7)

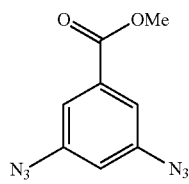

SOCl$_2$ (5.6 g, 47 mmol) was added slowly to MeOH (50 mL) under ice bath. The solution was stirred for 30 min, after which 3,5-diazido-benzoic acid (4, 6.4 g, 31 mmol) was added in one batch under room temperature. The suspension was then heated to reflux for 3 h. Then the solution was cooled to room temperature, concentrated, and dried in vacuo. The obtained waxy crude was purified by column chromatography (SiO$_2$, 1:1 hexanes:dichloromethane) to afford 7 (5.5 g, 38 mmol) as a pale yellow crystalline solid. Yield: 80%. $^1$H NMR (500 MHz, CDCl$_3$), δ=7.49 (d, J=2.1 Hz, 2H), 6.80 (t, J=2.1 Hz, 1H), 3.94 (s, 3H). $^{13}$C NMR (125 MHz, CDCl$_3$), (=165.35, 142.28, 133.24, 116.29, 113.86, 52.65. HR-CI-MS: C$_8$H$_7$N$_6$O$_2$ (M+H)$^+$, Calculated: 219.0630; Found: 219.0625.

Methyl 3-azido-5-(4-(4-(ethoxycarbonyl)phenyl)-1H-1,2,3-triazol-1-yl)benzoate (8)

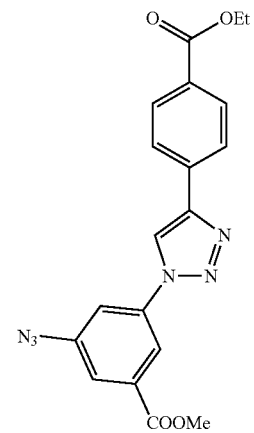 [SMILES: CCOC(=O)c1ccc(-c2cn(-c3cc(N=[N+]=[N-])cc(C(=O)OC)c3)nn2)cc1]

6 (0.15 g, 0.86 mmol), 7 (1.5 g, 6.9 mmol), and ligand TBTA (91.2 mg, 0.17 mmol) was dissolved in 3:3:1 THF:tBuOH:H$_2$O solvent mixture (860 mL). The solution was then heated to 60° C. and degassed under argon for 30 min, after which CuSO$_4$·5H$_2$O (43 mg, 0.17 mmol), and NaAsc (68 mg, 0.34 mmol) was added. The reaction mixture was stirred under argon for 2 h, then cooled to room temperature, and concentrated in vacuo. The resulting suspension was extracted with dichloromethane. The organic layer was separated, washed with brine, dried over Na$_2$SO$_4$, filtered over glass wool, and dried in vacuo. The obtained yellowish solid crude was purified by column chromatography (SiO$_2$, 20:1 to 4:1 dichloromethane:acetone) to afford 8 (0.28 g, 0.71 mmol) as a white solid. Yield: 83%. $^1$H NMR (500 MHz, CDCl$_3$), δ=8.35 (s, 1H), 8.15 (d, J=8.4 Hz, 2H), 8.14 (s, 1H), 7.99 (d, J=8.2 Hz, 2H), 7.82-7.77 (m, 1H), 7.78 (t, J=2.2 Hz, 1H), 4.41 (q, J=7.1 Hz, 2H), 4.00 (s, 3H), 1.43 (t, J=7.1 Hz, 3H). $^{13}$C NMR (125 MHz, CDCl$_3$), (=166.16, 164.92, 147.89, 142.81, 138.11, 133.89, 133.46, 130.51, 130.29, 125.67, 119.89, 118.23, 116.84, 115.15, 61.13, 52.90, 14.34. HR-CI-MS: C$_{19}$H$_{17}$N$_6$O$_4$ (M+H)$^+$, Calculated: 393.1306; Found: 393.1383.

Triazolotripod (3):

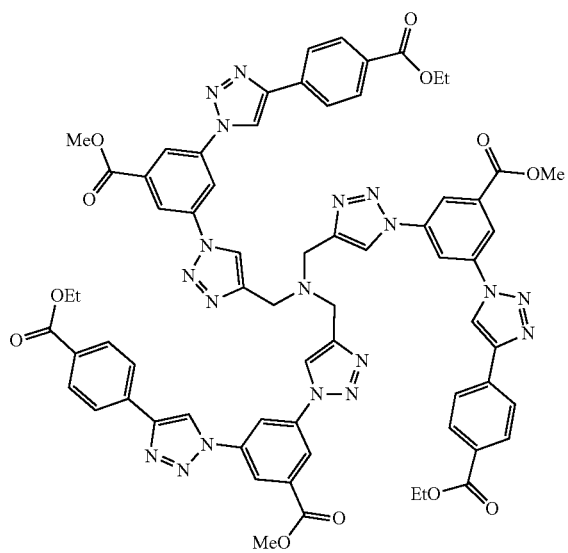 [SMILES: CCOC(=O)c1ccc(-c2cn(-c3cc(C(=O)OC)cc(-n4cc(CN(Cc5cn(-c6cc(C(=O)OC)cc(-n7cc(-c8ccc(C(=O)OCC)cc8)nn7)c6)nn5)Cc5cn(-c6cc(C(=O)OC)cc(-n7cc(-c8ccc(C(=O)OCC)cc8)nn7)c6)nn5)nn4)c3)nn2)cc1]

Tripropargylamine (22.2 mg, 0.17 mmol), 8 (0.2 g, 0.51 mmol), and ligand TBTA (17.9 mg, 0.039 mmol) was dissolved in 3:1:1 THF:tBuOH:H$_2$O solvent mixture (50 mL). The solution was then heated to 60° C. and degassed under argon for 30 min, after which CuSO$_4$·5H$_2$O (8.5 mg, 0.039 mmol), and NaAsc (13.4 mg, 0.068 mmol) was added. The reaction mixture was stirred under argon overnight, then cooled to room temperature, and concentrated in vacuo. The resulting suspension was extracted with dichloromethane. The organic layer was separated, washed with brine, dried over Na$_2$SO$_4$, filtered over glass wool, and dried in vacuo. The obtained yellowish solid crude was purified by column chromatography (SiO$_2$, dichloromethane to 50:1 dichloromethane:methanol) to afford 3 (0.19 g, 0.14 mmol) as a yellow solid. Yield: 85%. $^1$H NMR (500 MHz, CDCl$_3$), δ=8.51 (s, 3H), 8.48 (s, 3H), 8.45 (s, 3H), 8.34 (s, 6H), 8.00 (d, J=8.0 Hz, 6H), 7.87 (d, J=8.0 Hz, 6H), 4.34 (q, J=7.1 Hz, 6H), 3.99 (s, 6H), 3.93 (s, 9H), 1.38 (t, J=7.1 Hz, 9H). $^{13}$C NMR (125 MHz, CDCl$_3$), (=165.97, 164.34, 147.78, 145.69, 138.04, 137.82, 133.59, 133.46, 130.34, 130.10, 125.47, 121.93, 120.09, 119.93, 118.51, 115.29, 61.08, 52.99, 47.89, 14.26. HR-ESI-MS: C$_{66}$H$_{57}$N$_{19}$O$_{12}$Cl (M+Cl)$^-$, Calculated: 1342.4122; Found: 1342.4125.

Triazolocage (1) (T-Cage):

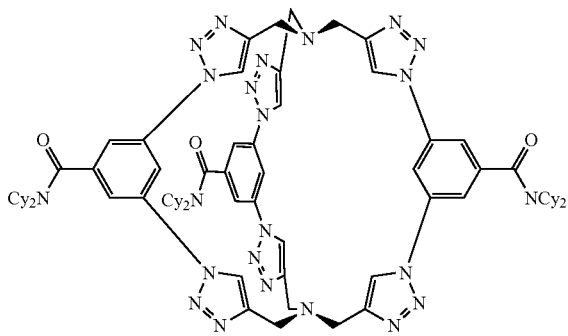

Ligand TBTA (95.3 mg, 0.18 mmol) and template TEACl (298 mg, 1.8 mmol) was dissolved in 3:1:1 THF:tBuOH:H$_2$O solvent mixture (850 mL). The solution was then heated to 60° C. and degassed under argon for 30 min, after which CuSO$_4$·5H$_2$O (45 mg, 0.18 mmol), and NaAsc (71.3 mg, 0.36 mmol) was added. Then tripropargylamine (235 mg, 1.8 mmol) and 5 (0.99 g, 2.7 mmol) were dissolved in a separate 3:1:1 THF:tBuOH:H$_2$O solvent mixture (50 mL), and injected slowly under argon to the solution containing ligand and template over 10 h. The reaction was continued for 3 days, the solution was then cooled to room temperature and concentrated in vacuo. The resulting suspension was extracted with DCM. The organic layer was separated, washed with brine, dried over Na$_2$SO$_4$, filtered, and concentrated in vacuo. The obtained yellowish solid crude was purified by column chromatography (SiO$_2$, 7% to 15% MeOH in dichloromethane) to afford 1·NaCl. NaCl was largely removed by dissolving the complex in dichloromethane and extensively washed with deionized water. The wet organic phase was concentrated and dried in vacuo overnight to afford 1 (0.19 g, 0.14 mmol, <0.4 wt % NaCl) as brown crystals. Yield: 30%. $^1$H NMR (600 MHz, CD$_2$Cl$_2$), δ=10.38 (s, 6H), 9.28 (s, 3H), 8.15 (s, 6H), 3.93 (s, 12H), 3.31 (s, 6H), 2.52 (br, 6H), 1.90-1.35 (m, 36H), 1.26 (br, 12H), 0.92 (br, 6H). $^{13}$C NMR (150 MHz, CDCl$_3$), δ=169.07, 148.79, 141.16, 138.41, 122.85, 115.35, 109.96, 60.57, 56.56, 50.16, 30.91, 29.66, 26.45, 25.38. HR-ESI-MS: C$_{75}$H$_{93}$N$_{23}$O$_3$Cl (M+Cl)$^-$, Calculated: 1398.7520; Found: 1398.7520.

E-Cage:

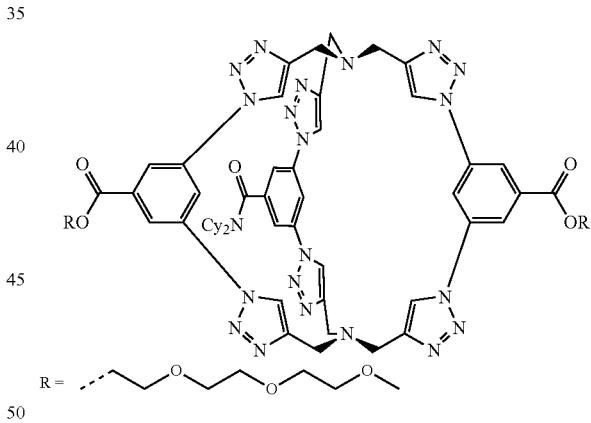

1,8-Diazabicyclo[5.4.0]undec-7-ene (DBU, 400 μL, 2.4 mmol) and template TBACl (222 mg, 0.8 mmol) was dissolved in 1:1 toluene:acetonitrile solvent mixture (800 mL). The solution was then heated to 60° C. and degassed under argon for 30 min, after which CuI (46 mg, 0.24 mmol) was added. Then tripropargylamine (105 mg, 0.8 mmol) and ethylene glycol-functionalized diazide (0.42 g, 1.2 mmol) were dissolved in a separate 1:1 toluene:acetonitrile solvent mixture (50 mL), and injected slowly under argon to the solution containing catalyst and template over 11 h. The reaction was stirred for 3 days. The solution was then cooled to room temperature and concentrated in vacuo. The resulting waxy crude was loaded onto a silica column and eluted with CH$_2$Cl$_2$:MeOH:Et$_3$N mixture (90:10:1) to afford the E-Cage as a NaCl complex.

Examples of Additional Cage Syntheses Reagents

The preparation of the R-substituted bisazide compound, reagent 1, follows general literature procedures. Typically, a 1,3,5-substituted benzene is selected as a starting material. The 1 and 3 positions are suitable functional groups (X) for conversion into azides, which could often be, but not limited to, bromo, iodo, and amino groups. The substituent at 5 position is a suitable functional group (Y) for substitution, such as, a phenolic hydroxyl group and a benzoic acid.

Reagent 1 can be made one of two ways: The first involves replacement of a halogen, e.g., bromo and iodo, with an azido group when Y is a hydroxyl group. The second involves converting an amino group into an azido group when Y is a benzoic acid.

The method of replacing halogens involves reaction between the dihalide and sodium azide, with appropriate copper catalyst, ligand, and solvent combinations. This 1,3-diazido phenol is then transformed into reagent 1 by substitution at the hydroxyl functional group. The substitution involves reaction of the hydroxyl group with an appropriate organohalide (e.g., dodecyl and benzyl) or tosylated ethylene glycol monomethyl ether under basic conditions.

When starting with amino groups, the conversion involves two steps in one pot. First, a diazonium intermediate is formed by reaction between diamino benzoic acid with appropriate nitrite (e.g., sodium nitrite and amyl nitrite). The resulting intermediate is used without isolation by addition of an azide source (e.g., sodium azide and trimethylsilyl azide). The resulting 1,3-diazido benzoic acid is then transformed into reagent 1 by substitution at the carboxylic acid functional group. The substitution involves converting the carboxylic acid group into acyl halides using more reactive halide donors (e.g., thionyl chloride and oxalyl chloride). The acyl halides are then subject to appropriate nucleophiles (e.g., organoamines and organoalcohols) under basic conditions.

The synthesis of the other Cage compounds of Formula (I) were made following the procedure outlined for T-Cage.

Example 2. Synthesis of Intermediate Macrocycle MC1-2 Using RXN 5

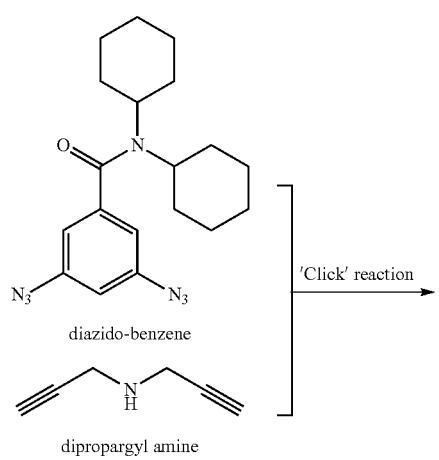

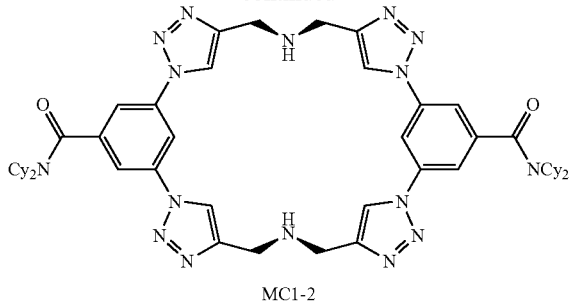

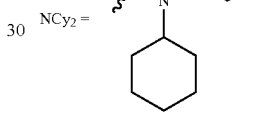

MC1-2: CuI (31 mg, 0.16 mmol), 1,8-diazabicyclo[5.4.0]undec-7-ene (DBU, 830 mg, 5.74 mmol), and tetraethylammonium chloride (TEACl, 4.5 g, 26.9 mmol) as template was suspended in 300 mL toluene with a three-necked flask. A solution of diazido-benzene (200 mg, 0.55 mmol) and dipropargyl amine (50 mg, 0.55 mmol) in toluene (50 mL) was prepared in an addition funnel. The reaction mixture was heated to 60° C. and degassed under argon for 30 min, after which the solution of 3,5-diazido-N,N-dicyclohexyl-benzamide and dipropargylamine was added into the reaction dropwise over 10 hours. After addition, the reaction was stirred for another 16 hours at 60° C. before cooling to room temperature. The solvent was concentrated under reduced pressure, and the crude was purified by column chromatography (SiO$_2$, 10% to 20% MeOH in dichloromethane) to afford the product as a yellowish solid (30%). $^1$H NMR (Complex with excess TEACl, 400 MHz, CD$_2$Cl$_2$): δ=10.23 (s, 4H, triazole CH), 9.24 (s, 2H, aryl CH), 8.13 (s, 4H, aryl CH), 4.10 (s, 8H, NCH$_2$), 3.41 (TEA-CH$_2$), 2.55 (m, 4H, NCH), 1.35-1.32 (m, CH$_2$ & CH$_3$). MS (ESI) m/z: calcd. for C$_{50}$H$_{64}$N$_{16}$O$_2$ at M$^+$: 921.2; found: 921.1.

Example 3. Synthesis of Intermediate Macrocycle MC2-2 Using RXN 3

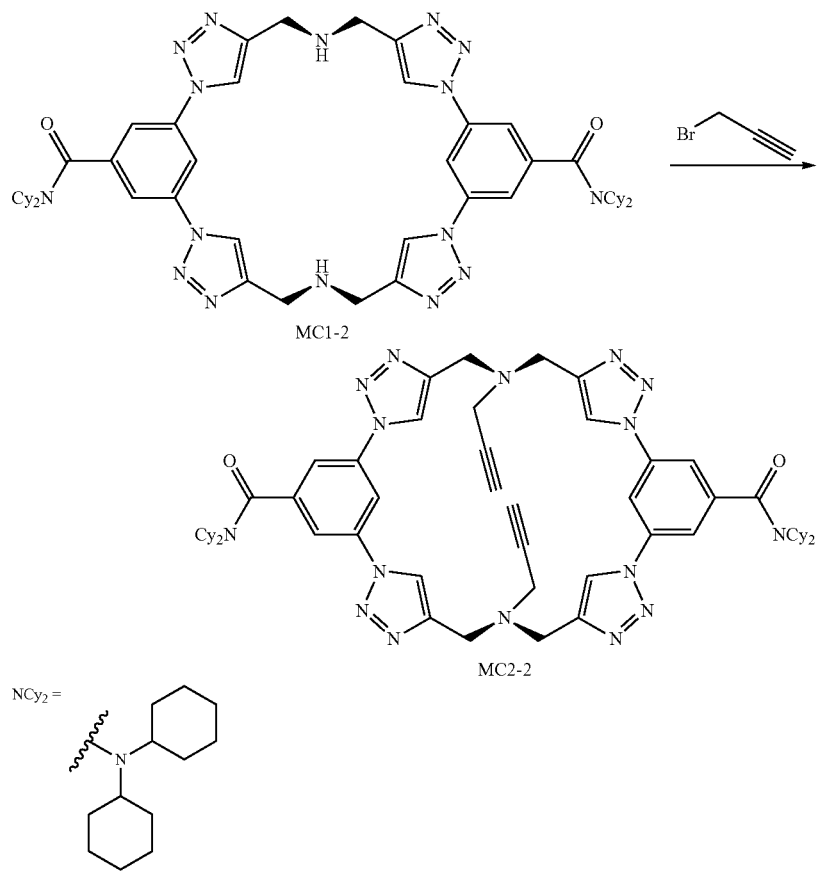

Preparation of macrocycle, MC2-2: Macrocycle MC1-2 (35 mg, 0.038 mmol) was dissolved in acetonitrile (10 mL) and tetrahydrofuran (10 mL) under argon, KOH (20 mg, 0.36 mmol) was added into the reaction. Then the mixture was stirred at room temperature for 30 minutes before propargyl bromide (28 mg, 0.24 mmol) was added. The reaction was heated to 80° C. and stirred over night before cooling to room temperature. The reaction mixture was filtered on celite to remove insoluble salts, and the filtrate concentrated under reduced pressure. The crude was purified by column chromatography (SiO$_2$, 10% methanol in dichloromethane) to afford a brown solid, MC2-2. MS (ESI) m/z: calcd. for $C_{56}H_{68}ClN_{16}O_2$ at [M+Cl]$^-$: 1031.5; found: 1031.3.

Example 4. Synthesis of T-cage-A$_2$B Using RXN 4

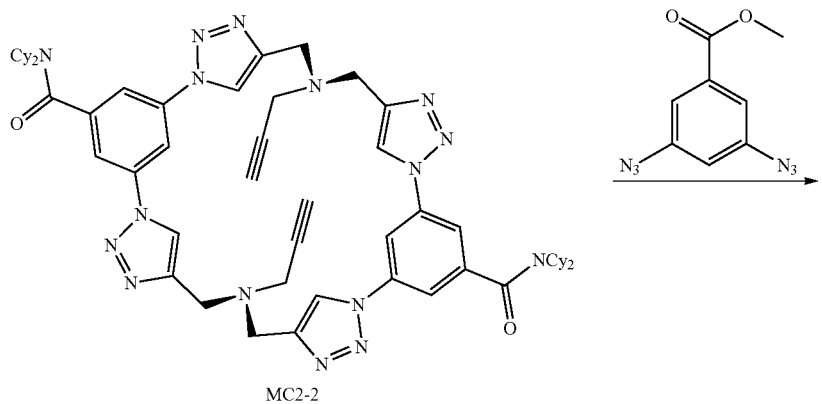

115

-continued

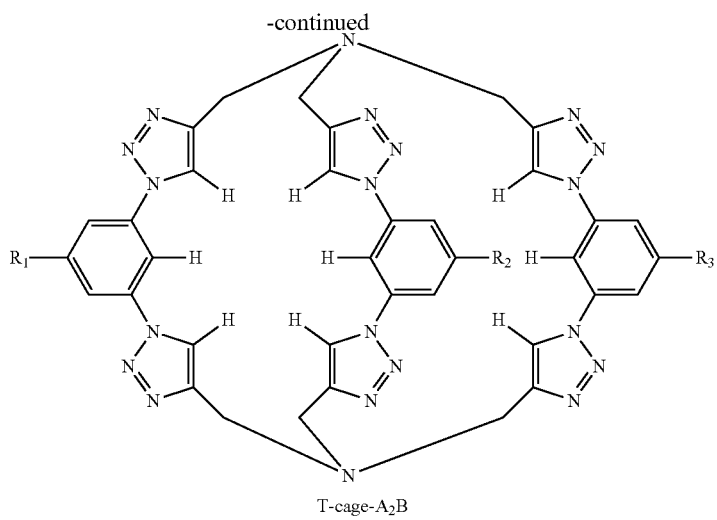
T-cage-A₂B

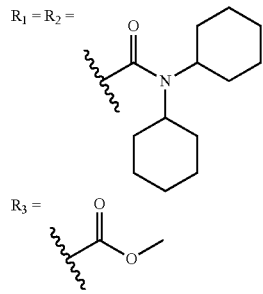

Preparation of T-cage-A₂B by click chemistry: CuI (5.7 mg, 0.03 mmol), DBU (13.7 mg, 0.09 mmol), tetraethylammonium chloride (50 mg, 0.30 mmol), methyl 3,5-diazidobenzoate (6.6 mg, 0.03 mmol) and MC2-2 (30 mg, 0.03 mmol) were dissolved in toluene (degassed, 350 mL) at room temperature. The reaction mixture was heated to 50° C. and the reaction was stirred overnight before cooling to room temperature. The solvent concentrated under reduced pressure, and the product of T-cage-A₂B was confirmed by mass spectroscopy. MS (ESI) m/z: calcd. for $C_{64}H_{74}ClN_{22}O_4$ at $[M+Cl]^-$: 1249.6; found: 1249.3.

Example 5. Synthesis of T-Cage-A₂B Using RXN 6

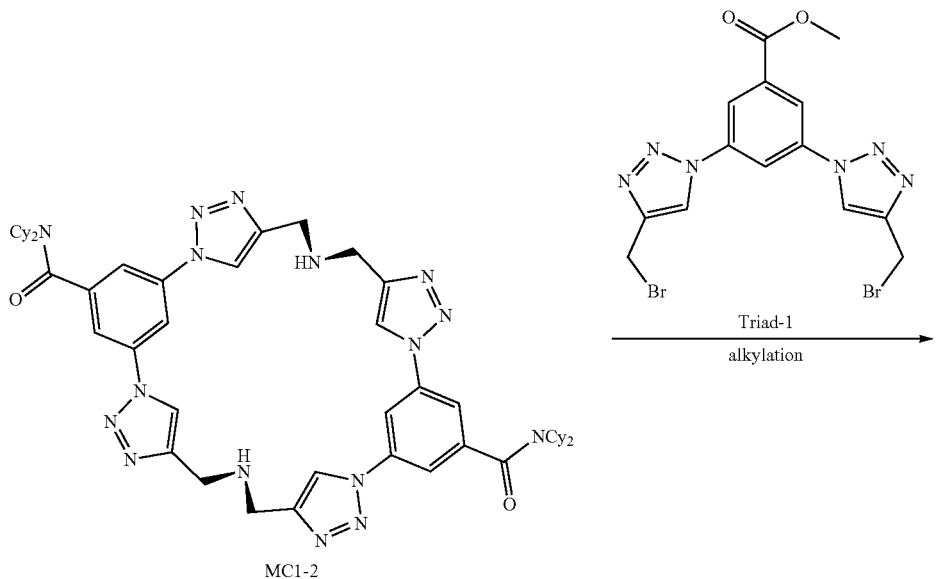

-continued

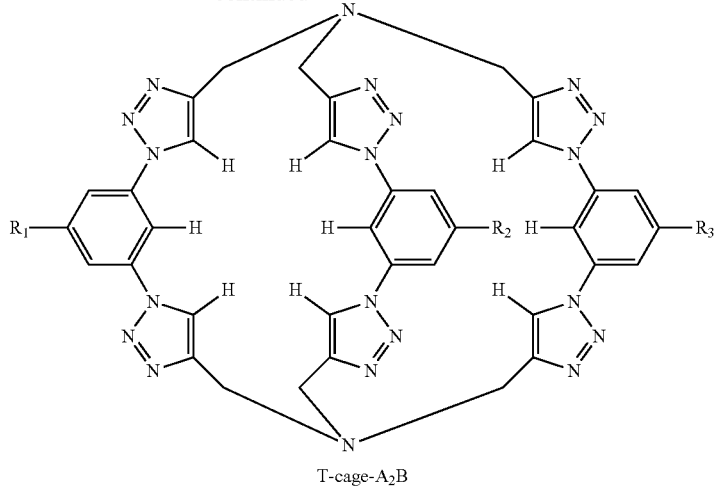
T-cage-A$_2$B $R_1 = R_2 =$
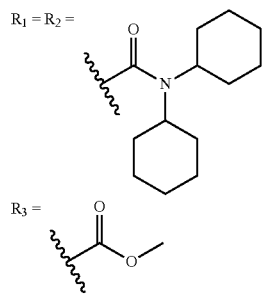

$R_3 =$

Preparation of T-cage-A$_2$B by alkylation: KOH (3.0 equiv.) is suspended in a large volume of dry acetonitrile (large volume), and the solution heat to 60° C. A solution of MC1-2 (1.0 equiv.) and dibromomethylene triad (Triad-1, 1.0 equiv.) in acetonitrile would be added into the KOH solution slowly over 10 hours. The reaction mixture was further stirred for another 24 hours and monitored by TLC until all the reactants are fully consumed. The reaction mixture would be filtered to remove insoluble salts, and the filtrate concentrate under reduced pressure. The crude material would be purified by column chromatography (SiO$_2$, methanol and dichloromethane) to afford the product, T-cage-A$_2$B.

Example 6. One-Pot Synthetic Strategy of Intermediate Macrocycles

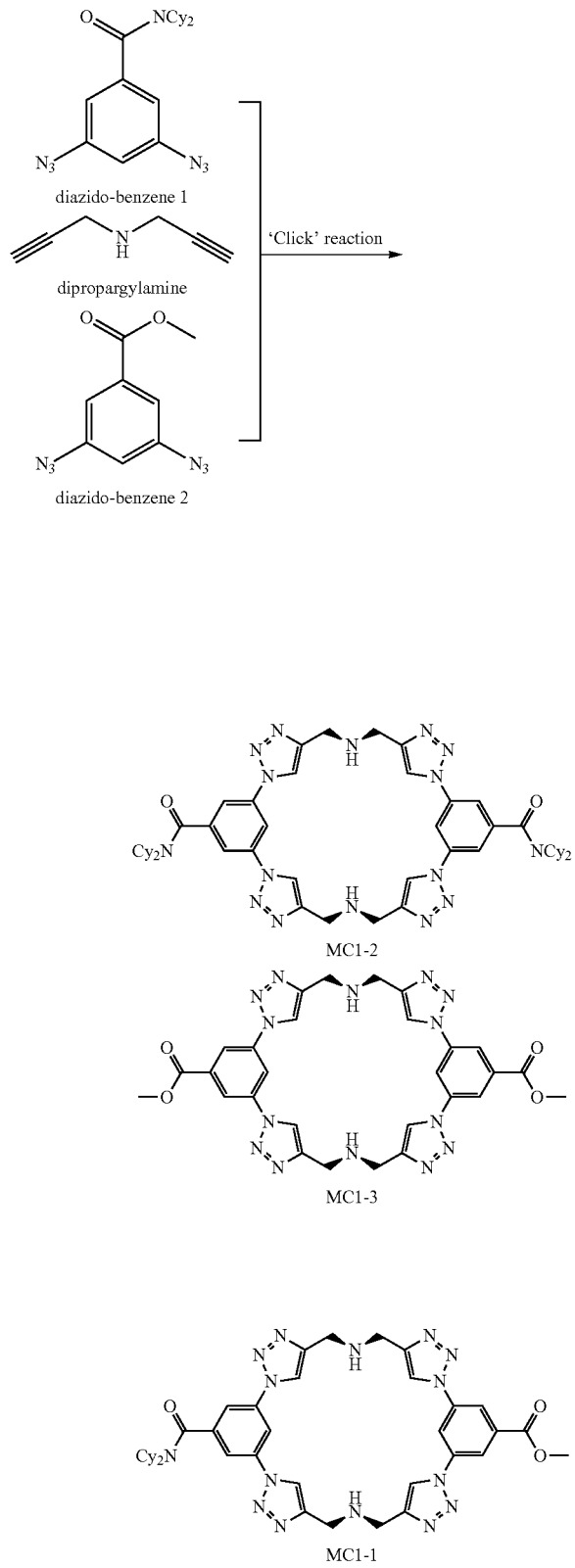

One-pot preparation of MC1-2, MC1-3, and MC1-4: CuI (0.5 equiv.), 1,8-diazabicyclo[5.4.0]undec-7-ene (5.0 equiv.), and tetraethylammonium chloride (50 equiv.) as template is suspended in a large volume of toluene with a three-necked flask. A solution of dipropargylamine (2.0 equiv), diazidobenzene building block diazido-benzene 1 (1.0 equiv.) and diazido-benzene 2 (1.0 equiv.) in toluene are prepared in an addition funnel. The reaction mixture is heated to 60° C. and is degassed under argon for 30 min, after which the solution in addition funnel is added into the reaction dropwise over 10 hours. After addition, the reaction is stirred for another 24 hours at 60° C. before cooling to room temperature. The solvents are concentrated under reduced pressure, and the crude material would be purified by column chromatography ($SiO_2$) to afford the different macrocycle products, MC1-2, MC1-3, and MC1-4.

Example 7. Step-Wise Synthetic Strategy of Nonsymmetric Macrocycle with RXN 1

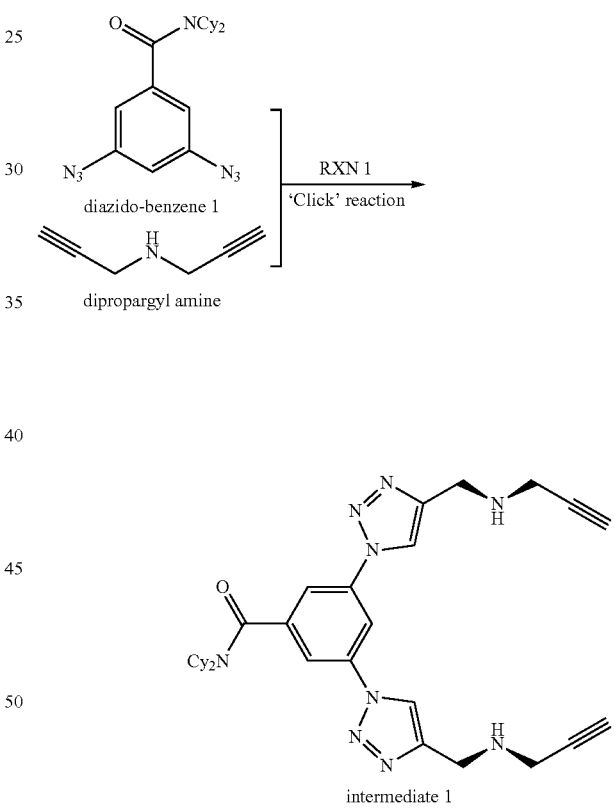

intermediate-1: Dipropargyl amine (253 mg, 2.72 mmol), CuI (52 mg, 0.27 mmol), and DBU (413 mg, 2.71 mmol) were dissolved in toluene (250 mL). The reaction is heated to 60° C. and degassed for 30 mins before diazido-benzene 1 (200 mg, 0.54 mmol) was added into the solution slowly. After addition, the reaction was stirred at 60° C. for 24 hours before cooling to room temperature. Subsequently, the solvents were concentrated under reduced pressure, the product, intermediate 1 was confirmed by mass spectroscopy. MS (ESI) m/z: calcd. for $C_{31}H_{40}N_9O$ at $[M+H]^+$: 554.6; found: 554.2.

Example 8. Step-Wise Synthetic Strategy of Nonsymmetric Macrocycle with RXN 1

Example 9. Step-Wise Synthetic Strategy of Nonsymmetric Macrocycle with RXN 2

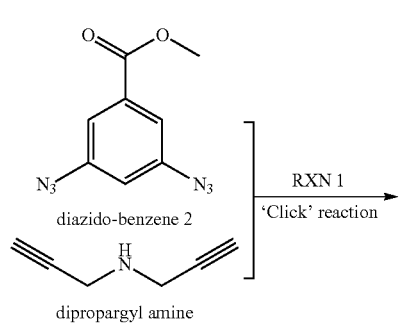
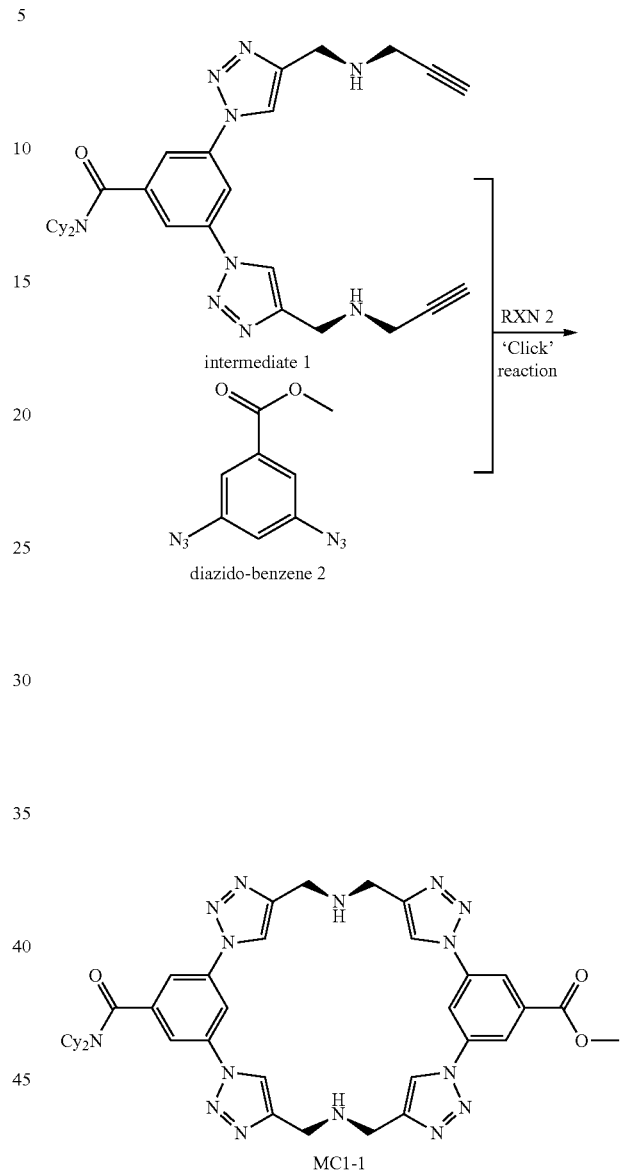

intermediate 2: Dipropargyl amine (0.71 mL, 6.90 mmol), CuI (131 mg, 0.69 mmol), and DBU (0.31 mL, 2.07 mmol) was dissolved in toluene. The reaction was heated to 60° C. and degassed for 30 mins before diazido-benzene 2 (300 mg, 1.38 mmol) was added into the solution slowly dropwise over 3 hours. After addition, the reaction was stirred at 60° C. for 24 hours before cooling to room temperature. Subsequently, the solvents was concentrated under reduced pressure and the crude materials purified by column chromatography (SiO$_2$, 1% to 5% MeOH in dichloromethane) to afford the product, intermediate 2 as brown solid (37%). $^1$H NMR (400 MHz, CD$_2$Cl$_2$): δ=8.52 (t, 1H, aryl CH), 8.42 (d, 2H, aryl CH), 8.14 (s, 2H, triazole CH), 4.09 (s, 4H, NCH$_2$), 4.00 (s, 3H, OCH$_3$), 3.51 (s, 4H, NCH$_2$), 2.32 (t, 2H, CCH). MS (ESI) m/z: calcd. for C$_{20}$H$_{21}$N$_8$O$_2$ at [M+H]$^+$: 405.2; found: 405.1.

MC1-4: CuI (24 mg, 0.13 mmol), DBU (0.06 mL, 0.38 mmol), and tetraethylammonium chloride (414 mg, 2.50 mmol) as template were dissolved in large volume of toluene (400 mL) with a three-necked flask. A solution of diazido-benzene 1 (92 mg, 0.25 mmol) and intermediate 2 (100 mg, 0.25 mmol) was prepared in an addition funnel. The reaction mixture was heated to 60° C. and degassed under argon for 30 min, after which the solution in the addition funnel was added into the reaction dropwise over 4 hours. After addition, the reaction was stirred for another 24 hours at 60° C. before cooling to room temperature. The solvent was concentrated under reduced pressure, and the crude material was purified by column chromatography (SiO$_2$, 5% to 20% MeOH in dichloromethane) to afford the product, MC1-4 as yellowish white solid. MS (ESI) m/z: calcd. for C$_{39}$H$_{45}$ClN$_{15}$O$_3$ at [M+Cl]$^-$: 806.4; found: 806.3.

Example 10. Step-Wise Synthetic Strategy of Nonsymmetric Macrocycle with RXN 3

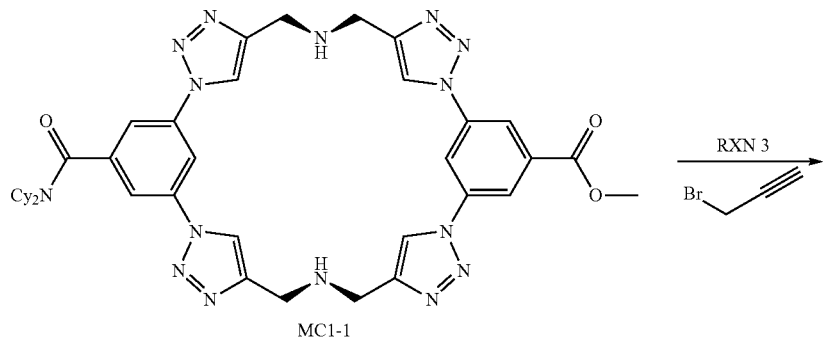

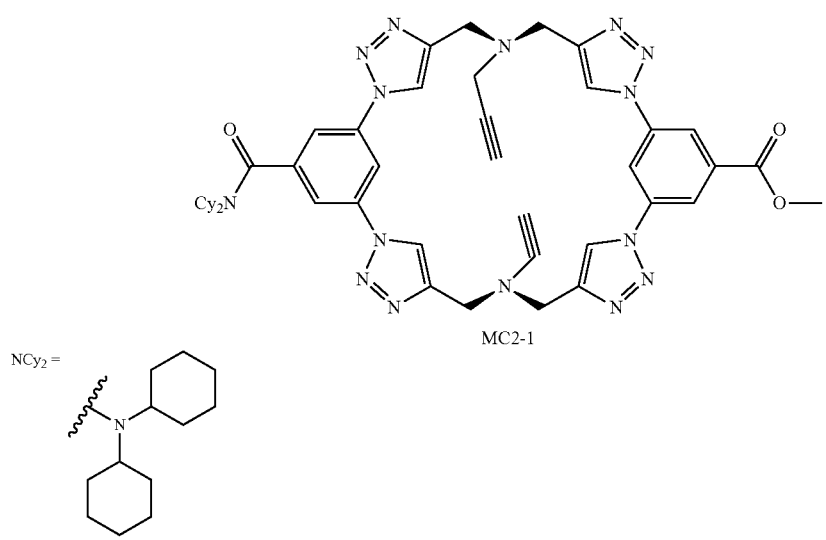

Preparation of macrocycle, MC2-1: Macrocycle MC1-4 (1.0 equiv.) is dissolved in acetonitrile, KOH (2.5 equiv.) is added into the reaction. Then the mixture would be stirred at room temperature for 30 minutes before propargyl bromide (2.5 equiv.) is added. The reaction would be heated to 80° C. and stirred for 24 hours before cooling to room temperature. The reaction mixture would be filtered to remove insoluble salts, and the filtrate concentrate under reduced pressure. The crude would be purified by column chromatography ($SiO_2$, methanol and dichloromethane) to afford the product, MC2-1.

Example 11. Step-Wise Synthetic Strategy of Nonsymmetric Macrocycle with RXN 4

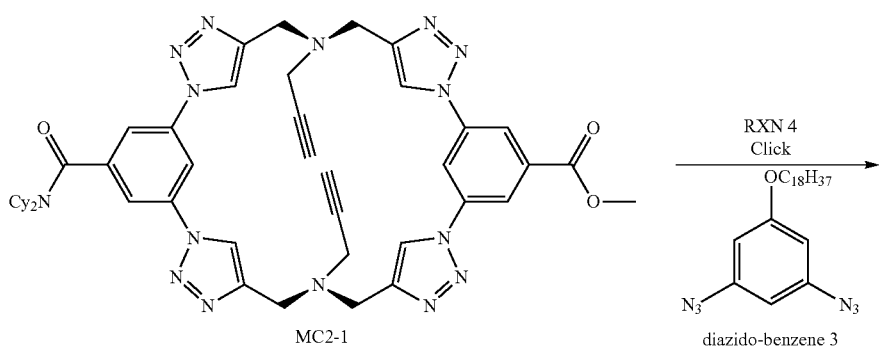

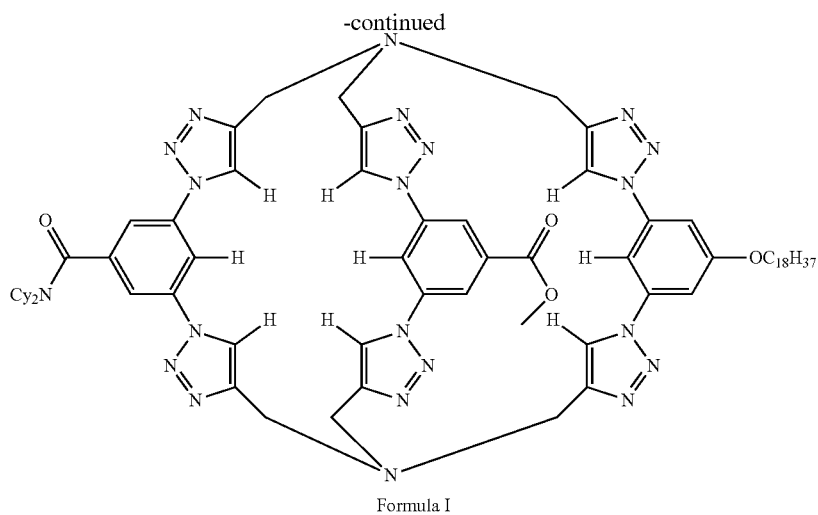

Formula I

MC2-1 is prepared as described previously herein. CuI (0.3 equiv.) and DBU (5.0 equiv.) are suspended in a large volume of toluene at room temperature. The reaction mixture was heated to 60° C. and degassed under argon for 30 min, a solution of diazido-benzene 3 (1.0 equiv.) and MC2-1 (1.0 equiv.) in toluene would be added into the reaction slowly over 10 hours. After addition, the reaction would be stirred for another 24 hours at 60° C. before cooling to room temperature. The solvent would be concentrated under reduced pressure, and the crude material would be purified by column chromatography (SiO$_2$, MeOH in dichloromethane) to afford the product, Formula (I).

Example 12. Step-Wise Synthetic Strategy of Formula (III): HHF-T-Cage with RXN 4

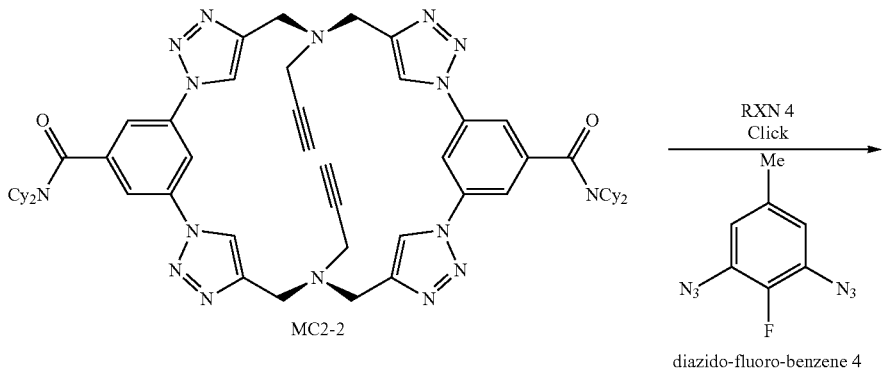

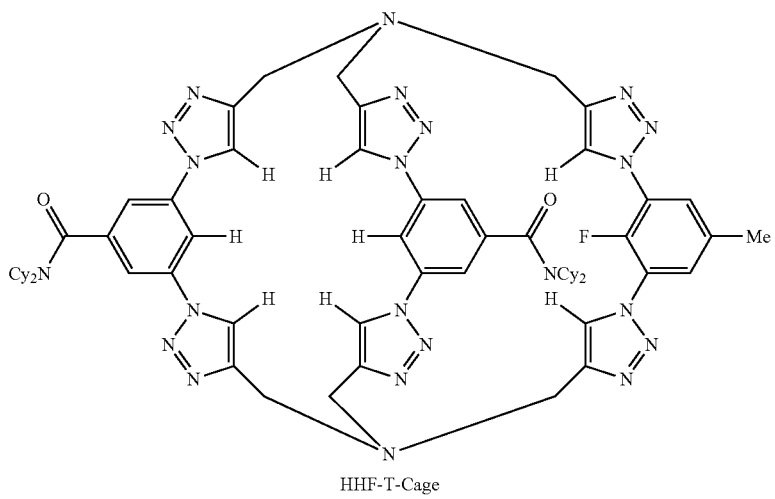

HHF-T-Cage

Preparation of HHF-T-cage by click chemistry: MC2-2 is prepared as described previously herein. CuI (0.3 equiv.) and DBU (5.0 equiv.) are suspended in a large volume of toluene at room temperature. The reaction mixture was heated to 60° C. and degassed under argon for 30 min, a solution of diazido-fluoro-benzene 4 (1.0 equiv.) and MC2-2 (1.0 equiv.) in toluene would be added into the reaction slowly over 10 hours. After addition, the reaction would be stirred for another 24 hours at 60° C. before cooling to room temperature. The solvent would be concentrated under reduced pressure, and the crude material would be purified by column chromatography ($SiO_2$, MeOH in dichloromethane) to afford the product, HHF-T-cage.

Example 13. Step-wise Synthetic Strategy of Formula (III): HHN-T-Cage with RXN 4

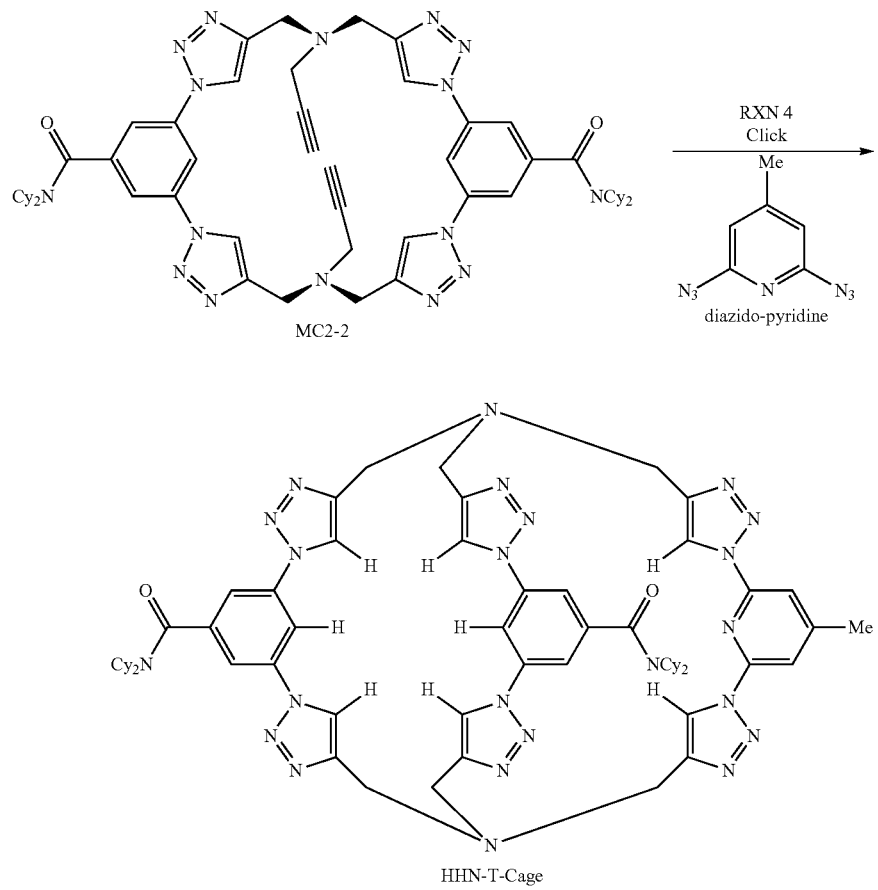

Preparation of HIHN-T-cage by click chemistry: MC2-2 is prepared as described previously herein. CuI (0.3 equiv.) and DBU (5.0 equiv.) are suspended in a large volume of toluene at room temperature. The reaction mixture was heated to 60° C. and degassed under argon for 30 min, a solution of diazido-pyridine (1.0 equiv.) and MC2-2 (1.0 equiv.) in toluene would be added into the reaction slowly over 10 hours. After addition, the reaction would be stirred for another 24 hours at 60° C. before cooling to room temperature. The solvent would be concentrated under reduced pressure, and the crude material would be purified by column chromatography ($SiO_2$, MeOH in dichloromethane) to afford the product, HHN-T-cage.

Example 14. Step-Wise Synthetic Strategy of Formula (IV): Monoalkyl-T-Cage with RXN 4

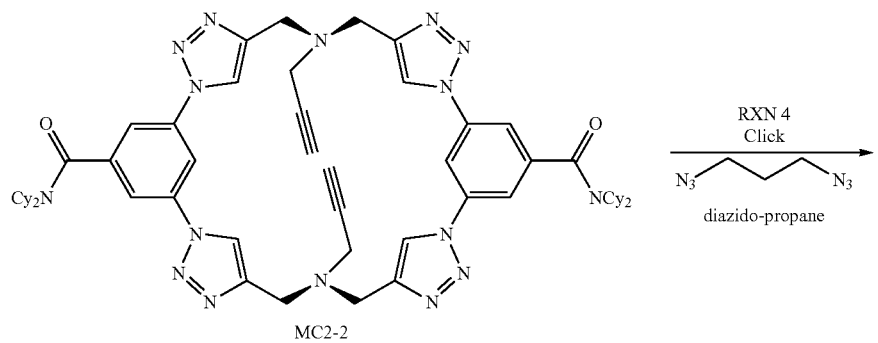

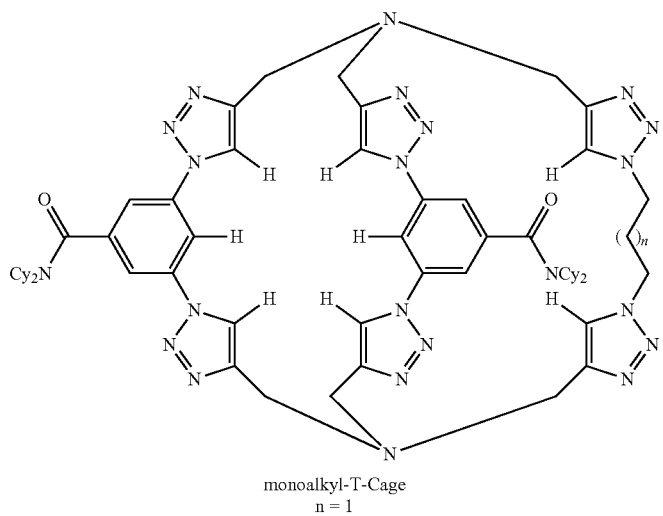

monoalkyl-T-Cage
n = 1

Preparation of monoalkyl-T-cage by click chemistry: MC2-2 is prepared as described previously herein. CuI (0.3 equiv.) and DBU (5.0 equiv.) are suspended in a large volume of toluene at room temperature. The reaction mixture was heated to 60° C. and degassed under argon for 30 min, a solution of diazido-propane (1.0 equiv.) and MC2-2 (1.0 equiv.) in toluene would be added into the reaction slowly over 10 hours. After addition, the reaction would be stirred for another 24 hours at 60° C. before cooling to room temperature. The solvent would be concentrated under reduced pressure, and the crude material would be purified by column chromatography (SiO$_2$, MeOH in dichloromethane) to afford the product, monoalkyl-T-cage.

Example 15. Step-Wise Synthetic Strategy of Formula (V): Biphenyl-T-Cage with RXN 4

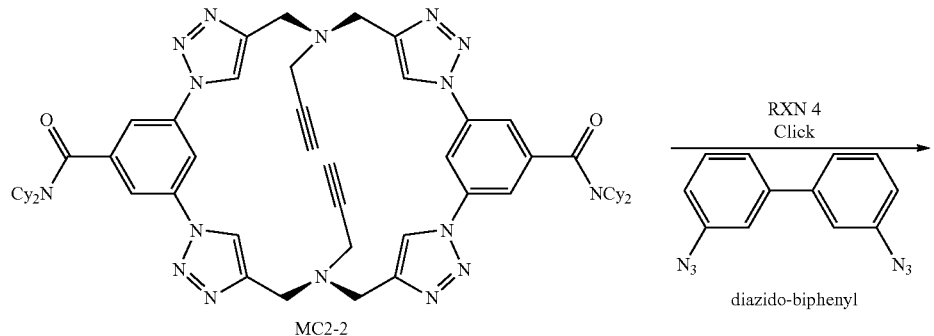

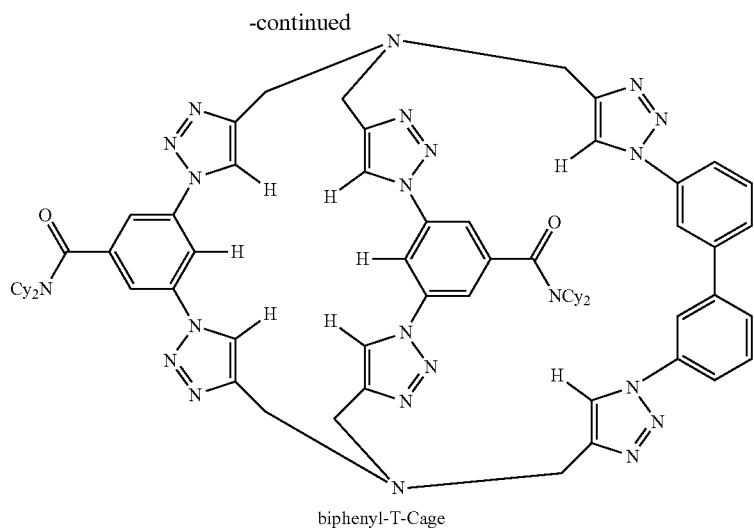

biphenyl-T-Cage

Preparation of biphenyl-T-cage by click chemistry: MC2-2 is prepared as described previously herein. CuI (0.3 equiv.) and DBU (5.0 equiv.) are suspended in a large volume of toluene at room temperature. The reaction mixture was heated to 60° C. and degassed under argon for 30 min, a solution of diazido-biphenyl (1.0 equiv.) and MC2-2 (1.0 equiv.) in toluene would be added into the reaction slowly over 10 hours. After addition, the reaction would be stirred for another 24 hours at 60° C. before cooling to room temperature. The solvent would be concentrated under reduced pressure, and the crude material would be purified by column chromatography ($SiO_2$, MeOH in dichloromethane) to afford the product, biphenyl-T-cage.

Example 16. Step-Wise Synthetic Strategy of Formula (VI): Carbazole-T-Cage with RXN 4

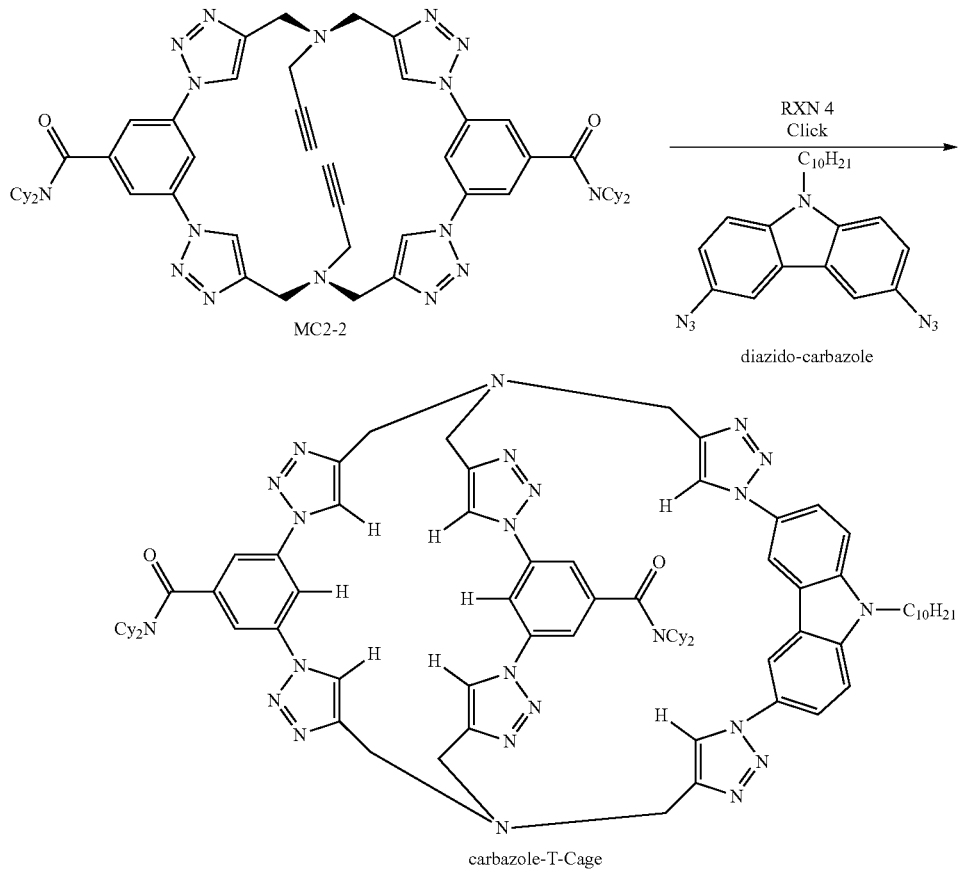

Preparation of carbazole-T-cage by click chemistry: MC2-2 is prepared as described previously herein. CuI (0.3 equiv.) and DBU (5.0 equiv.) are suspended in a large volume of toluene at room temperature. The reaction mixture was heated to 60° C. and degassed under argon for 30 mi, a solution of diazido-carbazole (1.0 equiv.) and MC2-2 (1.0 equiv.) in toluene would be added into the reaction slowly over 10 hours. After addition, the reaction would be stirred for another 24 hours at 60° C. before cooling to room temperature. The solvent would be concentrated under reduced pressure, and the crude material would be purified by column chromatography (SiO$_2$, MeOH in dichloromethane) to afford the product, carbazole-T-cage.

Example 17. Step-wise Synthetic Strategy of Formula (VII): Monoglycol-T-Cage with RXN 6

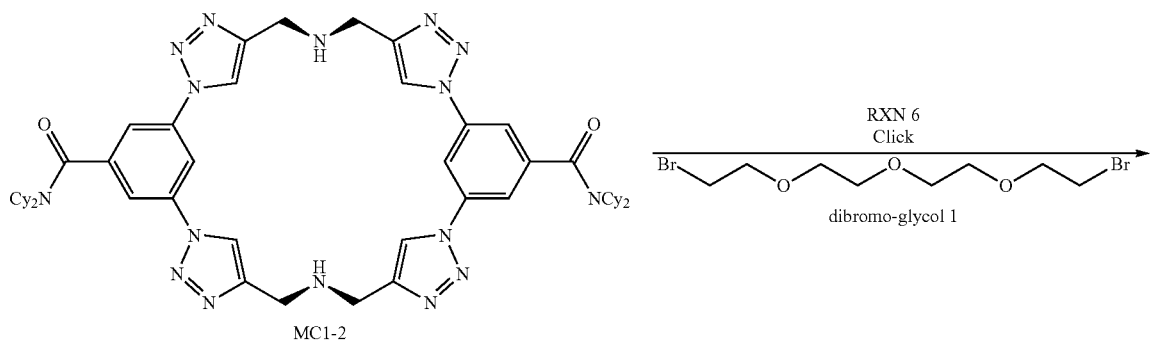

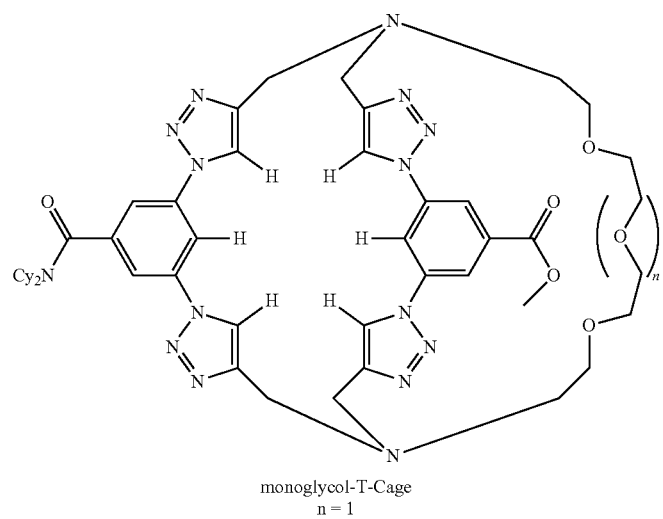

Preparation of monoglycol-T-cage by alkylation: MC1-2 is prepared as described previously herein. KOH (3.0 equiv.) are suspended in mixture of tetrahydrofuran and acetonitrile at room temperature. The reaction mixture was heated to 80° C., a solution of MC1-2 (1.0 equiv.) and dibromo-glycol 1 (1.0 equiv.) in tetrahydrofuran is added into the reaction slowly over 10 hours. After addition, the reaction would be stirred for another 24 hours at 80° C. before cooling to room temperature. The solvents would be filtrated over celite to remove inorganic salts, and the filtrate is concentrated under reduced pressure. The crude material would be purified by column chromatography ($SiO_2$, MeOH in dichloromethane) to afford the product, monoglycol-T-cage.

Example 18. Single Crystal X-Ray Structure of T-Cage·NaCl

A colorless crystal (approximate dimensions 0.382× 0.159×0.086 $mm^3$) was placed onto the tip of MiTeGen and mounted on an Apex Kappa Duo diffractometer and measured at 150 K. The data collection was carried out using Mo Kα radiation (graphite monochromator) with a frame time of 180 seconds and a detector distance of 5.0 cm. A randomly oriented region of reciprocal space was surveyed to achieve complete data with a redundancy of 4. Sections of frames were collected with 0.50° steps in ω and φ scans. Data to a resolution of 0.84 Å were considered in the reduction. Final cell constants were calculated from the xyz centroids of 9868 strong reflections from the actual data collection after integration (SAINT). The intensity data were corrected for absorption (SADABS) (Table 1).

direct-methods solution was calculated, which provided most non-hydrogen atoms from the E-map. Full-matrix least squares/difference Fourier cycles were performed, which located the remaining non-hydrogen atoms.

The disorders exhibited on chloroform solvent molecules and sodium cations were successfully modeled. Chloroform molecules were found in the special position and modeled to have equal occupancies. The sodium cations were found in three sites. Half of them are found in a pyramidal coordination sphere that is formed by one acetone, two triazoles and two amide carbonyl groups. The rest are found to be disordered between two different water-binding geometries, as well as two crystallographic sites with one in general position and one special. All non-hydrogen atoms were refined with anisotropic displacement parameters. The hydrogen atoms were placed in ideal positions and refined as riding atoms. The final full matrix least squares refinement converged to $R_1$=0.1040 and $wR_2$=0.3435 ($F^2$, all data). Severe disorder of n-hexane was not successfully modeled and was treated with Platon SQUEEZE.

Example 19. Liquid-Liquid Extraction of Salts

Extraction of salts was performed in 2-mL vials between 1 mL dichloromethane with or without T-Cage (0.2 mM) and 1 mL aqueous solution of salts (0.2 mM). The immiscible organic-water mixtures were vigorously shaken and allowed to settle for two days to ensure complete phase separation. The organic layers were collected, and solvents were evaporated under vacuum. The samples were dissolved in 400 μL 1:1 $CD_2Cl_2$:DMSO-$d_6$ for $^1H$ NMR measurements (298 K, 500 MHz). The solvent mixture was chosen to best sharpen proton peaks for accurate integration.

TABLE 1

| Crystal data and structure refinement for T-Cage·NaCl. | |
|---|---|
| Empirical formula (1·NaCl·$CHCl_3$·0.25$CH_2Cl_2$·1.5$H_2O$·0.5Acetone) | $C_{77.75}H_{100.50}Cl_{5.5}N_{23}NaO_5$ |
| Formula weight | 1655.27 |
| Crystal color, shape, size | colorless block, 0.382 × 0.159 × 0.086 $mm^3$ |
| Temperature | 150 K |
| Wavelength | 0.71073 Å |
| Crystal system, space group | Orthorhombic, Ccca |
| Unit cell dimensions | a = 25.494(3) Å    α = 90° |
|  | b = 47.385(6) Å    β = 90° |
|  | c = 35.772(5) Å    γ = 90° |
| Volume | 43220(10) $Å^3$ |
| Z | 16 |
| Density (calculated) | 1.018 Mg/$m^3$ |
| Absorption coefficient | 0.200 $mm^{-1}$ |
| F(000) | 13959.9 |
| Diffractometer | Bruker Apex Kappa Duo, Bruker |
| Theta range for data collection | 1.071 to 25.090°. |
| Index ranges | 0 ≤ h ≤ 30, 0 ≤ k ≤ 56, 0 ≤ l ≤ 42 |
| Reflections collected | 19143 |
| Independent reflections | 19143 [R(int) = 0.106] |
| Observed Reflections | 10857 |
| Completeness to theta = 25.090° | 99.4% |
| Absorption correction | Numerical |
| Max. and min. transmission | 0.98 and 0.97 |
| Solution | Direct methods |
| Refinement method | Full-matrix least-squares on $F^2$ |
| Weighting scheme | w = $[\sigma^2 F_o^2 + AP^2 + BP]^{-1}$, with P = $(F_o^2 + 2 F_c^2)/3$, A = 0.200, B = 0.000 |
| Data/restraints/parameters | 19054/80/980 |
| Goodness-of-fit on $F^2$ | 1.1515 |
| Final R indices [I > 2sigma(I)] | $R_1$ = 0.1040, $wR_2$ = 0.3005 |
| R indices (all data) | $R_1$ = 0.1463, $wR_2$ = 0.3435 |
| Largest diff. peak and hole | 1.56 and −1.25 e $Å^{-3}$ |

The space group Ccca was determined based on intensity statistics and systematic absences. The structure was solved using SIR-92 and refined (full-matrix-least squares) using the Oxford University Crystals for Windows system. A Samples of T-Cage initially contains 10 mol % of NaCl that cannot be removed by simple extraction. This was taken in to account in two ways. First, in extraction of chloride salts, the residual 10% chloride present in the cage sample was added onto the total salt concentration. Second, in extraction of other salts, the concentration of free cage sample is considered as 90% of total cage concentration; the 10% complex was considered as spectating, background species in this case based on the fact that this 10% can hardly be removed by the same extraction method.

Example 20. Anti-Corrosion Test of T-Cage

The surface of a mild stainless steel was polished and cleaned by washing with water and acetone. The steel was placed directly on a heating plate and warm to 40° C., after which a solution of T-Cage (5 mM, 2 mL, $CH_2Cl_2$) was added drop-wise onto the surface. Each successive drop was added after the previous drop was completely dried. After completion of addition, 10 mL of pure solvent ($CH_2Cl_2$) was added in a drop-wise manner to anneal the film on the metal surface. Finally, the metal with deposited film was naturally cooled to room temperature.

This partially covered stainless steel was placed at the bottom of a recrystallization dish, to which a saturated NaCl solution (5.4 M) was poured carefully to immense the steel. Then the top of the dish was covered to prevent fast evaporation but still allow for exchange of air. Appropriate amount of water was added every other day to compensate for water evaporation.

CITATIONS

1. G. S. Frankel, Pitting Corrosion of Metals. *J. Electrochem. Soc.* 145, 2186-2198 (1998). doi: 10.1149/1.1838615
2. T. R. Crompton, *Determination of anions in natural and treated waters*. (Spon Press, London; New York, 2002).
3. R. A. Sachleben et al., Surveying the Extraction of Cesium Nitrate by 1,3-Alternatecalix[4]Arene Crown-6 Ethers in 1,2-Dichloroethane. *Solvent Extr. Ion Exch.* 17, 1445-1459 (1999). doi: 10.1080/07366299908934657
4. Y. Marcus, M. J. Kamlet, R. W. Taft, Linear solvation energy relationships: standard molar Gibbs free energies and enthalpies of transfer of ions from water into nonaqueous solvents. *J Phys. Chem.* 92, 3613-3622 (1988). doi: 10.1021/j100323a057
5. H. K. Roobottom, H. D. B. Jenkins, J. Passmore, L. Glasser, Thermochemical Radii of Complex Ions. *J. Chem. Ed.* 76, 1570-1573 (1999). doi: 10.1021/ed076p1570
6. Y. Haketa, H. Maeda, From helix to macrocycle: anion-driven conformation control of pi-conjugated acyclic oligopyrroles. *Chem. Eur. J.* 17, 1485-1492 (2011). doi: 10.1002/chem.201002748
7. A. J. Ayling, M. N. Perez-Payin, A. P. Davis, New "Cholapod" Anionophores; High-Affinity Halide Receptors Derived from Cholic Acid. *J. Am. Chem. Soc.* 123, 12716-12717 (2001). doi: 10.1021/ja016796z
8. S. J. Edwards, H. Valkenier, N. Busschaert, P. A. Gale, A. P. Davis, High-affinity anion binding by steroidal squaramide receptors. *Angew. Chem. Int. Ed.* 54, 4592-4596 (2015). doi: 10.1002/anie.201411805
9. S. O. Kang, J. M. Llinares, V. W. Day, K. Bowman-James, Cryptand-like anion receptors. *Chem. Soc. Rev.* 39, 3980-4003 (2010). doi: 10.1039/c0cs00083c
10. J. M. Lehn, J. P. Sauvage, Cryptates. XVI. [2]-Cryptates. Stability and selectivity of alkali and alkaline-earth macrobicyclic complexes. *J Am. Chem. Soc.* 97, 6700-6707 (1975). doi: 10.1021/ja00856a018
11. S. O. Kang, J. M. Llinares, D. Powell, D. VanderVelde, K. Bowman-James, New polyamide cryptand for anion binding. *J Am. Chem. Soc.* 125, 10152-10153 (2003). doi: 10.1021/ja034969+
12. N. Lopez et al., Reversible reduction of oxygen to peroxide facilitated by molecular recognition. *Science* 335, 450-453 (2012). doi: 10.1126/science.1212678
13. C. Bucher, R. S. Zimmerman, V. Lynch, J. L. Sessler, First Cryptand-Like Calixpyrrole: Synthesis, X-ray Structure, and Anion Binding Properties of a Bicyclic[3,3,3] nonapyrrole. *J. Am. Chem. Soc.* 123, 9716-9717 (2001). doi: 10.1021/ja016629z

INCORPORATION BY REFERENCE

All literature, publications, patents, patent applications and related material cited here are incorporated by reference as if fully set forth herein.

What is claimed is:

1. An aryl-triazole bicyclic macrocycle of Formula (I):

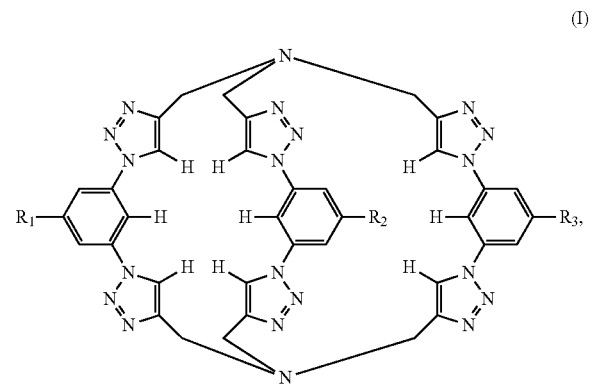

wherein $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

2. The aryl-triazole bicyclic macrocycle of claim 1, wherein $R^1$, $R^2$, and $R^3$ comprise N,N-dicyclohexylamide groups.

3. The aryl-triazole bicyclic macrocycle of claim 1, wherein the aryl-triazole bicyclic macrocycle having Formula (I) is selected from the following:

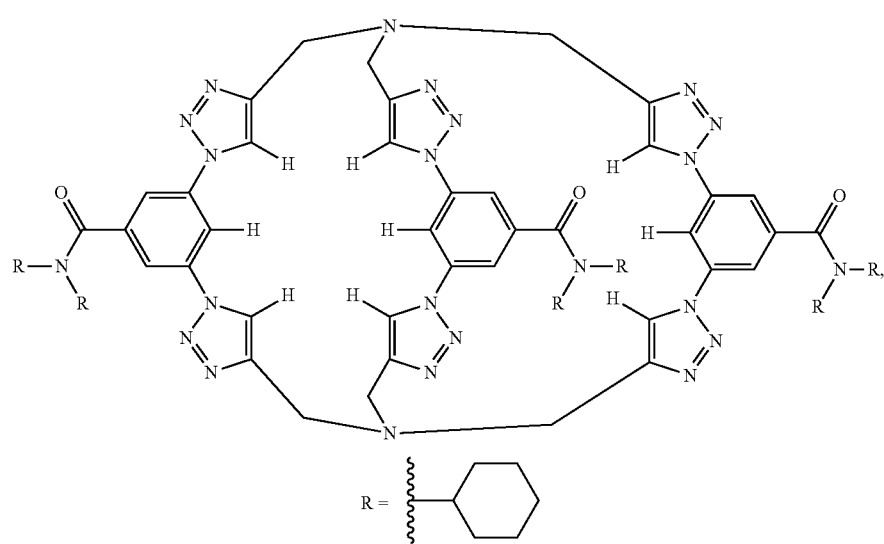
(T-Cage)
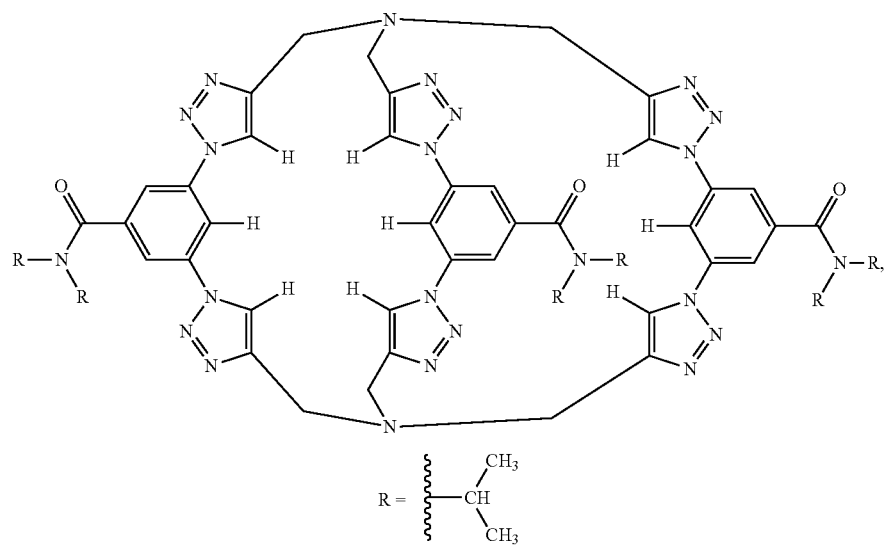
(I-Cage)

-continued
(B-Cage)
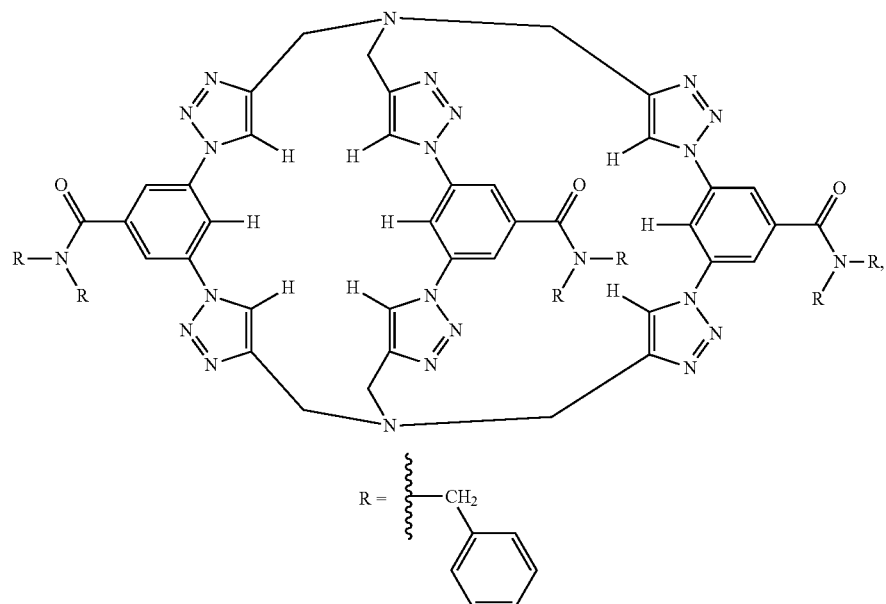
(E-Cage)
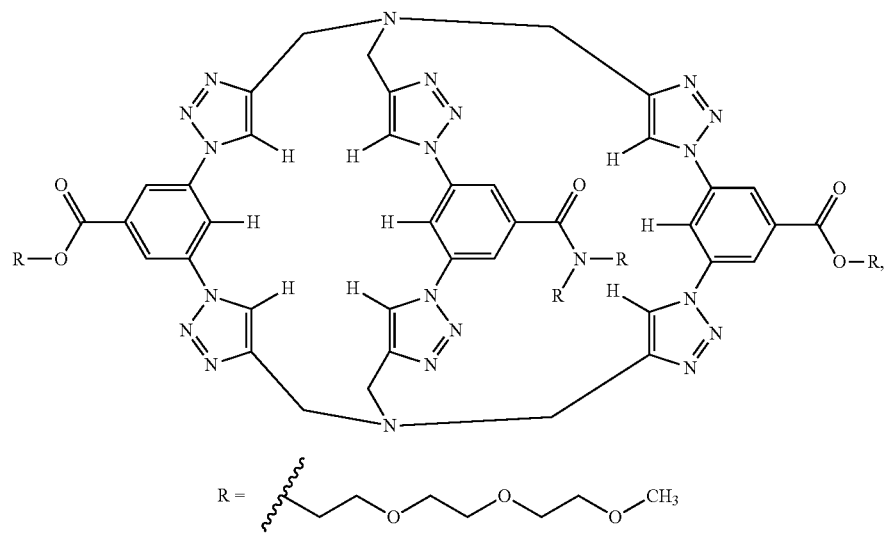
(G-Cage)
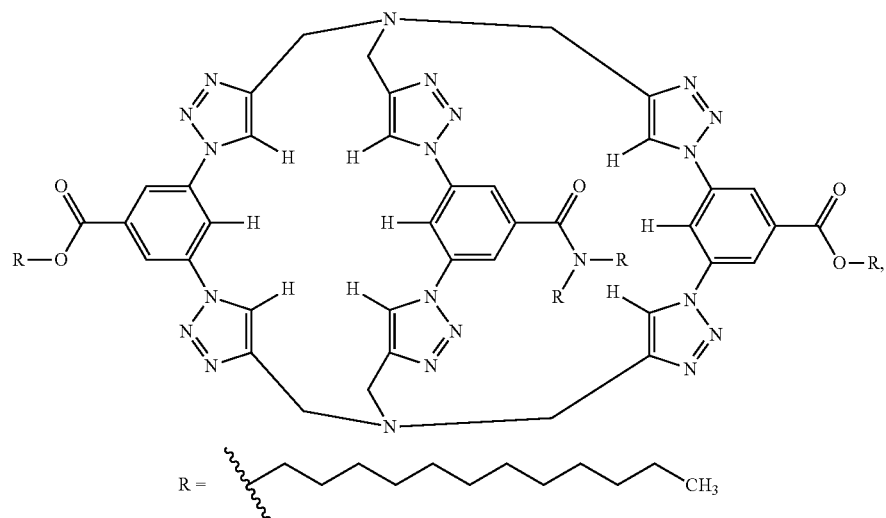

-continued
(P-Cage)
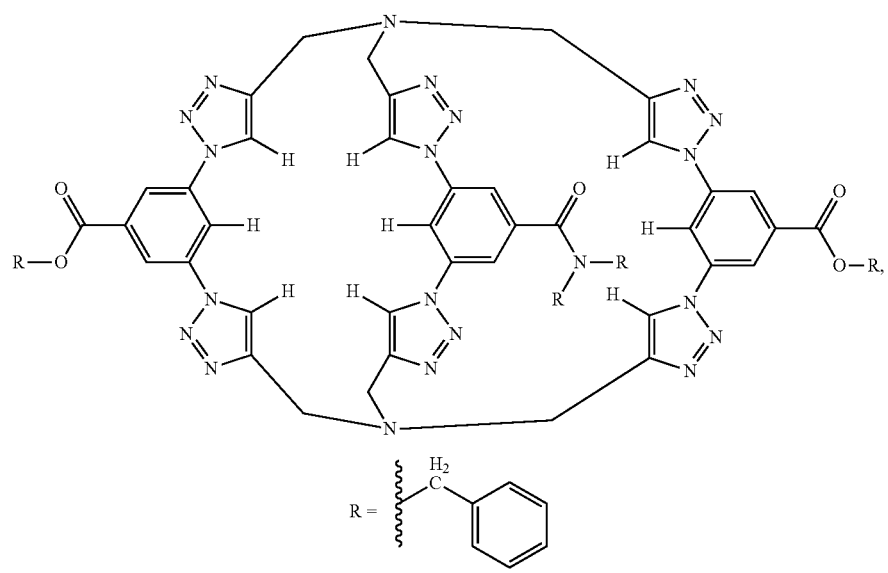
(A-Cage)
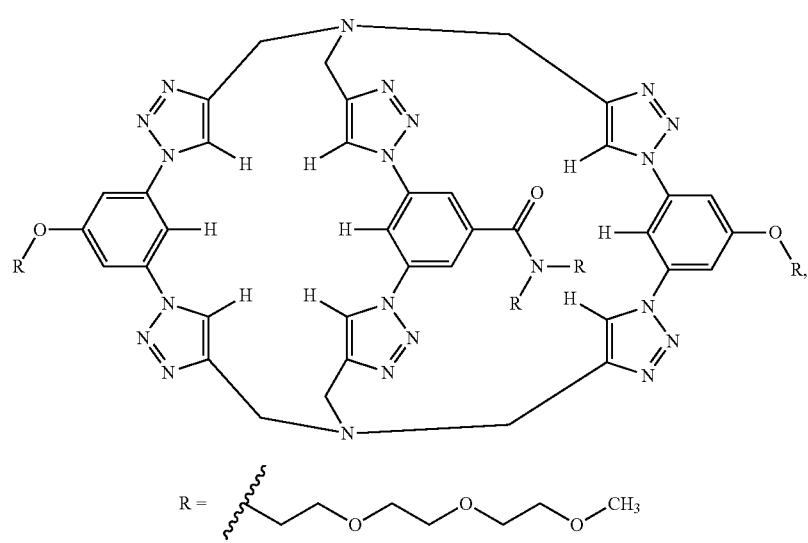
(D-Cage)
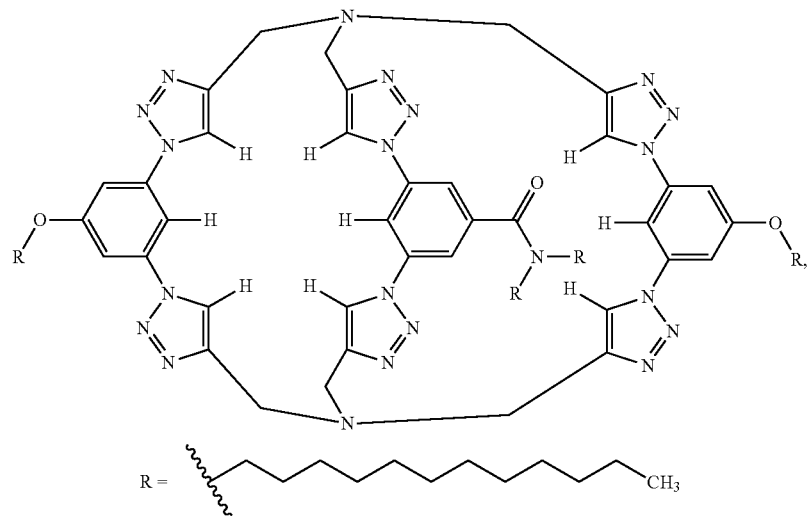

-continued
(Z-Cage)
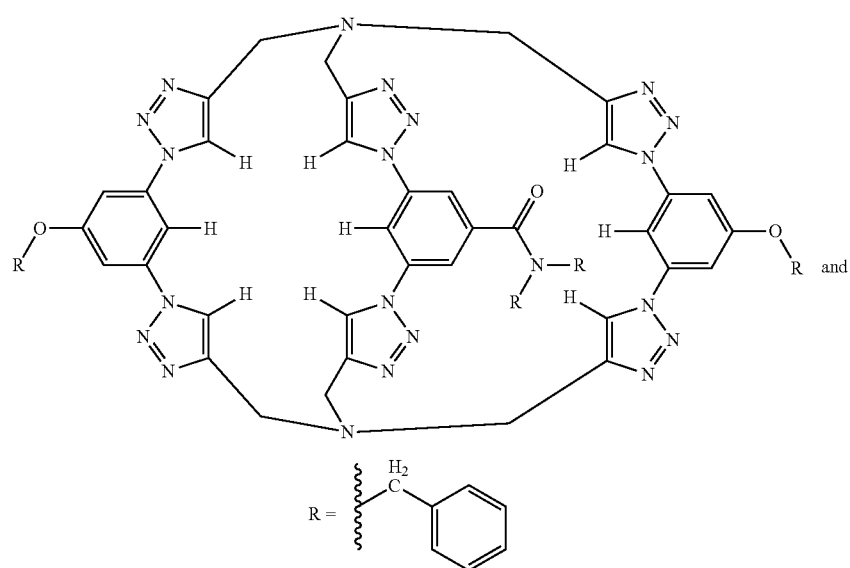
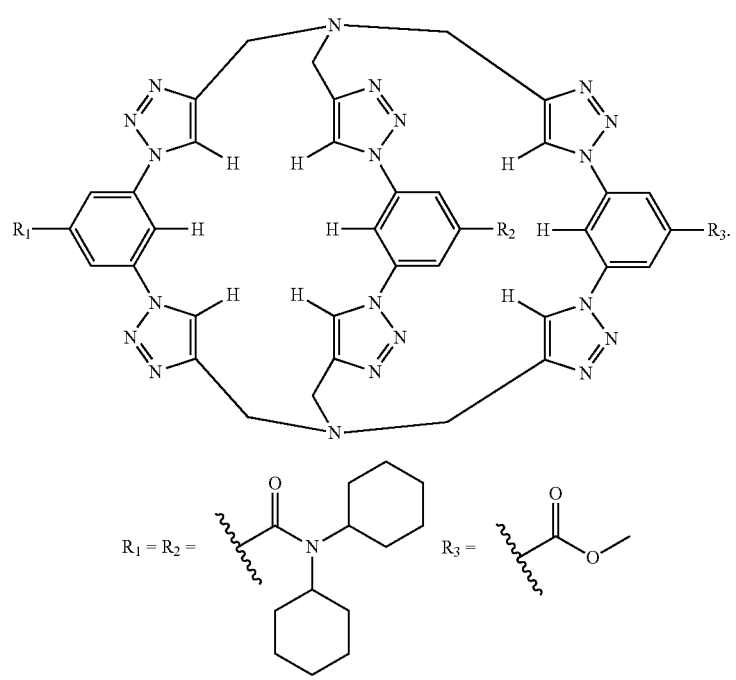

4. A method of synthesizing an aryl-triazole bicyclic macrocycle of Formula (II):

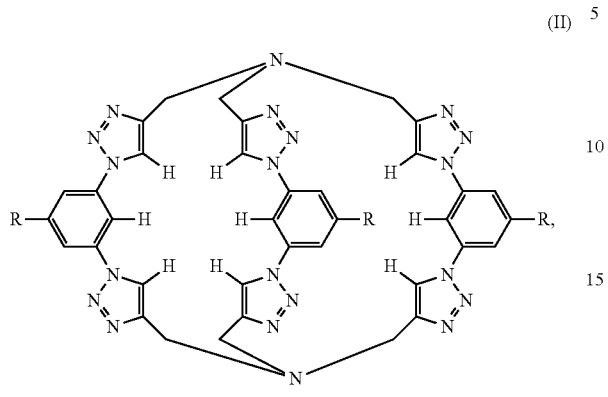
(II)

wherein R is independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, the method comprises:

forming a reaction mixture comprising:

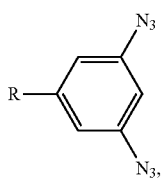

wherein

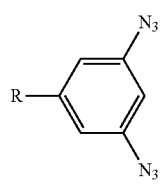

is selected from the group consisting of

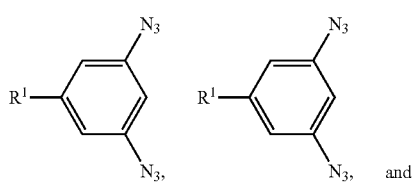

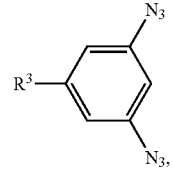

or a combination thereof, wherein $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen;

tripropargylamine; and a solvent;

incubating the reaction mixture at a reaction temperature above room temperature for a reaction time to form the aryl-triazole bicyclic macrocycle of Formula (II); and optionally purifying the aryl-triazole bicyclic macrocycle of Formula (II) from the reaction mixture to provide the aryl-triazole bicyclic macrocycle of Formula (II).

5. The method of claim 4, wherein R is selected from the group consisting of the following:

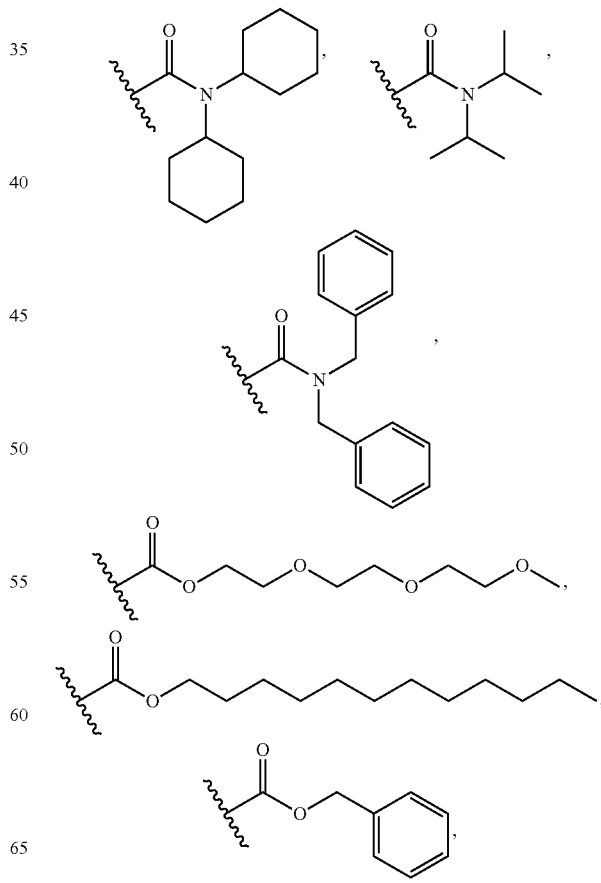

-continued

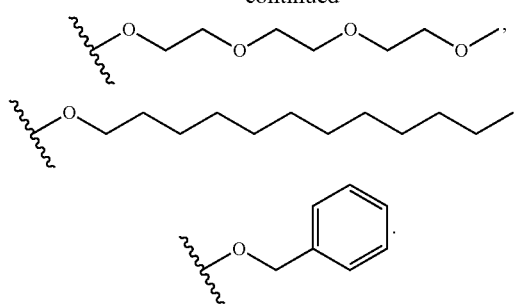

and

6. The method of claim 4, wherein the solvent comprises a Cu(I) source, a reducing reagent and a buffer.

7. The method of claim 6, wherein the Cu(I) source comprises $CuSO_4$.

8. The method of claim 6, wherein the reducing reagent comprises sodium ascorbate.

9. The method of claim 6, wherein the buffer comprises tris[(1-benzyl-1H-1,2,3-triazol-4-yl)methyl]amine (TBTA), tetrahydrofuran (THF), tert-butyl alcohol (t-BuOH), and water ($H_2O$).

10. The method of claim 4, wherein the solvent comprises $CuSO_4$, sodium ascorbate and tris[(1-benzyl-1H-1,2,3-triazol-4-yl)methyl]amine (TBTA), tetrahydrofuran (THF), tert-butyl alcohol (t-BuOH), and water ($H_2O$).

11. The method of claim 4, wherein the reaction temperature comprises a temperature in the range from about 50° C. to about 70° C.

12. The method of claim 4, wherein the reaction temperature comprises a temperature of about 60° C.

13. The method of claim 4, wherein the reaction time comprises a reaction time up to and including 5 days.

14. The method of claim 4, wherein the reaction time comprises a reaction time in a range from about 1 day to about 5 days.

15. The method of claim 4, wherein the reaction time comprises about 3 days.

16. The method of claim 4, wherein the step of purifying the aryl-triazole bicyclic macrocycle of Formula (I) comprises chromatography.

17. A method of synthesizing the aryl-triazole bicyclic macrocycle of Formula (I) according to claim 1,

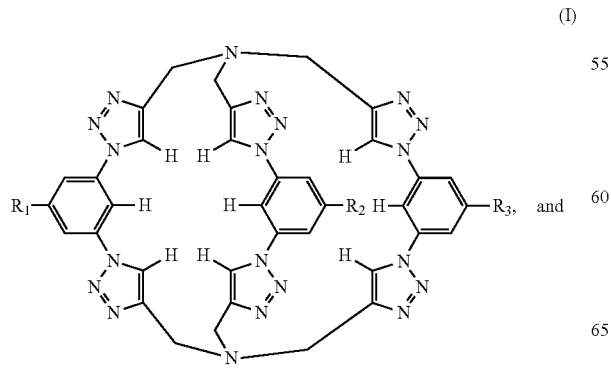

(I)

-continued

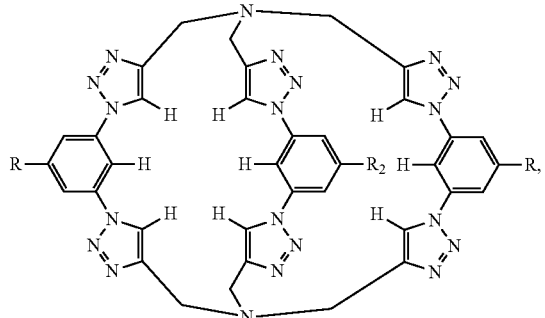

(II)

the method comprising a first sequence of step-wise reactions, a second sequence of step-wise reactions, a third sequence of step wise reactions, or a fourth sequence of step-wise reactions, wherein the first sequence of step-wise reactions comprises Reaction 1, Reaction 2, Reaction 3, and Reaction 4, wherein the second sequence of step-wise reactions comprises Reaction 5, Reaction 3, and Reaction 4, wherein the third sequence of step-wise reactions comprises Reaction 1, Reaction 2, and Reaction 6, wherein the fourth sequence of step-wise reactions comprises Reaction 5 and Reaction 6, wherein Reaction 1 comprises contacting two equivalents of dipropargyl amine with one equivalent of diazido-benzene 1

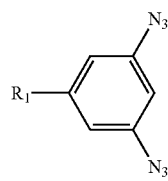

(diazido-benzene 1), to form intermediate 1

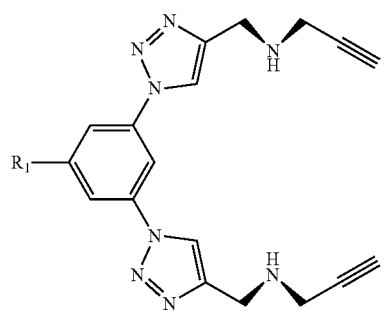

(intermediate 1),
wherein the Reaction 2 comprises contacting intermediate 1 with diazido-benzene 2

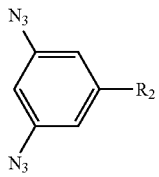

(diazido-benzene 2)
to form MC1-1

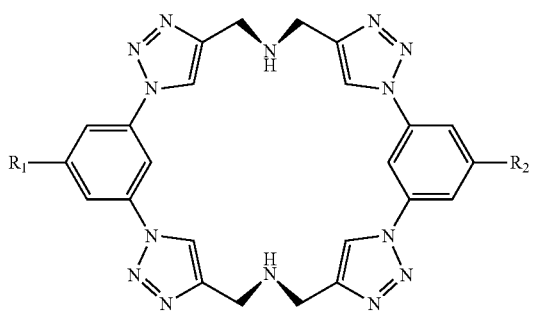

(MC1-1),
wherein Reaction 3 comprises contacting one equivalent of MC1-1 with two equivalents of propargyl bromide to form MC2-1

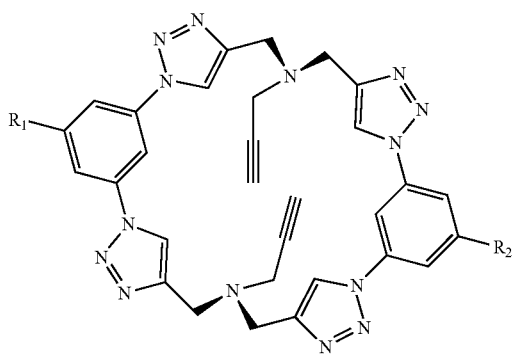

(MC2-1);
wherein Reaction 4 comprises contacting MC2-1 with diazido-benzene 3

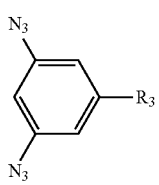

(diazido-benzene 3);
to form the aryl-triazole bicyclic macrocycle of Formulas (I);
wherein Reaction 5 comprises contacting one equivalent of diazido-benzene 1 with one equivalent of diazido-benzene 2 and two equivalents of dipropargyl amine to form MC1-1; and
wherein Reaction 6 comprises contacting MC1-1 with triad-1

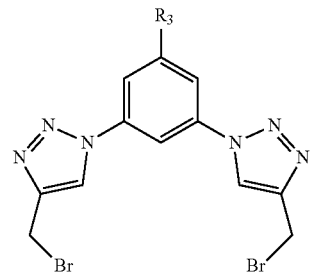

(triad 1)
to form the aryl-triazole bicyclic macrocycle of Formulas (I).

18. The method of claim 17, wherein the aryl-triazole bicyclic macrocycle is Formula (I), wherein at least one of $R^1$, $R^2$ and $R^3$ differs from the other two R-substituents.

19. The method of claim 17, wherein the aryl-triazole bicyclic macrocycle is Formula (I), wherein $R^1$, $R^2$ and $R^3$ differ from each other.

20. The method of claim 17, wherein the method comprises the first sequence of step-wise reactions.

21. The method of claim 17, wherein the method comprises a method of step-wise synthesis of the aryl-triazole bicyclic macrocycle of Formula (I) from macrocycle intermediate MC1-1 by an alkylation using Reaction 6.

22. The method of claim 17, wherein intermediate macrocycle MC1-1 is prepared in a one-pot synthesis using Reaction 5.

23. An aryl-triazole bicyclic macrocycle of Formula (III):

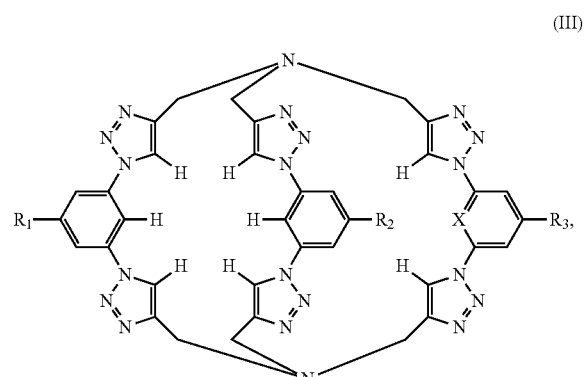

(III)

wherein X is independently selected from the group consisting of CH, CF and N,
wherein $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen.

24. The aryl-triazole bicyclic macrocycle of claim 23, wherein the aryl-triazole bicyclic macrocycle is selected from the group consisting of the following:

(HHF-T-Cage)

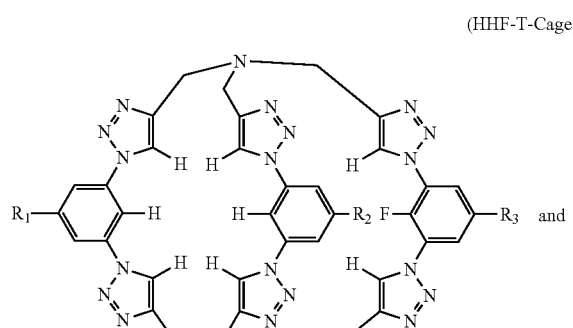

and (HHN-T-Cage)

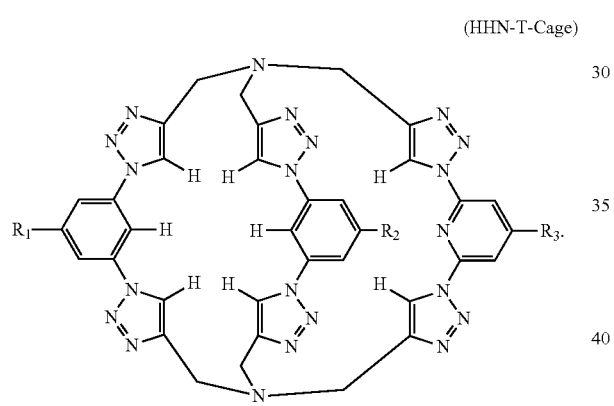

25. An aryl-triazole bicyclic macrocycle selected from the group consisting of Formula (IV), (V), (VI) and (VII):

(IV)

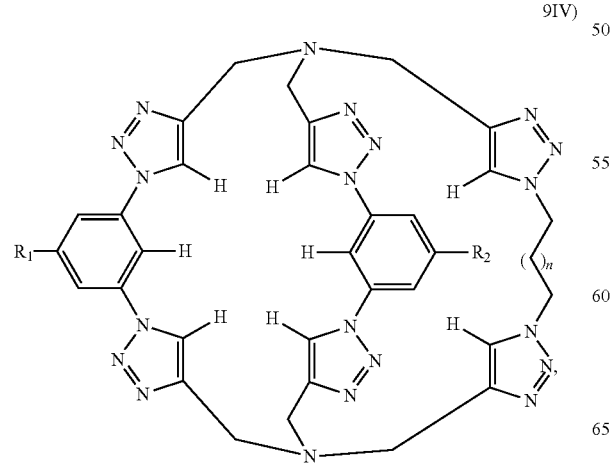

(V)

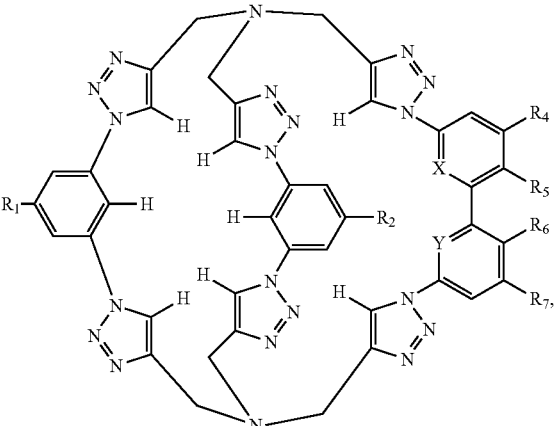

(VI)

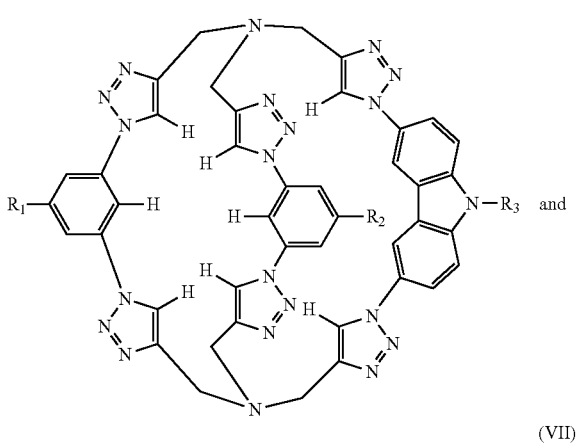

and (VII)

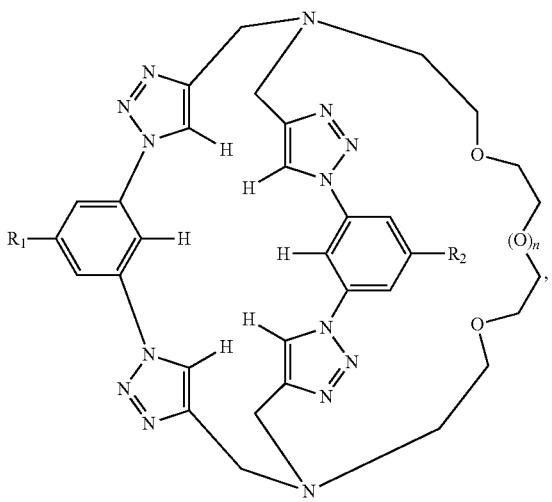

wherein for (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$—$N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen, wherein for (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^2R^3)$, wherein $R^8$, $R^9$, $R^{10}R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen, wherein for (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

26. A method of synthesizing an aryl-triazole bicyclic macrocycle selected from Formulas (III), (IV), (V) and (VI):

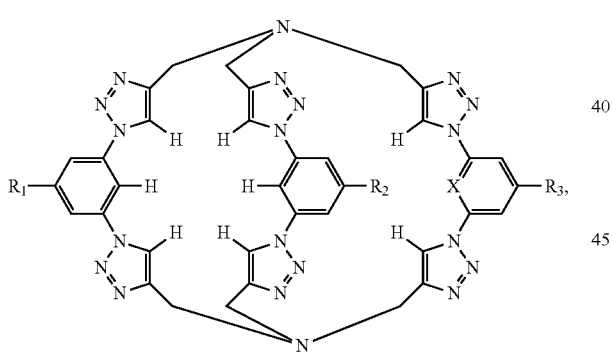

(III)

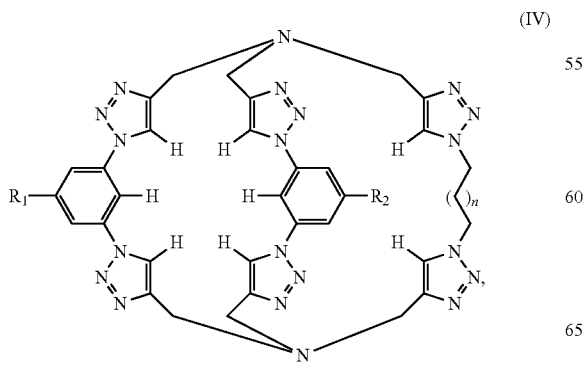

(IV)

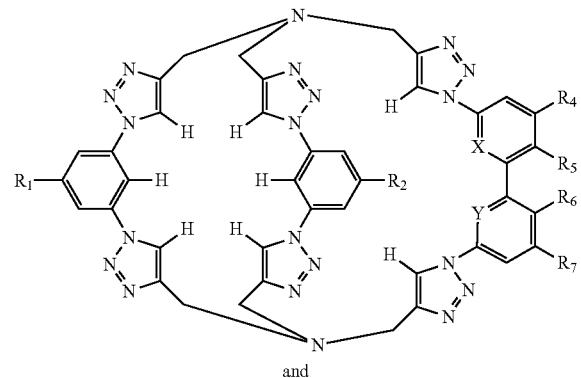

(V)

and

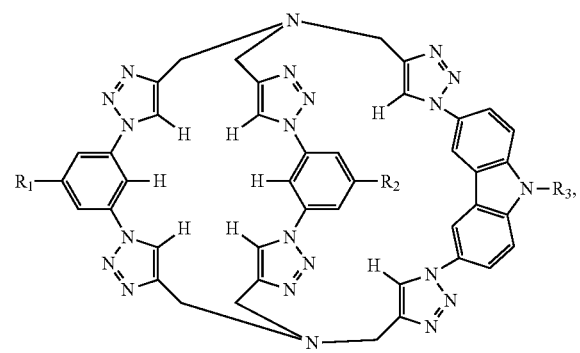

(VI)

wherein for (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen, wherein for (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^1$, $R^9$, $R^{10}$, $R^{11}$, $R^{12}$ and $R^{13}$ are each independently selected from the group consisting of alkenyl, alkyl, aryl, arylalkyl, cycloalkyl, heteroaryl, heterocycle, haloalkyl, and hydrogen, wherein for (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —N(R⁵R⁶), —CO₂R⁷, —C(O)—N(R⁸R⁹), wherein R⁴, R⁵, R⁶, R⁷, R⁸, and R⁹ are each independently selected from the group consisting of alkenyl, alkyl, aryl, arylalkyl, cycloalkyl, heteroaryl, heterocycle, haloalkyl, and hydrogen, the method comprises preparing macrocycle intermediate MC2-1

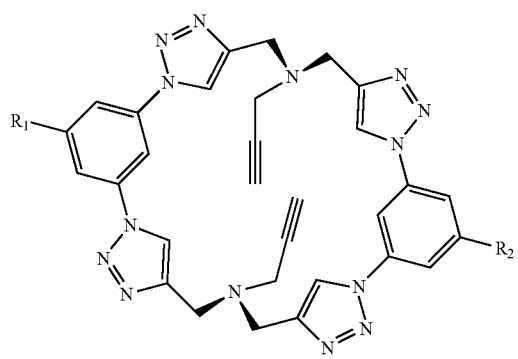

(MC2-1) and contacting MC2-1 with a diazido compound selected from

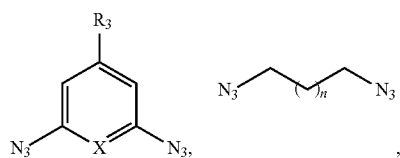

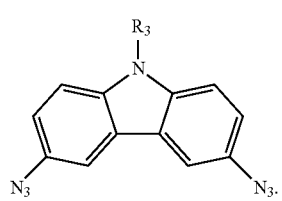

27. A method of synthesizing an aryl-triazole bicyclic macrocycle of Formula (VII):

(VII)

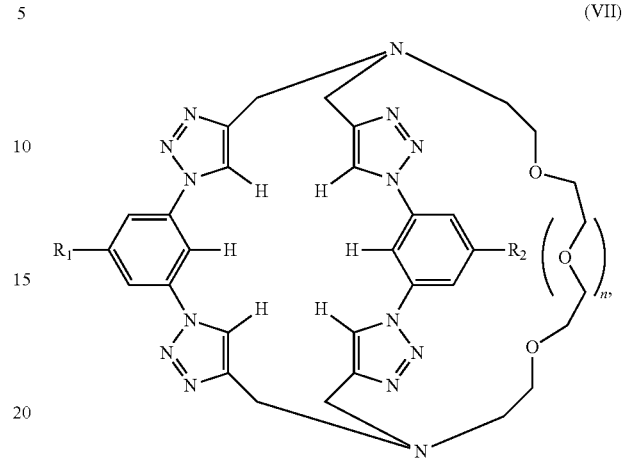

wherein n=1 to 4, and R¹ and R² are independently selected from the group consisting of alkenyl, alkyl, alkoxy, alkyl-NH-alkyl, aryl, cycloalkyl, heteroaryl, heterocycle, haloalkyl, hydrogen, iodo, —OR³, —N(R⁴R⁵), —CO₂R⁶, —C(O)—N(R⁷R⁸), wherein R³, R⁴, R⁵, R⁶, R⁷, and R⁸ are each independently selected from the group consisting of alkenyl, alkyl, aryl, arylalkyl, cycloalkyl, heteroaryl, heterocycle, haloalkyl, and hydrogen, the method comprises:

preparing macrocycle intermediate MC1-1:

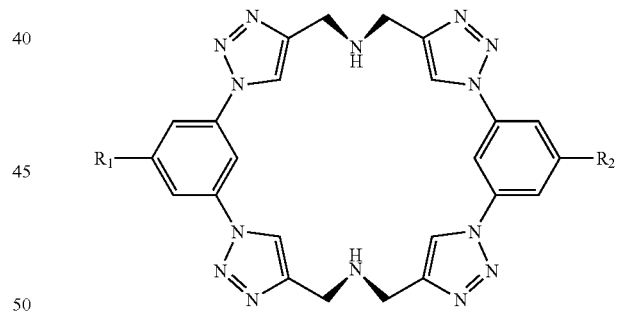

(MC1-1); and alkylating macrocycle intermediate MC1-1 to produce the aryl-triazole bicyclic macrocycle of Formula (VII).

28. A complex comprising:

(a) an anion, (b) a cation and (c) an aryl-triazole bicyclic macrocycle selected from the group consisting of Formulas (I), (III), (IV), (V), (VI) and (VII):

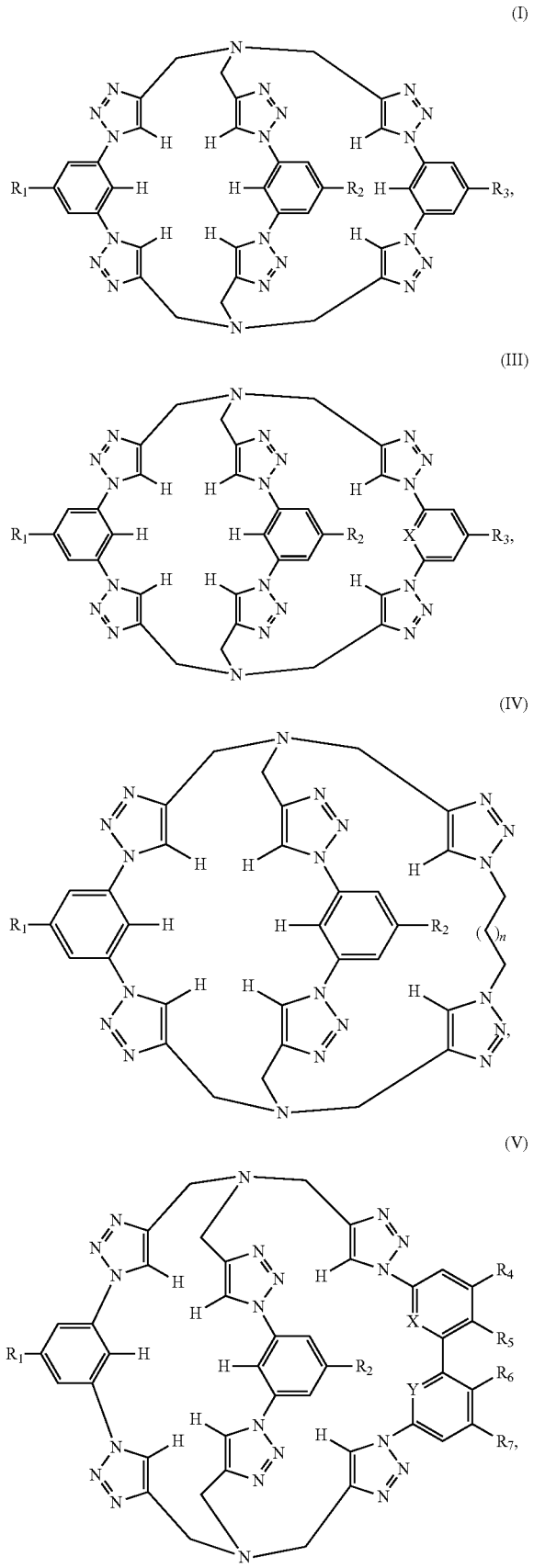

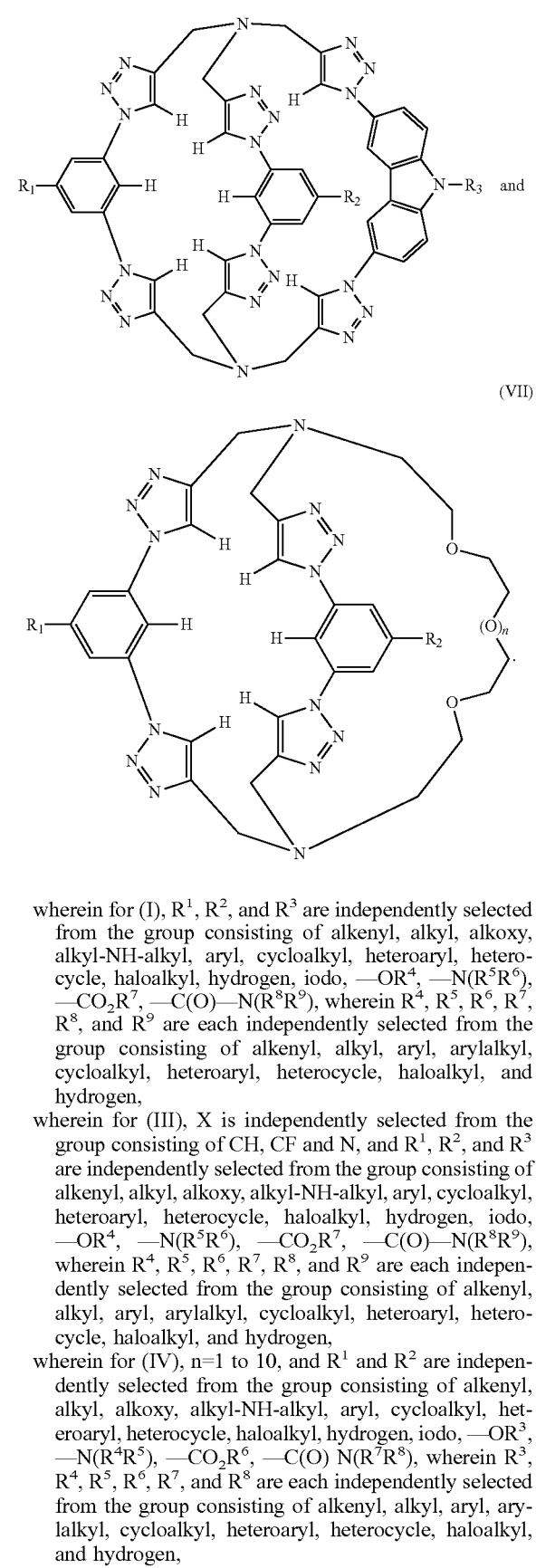

wherein for (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —$C(O)$—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —$C(O)$ $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen, wherein for (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^1$, $R^9$, $R^{10}$, $R^{11}$, $R^{12}$ and $R^{13}$ are each independently selected from the group consisting of alkenyl, alkyl, aryl, arylalkyl, cycloalkyl, heteroaryl, heterocycle, haloalkyl, and hydrogen, wherein for (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen.

29. The complex of claim 28, wherein the aryl-triazole bicyclic macrocycle is Formula (I) in which $R^1$, $R^2$, and $R^3$ comprise N,N-dicyclohexylamide groups.

30. The complex of claim 28, wherein the aryl-triazole bicyclic macrocycle is selected from the group consisting of the following species of Formula (I):

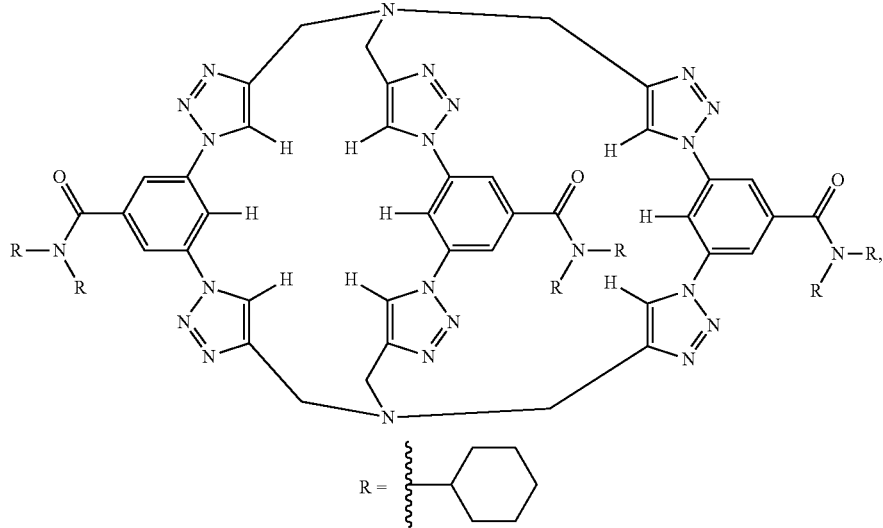

(T-Cage)

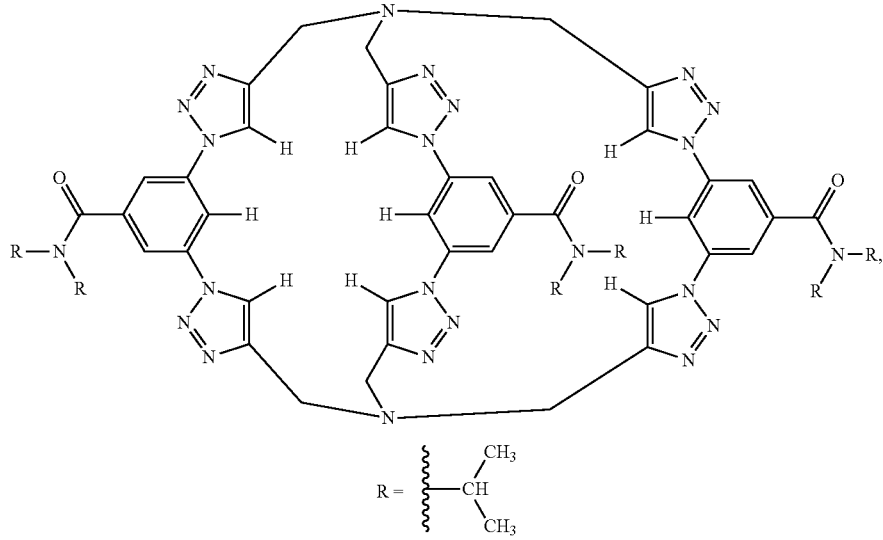

(I-Cage)

-continued
(B-Cage)
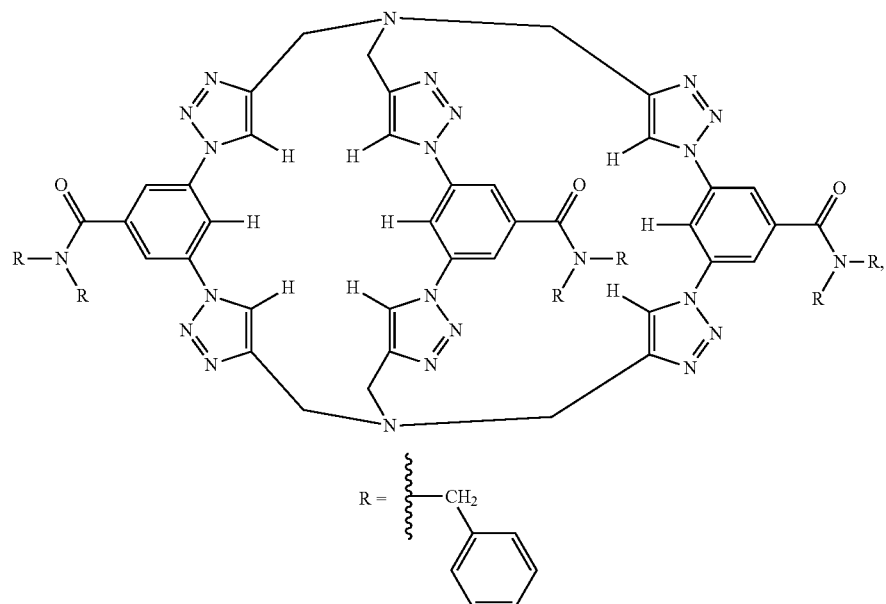
(E-Cage)
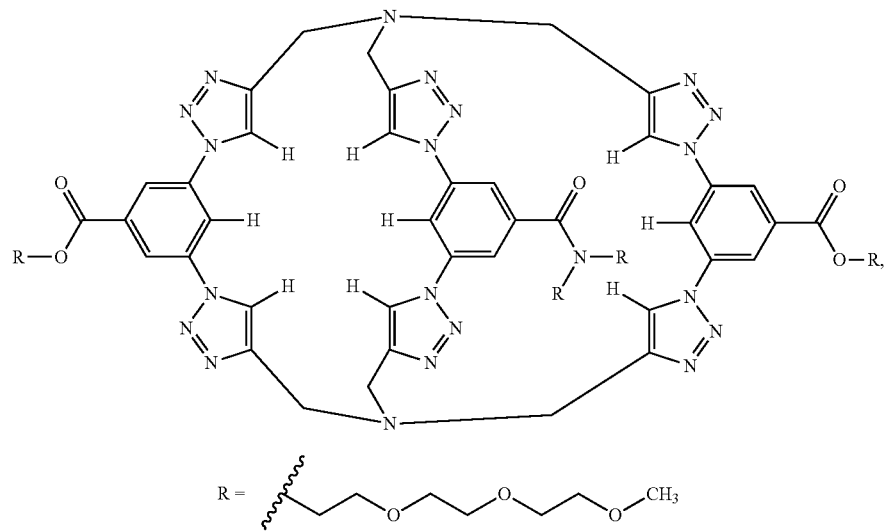
(G-Cage)
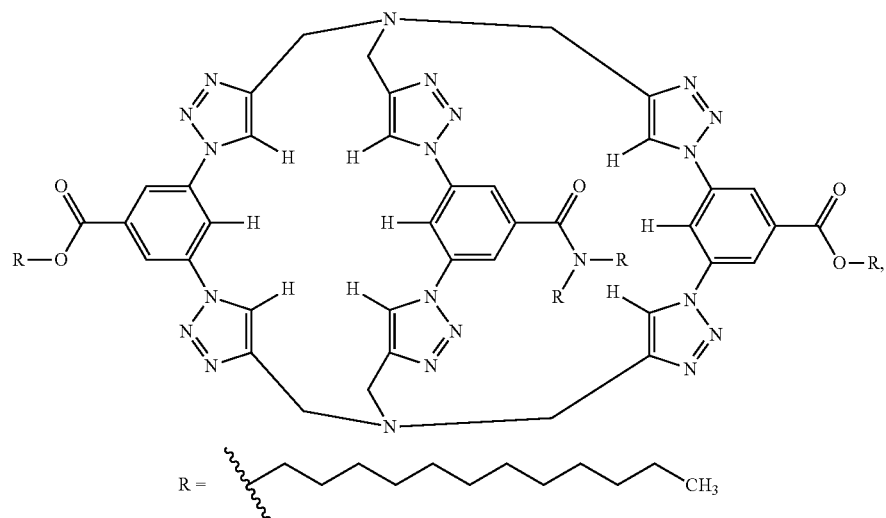

-continued
(P-Cage)
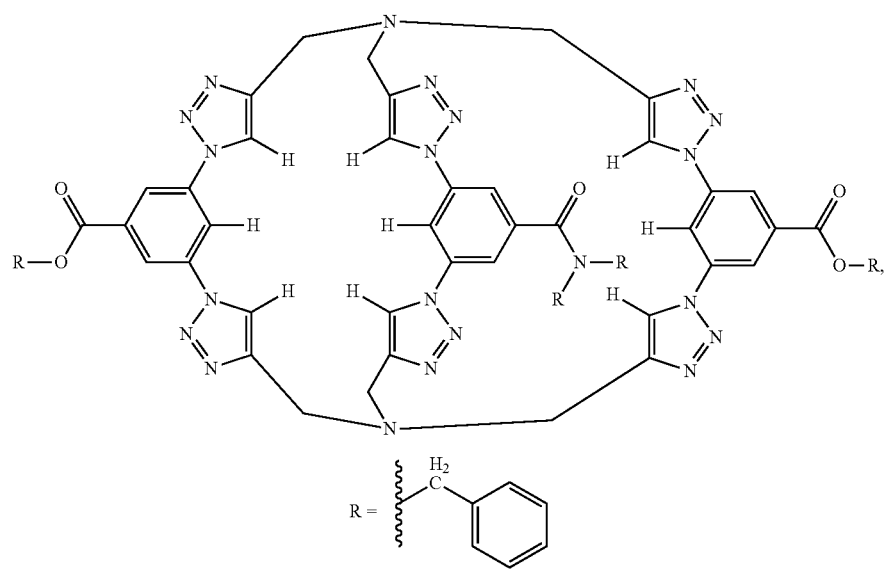
(A-Cage)
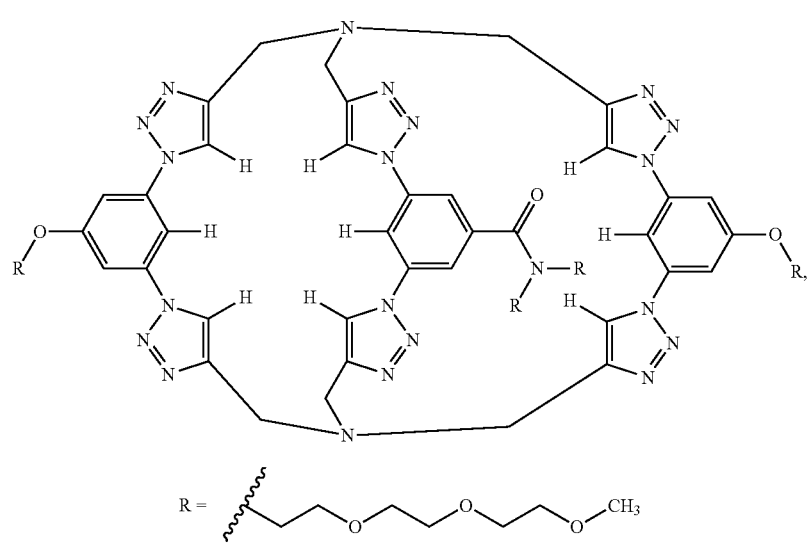
(D-Cage)
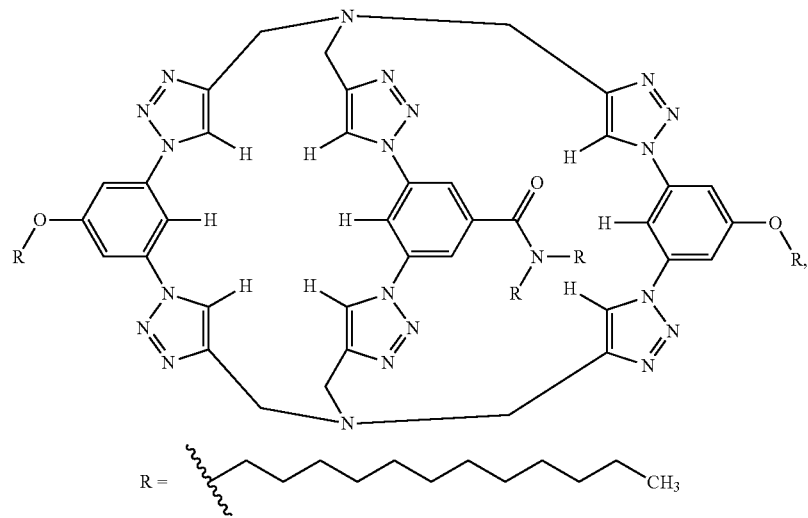

(Z-Cage)
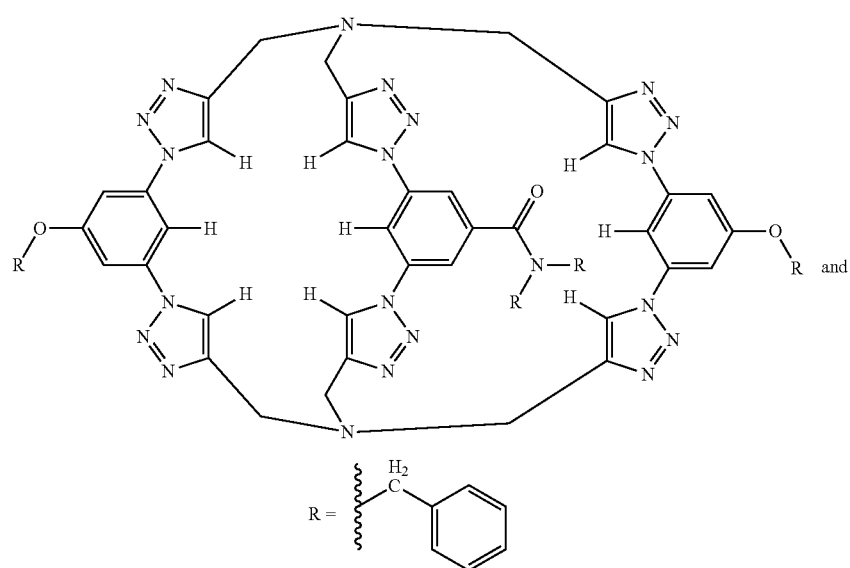
(T-cage-A₂B)
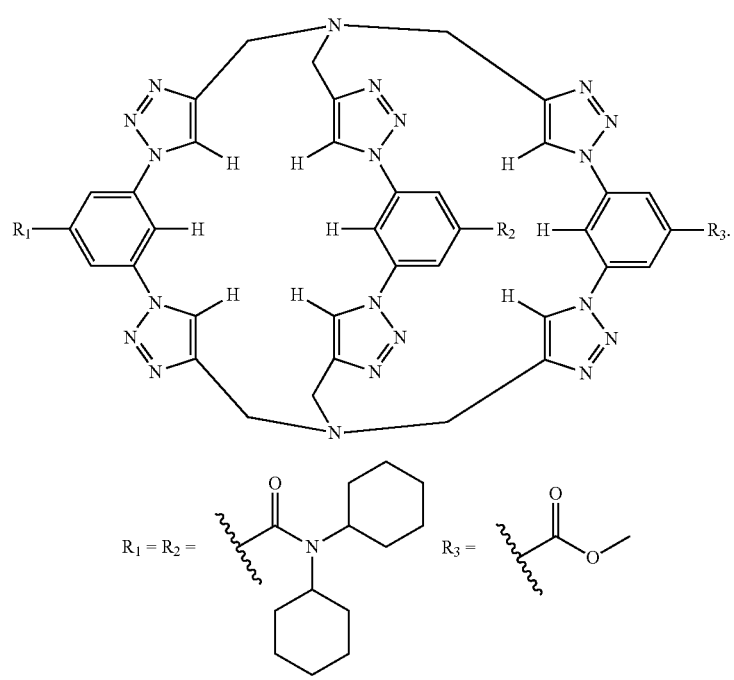

31. The complex of claim 28, wherein the anion is selected from $Cl^-$, $Br^-$, $I^-$, $CN^-$, $F^-$, $HF_2^-$, $SCN^-$, $N_3^-$, $O_2^{2-}$, $O_2^{2-}$, $NO_2^-$, $NO_3^-$, $CO_3^{2-}$, $HCO_3^-$, $S^{2-}$, $S_n^{x-}$, where $n = \geq 1$, and $x=1$ or 2, and $ArO^-$.

32. A method of removing an anion from aqueous solution containing the anion, comprising:
(a) contacting the aqueous solution with an immiscible organic solution comprising an aryl-triazole bicyclic macrocycle selected from the group consisting of Formulas (I), (III), (IV), (V), (VI) and (VII):

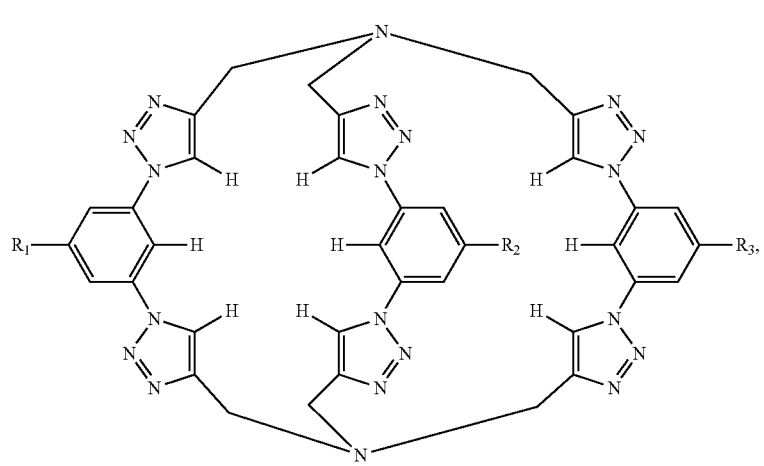
(I)

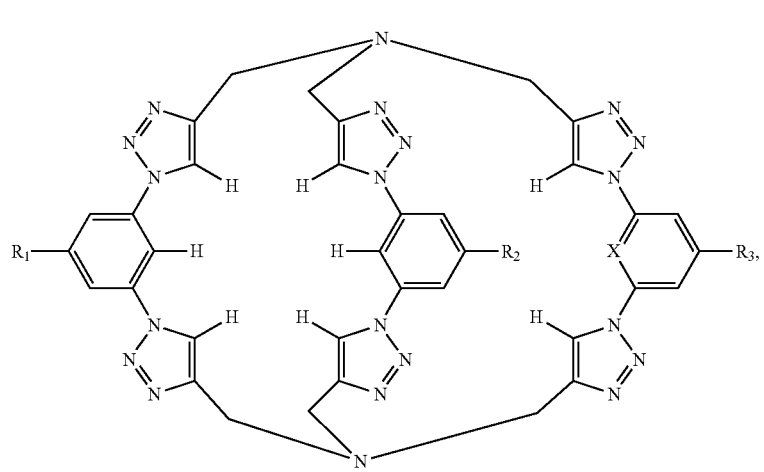
(III)

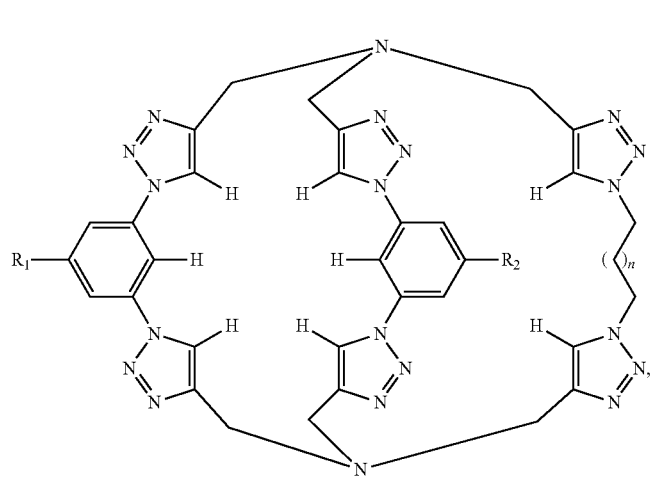
(IV)

-continued
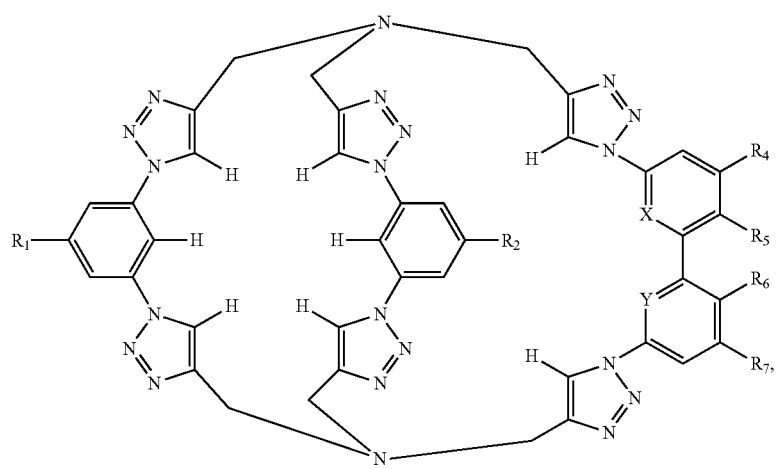
(V)
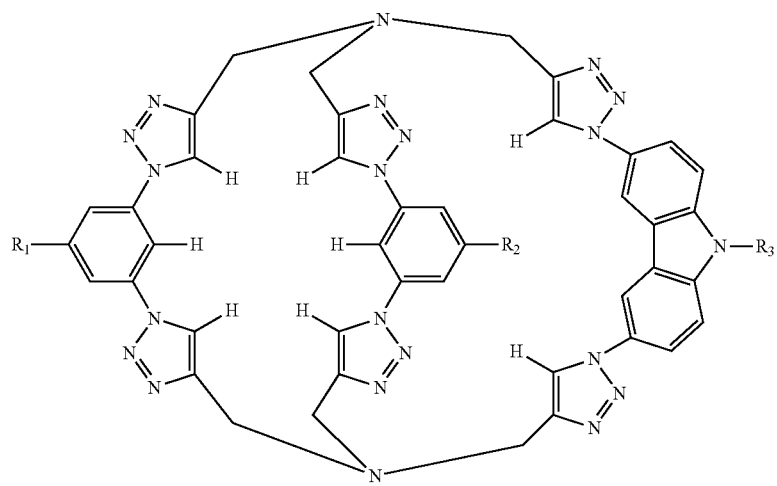
(VI)
and
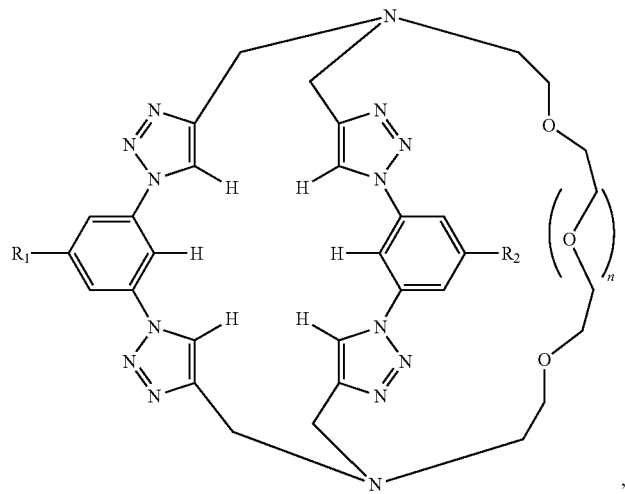
(VII)
, wherein for (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen, wherein for (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^1$, $R^9$, $R^{10}$, $R^{11}$, $R^{12}$ and $R^{13}$ are each independently selected from the group consisting of alkenyl, alkyl, aryl, arylalkyl, cycloalkyl, heteroaryl, heterocycle, haloalkyl, and hydrogen, wherein for (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R'$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen;

(b) forming a complex, said complex comprising the anion, a cation and the aryl-triazole bicyclic macrocycle in the organic layer; and (c) separating the organic layer from aqueous layer.

33. The method of claim 32, wherein the aryl-triazole bicyclic macrocycle is Formula (I) in which $R^1$, $R^2$, and $R^3$ comprise N,N-dicyclohexylamide groups.

34. The method of claim 32, wherein the aryl-triazole bicyclic macrocycle is selected from the group consisting of the following species of Formula (I):

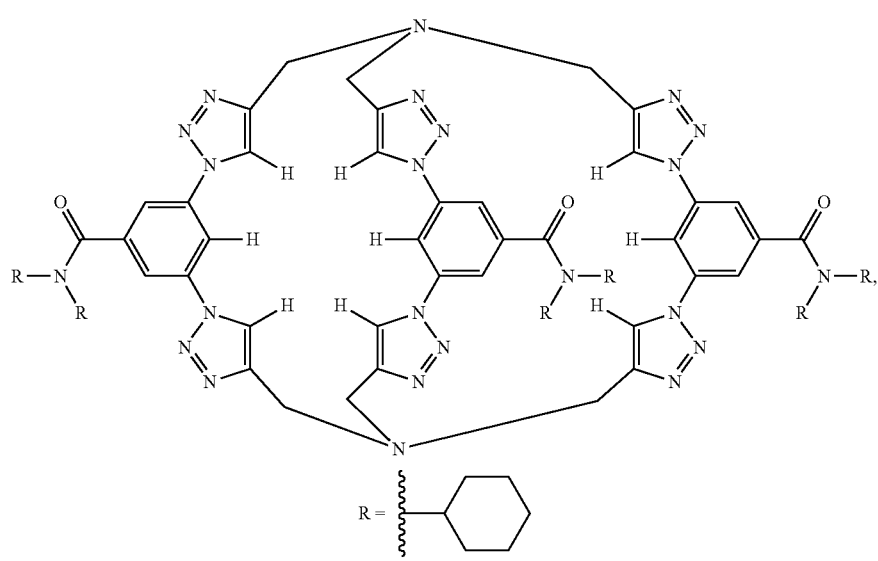

(T-Cage)

-continued
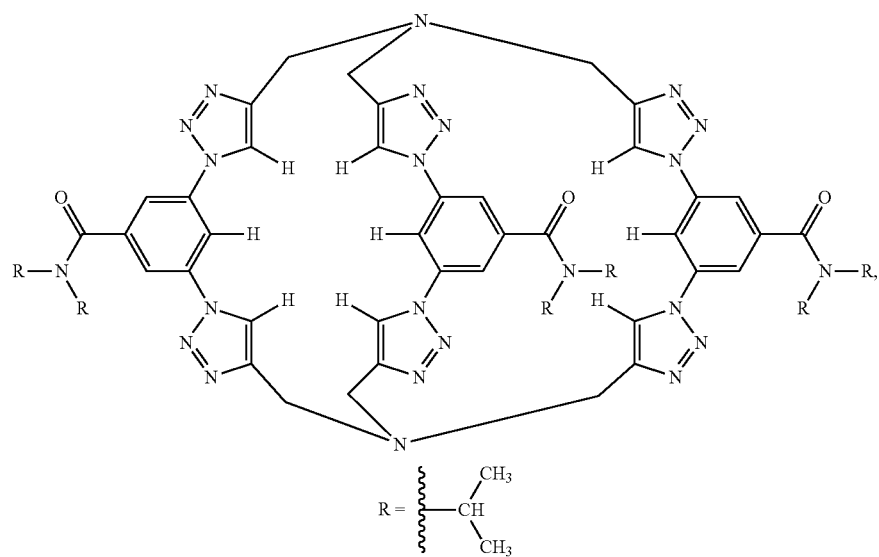
(I-Cage)
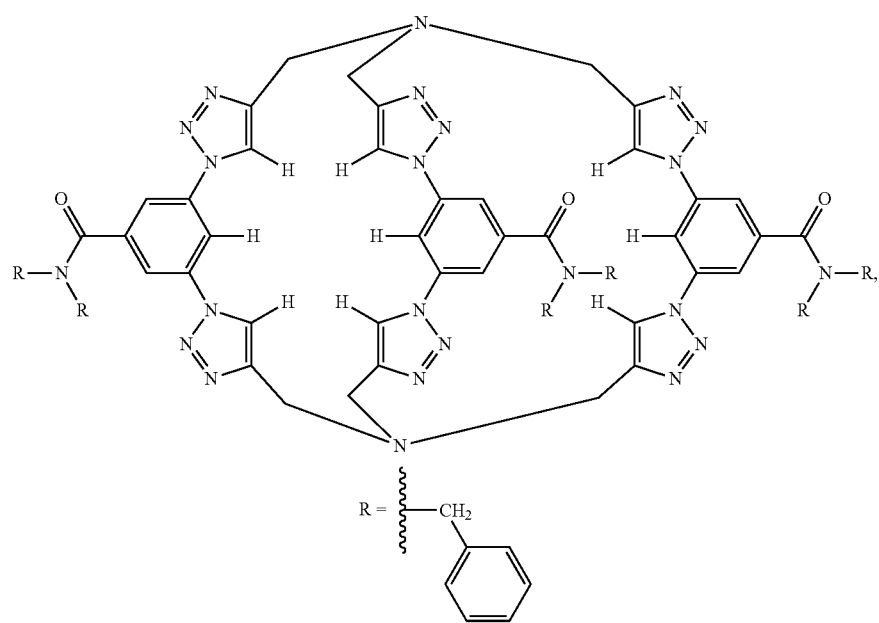
(B-Cage)

-continued
(E-Cage)
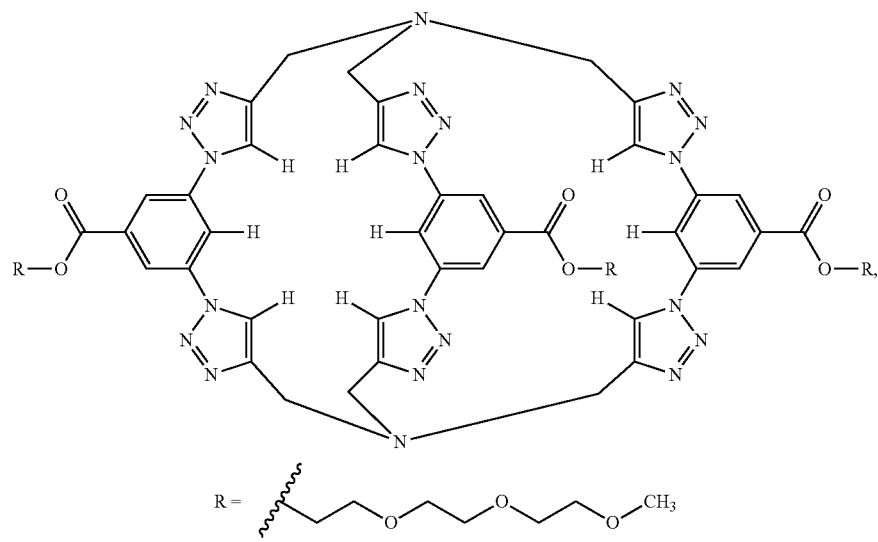
(G-Cage)
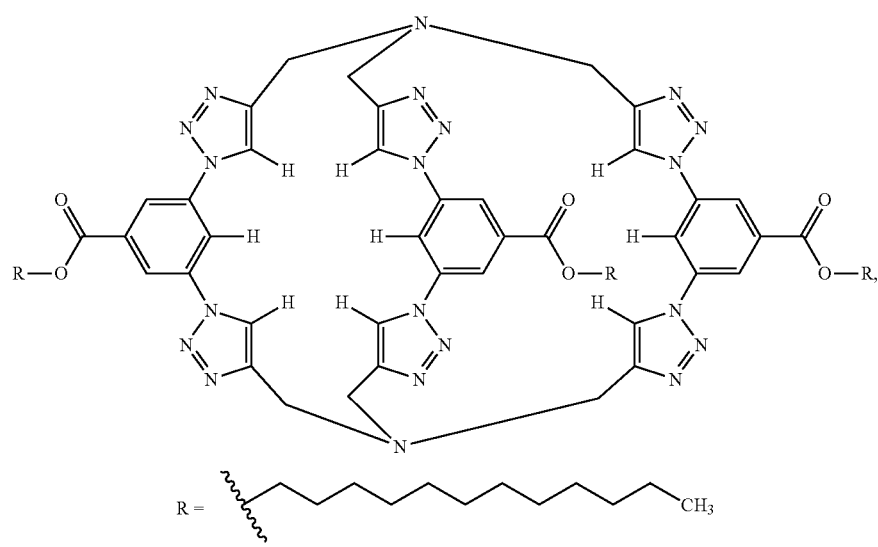
(P-Cage)
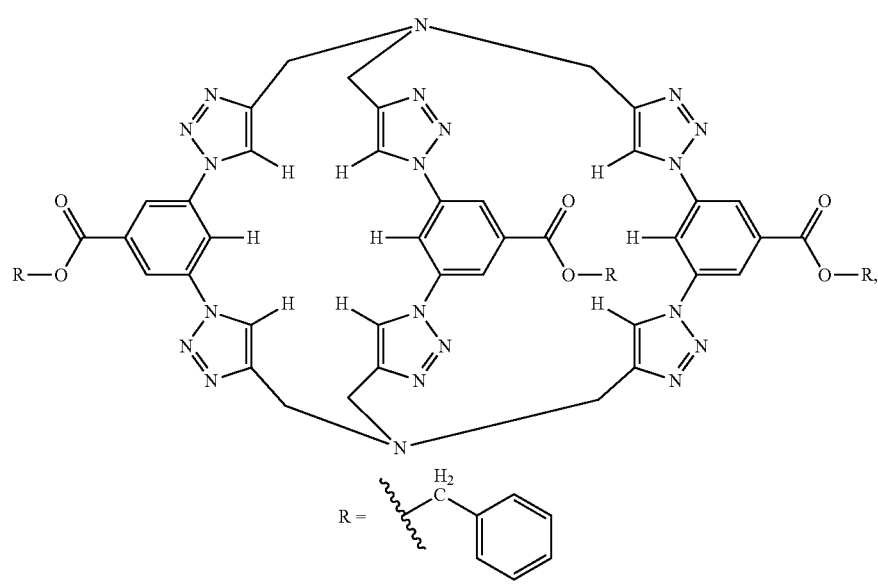

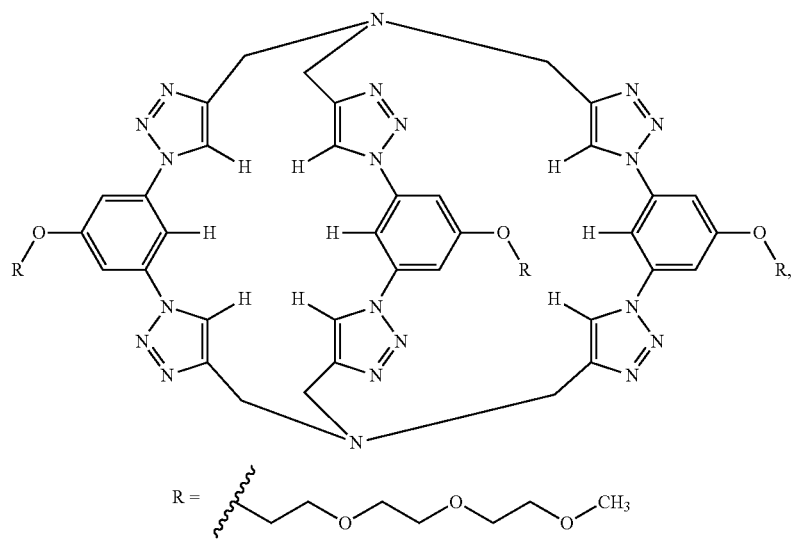
(A-Cage)
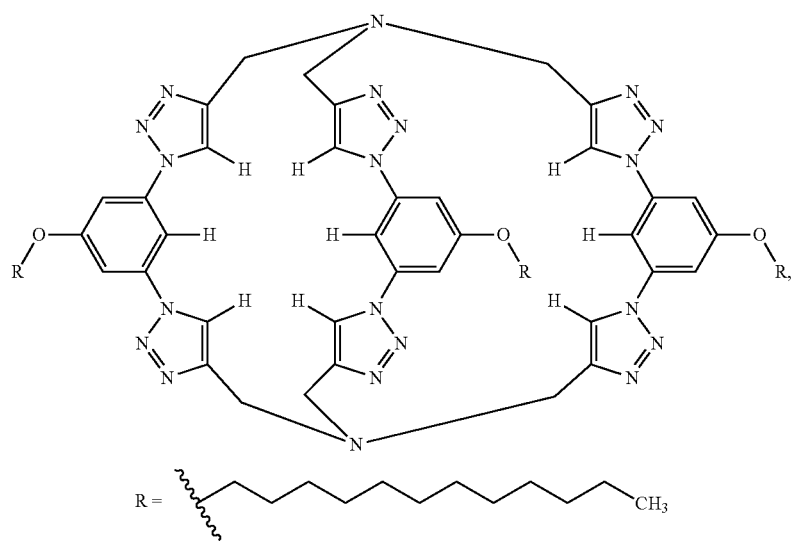
(D-Cage)
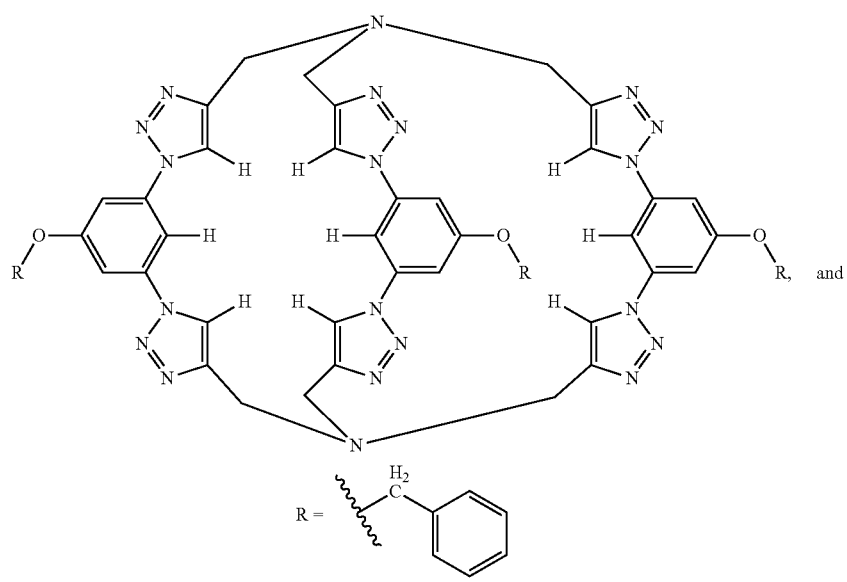
(Z-Cage) and (T-cage-A₂B)
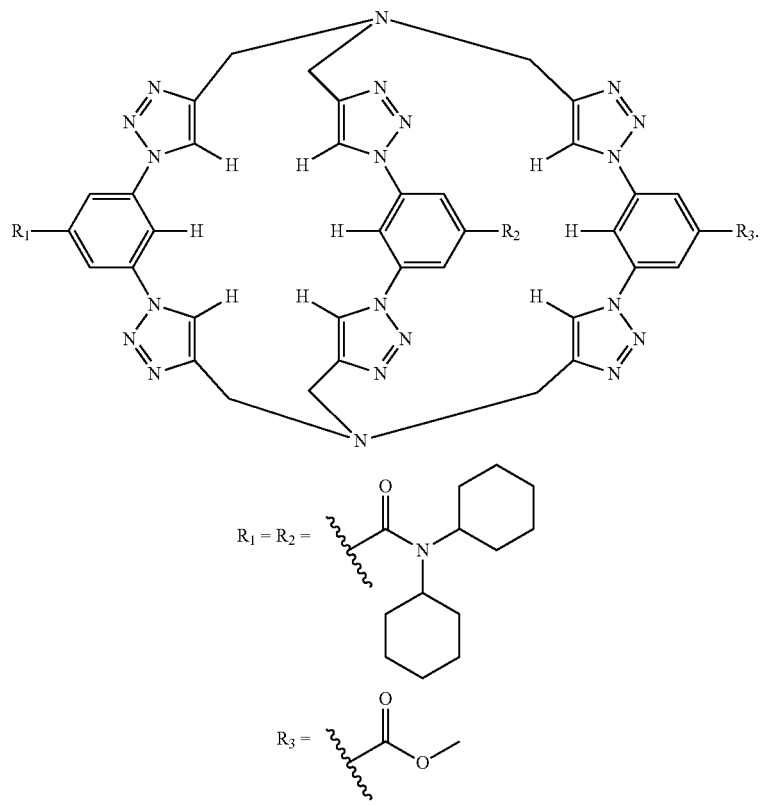
35. A method of preventing corrosion of a metal surface, comprising:
   (a) depositing a solution comprising an aryl-triazole bicyclic macrocycle in a solvent phase onto the metal surface to produce a coating on the metal surface, wherein the aryl-triazole bicyclic macrocycle is selected from the group consisting of Formulas (I), (III), (IV), (V), (VI) and (VII):
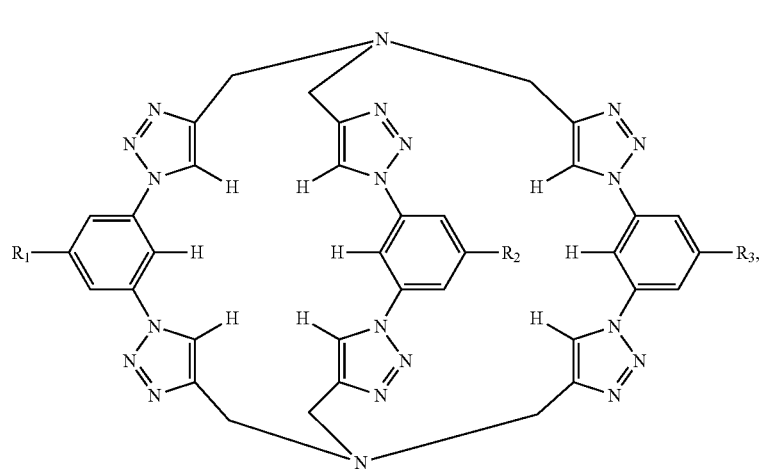

-continued
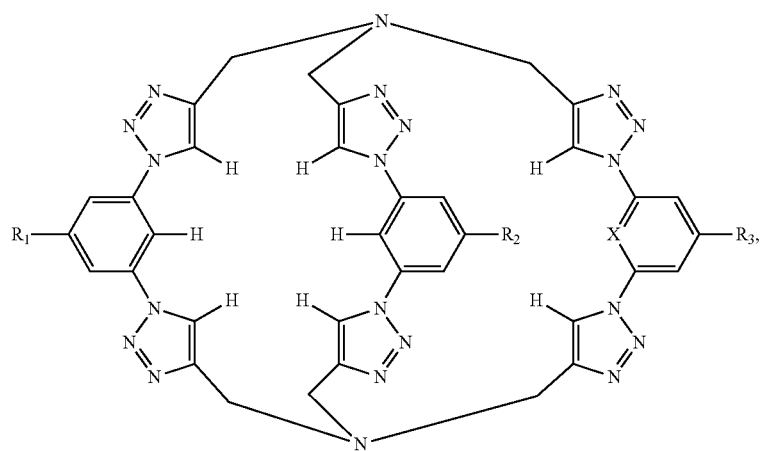
(III)
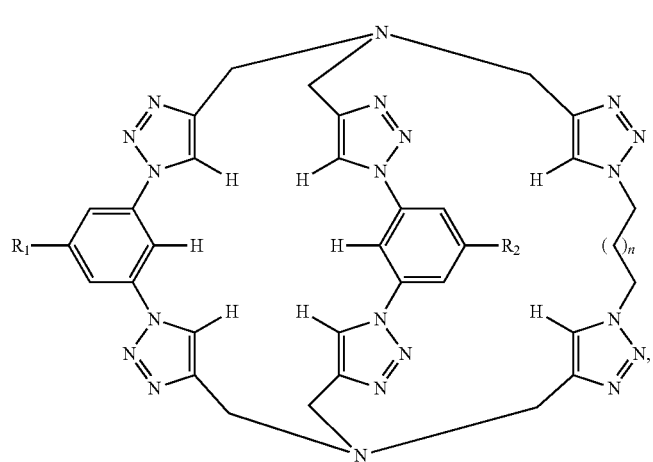
(IV)
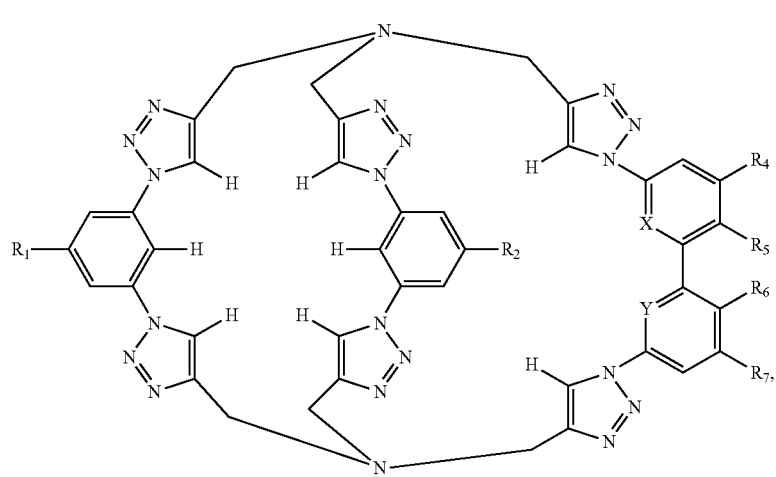
(V)

-continued

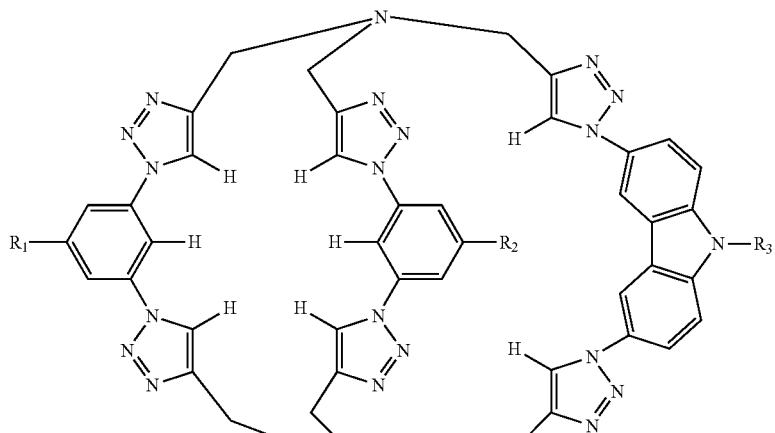

(VI)

and

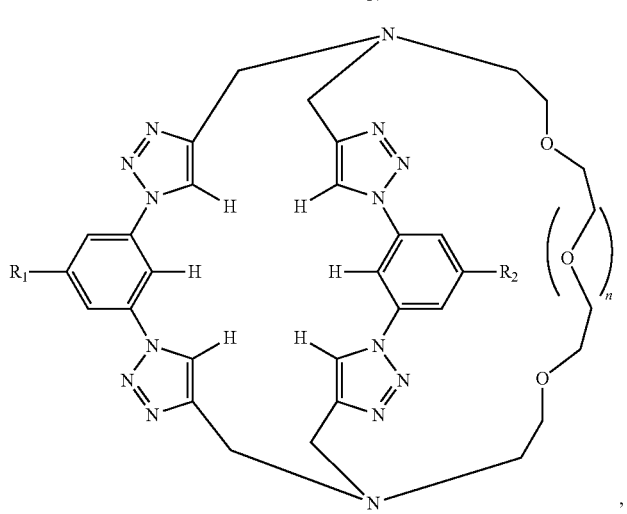

(VII)

wherein for (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen, wherein for (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^1$, $R^9$, $R^{10}$, $R^{11}$, $R^{12}$, and $R^{13}$ are each independently selected from the group consisting of alkenyl, alkyl, aryl, arylalkyl, cycloalkyl, heteroaryl, heterocycle, haloalkyl, and hydrogen, wherein for (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —OR$^3$, —N(R$^4$R$^5$), —CO$_2$R$^6$, —C(O) N(R$^7$R$^8$), wherein R$^3$, R$^4$, R$^5$, R$^6$, R$^7$, and R$^8$ are each independently selected from the group consisting of alkenyl, alkyl, aryl, arylalkyl, cycloalkyl, heteroaryl, heterocycle, haloalkyl, and hydrogen;

(b) removing the solvent phase from the coating to produce a metal surface having dried coating; and (c) annealing the dried coating onto the metal surface by applying a neat solvent to the metal surface having the dried coating of step (b).

36. The method of claim 35, wherein the aryl-triazole bicyclic macrocycle is Formula (I) in which R$^1$, R$^2$, and R$^3$ comprise N,N-dicyclohexylamide groups.

37. The method of claim 35, wherein the aryl-triazole bicyclic macrocycle is selected from the group consisting of the following species of Formula (I):

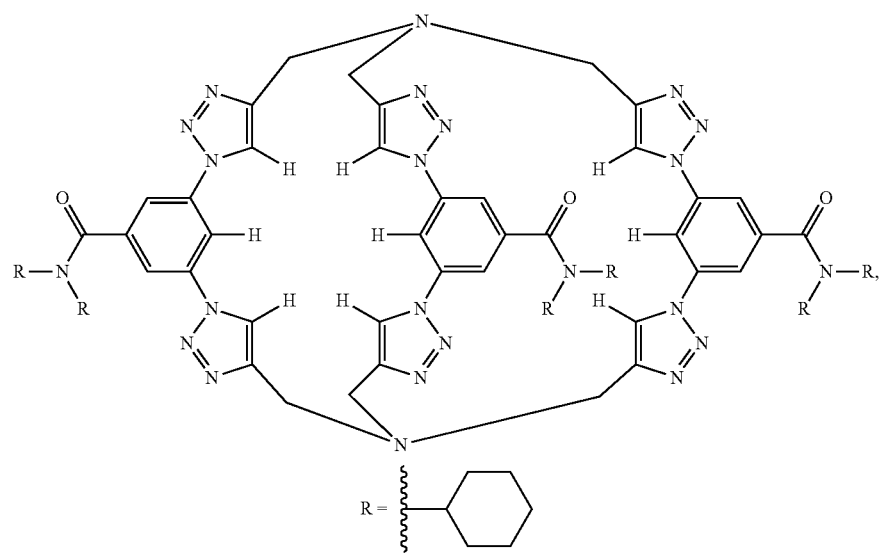

(T-Cage)

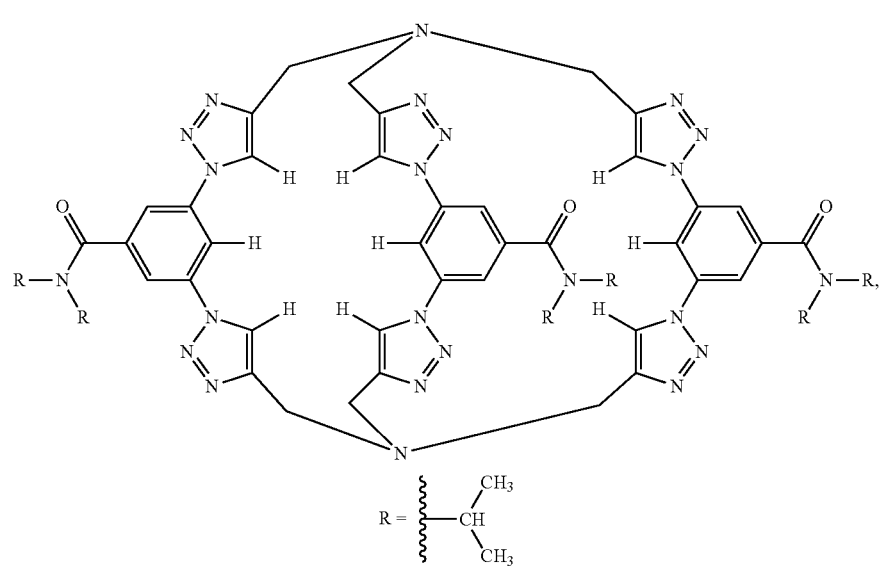

(I-Cage)

-continued
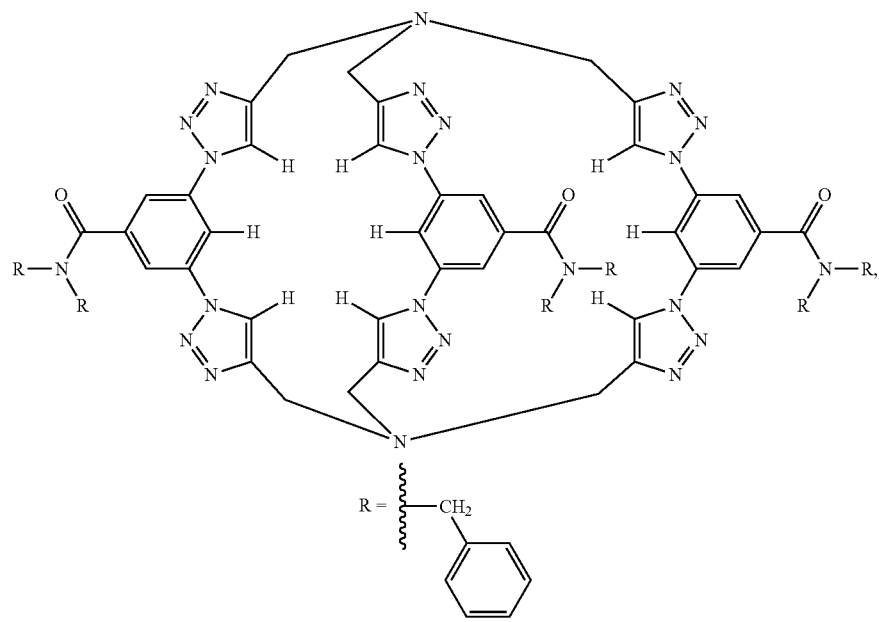
(B-Cage)
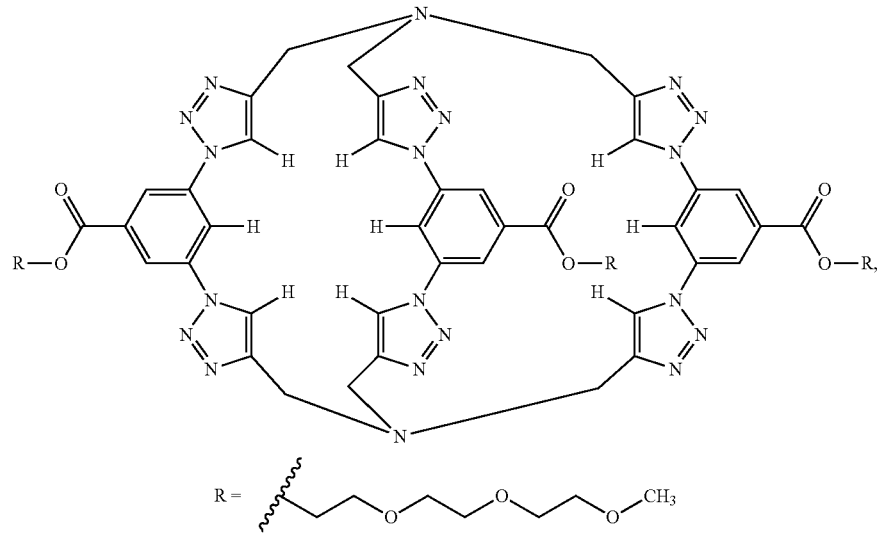
(E-Cage)

-continued
(G-Cage)
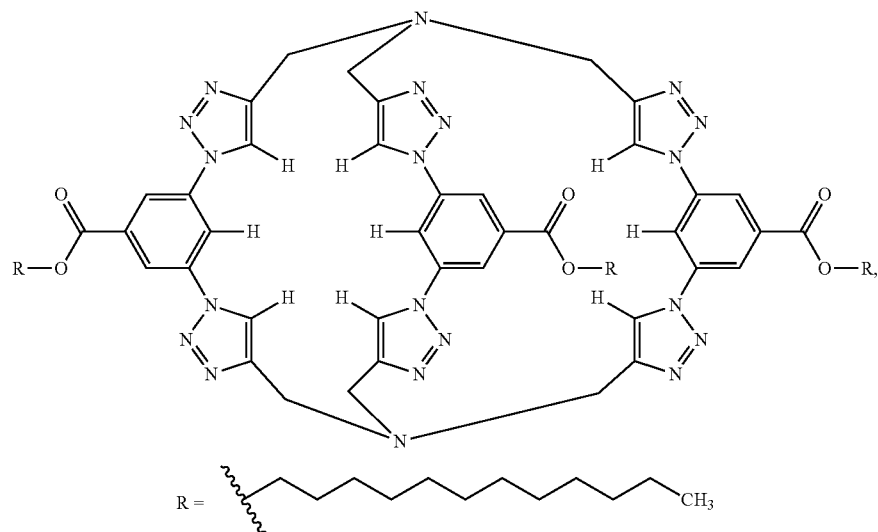
(P-Cage)
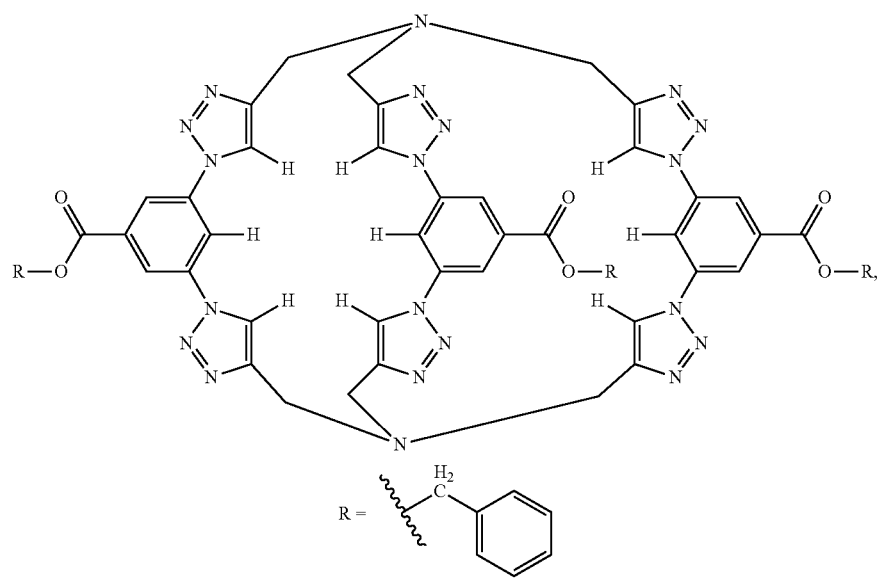
(A-Cage)
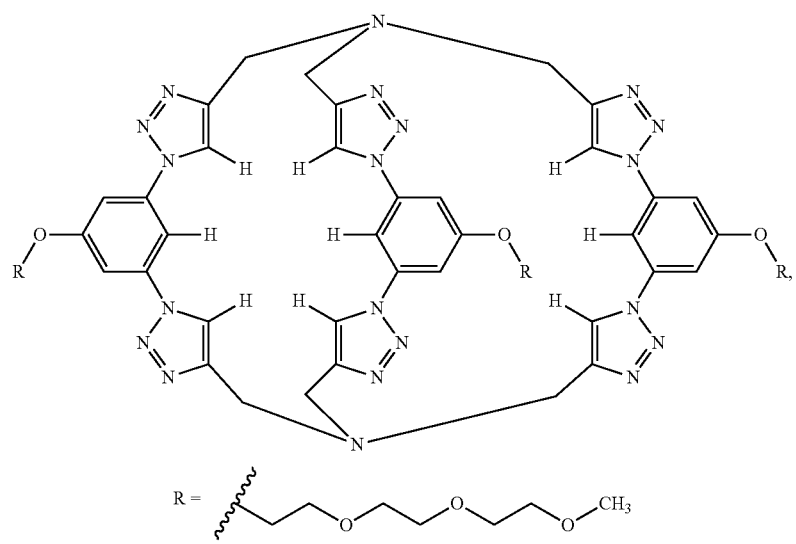

-continued
(D-Cage)
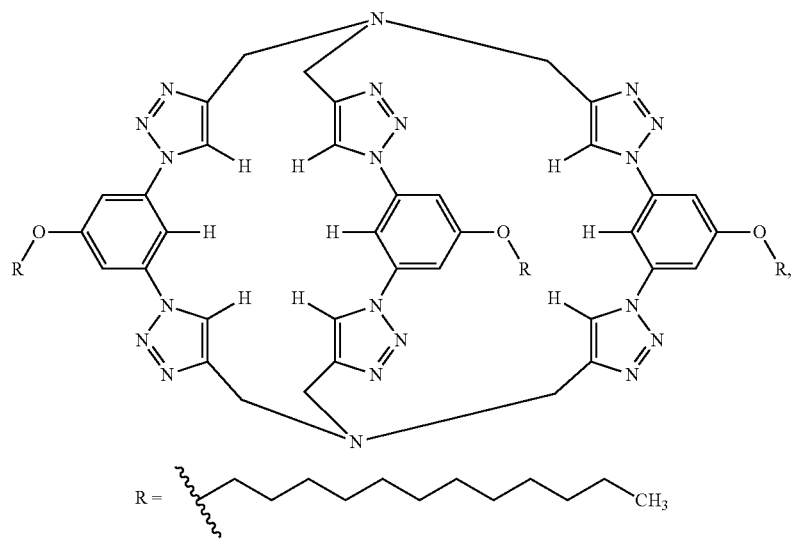
(Z-Cage)
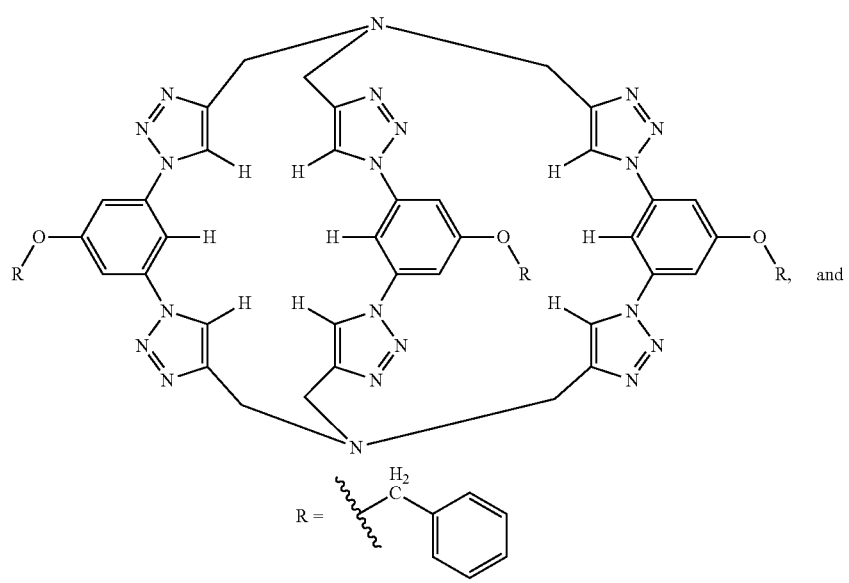
and

-continued
(T-cage-A₂B)
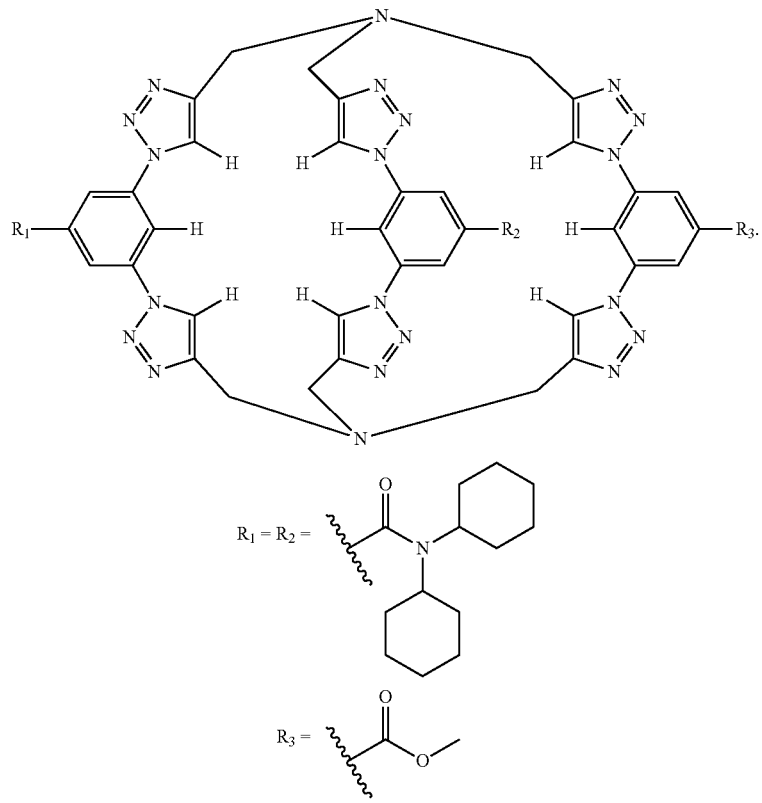
R₁ = R₂ =
R₃ =
38. A composition comprising a metal surface and a coating, wherein the coating comprises an aryl-triazole bicyclic macrocycle selected from the group consisting of Formulas (I), (III), (IV), (V), (VI) and (VII):
(I)
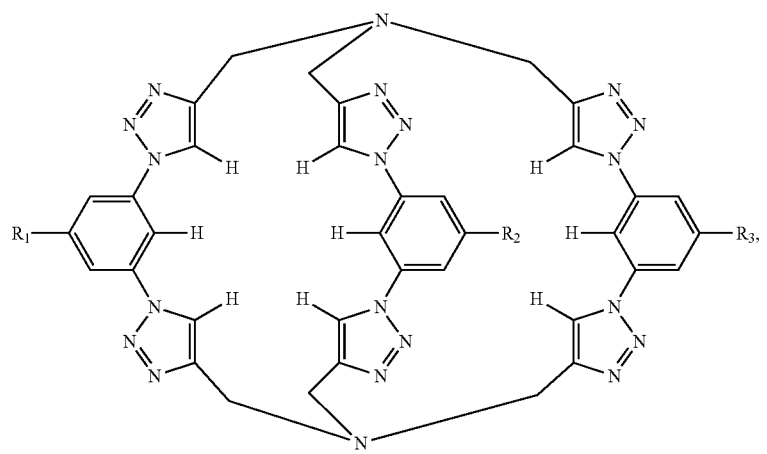

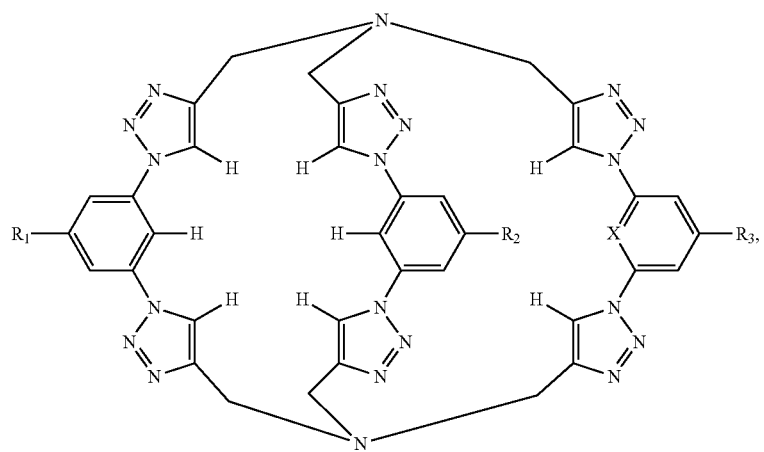
(III)
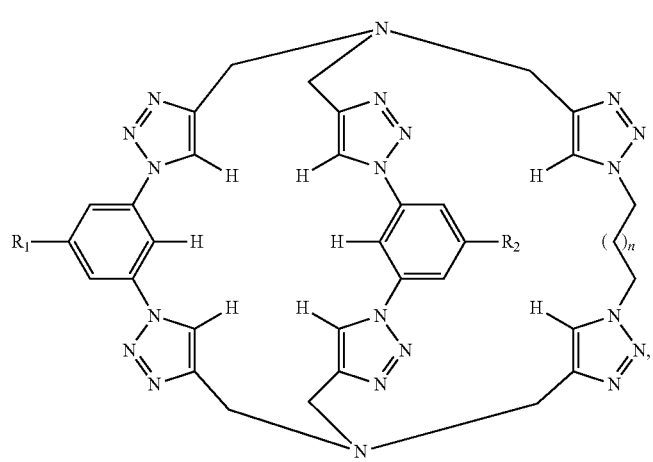
(IV)
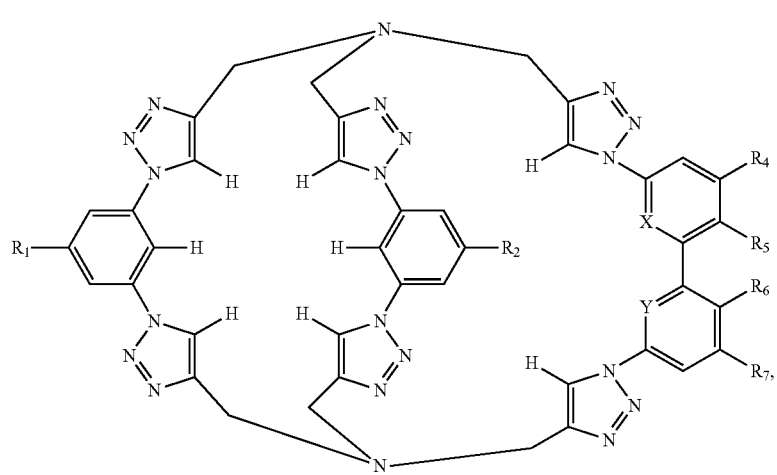
(V)

(VI)

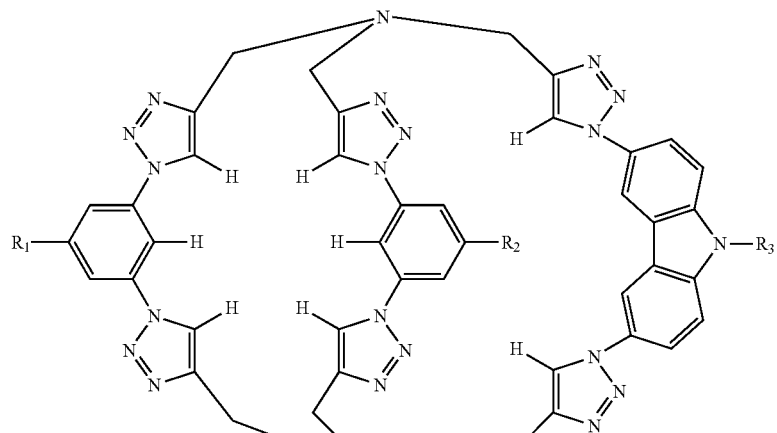

and (VII)

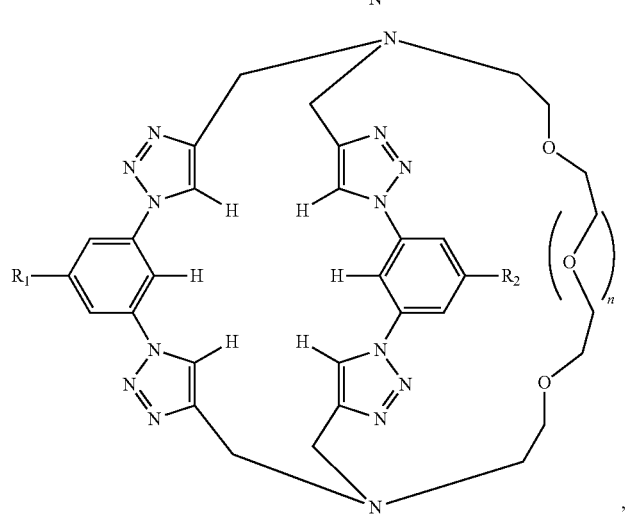

wherein for (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen, wherein for (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^1$, $R^9$, $R^{10}$, $R^{11}$, $R^{12}$ and $R^{13}$ are each independently selected from the group consisting of alkenyl, alkyl, aryl, arylalkyl, cycloalkyl, heteroaryl, heterocycle, haloalkyl, and hydrogen, wherein for (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —OR$^3$, —N(R$^4$R$^5$), —CO$_2$R$^6$, —C(O) N(R$^7$R$^8$), wherein R$^3$, R$^4$, R$^5$, R$^6$, R$^7$, and R$^8$ are each independently selected from the group consisting of alkenyl, alkyl, aryl, arylalkyl, cycloalkyl, heteroaryl, heterocycle, haloalkyl, and hydrogen.

39. The composition of claim 38, wherein the aryl-triazole bicyclic macrocycle is Formula (I) in which R$^1$, R$^2$, and R$^3$ comprise N,N-dicyclohexylamide groups.

40. The complex of claim 38, wherein the aryl-triazole bicyclic macrocycle is selected from the group consisting of the following species of Formula (I):

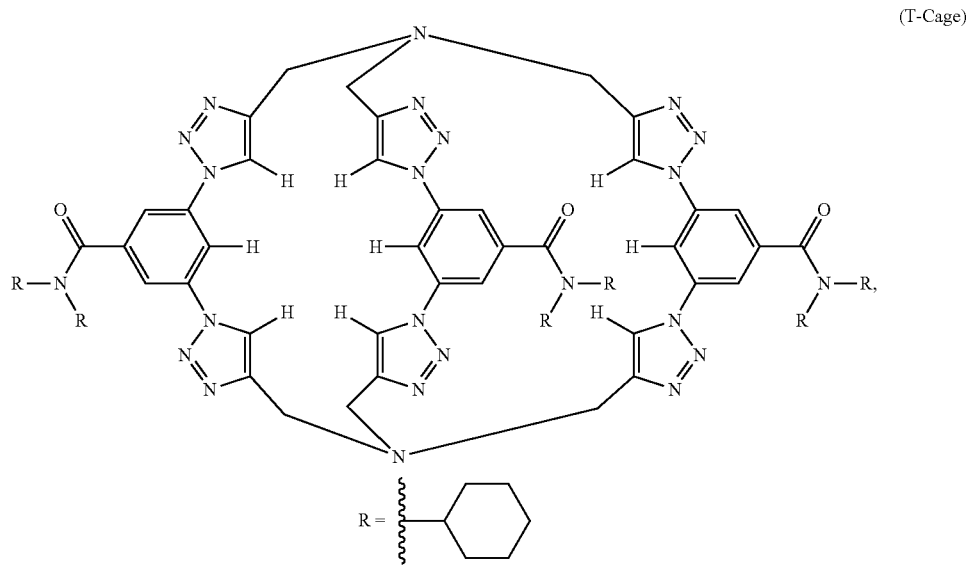

(T-Cage)

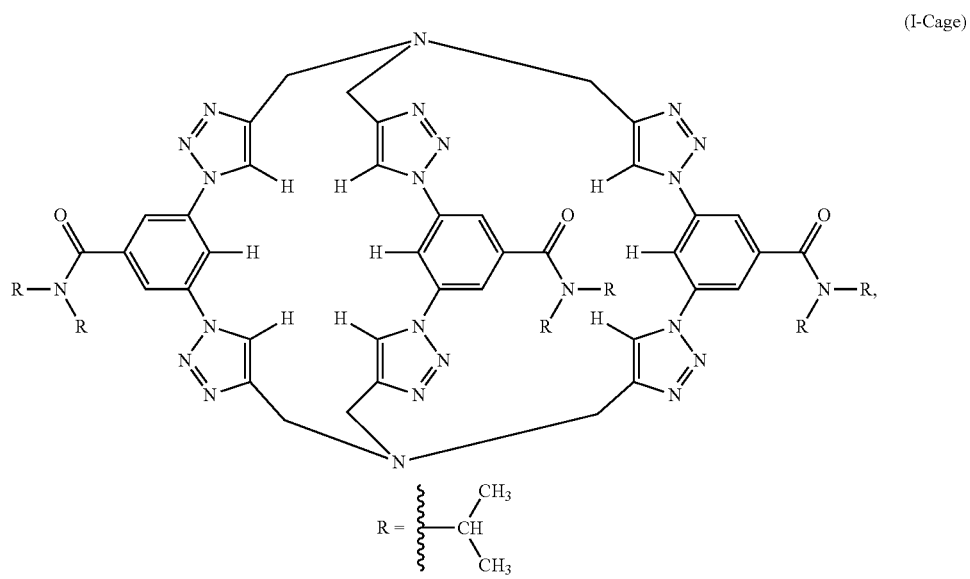

(I-Cage)

-continued
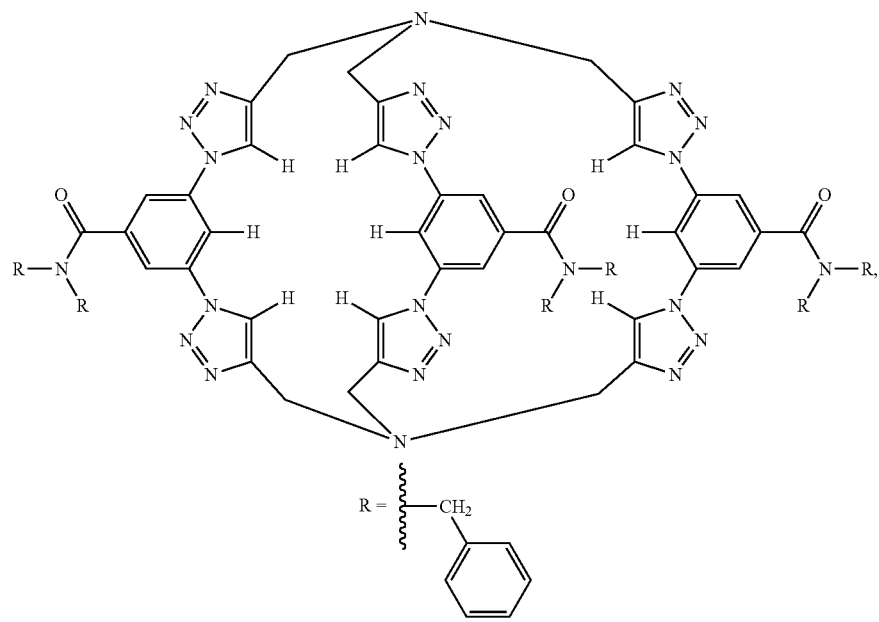
(B-Cage)
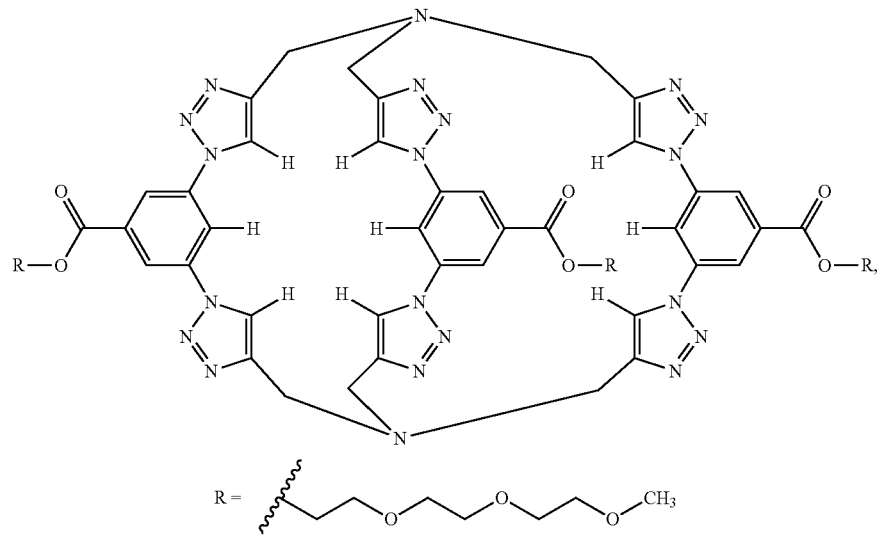
(E-Cage)

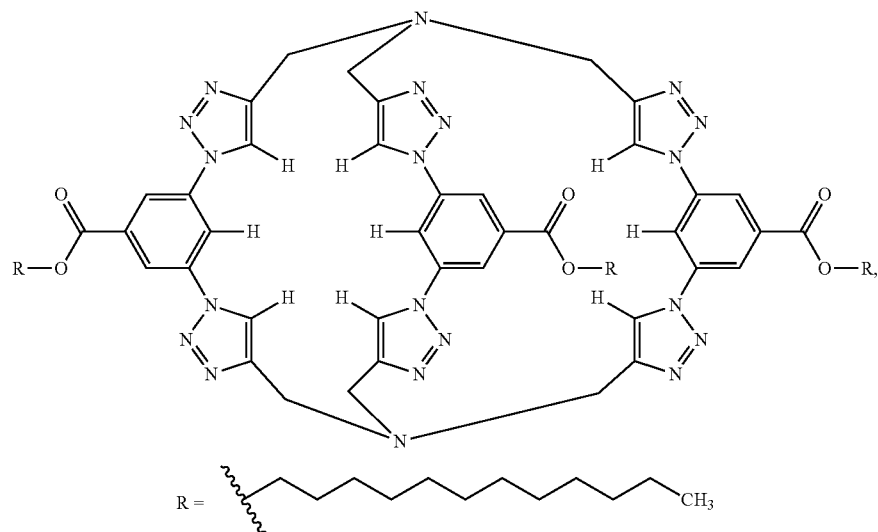
(G-Cage)
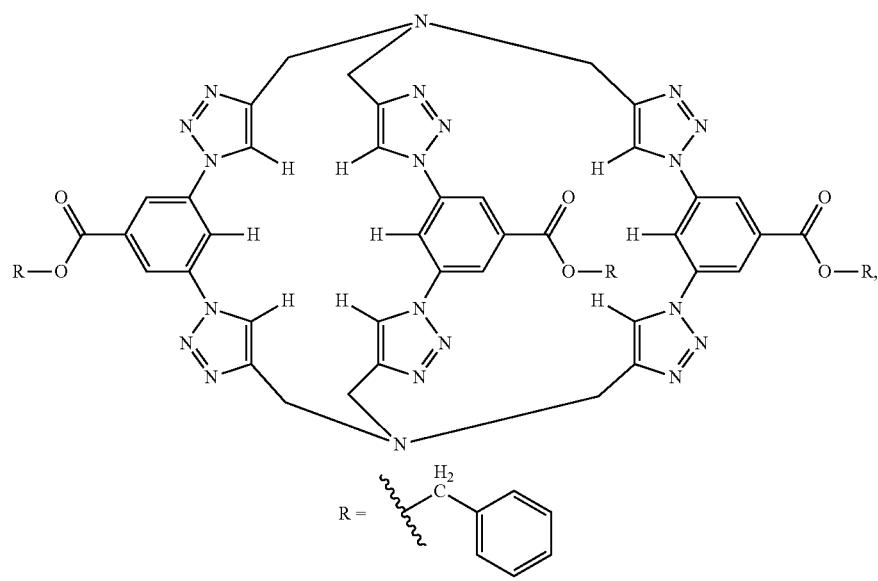
(P-Cage)
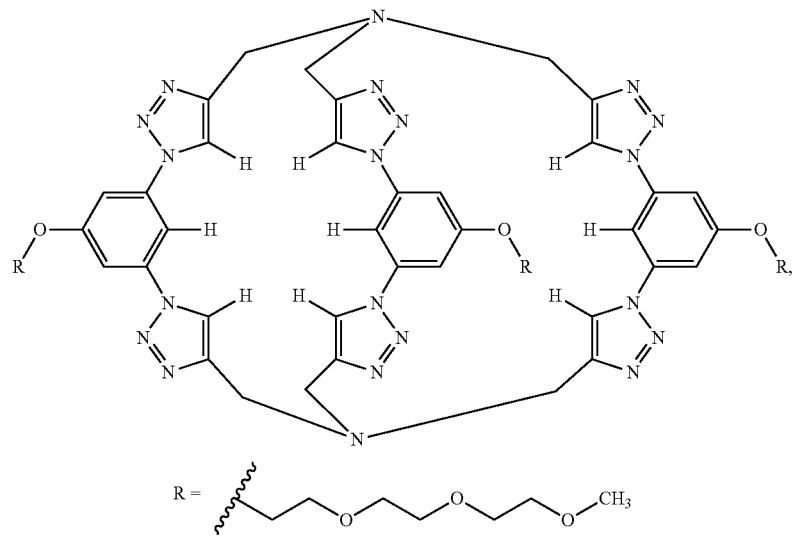
(A-Cage)

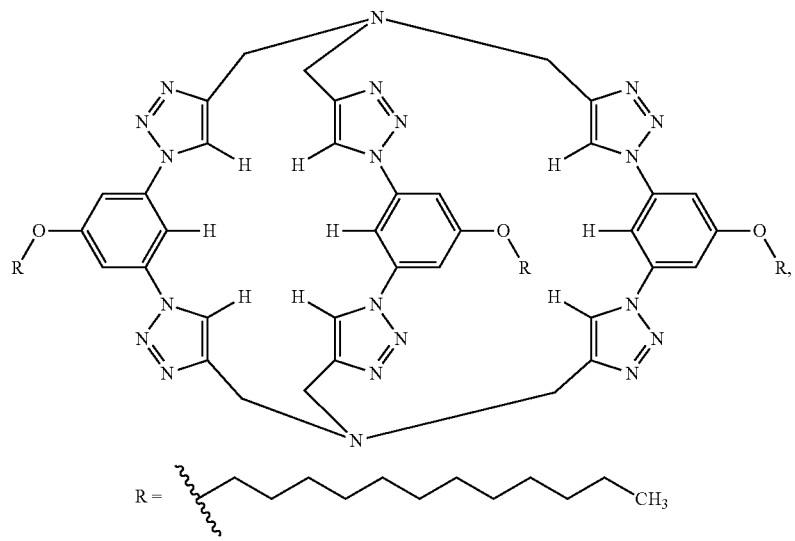
(D-Cage)
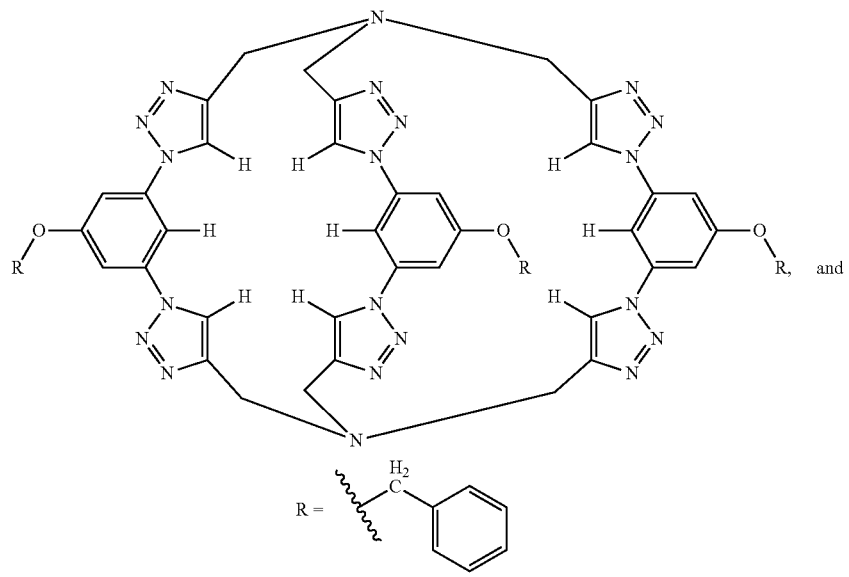
(Z-Cage) and (T-cage-A₂B)
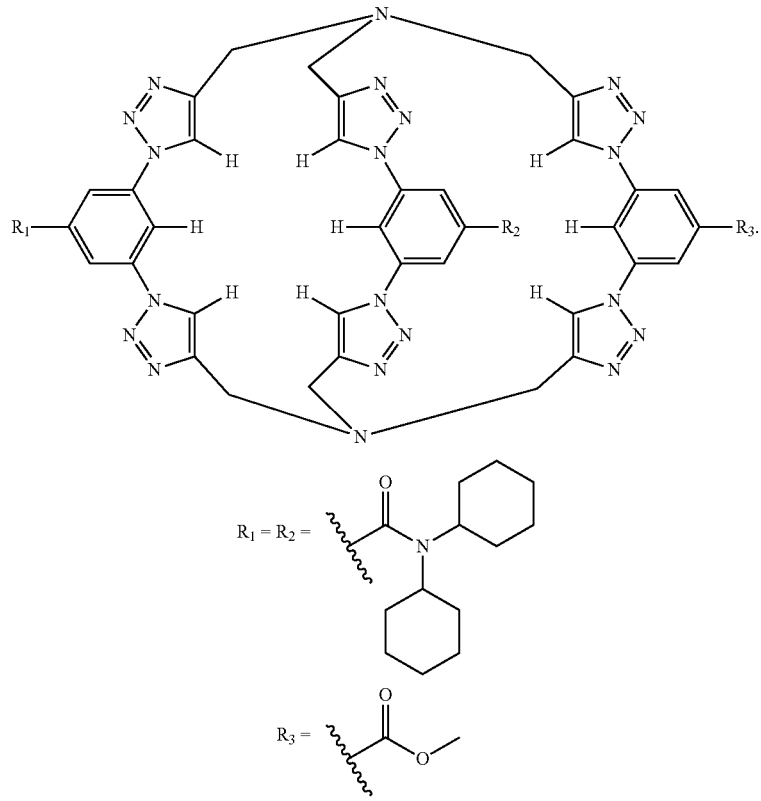
41. The composition of claim 38, wherein the metal surface comprises a metal composed of stainless steel.
42. A formulation, comprising:
   a coating; and
   an aryl-triazole bicyclic macrocycle selected from the group consisting of Formulas (I), (III), (IV), (V), (VI) and (VII):
(I)
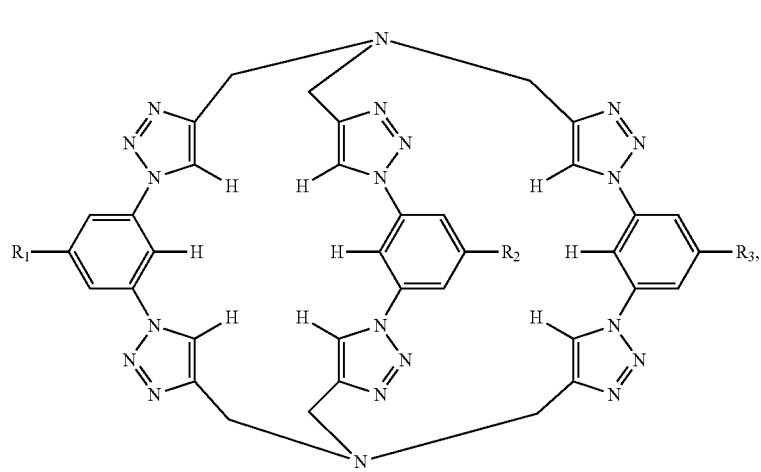

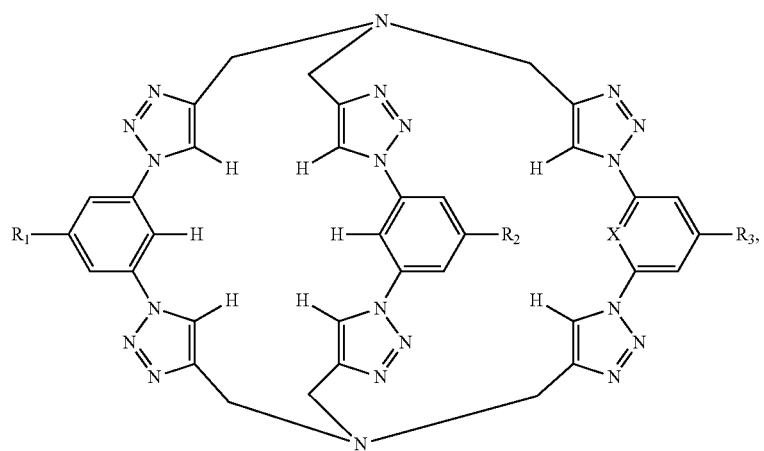
(III)
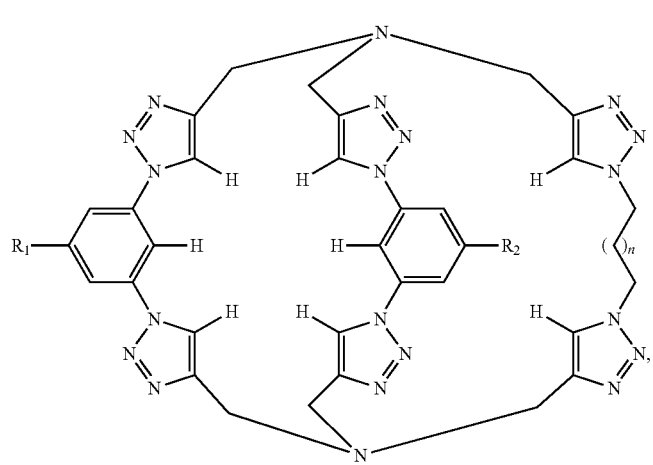
(IV)
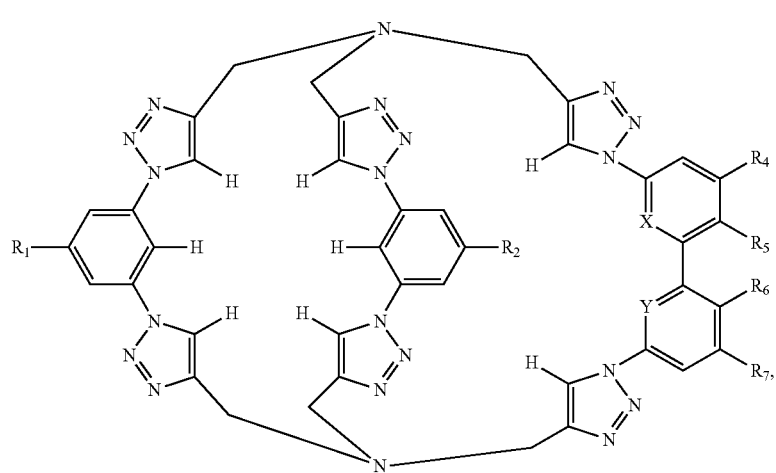
(V)

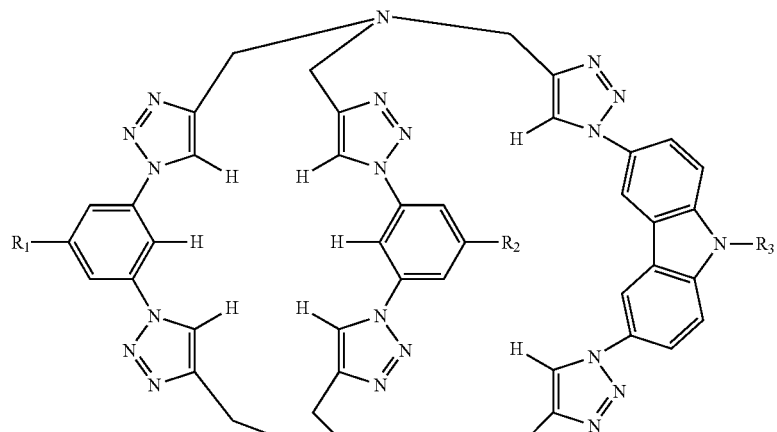

(VI)

and

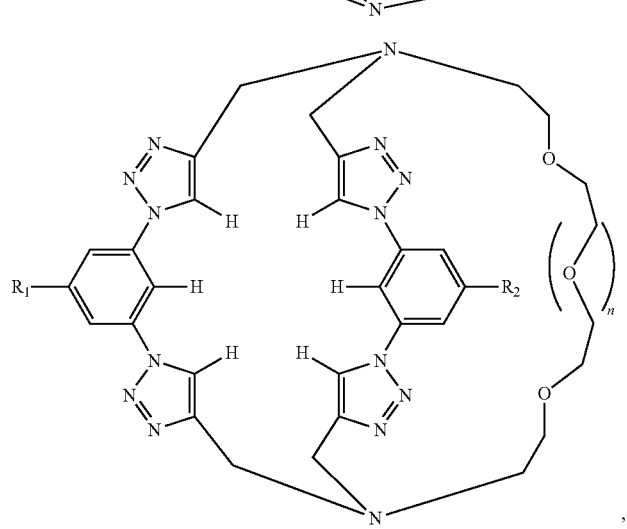

(VII)

wherein for (I), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (III), X is independently selected from the group consisting of CH, CF and N, and $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (IV), n=1 to 10, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^3$, —$N(R^4R^5)$, —$CO_2R^6$, —C(O) $N(R^7R^8)$, wherein $R^3$, $R^4$, $R^5$, $R^6$, $R^7$, and $R^8$ are each independently selected from the group consisting of alkenyl, alkyl, aryl, arylalkyl, cycloalkyl, heteroaryl, heterocycle, haloalkyl, and hydrogen, wherein for (V), X and Y are independently selected from the group consisting of CH, CF and N, and $R^1$, $R^2$, $R^4$, $R^5$, $R^6$ and $R^7$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^8$, —$N(R^9R^{10})$, —$CO_2R^{11}$, —C(O)—$N(R^{12}R^{13})$, wherein $R^8$, $R^9$, $R^{10}$, $R^{11}$, $R^{12}$ and $R^{13}$ are each independently selected from the group consisting of alkenyl, alkyl, aryl, arylalkyl, cycloalkyl, heteroaryl, heterocycle, haloalkyl, and hydrogen, wherein for (VI), $R^1$, $R^2$, and $R^3$ are independently selected from the group consisting of alkenyl, alkyl, alkoxy, alkyl-NH-alkyl, aryl, cycloalkyl, heteroaryl, heterocycle, haloalkyl, hydrogen, iodo, —$OR^4$, —$N(R^5R^6)$, —$CO_2R^7$, —C(O)—$N(R^8R^9)$, wherein $R^4$, $R^5$, $R^6$, $R^7$, $R^8$, and $R^9$ are each independently selected from the group consisting of alkenyl, alkyl, aryl, arylalkyl, cycloalkyl, heteroaryl, heterocycle, haloalkyl, and hydrogen, wherein for (VII), n=1 to 4, and $R^1$ and $R^2$ are independently selected from the group consisting of alkenyl, alkyl, alkoxy, alkyl-NH-alkyl, aryl, cycloalkyl, heteroaryl, heterocycle, haloalkyl, hydrogen, iodo, —OR$^3$, —N(R$^4$R$^5$), —CO$_2$R$^6$, —C(O) N(R$^7$R$^8$), wherein R$^3$, R$^4$, R$^5$, R$^6$, R$^7$, and R$^8$ are each independently selected from the group consisting of alkenyl, alkyl, aryl, arylalkyl, cycloalkyl, heteroaryl, heterocycle, haloalkyl, and hydrogen.

43. The formulation of claim 42, wherein the aryl-triazole bicyclic macrocycle is Formula (I) in which R$^1$, R$^2$, and R$^3$ comprise N,N-dicyclohexylamide groups.

44. The formulation of claim 42, wherein the aryl-triazole bicyclic macrocycle is selected from the group consisting of the following species of Formula (I):

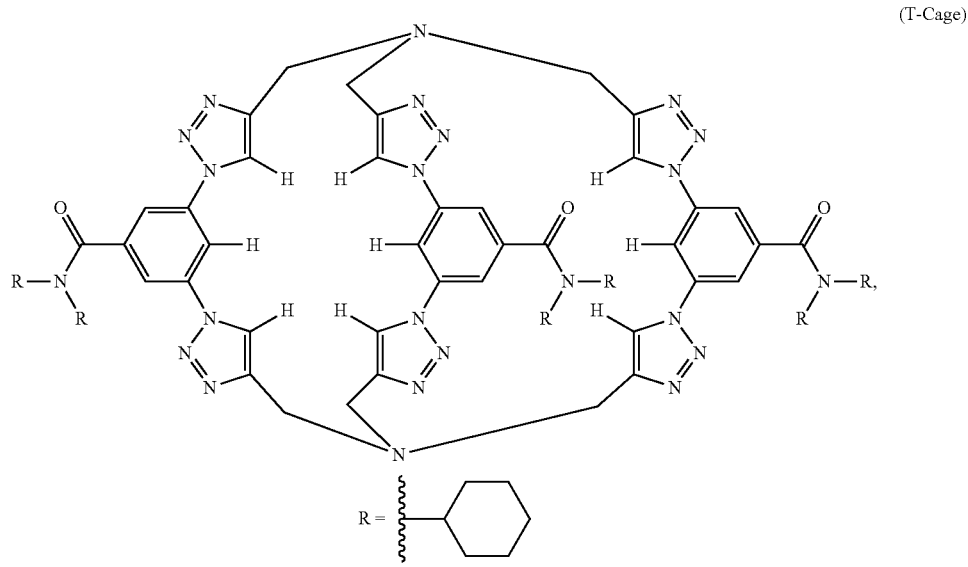

(T-Cage)

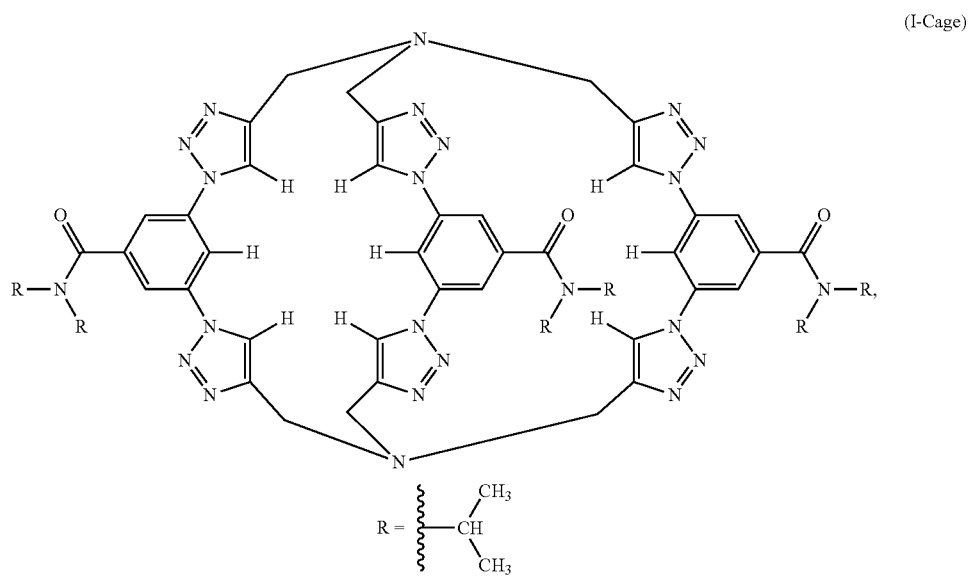

(I-Cage)

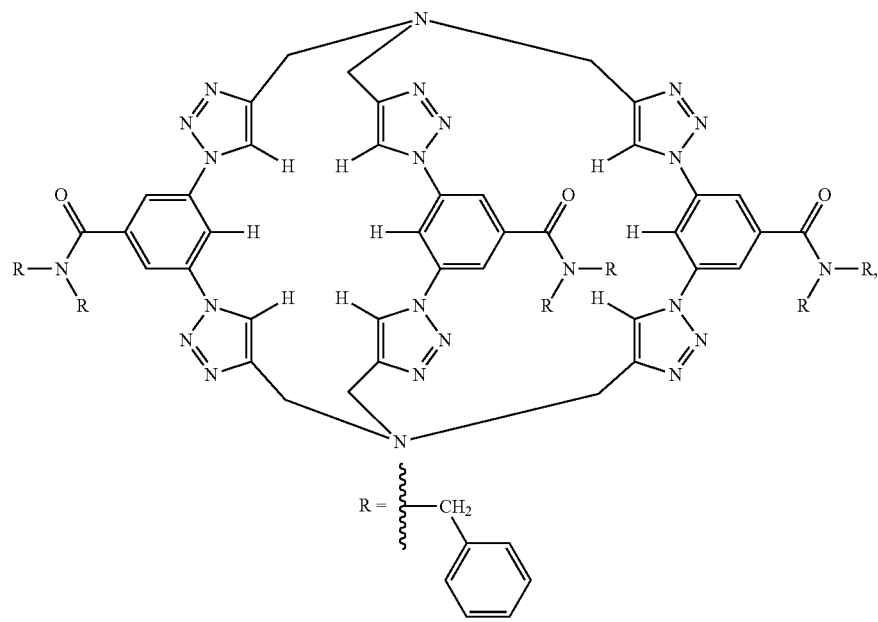
(B-Cage)
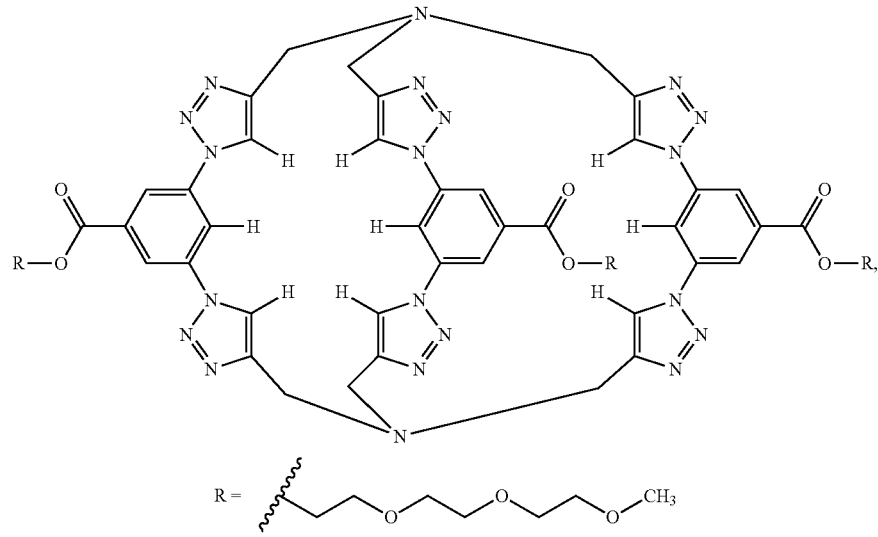
(E-Cage)

(G-Cage)
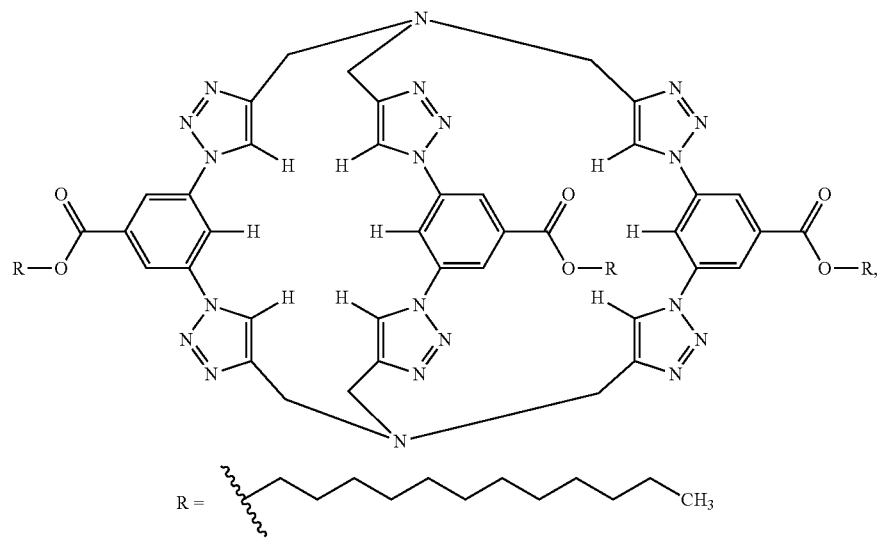
(P-Cage)
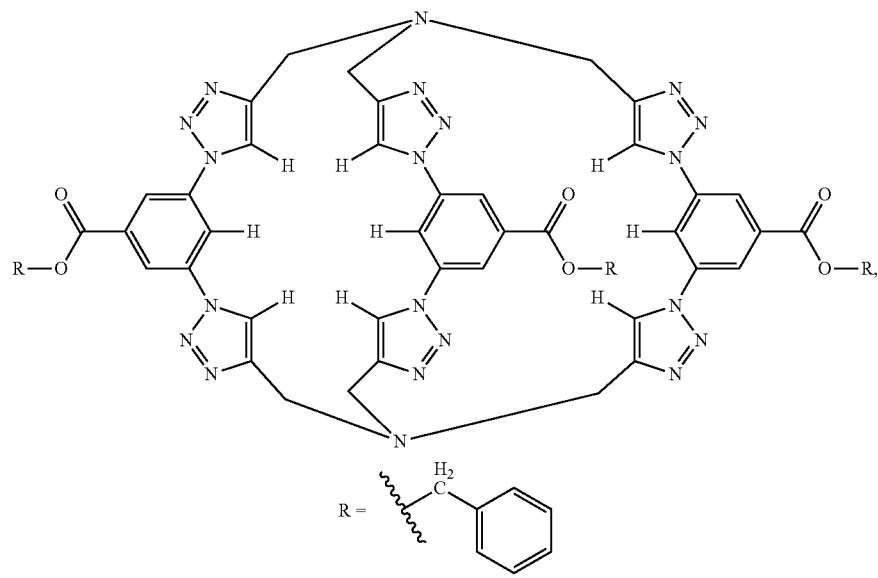
(A-Cage)
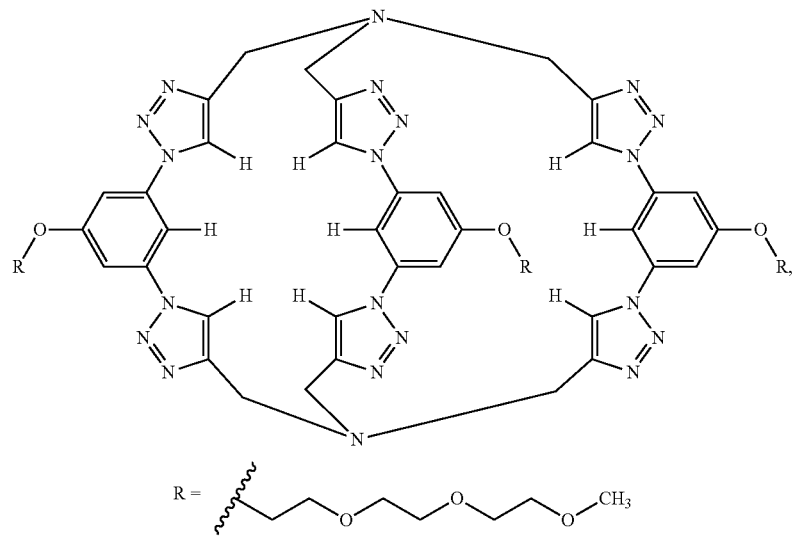

-continued
(D-Cage)
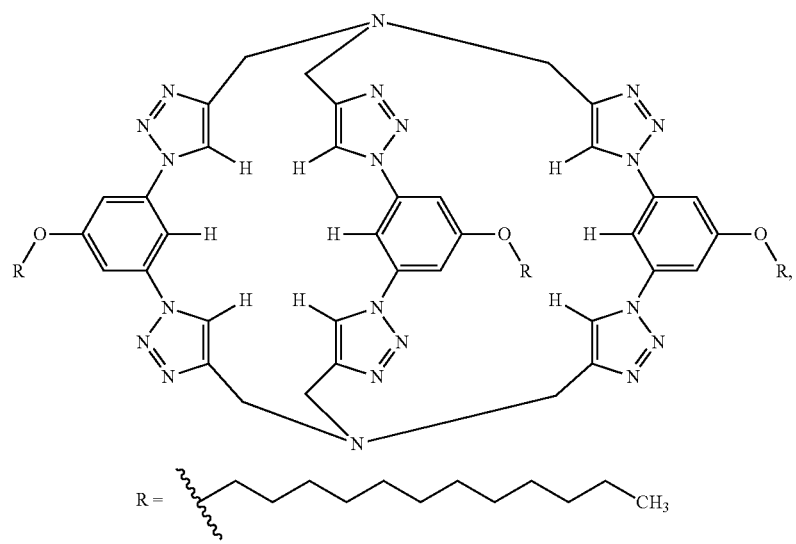
(Z-Cage)
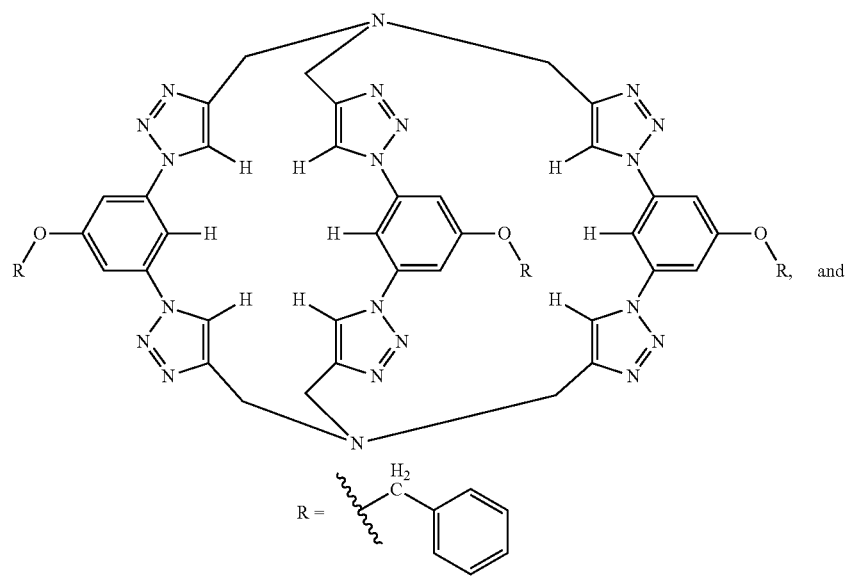
and

-continued (T-cage-A$_2$B)

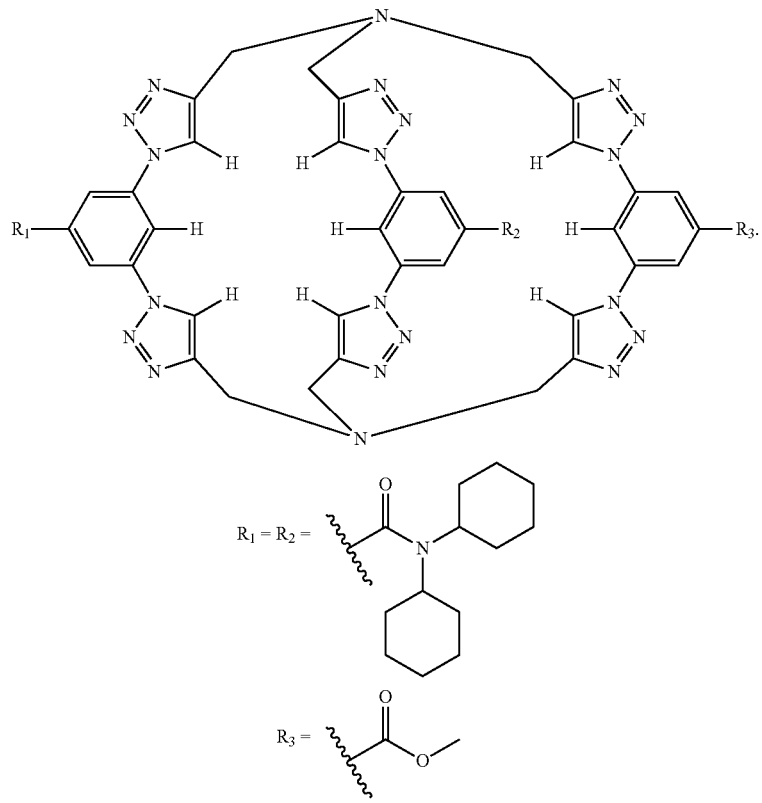

45. The formulation of claim 42, wherein the coating comprises a polymer.

46. The formulation of claim 45, wherein the polymer is selected from the group consisting of polymethyl methacrylate, polymethyl acrylate, acrylic polymers, latex, epoxy and polyester.

47. The formulation of claim 42, wherein the coating comprises a pigment.

48. The formulation of claim 47, wherein the pigment comprises a colorant.

* * * * *